(12) United States Patent
Kumada et al.

(10) Patent No.: US 11,136,609 B2
(45) Date of Patent: Oct. 5, 2021

(54) SEPARATING AGENT FOR HUMAN SERUM-DERIVED IGG POLYCLONAL ANTIBODIES, AND METHOD FOR SEPARATING HUMAN SERUM-DERIVED IGG POLYCLONAL ANTIBODIES USING SAME

(71) Applicants: NATIONAL UNIVERSITY CORPORATION KYOTO INSTITUTE OF TECHNOLOGY, Kyoto (JP); DAICEL CORPORATION, Osaka (JP)

(72) Inventors: Yoichi Kumada, Kyoto (JP); Yuya Hasegawa, Kyoto (JP); Seiichi Uchimura, Himeji (JP)

(73) Assignees: NATIONAL UNIVERSITY CORPORATION KYOTO INSTITUTE OF TECHNOLOGY, Kyoto (JP); DAICEL CORPORATION, Osaka (JP)

( * ) Notice: Subject to any disclaimer, the term of this patent is extended or adjusted under 35 U.S.C. 154(b) by 480 days.

(21) Appl. No.: 15/774,398

(22) PCT Filed: Nov. 7, 2016

(86) PCT No.: PCT/JP2016/082986
§ 371 (c)(1),
(2) Date: May 8, 2018

(87) PCT Pub. No.: WO2017/082213
PCT Pub. Date: May 18, 2017

(65) Prior Publication Data
US 2018/0327803 A1   Nov. 15, 2018

(30) Foreign Application Priority Data

Nov. 9, 2015 (JP) .............................. JP2015-219765
Feb. 10, 2016 (JP) .............................. JP2016-024016

(51) Int. Cl.
| | | |
|---|---|---|
| *C07K 1/22* | (2006.01) | |
| *C07K 16/42* | (2006.01) | |
| *C12P 21/00* | (2006.01) | |
| *C12Q 1/70* | (2006.01) | |
| *C12N 15/09* | (2006.01) | |
| *C07K 16/06* | (2006.01) | |
| *C12N 15/62* | (2006.01) | |

(52) U.S. Cl.
CPC .............. *C12P 21/005* (2013.01); *C07K 1/22* (2013.01); *C07K 16/065* (2013.01); *C07K 16/42* (2013.01); *C12N 15/09* (2013.01); *C12N 15/62* (2013.01); *C12Q 1/70* (2013.01); *C07K 2317/14* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 480,466 | A | 8/1892 | Hubbard |
| 4,618,589 | A | 10/1986 | Jefferis et al. |
| 4,806,466 | A | 2/1989 | Papahadjopoulos et al. |
| 2007/0231378 | A1 | 10/2007 | Chang et al. |
| 2008/0102474 | A1 | 5/2008 | Lenz et al. |
| 2009/0297534 | A1 | 12/2009 | Paul et al. |
| 2012/0070448 | A1 | 3/2012 | Tawara et al. |
| 2012/0208216 | A1 | 8/2012 | Essig et al. |
| 2016/0347826 | A1 * | 12/2016 | Knappik ............ B01D 15/3809 |

FOREIGN PATENT DOCUMENTS

| | | |
|---|---|---|
| JP | 57-501147 A | 7/1982 |
| JP | 9-506508 A | 6/1997 |
| JP | 2008-525766 A | 7/2008 |
| JP | 2009-501713 A | 1/2009 |
| JP | 2009-142269 A | 7/2009 |
| JP | 2013-508700 A | 3/2013 |
| JP | 2015-097496 A | 5/2015 |
| JP | 2015-145366 A | 8/2015 |
| WO | WO 95/15388 A1 | 6/1995 |
| WO | WO-2006059904 A1 * | 6/2006 ............... C07K 1/22 |

OTHER PUBLICATIONS

Ameer et al. "Single-chain antibody fragment-based adsorbent for the extracorporeal removal of B2-microglobulin" Kidney International, 65 (2004), pp. 310-322 (Year: 2004).*
Omidi et al. "Affinity purificaiton of tumor necrosis factor-alpha expressed in Raji cells by produced scFv antibody coupled CNBr-activated sepharose" Advanced Pharmaceutical Bulletin, 2013, 3(1) 19-23 (Year: 2013).*
Zhang et al. "Production and characterization of a human monoclonal anti-idiotype to anti-ribosomal P antibodies" Clinical Immunology 114 (2005) 130-136 (Year: 2005).*
English translation of International Preliminary Report on Patentability and Written Opinion dated May 24, 2018, in PCT International Application No. PCT/JP2016/082986.
Extended European Search Report, dated Nov. 6, 2018, for European Application No. 16864174.4.

(Continued)

*Primary Examiner* — Daniel E Kolker
*Assistant Examiner* — James L Rogers
(74) *Attorney, Agent, or Firm* — Birch, Stewart, Kolasch & Birch, LLP

(57) ABSTRACT

An object of the present invention is to provide a separation agent for separating a human serum-derived IgG polyclonal antibody. This object is achieved by a separation agent for separating a human serum-derived IgG polyclonal antibody, the separation agent including: a carrier; and a single-chain antibody which has a dissociation constant for a human serum-derived IgG polyclonal antibody of not more than $3.0 \times 10^{-8}$ M and which binds to the surface of the carrier via a chemical bond.

10 Claims, 36 Drawing Sheets

Specification includes a Sequence Listing.

(56) References Cited

OTHER PUBLICATIONS

Kumada, "Site-specific Immobilization of Recombinant Antibody Fragments through Material-binding Peptides for the Sensitive Detection of Antigens in Enzyme Immunoassays," Biochimica et Biophysica Acta, vol. 1844, No. 11, 2014 (Available online Aug. 8, 2014), pp. 1960-1969, XP029050317.
Boder et al., "Directed evolution of antibody fragments with monovalent femtomolar antigen-binding affinity," PNAS, vol. 97, No. 20, Sep. 26, 2000, pp. 10701-10705, XP002185398.
European Communication pursuant to Article 94(3) EPC for European Application No. 16864174.4, dated Oct. 16, 2019.
Kuan et al., "Recombinant single-chain variable fragment antibodies against extracellular epitopes of human multidrug resistance protein MRP3 for targeting malignant gliomas," International Journal of Cancer, vol. 127, 2010 (published online Nov. 23, 2009), pp. 598-611.
International Search Report (PCT/ISA/210) issued in PCT/JP2016/082986, dated Feb. 7, 2017.
Kumada et al., "Application of protein-coupled liposomes to effective affinity screening from phage library", Journal of Chromatography A, vol. 1080, 2005, pp. 22-28.
Written Opinion (PCT/ISA/237) issued in PCT/JP2016/082986, dated Feb. 7, 2017.

\* cited by examiner

| Rank | Clone No. | koff (s⁻¹) | FR1 | CDR1 | FR2 | CDR2 | V_H FR3 | CDR3 | FR4 | SEQ ID NO. |
|---|---|---|---|---|---|---|---|---|---|---|
| 1 | III-75 | 4.00E-04 | QSVKESGGGLVQPGGTPLRLSCTV | SGIBLSSMA | MGWVRQAPGEGLEWIGT | ISIVGKT | VFASWAKGRFTISKI STTVDLKITSPTTEDTATYFC | ATKVDSFGYAYNYWFGTLW | GPGTLVTVTS | 12 |
| 2 | III-23 | 2.78E-04 | QSVKESEGRLVTPGTPLTLTCTV | SGFSLSRYA | VSWVRQAPGKGLEWIG | IGSGGST | SYATWAKGRFTISKT STTVDLKITSPTTEDTVTYFC | GSYVDSMGYAY | VSLW | GPGTLVTVTS | 13 |
| 3 | III-26 | 5.71E-04 | SEGLVESEGGLVKPGGTLTLTCTV | SGIDLSSYA | MGWVRQVPGKGLEWIG | IGSGHET | AYANWAKGRFTISKISSTTVDLKWTSLTTEDTATYFC | ATDVGIVGYAY | GHLW | GPGTLVTVTS | 14 |
| 4 | III-43 | 6.41E-04 | | | | | | | | |
| 5 | III-58 | 7.42E-04 | QQQLRESGGRLVTPGGSLTLTCTV | SGIDLNSYA | MGWVRQAPGKGLEYIG | IRNSGNT | VYASWAKGRFTISKTSSTTVDLKWTSLTTEDTATYFC | ARYSGBNGGALN | LW | GPGTLVTVTS | 15 |
| 6 | II-18 | 8.00E-04 | QSLEESGGRLVTPGGTPLTLTCTV | SGIBLSSMA | MTWVRQAPCGEGLEWIGT | ISTGGST | VFASWAKGRFTISKT STTVDLKITSPTTEDTATYFC | ATKVDSYGYAYNYWFGTLW | GPGTLVTVTS | 16 |
| 7 | II-16 | 8.33E-04 | VKESEGRLVTPGTPLTLTCTV | SGFSLSSYA | MGWVRQAPGKGLRYIG | ISSSGST | VYASWAKGRFTISKT STTVDLKITSPTTEDTATYFC | ARYSGONGGALN | LW | GPGTLVTVTS | 17 |
| 8 | I-27 | 8.59E-04 | QQQLMESGGGLVTPGTPLTLTCTV | SGIBLRNYA | MGWVRQAPCGKGLEWIG | IASGNTD | VASWAKGRFTISHT STTVDLKITSPTTEDTATYFC | ARYSGBNGGTLN | LW | GPGTLVTVTS | 18 |
| 11 | III-9 | 8.80E-04 | QSLEESGGRLVTPGTPLTLTCTV | SGIDLSSMA | MTWVRQAPCGEGLEWIG | ISTGGST | VFASWAKGRFTISKT STTVDLKITSPTTEDTATYFC | ATNVDSYGYAYNYWFGTLW | LW | GPGTLATVTT | 19 |
| 63 | I-7 | 1.75E-03 | QSLEESGGRLVTPGTPLTLTCTV | SGIDLRRYA | MGWVRQAPGKGLQWIG | IASGNTD | YASWAKGRFTISAI STTVDLKITSFTIEDTATYFC | ARYSGBNGGTLN | LW | GPGTLVTVTS | 20 |

Fig. 8-1

| Rank | Clone No. | koff (s^-1) | FR1 | CDR1 | FR2 | CDR2 | FR3 | CDR3 | FR4 | SEQ ID NO. |
|---|---|---|---|---|---|---|---|---|---|---|
| 1 | III-75 | 4.08E-03 | ELDLTQPPSVSGAVGGTVTIKCQAS | ENINSE | LAWYQQKPGQRPKLLIY | DAS | KLASGVPSRFSGSGSGTEYTLTISGMQCDDAATYYC | QSTYYDGNYVYA | FGGGTEVDVTKS | 21 |
| 2 | III-23 | 2.78E-03 | ELVLTQTPSPVSGSAVGGTVTIRCQAS | QSISTA | LAWYQQKPGQPPKLLIY | SAS | TLASGVSSRFKGSGSGTGFTLTISDLECADAATYYC | QSVYGSSSD NA | PGGGTEVIKRS | 22 |
| 3 | III-26 | 5.73E-04 | ELVMTQIASPVSAAVGGTVTIKCQAS | QSISTA | LAWYQQKPGQPPKLLIY | DAS | TLASWSSRFKGSGSGTEFTLTISDLECADAATYYC | QTVPGSDID NA | PEGGTEVRITGS | 23 |
| 4 | III-43 | 6.91E-04 | | | | | | | | |
| 5 | III-58 | 2.42E-04 | ELVMTQTAASVSGPVGGTVTIKCQAS | EFIRNY | LAWYQQKPGQPPKLLIY | TTS | NLASGVPSRFSGSGSGTEYTLTISDLECADAATYYC | QNYYDISTYGNA | PGGGTEVVTKGS | 24 |
| 6 | II-18 | 9.08E-04 | ELVMTQTAASVSEPVGGTVTIKCQSS | QNINNE | LAWYQQKPGQPPKLLIY | DAS | KLASGVPSRFSGSGSGTEFTLTISGMQCDDAATYYC | QSTYYDGNYVYA | PGGGTEVRVTKGS | 25 |
| 7 | II-16 | 8.39E-04 | ELVMTQTAASVSEHPVGGTVTIKCQSS | QHIRSY | LAWYQQKPGQPPKLLIS | AAS | TLASGVSSRFKGSGSGTEFTLTISDLECADAATYYC | QRVYDIRNYGMG | PGGGTEVRITGS | 26 |
| 8 | I-27 | 8.59E-04 | ELVMTQIAASVSEPVGGIVTIKCQAS | EHIKNY | LAWYQQKPGQPPKLLIY | TTS | NLASGVPSRFSGSGSGTEYTLTISDLECADAATYYC | QNYDISTYGNT | PGGGTEVDYKGS | 27 |
| 11 | III-8 | 9.00E-04 | ELVMTQTAASVSEPVGGTVTIKCQAS | QSISDE | LAWYQQKPGQRPKLLIY | DAS | DLASGVPSRFSGSGSGTEFTLTISEVQCDDAATYYC | QSAYYDNRVYA | PGGGTEVEVTGS | 28 |
| 23 | C-7 | 1.75E-03 | ELVMTQTAASVSEPVGGTVTIKCQAS | QSISSY | LAWYQQKPGQPPKLLIY | AAS | NLASGVSSRFKGSGSGTEFTLTISDLECADAATYYC | QSVYSISSYGNT | PGGGTEVEITGS | 29 |

Fig. 8-2

At the completion of Round 1

| Clone No. | FR1 | CDR1 | FR2 | CDR2 | FR3 | CDR3 | FR4 | SEQ ID NO | Remarks |
|---|---|---|---|---|---|---|---|---|---|
| IgA H1-1 | GGLEESGGGLVKPGGSLRLSCTA | SGFSLSSYA | MGWVRQAPGKGLEWIGI | IGSGGT | YYASPASGRFTISRT AIYPQLKAISSPFYEDTAIYFC | ARAGRDFVIGDHLW | GPGTLVTVTS | 36 | |
| IgA R1-2 | | | | | | | | | |
| IgA H1-3 | SRRESPGGSLVTPGTPELTICTV | SGIDLSSYA | MIRYRGSPGSGLEYIGI | ISSTGGSA | YYASRASGARFAIANT SITMPLKMISPFTERIATEC | GRYINGGFNPHR | GPGILVTVIS | 37 | |
| IgA R1-4 | | | | | | | | | |
| IgA H1-5 | | | | | | | | 38 | |
| IgA R1-6 | | | | | | | | | |
| IgA H1-7 | GGLEESGGGLVTPGGSLRLICTV | SGIDLSSYA | MGWVRQAPGKGLEWIGI | KGTGGSA | DYARASGRFISRT SITVDLAISPFYEDIATYFC | VRDNKPWGGSAR | GPGRLVTVIS | 39 | |
| IgA H1-8 | | | | | | | PRAILVTVTS | 40 | |
| IgA H1-9 | | | | | | | | | |
| IgA R1-10 | GVESSGGRLVTPGTPLTLICTV | SGIDLNSPF | MSWVRQAPGKGLEWIGI | FWIGASA | YYASREGRFTERT SSTVDLAISPFTERTATYFC | ARGVPSYGGGAYIN | GPGILVTVIS | 41 | |
| IgA R1-11 | | | | | | | | | |
| IgA R1-12 | | | | | | | PRAILVTVTS | | |
| IgA R1-13 | | | | | | | | | |
| IgA H1-14 | GDGLNESGGRL VTPGIPLTLSCTV | SGIDLSGYA | MGGVRQAPGKGLAWIGI | SGATGST | YYASRAMGRFIERA SSTVDLAIESPFTEBIATFC | ARNSDTMGGAPHLW | GPGTLVTVTS | 42 | |
| IgA R1-15 | | | | | | | PRAILVTVTS | 43 | |
| IgA R1-16 | | | | | | | | | |
| IgA R1-17 | | | | | | | | | |
| IgA H1-18 | CSLEESGGGLVTPGTRLSLSCTV | SGFSLSSYY | MIRVRGQAPGGGLSWIGA | IYRGGHT | HFASSRAMGRFTEKT SITVDLKLTSLITEDIATEC | AGDWSILVPKCW | GPGTLVTVIS | 44 | |
| IgA R1-19 | KSVKESKERLVTPGIPLTLICFV | SGFSLSTYE | ISGPVRQAPGGGLEYIGI | IESSGST | YVANVARGRFTERT SSTVDLKMTSALTEDIATYFC | ARGGTYSDSWYIGMAPQPW | GPGILVTVIS | 45 | |
| IgA R1-20 | GBQLESGSGRLVTPGGGLRLICTV | SGIDLSSYA | MGPVRQAPGKGLEYIGI | ISSSGSI | YYASRANGRFTSRT SITVDKAMTSALPEDFAIYFC | ARYSGUROGFLRLM | GPGILVTVTS | |  |
| IgA R1-21 | | | | | | | | | |
| IgA H1-22 | GSVEESGGGLVTPGTPLILICTV | SGFSLSSYY | MIRVRGAPENGLSYIGI | ID2YGGSA | YYASRAMGRFTPSRA SITVDLKTMTSLTADDIATYFC | ARVYGYSFDLW | GPGTLVTVIS | 46 | |
| IgA R1-23 | | | | | | | | | |
| IgA R1-24 | | | | | | | | | |
| IgA R1-25 | KSVKEGIKERLVTPGIPLTLICTA | SGFSLSSBA | ASGPVRQAFGKGLEWIGI | INTGGFT | YRASRANGRFTISRT SITVDLAGTSLITEDIATYFC | ARWHLK | GPGILVFVIS | 47 | |
| IgA R1-26 | | | | | | | | | |
| IgA R1-27 | GBQLESGSGRLVTPGGGLRLICFV | SGISLSSYA | MGPVRQAFGKGLEYIGI | ISSSGST | YYASRANGRFTSRT SITVDLAMTSALPEDFATYFC | ARYSGUHGGFLRLW | GPGILVTVIS | 48 | |
| IgA R1-28 | | | | | | | | | |
| IgA H1-29 | GSLLESKGGRLVTPGTPLTLICTV | SGLYLSSBA | MIRVRQAFGKGLEWIGI | FFASGST | YVASRANGRFTSKT SITVDLKTISPFTERNATYCA | ARVKSMGRKVMDLW | GPGTLVTVTS | 49 | |
| IgA R1-30 | | | | | | | | | |
| IgA H1-31 | KSVEESGGRLVTPGTPLTLICII | SGFSLNIYE | IMPVRGAFGKGLEWIAA | INYBSGHT | DNSKRANGRFIGRG SITVLARGTSLFTRDYASYFC | ARVSGUHGGTFHLW | GPGILVTVIS | 50 | |
| IgA R1-32 | GGLSESGGRLVTPGTPLTLICTV | SGFISSYA | MIRVRGAFGKGLEWIGA | IGSSGIT | YYASRAKGRFTSRT AIYVDLANTSLITEDIATYPC | ARAPVRAAYPDLW | GPGILVTVTS | 51 | |

Fig. 17-1

At the completion of Round 1

| Sequence of CDR3 | Number of residues | Number of emergences | Probability of emergence (%) | SEQ ID NO |
|---|---|---|---|---|
| ARGGYSDSNYYIGYAFDPW | 19 | 1 | 3.1 | 52 |
| ARAGNDRYIGDNLW | 14 | 1 | 3.1 | 53 |
| ARGVPSYGGGAYIW | 14 | 1 | 3.1 | 54 |
| ARYSGYNGGAFNLW | 14 | 1 | 3.1 | 55 |
| ARVSGDNGGTLNLW | 14 | 1 | 3.1 | 56 |
| ARVRSNGHYYFDLW | 14 | 1 | 3.1 | 57 |
| ARYSGDNGGTFNLW | 14 | 1 | 3.1 | 58 |
| ARADYNTAAYFDLW | 14 | 1 | 3.1 | 59 |
| GRYINGCYFDLW | 12 | 1 | 3.1 | 60 |
| VRDEHGNIGSLW | 12 | 1 | 3.1 | 61 |
| AGDWDTLPFKFW | 12 | 1 | 3.1 | 62 |
| ARVDYGVSFDLW | 12 | 1 | 3.1 | 63 |
| ARPWNLW | 7 | 1 | 3.1 | 64 |
| Negative clones | | 19 | 59.4 | |

At the completion of Round 2

| Sequence of CDR3 | Number of residues | Number of emergences | Probability of emergence (%) | SEQ ID NO |
|---|---|---|---|---|
| ATRYDSYGYAYNYWFGTLW | 19 | 8 | 25.0 | 91 |
| ARGNIGIGWGSYYFNFW | 17 | 1 | 3.1 | 92 |
| ARGDYDNYGYGYAINFW | 17 | 1 | 3.1 | 93 |
| ARGDTGGSLYRHFNLW | 16 | 1 | 3.1 | 94 |
| ARGGAGYNTVGLNLW | 15 | 1 | 3.1 | 95 |
| ARGDYNNNWDYFNLW | 15 | 1 | 3.1 | 96 |
| ARADYNTVAYFDLW | 14 | 1 | 3.1 | 97 |
| VRADYNTVSYFDLW | 14 | 2 | 6.3 | 98 |
| ARAIGDNGGYFNLW | 14 | 1 | 3.1 | 99 |
| ARYSGDNGGTFNLW | 14 | 1 | 3.1 | 100 |
| ARAGDSVSTLALW | 13 | 1 | 3.1 | 101 |
| ATALYADDGNTLW | 13 | 1 | 3.1 | 102 |
| AKNDDPFETYDLW | 13 | 1 | 3.1 | 103 |
| VRGVIGATGDLW | 12 | 1 | 3.1 | 104 |
| VRHDDDLTFNLW | 12 | 1 | 3.1 | 105 |
| ARDVDGGYALW | 11 | 2 | 6.3 | 106 |
| ARGWLYFDLW | 10 | 1 | 3.1 | 107 |
| Negative clones | | 4 | 12.5 | |

At the completion of Round 3

| Sequence of CDR3 | Number of residues | Number of emergences | Probability of emergence (%) | SEQ ID NO |
|---|---|---|---|---|
| ATRYDSYGYAYNYWRGTLW | 19 | 26 | 81.3 | 140 |
| ARADYNTVAYFDLW | 14 | 2 | 6.3 | 141 |
| ARADYNTAAYFDLW | 14 | 2 | 6.3 | 142 |
| VRADYNTVSYFDLW | 14 | 1 | 3.1 | 143 |
| ARGFDNYNLW | 10 | 1 | 3.1 | 144 |
| Negative clones | - | 0 | 0 | |

At the completion of Round 1

| | Number of clones |
|---|---|
| Common 1 | 0 |
| Common 2 | 0 |
| Common 3 (Identical to R3-75) | 0 |
| Common 4 (Identical to R2-18) | 0 |
| Common 5 | 0 |
| Common 6 | 0 |
| Common 7 | 0 |

Fig. 17-8

At the completion of Round 2

| | Number of clones |
|---|---|
| Common 1 | 2 |
| Common 2 | 3 |
| Common 3 (Identical to R3-75) | 0 |
| Common 4 (Identical to R2-18) | 0 |
| Common 5 | 0 |
| Common 6 | 1 |
| Common 7 | 2 |

Fig. 17-9

At the completion of Round 3

| | Number of clones |
|---|---|
| Common 1 | 12 |
| Common 2 | 8 |
| Common 3 (Identical to R3-75) | 2 |
| Common 4 (Identical to R2-18) | 2 |
| Common 5 | 2 |
| Common 6 | 1 |
| Common 7 | 1 |

Fig. 17-10

SEQUENCE LISTING

<160> NUMBER OF SEQ ID NOS: 173

<210> SEQ ID NO 1
<211> LENGTH: 36
<212> TYPE: DNA
<213> ORGANISM: Artificial Sequence
<220> FEATURE:
<223> OTHER INFORMATION: primer

<400> SEQUENCE: 1
aaaaaggcca tggcccagtc ggtggaggag tccrgg      36

<210> SEQ ID NO 2
<211> LENGTH: 36
<212> TYPE: DNA
<213> ORGANISM: Artificial Sequence
<220> FEATURE:
<223> OTHER INFORMATION: primer

<400> SEQUENCE: 2
aaaaaggcca tggcccagtc ggtgaaggag tccgag      36

<210> SEQ ID NO 3
<211> LENGTH: 36
<212> TYPE: DNA
<213> ORGANISM: Artificial Sequence
<220> FEATURE:
<223> OTHER INFORMATION: primer

<400> SEQUENCE: 3
aaaaaggcca tggcccagtc gytggaggag tccggg      36

<210> SEQ ID NO 4
<211> LENGTH: 38

```
<212> TYPE: DNA
<213> ORGANISM: Artificial Sequence
<220> FEATURE:
<223> OTHER INFORMATION: primer

<400> SEQUENCE: 4
aaaaaggcca tggcccagsa gcagctgrwg gagtccgg                                    38

<210> SEQ ID NO 5
<211> LENGTH: 27
<212> TYPE: DNA
<213> ORGANISM: Artificial Sequence
<220> FEATURE:
<223> OTHER INFORMATION: primer

<400> SEQUENCE: 5
tccaccacta gtgacggtga csagggt                                                27

<210> SEQ ID NO 6
<211> LENGTH: 36
<212> TYPE: DNA
<213> ORGANISM: Artificial Sequence
<220> FEATURE:
<223> OTHER INFORMATION: primer

<400> SEQUENCE: 6
aattaaggat ccgagctcgt gmtgacccag actsca                                      36

<210> SEQ ID NO 7
<211> LENGTH: 36
<212> TYPE: DNA
<213> ORGANISM: Artificial Sequence
<220> FEATURE:
<223> OTHER INFORMATION: primer

<400> SEQUENCE: 7
aattaaggat ccgagctcga tmtgacccag actsca                                      36

<210> SEQ ID NO 8
<211> LENGTH: 36
<212> TYPE: DNA
<213> ORGANISM: Artificial Sequence
<220> FEATURE:
<223> OTHER INFORMATION: primer

<400> SEQUENCE: 8
aattaaggat ccgagctcgt gatgacccag actgca                                      36

<210> SEQ ID NO 9
<211> LENGTH: 38
<212> TYPE: DNA
<213> ORGANISM: Artificial Sequence
<220> FEATURE:
<223> OTHER INFORMATION: primer

<400> SEQUENCE: 9
aattaaggat ccgagctcgt gctgactcag tcgycctc                                    38

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10
```

```
tatatatgcg gccgccgaac stktgayswc cac                                        33
```

<210> SEQ ID NO 11
<211> LENGTH: 35
<212> TYPE: DNA
<213> ORGANISM: Artificial Sequence
<220> FEATURE:
<223> OTHER INFORMATION: primer

<400> SEQUENCE: 11

```
tttaaatttg cggccgccga acctgtgacg gtcag                                      35
```

<210> SEQ ID NO 12
<211> LENGTH: 121
<212> TYPE: PRT
<213> ORGANISM: Oryctolagus cuniculus

<400> SEQUENCE: 12

Gln Ser Val Lys Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Ser Trp Val Arg Gln Ala Pro Gly Glu Gly Leu Glu Trp Ile Gly
        35                  40                  45

Thr Ile Ser Thr Val Gly Lys Thr Tyr Phe Ala Ser Trp Ala Lys Gly
    50                  55                  60

Arg Phe Thr Ile Ser Lys Thr Ser Thr Thr Val Asp Leu Arg Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
        115                 120

<210> SEQ ID NO 13
<211> LENGTH: 117
<212> TYPE: PRT
<213> ORGANISM: Oryctolagus cuniculus

<400> SEQUENCE: 13

Gln Ser Val Lys Glu Ser Glu Gly Arg Leu Val Thr Pro Gly Thr Pro
1               5                   10                  15

Leu Thr Leu Thr Cys Thr Val Ser Gly Phe Ser Leu Ser Arg Tyr Ala
            20                  25                  30

Val Ser Trp Val Arg Gln Ala Pro Gly Lys Gly Leu Glu Trp Ile Gly
        35                  40                  45

Ile Ile Gly Ser Gly Gly Ser Thr Ser Tyr Ala Thr Trp Ala Arg Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Val Thr Tyr Phe Cys Gly Ser Tyr Tyr
                85                  90                  95

Asp Ser His Gly Tyr Ala Tyr Val Ser Leu Trp Gly Pro Gly Thr Leu
            100                 105                 110

Val Thr Val Thr Ser
        115

<210> SEQ ID NO 14
<211> LENGTH: 119
<212> TYPE: PRT
<213> ORGANISM: Oryctolagus cuniculus

<400> SEQUENCE: 14

Gln Glu Gln Leu Val Glu Ser Gly Gly Gly Leu Val Lys Pro Gly Gly
1               5                   10                  15

Thr Leu Thr Leu Thr Cys Thr Val Ser Gly Ile Asp Leu Ser Ser Tyr
            20                  25                  30

Ala Met Ser Trp Val Arg Gln Val Pro Gly Lys Gly Leu Glu Trp Ile
        35                  40                  45

Gly Ile Ile Gly Ser Gly Gly Thr Ala Tyr Ala Asn Trp Ala Lys
    50                  55                  60

Gly Arg Phe Thr Ile Ser Lys Thr Ser Ser Thr Val Asp Leu Lys
65                  70                  75                  80

Met Thr Ser Leu Thr Thr Glu Asp Thr Ala Thr Tyr Phe Cys Ala Thr
                85                  90                  95

Asp Tyr Gly Ile Tyr Gly Tyr Ala Tyr Gly His Leu Trp Gly Pro Gly
            100                 105                 110

Thr Leu Val Thr Val Thr Ser
        115

<210> SEQ ID NO 15
<211> LENGTH: 118
<212> TYPE: PRT
<213> ORGANISM: Oryctolagus cuniculus

<400> SEQUENCE: 15

Gln Gln Gln Leu Met Glu Ser Gly Gly Arg Leu Val Thr Pro Gly Gly
1               5                   10                  15

Ser Leu Thr Leu Thr Cys Thr Val Ser Gly Ile Asp Leu Asn Ser Tyr
            20                  25                  30

Ala Met Gly Trp Val Arg Gln Ala Pro Gly Lys Gly Leu Glu Tyr Ile
        35                  40                  45

Gly Ile Ile Arg Asn Ser Gly Asn Thr Tyr Tyr Ala Ser Trp Ala Lys
    50                  55                  60

Gly Arg Phe Thr Ile Ser Lys Thr Ser Ser Thr Val Asp Leu Lys
65                  70                  75                  80

Met Thr Ser Leu Thr Thr Glu Asp Thr Ala Thr Tyr Phe Cys Ala Arg
                85                  90                  95

Tyr Ser Gly Asp Asn Gly Gly Ala Leu Asn Leu Trp Gly Pro Gly Thr
            100                 105                 110

Leu Val Thr Val Thr Ser
        115

<210> SEQ ID NO 16
<211> LENGTH: 121
<212> TYPE: PRT
<213> ORGANISM: Oryctolagus cuniculus

<400> SEQUENCE: 16

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Thr Trp Val Arg Gln Ala Pro Gly Glu Gly Leu Glu Trp Ile Gly
        35                  40                  45

Thr Ile Ser Thr Gly Gly Ser Thr Tyr Phe Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
            115                 120

<210> SEQ ID NO 17
<211> LENGTH: 116
<212> TYPE: PRT
<213> ORGANISM: Oryctolagus cuniculus

<400> SEQUENCE: 17

Gln Ser Val Lys Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Gly Trp Val Arg Gln Ala Pro Gly Lys Gly Leu Glu Tyr Ile Gly
        35                  40                  45

Ile Ile Ser Ser Ser Gly Ser Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Tyr Ser
                85                  90                  95

Gly Asp Asn Gly Gly Ala Leu Asn Leu Trp Gly Pro Gly Thr Leu Val
            100                 105                 110

Thr Val Thr Ser
        115

<210> SEQ ID NO 18
<211> LENGTH: 116
<212> TYPE: PRT
<213> ORGANISM: Oryctolagus cuniculus

<400> SEQUENCE: 18

Gln Gln Gln Leu Met Glu Ser Gly Gly Leu Val Thr Pro Gly Thr
1               5                   10                  15

Pro Leu Thr Leu Thr Cys Thr Val Ser Gly Ile Asp Leu Arg Arg Tyr
            20                  25                  30

Ala Met Gly Trp Val Arg Gln Ala Pro Gly Lys Gly Leu Gln Trp Ile
        35                  40                  45

Gly Ile Ile Ala Ser Gly Asn Thr Asp Tyr Ala Ser Trp Ala Lys Gly
    50                  55                  60

Arg Phe Thr Ile Ser Ala Thr Ser Thr Thr Val Asp Leu Lys Ile Thr
65                  70                  75                  80

Ser Ser Thr Thr Glu Asp Thr Ala Thr Tyr Phe Cys Ala Arg Tyr Ser
                85                  90                  95

Gly Asp Asn Gly Gly Thr Leu Asn Leu Trp Gly Pro Gly Thr Leu Ala
            100                 105                 110

Thr Val Thr Thr
        115

```
<210> SEQ ID NO 19
<211> LENGTH: 121
<212> TYPE: PRT
<213> ORGANISM: Oryctolagus cuniculus

<400> SEQUENCE: 19

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Thr Trp Val Arg Gln Ala Pro Gly Glu Gly Leu Glu Trp Ile Gly
        35                  40                  45

Thr Ile Ser Thr Gly Gly Ser Thr Tyr Phe Ala Ser Trp Ala Lys Gly
    50                  55                  60

Arg Phe Thr Ile Ser Lys Thr Ser Thr Val Asp Leu Lys Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
        115                 120

<210> SEQ ID NO 20
<211> LENGTH: 115
<212> TYPE: PRT
<213> ORGANISM: Oryctolagus cuniculus

<400> SEQUENCE: 20

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Arg Arg Tyr Ala
            20                  25                  30

Met Gly Trp Val Arg Gln Ala Pro Gly Lys Gly Leu Gln Trp Ile Gly
        35                  40                  45

Ile Ile Ala Ser Gly Asn Thr Asp Tyr Ala Ser Trp Ala Lys Gly Arg
    50                  55                  60

Phe Thr Ile Ser Ala Thr Ser Thr Thr Val Asp Leu Lys Ile Thr Ser
65                  70                  75                  80

Pro Thr Thr Glu Asp Thr Ala Thr Tyr Phe Cys Ala Arg Tyr Ser Gly
                85                  90                  95

Asp Asn Gly Gly Thr Leu Asn Leu Trp Gly Pro Gly Thr Leu Val Thr
            100                 105                 110

Val Thr Ser
        115

<210> SEQ ID NO 21
<211> LENGTH: 112
<212> TYPE: PRT
<213> ORGANISM: Oryctolagus cuniculus

<400> SEQUENCE: 21

Glu Leu Asp Leu Thr Gln Thr Pro Pro Ser Val Ser Gly Ala Val Gly
1               5                   10                  15

Gly Thr Val Thr Ile Lys Cys Gln Ala Ser Glu Asn Ile Asn Ser Glu
            20                  25                  30
```

```
Leu Ala Trp Tyr Gln Gln Lys Pro Gly Gln Arg Pro Lys Leu Leu Ile
            35                  40                  45

Tyr Asp Ala Ser Lys Leu Ala Ser Gly Val Pro Ser Arg Phe Ser Gly
    50                  55                  60

Ser Gly Ser Gly Thr Glu Tyr Thr Leu Thr Ile Ser Gly Met Gln Cys
65                  70                  75                  80

Asp Asp Ala Ala Thr Tyr Tyr Cys Gln Ser Thr Tyr Tyr Asp Gly Asn
                    85                  90                  95

Tyr Val Tyr Ala Phe Gly Gly Gly Thr Glu Val Asp Val Thr Arg Ser
                100                 105                 110
```

<210> SEQ ID NO 22
<211> LENGTH: 111
<212> TYPE: PRT
<213> ORGANISM: Oryctolagus cuniculus

<400> SEQUENCE: 22

```
Glu Leu Val Leu Thr Gln Thr Pro Ser Pro Val Ser Gly Ala Val Gly
1               5                   10                  15

Gly Thr Val Thr Ile Asn Cys Gln Ala Ser Gln Ser Ile Ser Thr Ala
                20                  25                  30

Leu Ala Trp Tyr Gln Gln Lys Pro Gly Gln Pro Pro Lys Leu Leu Ile
            35                  40                  45

Tyr Ser Ala Ser Thr Leu Ala Ser Gly Val Ser Arg Phe Lys Gly
    50                  55                  60

Ser Gly Ser Gly Thr Gly Phe Thr Leu Thr Ile Ser Asp Leu Glu Cys
65                  70                  75                  80

Ala Asp Ala Ala Thr Tyr Tyr Cys Gln Ser Tyr Tyr Gly Ser Ser Ser
                    85                  90                  95

Asp Asn Ala Phe Gly Gly Gly Thr Glu Val Val Ile Lys Arg Ser
                100                 105                 110
```

<210> SEQ ID NO 23
<211> LENGTH: 111
<212> TYPE: PRT
<213> ORGANISM: Oryctolagus cuniculus

<400> SEQUENCE: 23

```
Glu Leu Val Met Thr Gln Thr Ala Ser Pro Val Ser Ala Ala Val Gly
1               5                   10                  15

Gly Thr Val Thr Ile Lys Cys Gln Ala Ser Gln Ser Ile Ser Thr Ala
                20                  25                  30

Leu Ala Trp Tyr Gln Gln Arg Pro Gly Gln Pro Pro Lys Leu Leu Ile
            35                  40                  45

Tyr Asp Ala Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Thr Tyr Phe Gly Ser Asp Thr
                    85                  90                  95

Asp Asn Ala Phe Gly Glu Gly Thr Glu Val Glu Ile Thr Gly Ser
                100                 105                 110
```

<210> SEQ ID NO 24
<211> LENGTH: 113
<212> TYPE: PRT
<213> ORGANISM: Oryctolagus cuniculus

<400> SEQUENCE: 24

Glu Leu Val Met Thr Gln Thr Ala Ala Ser Val Ser Gly Pro Val Gly
1               5                   10                  15

Gly Thr Val Thr Ile Lys Cys Gln Ala Ser Glu Phe Ile Arg Asn Tyr
            20                  25                  30

Leu Ala Trp Tyr Gln Gln Lys Pro Gly Gln Pro Pro Lys Leu Leu Ile
        35                  40                  45

Tyr Thr Thr Ser Asn Leu Ala Ser Gly Val Pro Ser Arg Phe Ser Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Asn Tyr Tyr Asp Ile Ser Thr
                85                  90                  95

Tyr Gly Asn Ala Phe Gly Gly Gly Thr Glu Val Val Val Ile Lys Gly
            100                 105                 110

Ser

<210> SEQ ID NO 25
<211> LENGTH: 112
<212> TYPE: PRT
<213> ORGANISM: Oryctolagus cuniculus

<400> SEQUENCE: 25

Glu Leu Val Met Thr Gln Thr Ala Ala Ser Val Ser Glu Pro Val Gly
1               5                   10                  15

Gly Thr Val Thr Ile Lys Cys Gln Ala Ser Gln Asn Ile Asn Asn Glu
            20                  25                  30

Leu Ala Trp Tyr Gln Gln Lys Pro Gly Gln Arg Pro Lys Leu Leu Ile
        35                  40                  45

Tyr Asp Ala Ser Lys Leu Ala Ser Gly Val Pro Ser Arg Phe Ser Gly
    50                  55                  60

Ser Gly Ser Gly Thr Glu Phe Thr Leu Thr Ile Ser Gly Met Gln Cys
65                  70                  75                  80

Asp Asp Ala Ala Thr Tyr Tyr Cys Gln Ser Thr Tyr Tyr Asp Gly Asn
                85                  90                  95

Tyr Val Tyr Ala Phe Gly Gly Gly Thr Glu Val Asp Val Lys Gly Ser
            100                 105                 110

<210> SEQ ID NO 26
<211> LENGTH: 112
<212> TYPE: PRT
<213> ORGANISM: Oryctolagus cuniculus

<400> SEQUENCE: 26

Glu Leu Asp Leu Thr Gln Thr Ala Ala Ser Val Ser Glu Pro Val Gly
1               5                   10                  15

Gly Thr Val Thr Ile Ser Cys Gln Ser Ser Gln His Ile Arg Ser Tyr
            20                  25                  30

Leu Ala Trp Tyr Gln Gln Lys Pro Gly Gln Pro Pro Lys Leu Leu Ile
        35                  40                  45

Ser Ala Ala Ser Thr Leu Ala Ser Gly Val Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Arg Tyr Tyr Asp Ile Arg Asn
                85                  90                  95

Tyr Gly Asn Gly Phe Gly Gly Thr Glu Val Glu Ile Thr Gly Ser
            100                 105                 110

<210> SEQ ID NO 27
<211> LENGTH: 112
<212> TYPE: PRT
<213> ORGANISM: Oryctolagus cuniculus

<400> SEQUENCE: 27

Glu Leu Val Met Thr Gln Thr Ala Ala Ser Val Ser Glu Pro Val Gly
1               5                   10                  15

Gly Thr Val Thr Ile Lys Cys Gln Ala Ser Glu His Ile Arg Asn Tyr
            20                  25                  30

Leu Ala Trp Tyr Gln Gln Lys Pro Gly Gln Pro Pro Lys Leu Leu Ile
        35                  40                  45

Tyr Thr Thr Ser Asn Leu Ala Ser Gly Val Pro Ser Arg Phe Ser Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Asn Tyr Tyr Asp Ile Ser Thr
                85                  90                  95

Tyr Gly Asn Thr Phe Gly Gly Gly Thr Glu Val Asp Val Lys Gly Ser
            100                 105                 110

<210> SEQ ID NO 28
<211> LENGTH: 112
<212> TYPE: PRT
<213> ORGANISM: Oryctolagus cuniculus

<400> SEQUENCE: 28

Glu Leu Val Met Thr Gln Thr Ala Ala Ser Val Ser Glu Pro Val Gly
1               5                   10                  15

Gly Thr Val Thr Ile Asn Cys Gln Ala Ser Gln Ser Ile Ser Asp Glu
            20                  25                  30

Leu Ala Trp Tyr Gln Gln Lys Pro Gly Gln Arg Pro Lys Leu Leu Ile
        35                  40                  45

Tyr Asp Ala Ser Asp Leu Ala Ser Gly Val Pro Ser Arg Phe Ser Gly
    50                  55                  60

Ser Gly Ser Gly Thr Glu Phe Thr Leu Thr Ile Ser Gly Val Gln Cys
65                  70                  75                  80

Asp Asp Ala Ala Thr Tyr Tyr Cys Gln Ser Ala Tyr Tyr Asp Gly Arg
                85                  90                  95

Tyr Val Tyr Ala Phe Gly Gly Gly Thr Glu Val Glu Val Thr Gly Ser
            100                 105                 110

<210> SEQ ID NO 29
<211> LENGTH: 112
<212> TYPE: PRT
<213> ORGANISM: Oryctolagus cuniculus

<400> SEQUENCE: 29

Glu Leu Val Met Thr Gln Thr Ala Ala Ser Val Ser Glu Pro Val Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly Gln Pro Pro Lys Leu Leu Ile
        35                  40                  45

```
Tyr Ala Ala Ser Asn Leu Ala Ser Gly Val Ser Ser Arg Phe Lys Gly
         50                  55                  60
Ser Gly Ser Gly Thr Glu Phe Thr Leu Thr Ile Ser Asp Leu Glu Cys
 65                  70                  75                  80
Ala Asp Ala Ala Thr Tyr Tyr Cys Gln Ser Tyr Tyr Ser Ile Ser Ser
                 85                  90                  95
Tyr Gly Asn Thr Phe Gly Gly Gly Thr Glu Val Glu Ile Thr Gly Ser
            100                 105                 110
```

<210> SEQ ID NO 30
<211> LENGTH: 19
<212> TYPE: PRT
<213> ORGANISM: Oryctolagus cuniculus

<400> SEQUENCE: 30

```
Ala Thr Arg Tyr Asp Ser Tyr Gly Tyr Ala Tyr Asn Tyr Trp Phe Gly
 1               5                  10                  15
Thr Leu Trp
```

<210> SEQ ID NO 31
<211> LENGTH: 15
<212> TYPE: PRT
<213> ORGANISM: Oryctolagus cuniculus

<400> SEQUENCE: 31

```
Gly Ser Tyr Tyr Asp Ser His Gly Tyr Ala Tyr Val Ser Leu Trp
 1               5                  10                  15
```

<210> SEQ ID NO 32
<211> LENGTH: 15
<212> TYPE: PRT
<213> ORGANISM: Oryctolagus cuniculus

<400> SEQUENCE: 32

```
Ala Thr Asp Tyr Gly Ile Tyr Gly Tyr Ala Tyr Gly His Leu Trp
 1               5                  10                  15
```

<210> SEQ ID NO 33
<211> LENGTH: 14
<212> TYPE: PRT
<213> ORGANISM: Oryctolagus cuniculus

<400> SEQUENCE: 33

```
Ala Arg Tyr Ser Gly Asp Asn Gly Gly Thr Leu Asn Leu Trp
 1               5                  10
```

<210> SEQ ID NO 34
<211> LENGTH: 14
<212> TYPE: PRT
<213> ORGANISM: Oryctolagus cuniculus

<400> SEQUENCE: 34

```
Ala Arg Tyr Ser Gly Asp Asn Gly Gly Ala Leu Asn Leu Trp
 1               5                  10
```

<210> SEQ ID NO 35
<211> LENGTH: 8
<212> TYPE: PRT
<213> ORGANISM: Artificial Sequence
<220> FEATURE:
<223> OTHER INFORMATION: octapeptide

<400> SEQUENCE: 35

```
Phe Val Asn Gln His Leu Cys Lys
1               5

<210> SEQ ID NO 36
<211> LENGTH: 115
<212> TYPE: PRT
<213> ORGANISM: Oryctolagus cuniculus

<400> SEQUENCE: 36

Gln Ser Leu Glu Glu Ser Gly Gly Arg Leu Val Lys Pro Asp Glu Thr
1               5                   10                  15

Leu Thr Ile Thr Cys Thr Ala Ser Gly Phe Ser Leu Ser Ser Tyr Ala
            20                  25                  30

Met Gly Trp Val Arg Gln Ala Pro Gly Lys Gly Leu Glu Trp Ile Gly
        35                  40                  45

Ile Ile Gly Ser Gly Asp Thr Tyr Tyr Ala Ser Trp Ala Lys Gly Arg
    50                  55                  60

Phe Thr Ile Ser Lys Thr Ala Thr Thr Val Asp Leu Lys Ile Thr Ser
65                  70                  75                  80

Pro Thr Thr Glu Asp Thr Ala Thr Tyr Phe Cys Ala Arg Ala Gly Asn
                85                  90                  95

Asp Arg Tyr Ile Gly Asp Asn Leu Trp Gly Pro Gly Thr Leu Val Thr
            100                 105                 110

Val Thr Ser
        115

<210> SEQ ID NO 37
<211> LENGTH: 114
<212> TYPE: PRT
<213> ORGANISM: Oryctolagus cuniculus

<400> SEQUENCE: 37

Ser Arg Trp Arg Ser Pro Gly Gly Arg Leu Val Thr Pro Gly Thr Pro
1               5                   10                  15

Leu Thr Ile Thr Cys Thr Val Ser Gly Ile Asp Leu Ser Ser Tyr Ala
            20                  25                  30

Met Ile Trp Val Arg Gln Ser Pro Gly Glu Gly Leu Glu Tyr Ile Gly
        35                  40                  45

Ile Ile Ser Ser Thr Gly Ser Ala Tyr Tyr Ala Ser Trp Ala Lys Gly
    50                  55                  60

Arg Phe Ala Ile Ala Lys Thr Ser Thr Thr Met Asp Leu Lys Met Thr
65                  70                  75                  80

Ser Pro Thr Thr Glu Asp Thr Ala Thr Tyr Phe Cys Gly Arg Tyr Ile
                85                  90                  95

Asn Gly Gly Tyr Phe Asp Leu Trp Gly Pro Gly Thr Leu Val Thr Val
            100                 105                 110

Thr Ser

<210> SEQ ID NO 38
<211> LENGTH: 10
<212> TYPE: PRT
<213> ORGANISM: Oryctolagus cuniculus

<400> SEQUENCE: 38

Pro Arg Ala Thr Leu Val Thr Val Thr Ser
1               5                   10

<210> SEQ ID NO 39
```

```
<211> LENGTH: 114
<212> TYPE: PRT
<213> ORGANISM: Oryctolagus cuniculus

<400> SEQUENCE: 39

Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Leu Ser Ser Tyr Ala
            20                  25                  30

Met Gly Trp Val Arg Gln Ala Pro Gly Lys Gly Leu Glu Trp Ile Gly
        35                  40                  45

Ile Val Glu Thr Gly Gly Ser Ala Asp Tyr Ala Ala Trp Ala Lys Gly
    50                  55                  60

Arg Phe Thr Ile Ser Arg Thr Ser Thr Thr Val Asp Leu Lys Ile Thr
65                  70                  75                  80

Ser Pro Thr Thr Glu Asp Thr Ala Thr Tyr Phe Cys Val Arg Asp Glu
                85                  90                  95

His Gly Asn Ile Gly Ser Leu Trp Gly Pro Gly Thr Leu Val Thr Val
            100                 105                 110

Thr Ser

<210> SEQ ID NO 40
<211> LENGTH: 10
<212> TYPE: PRT
<213> ORGANISM: Oryctolagus cuniculus

<400> SEQUENCE: 40

Pro Arg Ala Thr Leu Val Thr Val Thr Ser
1               5                   10

<210> SEQ ID NO 41
<211> LENGTH: 117
<212> TYPE: PRT
<213> ORGANISM: Oryctolagus cuniculus

<400> SEQUENCE: 41

Gln Ser Val Glu Glu Ser Arg Gly Arg Leu Val Thr Pro Gly Thr Pro
1               5                   10                  15

Leu Thr Leu Thr Cys Thr Val Ser Gly Ile Asp Leu Asn Ser Trp Pro
            20                  25                  30

Met Ser Trp Val Arg Gln Ala Pro Gly Lys Gly Leu Glu Trp Ile Gly
        35                  40                  45

Ile Ile Asn Thr Gly Gly Ser Ala Tyr Tyr Ala Ser Trp Ala Glu Gly
    50                  55                  60

Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Arg Gly
                85                  90                  95

Val Pro Ser Tyr Gly Gly Ala Tyr Ile Trp Gly Pro Gly Thr Leu
            100                 105                 110

Val Thr Val Thr Ser
        115

<210> SEQ ID NO 42
<211> LENGTH: 118
<212> TYPE: PRT
<213> ORGANISM: Oryctolagus cuniculus

<400> SEQUENCE: 42
```

```
Gln Gln Gln Leu Met Glu Ser Gly Gly Arg Leu Val Thr Pro Gly Thr
1               5                   10                  15

Pro Leu Thr Leu Thr Cys Thr Val Ser Gly Ile Asp Leu Ser Gly Tyr
                20                  25                  30

Ala Met Gly Trp Val Arg Gln Ala Pro Gly Lys Gly Leu Glu Tyr Ile
            35                  40                  45

Gly Ile Ile Asp Ala Thr Asp Val Thr Tyr Ala Ser Trp Ala Lys
50                      55                  60

Gly Arg Phe Thr Ile Ser Lys Ala Ser Ser Thr Val Asp Leu Lys
65              70                  75                  80

Leu Thr Ser Pro Thr Thr Glu Asp Thr Ala Thr Tyr Phe Cys Ala Arg
                85                  90                  95

Tyr Ser Gly Tyr Asn Gly Gly Ala Phe Asn Leu Trp Gly Pro Gly Thr
            100                 105                 110

Leu Val Thr Val Thr Ser
            115

<210> SEQ ID NO 43
<211> LENGTH: 10
<212> TYPE: PRT
<213> ORGANISM: Oryctolagus cuniculus

<400> SEQUENCE: 43

Pro Arg Ala Thr Leu Val Thr Val Thr Ser
1               5                   10

<210> SEQ ID NO 44
<211> LENGTH: 114
<212> TYPE: PRT
<213> ORGANISM: Oryctolagus cuniculus

<400> SEQUENCE: 44

Gln Ser Leu Glu Glu Ser Gly Gly Arg Leu Val Thr Pro Gly Thr Pro
1               5                   10                  15

Leu Thr Leu Ser Cys Thr Val Ser Gly Ile Asp Leu Ser Ser Asn Ala
                20                  25                  30

Met Ser Trp Val Arg Gln Ala Pro Gly Glu Gly Leu Glu Trp Ile Gly
            35                  40                  45

Ala Ile Tyr Arg Gly Gly Asn Thr Glu Phe Ala Ser Trp Ala Asn Gly
        50                  55                  60

Arg Phe Thr Ile Ser Lys Thr Ser Thr Thr Val Asp Leu Lys Leu Thr
65              70                  75                  80

Ser Leu Thr Thr Glu Asp Thr Ala Thr Tyr Phe Cys Ala Gly Asp Trp
                85                  90                  95

Asp Thr Leu Pro Phe Lys Phe Trp Gly Pro Gly Thr Leu Val Thr Val
            100                 105                 110

Thr Ser

<210> SEQ ID NO 45
<211> LENGTH: 122
<212> TYPE: PRT
<213> ORGANISM: Oryctolagus cuniculus

<400> SEQUENCE: 45

Gln Ser Val Glu Glu Ser Arg Gly Arg Leu Val Thr Pro Gly Thr Pro
1               5                   10                  15

Leu Thr Leu Thr Cys Thr Val Ser Gly Phe Ser Leu Ser Thr Tyr Gly
```

```
                    20                  25                  30
Val Ser Trp Val Arg Gln Ala Pro Gly Lys Gly Leu Glu Tyr Ile Gly
            35                  40                  45
Ile Ile Ser Ser Ser Gly Ser Thr Tyr Tyr Ala Asn Trp Ala Lys Gly
        50                  55                  60
Arg Phe Thr Ile Ser Lys Thr Ser Ser Thr Thr Val Asp Leu Lys Met
65                  70                  75                  80
Thr Ser Leu Thr Thr Glu Asp Thr Ala Thr Tyr Phe Cys Ala Arg Gly
                85                  90                  95
Gly Tyr Ser Asp Ser Asn Tyr Tyr Ile Gly Tyr Ala Phe Asp Pro Trp
            100                 105                 110
Gly Pro Gly Thr Leu Val Thr Val Thr Ser
            115                 120

<210> SEQ ID NO 46
<211> LENGTH: 115
<212> TYPE: PRT
<213> ORGANISM: Oryctolagus cuniculus

<400> SEQUENCE: 46

Gln Ser Val Glu Glu Ser Gly Gly Arg Leu Val Ser Pro Gly Thr Pro
1               5                   10                  15
Leu Thr Leu Thr Cys Thr Val Ser Gly Phe Ser Leu Ser Ser Tyr Tyr
            20                  25                  30
Met Ile Trp Val Arg Gln Ala Pro Gly Lys Gly Leu Glu Tyr Ile Gly
            35                  40                  45
Ile Ile Asp Gly Tyr Gly Ser Ala Tyr Tyr Ala Ser Trp Ala Lys
        50                  55                  60
Gly Arg Phe Thr Phe Ser Arg Ala Ser Thr Thr Val Asp Leu Thr Met
65                  70                  75                  80
Thr Ser Leu Thr Ala Ala Asp Thr Ala Thr Tyr Phe Cys Ala Arg Val
                85                  90                  95
Asp Tyr Gly Val Ser Phe Asp Leu Trp Gly Pro Gly Thr Leu Val Thr
            100                 105                 110
Val Thr Ser
        115

<210> SEQ ID NO 47
<211> LENGTH: 109
<212> TYPE: PRT
<213> ORGANISM: Oryctolagus cuniculus

<400> SEQUENCE: 47

Gln Ser Val Lys Glu Ser Arg Gly Arg Leu Val Thr Pro Gly Thr Pro
1               5                   10                  15
Leu Thr Leu Thr Cys Thr Ala Ser Gly Phe Ser Leu Ser Ser Asn Ala
            20                  25                  30
Met Ser Trp Val Arg Gln Ala Pro Gly Glu Gly Leu Glu Trp Ile Gly
            35                  40                  45
Thr Ile Asn Thr Gly Gly Thr Thr Tyr Tyr Ala Ser Trp Ala Lys Gly
        50                  55                  60
Arg Phe Thr Ile Ser Lys Thr Ser Thr Thr Val Asp Leu Lys Met Thr
65                  70                  75                  80
Gly Leu Thr Thr Glu Asp Thr Ala Thr Tyr Phe Cys Ala Arg Phe Trp
                85                  90                  95
Asn Leu Trp Gly Pro Gly Thr Leu Val Thr Val Thr Ser
```

<210> SEQ ID NO 48
<211> LENGTH: 118
<212> TYPE: PRT
<213> ORGANISM: Oryctolagus cuniculus

<400> SEQUENCE: 48

Gln Glu Gln Leu Glu Glu Ser Gly Gly Arg Leu Val Thr Pro Gly Gly
1               5                   10                  15

Ser Leu Thr Leu Thr Cys Thr Val Ser Gly Ile Asp Leu Ser Ser Tyr
            20                  25                  30

Ala Met Gly Trp Val Arg Gln Ala Pro Gly Lys Gly Leu Glu Tyr Ile
        35                  40                  45

Gly Ile Ile Ser Ser Ser Gly Ser Thr Tyr Tyr Ala Ser Trp Ala Arg
    50                  55                  60

Gly Arg Phe Thr Ile Ser Lys Thr Ser Ser Thr Thr Val Asp Leu Lys
65                  70                  75                  80

Met Thr Ser Leu Thr Pro Glu Asp Thr Ala Thr Tyr Phe Cys Ala Arg
                85                  90                  95

Tyr Ser Gly Asp Asn Gly Gly Thr Leu Asn Leu Trp Gly Pro Gly Thr
            100                 105                 110

Leu Val Thr Val Thr Ser
        115

<210> SEQ ID NO 49
<211> LENGTH: 117
<212> TYPE: PRT
<213> ORGANISM: Oryctolagus cuniculus

<400> SEQUENCE: 49

Gln Ser Leu Glu Glu Ser Gly Gly Arg Leu Val Thr Pro Gly Thr Pro
1               5                   10                  15

Leu Thr Leu Thr Cys Thr Val Ser Gly Leu Tyr Leu Ser Ser Asp Ala
            20                  25                  30

Met Ile Trp Val Arg Gln Ala Pro Gly Lys Gly Leu Glu Trp Ile Gly
        35                  40                  45

Ile Ile Tyr Ala Ser Gly Ser Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Ala Arg Val
                85                  90                  95

Arg Ser Asn Gly His Tyr Tyr Phe Asp Leu Trp Gly Pro Gly Thr Leu
            100                 105                 110

Val Thr Val Thr Ser
        115

<210> SEQ ID NO 50
<211> LENGTH: 116
<212> TYPE: PRT
<213> ORGANISM: Oryctolagus cuniculus

<400> SEQUENCE: 50

Gln Ser Val Glu Glu Ser Gly Gly Arg Leu Val Thr Pro Gly Thr Pro
1               5                   10                  15

Leu Thr Leu Thr Cys Thr Ile Ser Gly Phe Ser Leu Asn Ile Tyr Glu
            20                  25                  30

Ile Asn Trp Val Arg Gln Ala Pro Gly Lys Gly Leu Glu Trp Ile Ala
            35                  40                  45

Ala Ile Trp Arg Glu Gly His Thr Asp Tyr Ser Asn Trp Ala Lys Gly
 50                  55                  60

Arg Phe Thr Ile Ser Lys Ser Ser Thr Val Glu Leu Arg Met Thr
65                  70                  75                  80

Ser Leu Thr Thr Glu Asp Thr Ala Thr Tyr Phe Cys Ala Arg Tyr Ser
                85                  90                  95

Gly Asp Asn Gly Gly Thr Phe Asn Leu Trp Gly Pro Gly Thr Leu Val
                100                 105                 110

Thr Val Thr Ser
        115

<210> SEQ ID NO 51
<211> LENGTH: 116
<212> TYPE: PRT
<213> ORGANISM: Oryctolagus cuniculus

<400> SEQUENCE: 51

Gln Ser Leu Glu Glu Ser Gly Gly Arg Leu Val Thr Pro Gly Thr Pro
1               5                   10                  15

Leu Thr Leu Thr Cys Thr Val Ser Gly Phe Thr Ile Ser Ser Tyr Ala
            20                  25                  30

Met Ile Trp Val Arg Gln Ala Pro Gly Lys Gly Leu Glu Trp Ile Gly
            35                  40                  45

Ala Ile Ser Ser Gly Ile Thr Tyr Tyr Ala Ser Trp Ala Lys Gly
 50                  55                  60

Arg Phe Thr Ile Ser Lys Thr Ala Thr Val Asp Leu Lys Met Thr
65                  70                  75                  80

Ser Leu Thr Thr Glu Asp Thr Ala Thr Tyr Phe Cys Ala Arg Ala Asp
                85                  90                  95

Tyr Asn Thr Ala Ala Tyr Phe Asp Leu Trp Gly Pro Gly Thr Leu Val
                100                 105                 110

Thr Val Thr Ser
        115

<210> SEQ ID NO 52
<211> LENGTH: 19
<212> TYPE: PRT
<213> ORGANISM: Oryctolagus cuniculus

<400> SEQUENCE: 52

Ala Arg Gly Gly Tyr Ser Asp Ser Asn Tyr Ile Gly Tyr Ala Phe
1               5                   10                  15

Asp Pro Trp

<210> SEQ ID NO 53
<211> LENGTH: 14
<212> TYPE: PRT
<213> ORGANISM: Oryctolagus cuniculus

<400> SEQUENCE: 53

Ala Arg Ala Gly Asn Asp Arg Tyr Ile Gly Asp Asn Leu Trp
1               5                   10

<210> SEQ ID NO 54
<211> LENGTH: 14
<212> TYPE: PRT

<213> ORGANISM: Oryctolagus cuniculus

<400> SEQUENCE: 54

Ala Arg Gly Val Pro Ser Tyr Gly Gly Gly Ala Tyr Ile Trp
1               5                   10

<210> SEQ ID NO 55
<211> LENGTH: 14
<212> TYPE: PRT
<213> ORGANISM: Oryctolagus cuniculus

<400> SEQUENCE: 55

Ala Arg Tyr Ser Gly Tyr Asn Gly Gly Ala Phe Asn Leu Trp
1               5                   10

<210> SEQ ID NO 56
<211> LENGTH: 14
<212> TYPE: PRT
<213> ORGANISM: Oryctolagus cuniculus

<400> SEQUENCE: 56

Ala Arg Tyr Ser Gly Asp Asn Gly Gly Thr Leu Asn Leu Trp
1               5                   10

<210> SEQ ID NO 57
<211> LENGTH: 14
<212> TYPE: PRT
<213> ORGANISM: Oryctolagus cuniculus

<400> SEQUENCE: 57

Ala Arg Val Arg Ser Asn Gly His Tyr Tyr Phe Asp Leu Trp
1               5                   10

<210> SEQ ID NO 58
<211> LENGTH: 14
<212> TYPE: PRT
<213> ORGANISM: Oryctolagus cuniculus

<400> SEQUENCE: 58

Ala Arg Tyr Ser Gly Asp Asn Gly Gly Thr Phe Asn Leu Trp
1               5                   10

<210> SEQ ID NO 59
<211> LENGTH: 14
<212> TYPE: PRT
<213> ORGANISM: Oryctolagus cuniculus

<400> SEQUENCE: 59

Ala Arg Ala Asp Tyr Asn Thr Ala Ala Tyr Phe Asp Leu Trp
1               5                   10

<210> SEQ ID NO 60
<211> LENGTH: 12
<212> TYPE: PRT
<213> ORGANISM: Oryctolagus cuniculus

<400> SEQUENCE: 60

Gly Arg Tyr Ile Asn Gly Gly Tyr Phe Asp Leu Trp
1               5                   10

<210> SEQ ID NO 61
<211> LENGTH: 12
<212> TYPE: PRT
<213> ORGANISM: Oryctolagus cuniculus

<400> SEQUENCE: 61

Val Arg Asp Glu His Gly Asn Ile Gly Ser Leu Trp
1               5                   10

<210> SEQ ID NO 62
<211> LENGTH: 12
<212> TYPE: PRT
<213> ORGANISM: Oryctolagus cuniculus

<400> SEQUENCE: 62

Ala Gly Asp Trp Asp Thr Leu Pro Phe Lys Phe Trp
1               5                   10

<210> SEQ ID NO 63
<211> LENGTH: 12
<212> TYPE: PRT
<213> ORGANISM: Oryctolagus cuniculus

<400> SEQUENCE: 63

Ala Arg Val Asp Tyr Gly Val Ser Phe Asp Leu Trp
1               5                   10

<210> SEQ ID NO 64
<211> LENGTH: 7
<212> TYPE: PRT
<213> ORGANISM: Oryctolagus cuniculus

<400> SEQUENCE: 64

Ala Arg Phe Trp Asn Leu Trp
1               5

<210> SEQ ID NO 65
<211> LENGTH: 122
<212> TYPE: PRT
<213> ORGANISM: Oryctolagus cuniculus

<400> SEQUENCE: 65

Gln Glu Gln Leu Met Glu Ser Gly Gly Arg Leu Val Thr Pro Gly Thr
1               5                   10                  15

Pro Leu Thr Leu Thr Cys Thr Val Ser Gly Phe Ser Leu Ser Gly Tyr
            20                  25                  30

Ala Val Thr Trp Val Arg Gln Ala Pro Gly Glu Gly Leu Glu Trp Ile
        35                  40                  45

Gly Thr Ile Ser Thr Val Gly Ser Thr Tyr Phe Ala Ser Trp Ala Lys
    50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Thr Arg
                85                  90                  95

Tyr Asp Ser Tyr Gly Tyr Ala Tyr Asn Tyr Trp Phe Gly Thr Leu Trp
            100                 105                 110

Gly Pro Gly Thr Leu Val Thr Val Thr Ser
        115                 120

<210> SEQ ID NO 66
<211> LENGTH: 122
<212> TYPE: PRT
<213> ORGANISM: Oryctolagus cuniculus

<400> SEQUENCE: 66

Gln Gln Gln Leu Met Glu Ser Gly Gly Arg Leu Val Thr Pro Gly Thr

```
                  1               5                  10                 15
            Pro Leu Thr Leu Thr Cys Thr Val Ser Gly Ile Asp Leu Ser Ser Asn
                            20                 25                 30

Ala Met Thr Trp Val Arg Gln Ala Pro Gly Glu Gly Leu Glu Trp Ile
                            35                 40                 45

Gly Thr Ile Ser Thr Gly Gly Ser Thr Tyr Phe Ala Ser Trp Ala Lys
                            50                 55                 60

Gly Arg Phe Thr Ile Ser Lys Thr Ser Thr Val Asp Leu Lys Ile
            65                  70                 75                  80

Thr Ser Pro Thr Thr Glu Asp Thr Ala Thr Tyr Phe Cys Ala Thr Arg
                            85                 90                 95

Tyr Asp Ser Tyr Gly Tyr Ala Tyr Asn Tyr Trp Phe Gly Thr Leu Trp
                            100                105                110

Gly Pro Gly Thr Leu Val Thr Val Thr Ser
                            115                120

<210> SEQ ID NO 67
<211> LENGTH: 117
<212> TYPE: PRT
<213> ORGANISM: Oryctolagus cuniculus

<400> SEQUENCE: 67

Gln Ser Val Glu Glu Ser Gly Gly Arg Leu Val Ser Pro Gly Thr Pro
            1               5                  10                 15

Leu Thr Leu Thr Cys Thr Val Ser Gly Phe Ser Leu Ser Ser Tyr Tyr
                            20                 25                 30

Met Ile Trp Val Arg Gln Ala Pro Gly Lys Gly Leu Glu Tyr Ile Gly
                            35                 40                 45

Met Ile Asp Gly Tyr Gly Gly Asn Ala Tyr Tyr Ala Asn Trp Ala Lys
                            50                 55                 60

Gly Arg Phe Thr Val Ser Lys Ala Ala Thr Thr Val Asp Leu Lys Met
            65                  70                 75                  80

Thr Ser Leu Thr Thr Glu Asp Thr Ala Thr Tyr Phe Cys Val Arg Ala
                            85                 90                 95

Asp Tyr Asn Thr Val Ser Tyr Phe Asp Leu Trp Gly Pro Gly Thr Leu
                            100                105                110

Val Thr Val Thr Ser
                    115

<210> SEQ ID NO 68
<211> LENGTH: 121
<212> TYPE: PRT
<213> ORGANISM: Oryctolagus cuniculus

<400> SEQUENCE: 68

Gln Ser Leu Glu Glu Ser Gly Gly Arg Leu Val Thr Pro Gly Thr Pro
            1               5                  10                 15

Leu Thr Leu Thr Cys Thr Val Ser Gly Ile Asp Leu Ser Asn Ala
                            20                 25                 30

Met Thr Trp Val Arg Gln Ala Pro Gly Glu Gly Leu Glu Trp Ile Gly
                            35                 40                 45

Thr Ile Ser Thr Gly Gly Ser Thr Tyr Phe Ala Ser Trp Ala Lys Gly
                            50                 55                 60

Arg Phe Thr Ile Ser Lys Thr Ser Thr Val Asp Leu Lys Ile Thr
            65                  70                 75                  80

Ser Pro Thr Thr Glu Asp Thr Ala Thr Tyr Phe Cys Ala Thr Arg Tyr
```

Asp Ser Tyr Gly Tyr Ala Tyr Asn Tyr Trp Phe Gly Thr Leu Trp Gly
            100                 105                 110

Pro Gly Thr Leu Val Thr Val Thr Ser
        115                 120

<210> SEQ ID NO 69
<211> LENGTH: 121
<212> TYPE: PRT
<213> ORGANISM: Oryctolagus cuniculus

<400> SEQUENCE: 69

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Asp Tyr Ala
            20                  25                  30

Val Thr Trp Val Arg Gln Ala Pro Gly Lys Gly Leu Glu Trp Ile Gly
        35                  40                  45

Thr Ile Ser Thr Tyr Thr Asn Thr Tyr Tyr Ala Ser Trp Ala Lys Gly
    50                  55                  60

Arg Phe Thr Ile Ser Arg Thr Ser Thr Val Asp Leu Lys Ile
65                  70                  75                  80

Ser Pro Thr Thr Glu Asp Thr Ala Thr Tyr Phe Cys Ala Thr Arg Tyr
            85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
        115                 120

<210> SEQ ID NO 70
<211> LENGTH: 122
<212> TYPE: PRT
<213> ORGANISM: Oryctolagus cuniculus

<400> SEQUENCE: 70

Gln Gln Gln Leu Met Glu Ser Gly Gly Arg Leu Val Thr Pro Gly Thr
1               5                   10                  15

Pro Leu Thr Leu Thr Cys Thr Val Ser Gly Ile Asp Leu Ser Ser Asn
            20                  25                  30

Ala Met Thr Trp Val Arg Gln Ala Pro Gly Glu Gly Leu Glu Trp Ile
        35                  40                  45

Gly Thr Ile Ser Thr Gly Gly Ser Thr Tyr Phe Ala Ser Trp Ala Lys
    50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Thr Arg
            85                  90                  95

Tyr Asp Ser Tyr Gly Tyr Ala Tyr Asn Tyr Trp Phe Gly Thr Leu Trp
            100                 105                 110

Gly Pro Gly Thr Leu Val Thr Val Thr Ser
        115                 120

<210> SEQ ID NO 71
<211> LENGTH: 115
<212> TYPE: PRT
<213> ORGANISM: Oryctolagus cuniculus

<400> SEQUENCE: 71

Gln Ser Leu Glu Glu Ser Gly Gly Gly Leu Val Thr Pro Gly Gly Ser
1               5                   10                  15

Leu Thr Leu Ala Cys Thr Val Ser Gly Ile Asp Leu Ser Ser Asn Ala
                20                  25                  30

Met Gly Trp Val Arg Gln Ala Pro Gly Lys Gly Leu Glu Trp Ile Gly
            35                  40                  45

Leu Ile Asn Ser Gly Gly Asn Thr Tyr Tyr Ala Ser Trp Ala Lys Gly
        50                  55                  60

Arg Phe Thr Ile Ser Arg Thr Ser Thr Val Asp Leu Gln Met Thr
65                  70                  75                  80

Ser Pro Thr Thr Glu Asp Thr Ala Thr Tyr Phe Cys Ala Arg Ala Gly
                85                  90                  95

Asp Ser Val Ser Thr Leu Ala Leu Trp Gly Pro Gly Thr Leu Val Thr
                100                 105                 110

Val Thr Ser
        115

<210> SEQ ID NO 72
<211> LENGTH: 117
<212> TYPE: PRT
<213> ORGANISM: Oryctolagus cuniculus

<400> SEQUENCE: 72

Gln Ser Val Glu Glu Ser Gly Gly Arg Leu Val Ser Pro Gly Thr Pro
1               5                   10                  15

Leu Thr Leu Thr Cys Thr Ala Ser Gly Phe Ser Leu Ser Thr Tyr Tyr
                20                  25                  30

Met Ile Trp Val Arg Gln Ala Pro Gly Lys Gly Leu Glu Tyr Ile Gly
            35                  40                  45

Ser Ile Asp Gly Tyr Asp Gly Asp Thr Tyr Tyr Ala Thr Trp Ala Lys
        50                  55                  60

Gly Arg Phe Thr Val Ser Lys Thr Ala Thr Thr Val Asp Leu Lys Met
65                  70                  75                  80

Thr Ser Leu Thr Thr Glu Asp Thr Ala Thr Tyr Phe Cys Ala Arg Ala
                85                  90                  95

Asp Tyr Asn Thr Val Ala Tyr Phe Asp Leu Trp Gly Pro Gly Thr Leu
                100                 105                 110

Val Thr Val Thr Ser
        115

<210> SEQ ID NO 73
<211> LENGTH: 122
<212> TYPE: PRT
<213> ORGANISM: Oryctolagus cuniculus

<400> SEQUENCE: 73

Gln Gln Gln Leu Met Glu Ser Gly Gly Arg Leu Val Thr Pro Gly Thr
1               5                   10                  15

Pro Leu Thr Leu Thr Cys Thr Val Ser Gly Ile Asp Leu Ser Ser Asn
                20                  25                  30

Ala Met Thr Trp Val Arg Gln Ala Pro Gly Glu Gly Leu Glu Trp Ile
            35                  40                  45

Gly Thr Ile Ser Thr Gly Gly Ser Thr Tyr Phe Ala Ser Trp Ala Lys
        50                  55                  60

Gly Arg Phe Thr Ile Ser Lys Thr Ser Thr Thr Val Asp Leu Lys Ile
65                  70                  75                  80

```
Thr Ser Pro Thr Thr Glu Asp Thr Ala Thr Tyr Phe Cys Ala Thr Arg
                85                  90                  95

Tyr Asp Ser Tyr Gly Tyr Ala Tyr Asn Tyr Trp Phe Gly Thr Leu Trp
            100                 105                 110

Gly Pro Gly Thr Leu Val Thr Val Thr Ser
        115                 120

<210> SEQ ID NO 74
<211> LENGTH: 119
<212> TYPE: PRT
<213> ORGANISM: Oryctolagus cuniculus

<400> SEQUENCE: 74

Gln Ser Val Glu Glu Ser Arg Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Gly Trp Phe Arg Leu Ala Pro Gly Lys Gly Leu Glu Trp Ile Gly
        35                  40                  45

Ile Ile Thr Ile Gly Asp Ser Ile Tyr Tyr Ala Asn Trp Ala Lys Gly
50                  55                  60

Arg Phe Thr Ile Ser Lys Thr Ser Thr Thr Val Asp Leu Arg Ile Thr
65                  70                  75                  80

Ser Pro Thr Thr Ala Asp Thr Ala Thr Tyr Phe Cys Ala Arg Gly Asn
                85                  90                  95

Ile Gly Ile Gly Trp Gly Ser Tyr Tyr Phe Asn Phe Trp Gly Pro Gly
            100                 105                 110

Thr Leu Val Thr Val Thr Ser
        115

<210> SEQ ID NO 75
<211> LENGTH: 115
<212> TYPE: PRT
<213> ORGANISM: Oryctolagus cuniculus

<400> SEQUENCE: 75

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ala
            20                  25                  30

Met Ser Trp Val Arg Gln Ala Pro Gly Lys Gly Leu Glu Trp Ile Gly
        35                  40                  45

Tyr Ile Thr Thr Arg Asp Lys Thr Tyr Tyr Thr Asn Trp Ala Asn Gly
50                  55                  60

Arg Phe Thr Ile Ser Lys Thr Ser Thr Ser Val Ser Leu Arg Ile Ala
65                  70                  75                  80

Ser Pro Thr Thr Glu Asp Thr Ala Thr Tyr Phe Cys Ala Thr Ala Leu
                85                  90                  95

Tyr Ala Asp Asp Gly Asn Thr Leu Trp Gly Pro Gly Thr Leu Val Thr
            100                 105                 110

Val Thr Ser
        115

<210> SEQ ID NO 76
<211> LENGTH: 114
<212> TYPE: PRT
<213> ORGANISM: Oryctolagus cuniculus
```

```
<400> SEQUENCE: 76

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Pro
                20                  25                  30

Met Gly Trp Phe Arg Gln Ala Pro Gly Lys Gly Leu Glu Tyr Ile Gly
            35                  40                  45

Ala Ile Asn Thr Gly Gly Ser Thr Tyr Tyr Ala Ser Trp Ala Arg Gly
    50                  55                  60

Arg Phe Thr Val Ser Arg Thr Ser Thr Thr Val Asp Leu Lys Met Thr
65                  70                  75                  80

Ser Leu Thr Ala Glu Asp Thr Ala Thr Tyr Phe Cys Val Arg His Asp
                85                  90                  95

Asp Asp Leu Thr Phe Asn Leu Trp Gly Pro Gly Thr Leu Val Thr Val
                100                 105                 110

Thr Ser

<210> SEQ ID NO 77
<211> LENGTH: 114
<212> TYPE: PRT
<213> ORGANISM: Oryctolagus cuniculus

<400> SEQUENCE: 77

Gln Gln Gln Leu Val Glu Ser Gly Gly Arg Leu Val Thr Pro Gly Thr
1               5                   10                  15

Pro Leu Thr Leu Thr Cys Thr Ala Ser Gly Phe Ser Leu Ser Asn Tyr
                20                  25                  30

Tyr Met Gly Trp Val Arg Gln Ala Pro Gly Lys Gly Leu Gln Trp Ile
            35                  40                  45

Ala Tyr Ile Met Gln Ser Gly Thr Ala Tyr Tyr Ala Ser Trp Ala Arg
    50                  55                  60

Gly Arg Phe Thr Ile Ser Arg Thr Ser Thr Thr Val Asp Leu Lys Met
65                  70                  75                  80

Pro Ser Leu Thr Ala Ala Asp Thr Ala Ala Tyr Phe Cys Ala Arg Asp
                85                  90                  95

Val Asp Gly Gly Tyr Ala Leu Trp Gly Pro Gly Thr Leu Val Thr Val
                100                 105                 110

Thr Ser

<210> SEQ ID NO 78
<211> LENGTH: 114
<212> TYPE: PRT
<213> ORGANISM: Oryctolagus cuniculus

<400> SEQUENCE: 78

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
                20                  25                  30

Met Ser Trp Val Arg Gln Ala Pro Gly Lys Gly Leu Glu Trp Ile Gly
            35                  40                  45

Ser Ile Asp Thr Asn Ser Asn Thr Tyr Tyr Ala Ser Trp Val Lys Gly
    50                  55                  60

Arg Phe Thr Ile Ser Lys Thr Ser Thr Thr Val Asp Leu Lys Met Thr
65                  70                  75                  80
```

-continued

Ser Pro Thr Thr Glu Asp Thr Ala Thr Tyr Phe Cys Val Arg Gly Val
                85                  90                  95

Ile Gly Ala Thr Gly Asp Leu Trp Gly Pro Gly Thr Leu Val Thr Val
            100                 105                 110

Thr Ser

<210> SEQ ID NO 79
<211> LENGTH: 117
<212> TYPE: PRT
<213> ORGANISM: Oryctolagus cuniculus

<400> SEQUENCE: 79

Gln Ser Val Glu Glu Ser Arg Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Ile Ser Trp Val Arg Gln Ala Pro Gly Lys Gly Leu Glu Trp Ile Gly
        35                  40                  45

Tyr Ile Leu Ala Gly Gly Ser Ala Tyr Tyr Ala Asn Trp Ala Lys Gly
    50                  55                  60

Arg Phe Thr Ile Ser Lys Thr Ser Thr Thr Val Glu Leu Lys Val Thr
65                  70                  75                  80

Ser Pro Thr Thr Glu Asp Thr Ala Thr Tyr Phe Cys Ala Arg Gly Gly
                85                  90                  95

Ala Gly Tyr Asn Thr Val Gly Leu Asn Leu Trp Gly Pro Gly Thr Leu
            100                 105                 110

Val Thr Val Thr Ser
            115

<210> SEQ ID NO 80
<211> LENGTH: 122
<212> TYPE: PRT
<213> ORGANISM: Oryctolagus cuniculus

<400> SEQUENCE: 80

Gln Glu Gln Leu Met Glu Ser Gly Gly Arg Leu Val Thr Pro Gly Thr
1               5                   10                  15

Pro Leu Thr Leu Thr Cys Thr Val Ser Gly Phe Ser Leu Ser Gly Tyr
            20                  25                  30

Ala Val Thr Trp Val Arg Gln Ala Pro Gly Glu Gly Leu Glu Trp Ile
        35                  40                  45

Gly Thr Ile Ser Thr Val Gly Ser Thr Tyr Phe Ala Ser Trp Ala Lys
    50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Thr Arg
                85                  90                  95

Tyr Asp Ser Tyr Gly Tyr Ala Tyr Asn Tyr Trp Phe Gly Thr Leu Trp
            100                 105                 110

Gly Pro Gly Thr Leu Val Thr Val Thr Ser
            115                 120

<210> SEQ ID NO 81
<211> LENGTH: 117
<212> TYPE: PRT
<213> ORGANISM: Oryctolagus cuniculus

```
<400> SEQUENCE: 81

Gln Ser Val Glu Glu Ser Gly Gly Arg Leu Val Ser Pro Thr Pro
1               5                   10                  15

Leu Thr Leu Thr Cys Thr Val Ser Gly Phe Ser Leu Ser Ser Tyr Tyr
            20                  25                  30

Met Ile Trp Val Arg Gln Ala Pro Gly Lys Gly Leu Glu Tyr Ile Gly
            35                  40                  45

Met Ile Asp Gly Tyr Gly Gly Asn Ala Tyr Tyr Ala Asn Trp Ala Lys
        50                  55                  60

Gly Arg Phe Thr Val Ser Lys Ala Ala Thr Thr Val Asp Leu Lys Met
65                  70                  75                  80

Thr Ser Leu Thr Thr Glu Asp Thr Ala Thr Tyr Phe Cys Val Arg Ala
                85                  90                  95

Asp Tyr Asn Thr Val Ser Tyr Phe Asp Leu Trp Gly Pro Gly Thr Leu
                100                 105                 110

Val Thr Val Thr Ser
            115

<210> SEQ ID NO 82
<211> LENGTH: 115
<212> TYPE: PRT
<213> ORGANISM: Oryctolagus cuniculus

<400> SEQUENCE: 82

Gln Ser Val Lys Glu Ser Glu Gly Arg Leu Val Thr Pro Gly Thr Pro
1               5                   10                  15

Leu Thr Leu Thr Cys Thr Val Ser Gly Phe Ser Leu Ser Asn Tyr Asn
            20                  25                  30

Met Gln Trp Val Arg Gln Ala Pro Gly Lys Gly Leu Glu Tyr Ile Gly
            35                  40                  45

Ala Ile Tyr Ser Ser Gly Pro Thr Tyr Tyr Ala Ser Trp Ala Lys Gly
        50                  55                  60

Arg Phe Thr Ile Ser Lys Thr Ser Thr Thr Val Asp Leu Glu Met Thr
65                  70                  75                  80

Ser Leu Thr Ser Glu Asp Thr Ala Thr Tyr Phe Cys Ala Lys Asn Asp
                85                  90                  95

Asp Pro Phe Glu Thr Tyr Asp Leu Trp Gly Pro Gly Thr Leu Val Thr
                100                 105                 110

Val Thr Ser
    115

<210> SEQ ID NO 83
<211> LENGTH: 116
<212> TYPE: PRT
<213> ORGANISM: Oryctolagus cuniculus

<400> SEQUENCE: 83

Gln Ser Val Glu Glu Ser Arg Gly Arg Leu Val Thr Pro Gly Thr Pro
1               5                   10                  15

Leu Thr Leu Thr Cys Thr Val Ser Gly Ile Asp Leu Met Ser Asn Ala
            20                  25                  30

Met Gly Trp Val Arg Gln Ala Pro Gly Lys Gly Leu Glu Tyr Ile Gly
            35                  40                  45

Ile Ile Ser Ser Ser Gly Ser Thr Tyr Tyr Ala Ser Trp Ala Lys Gly
        50                  55                  60

Arg Phe Thr Ile Ser Lys Thr Ser Thr Thr Val Asp Leu Lys Ile Thr
```

```
                65                  70                  75                  80
Ser Pro Thr Thr Glu Asp Ala Ala Thr Tyr Phe Cys Ala Arg Ala Ile
                    85                  90                  95

Gly Asp Asn Gly Gly Tyr Phe Asn Leu Trp Gly Pro Gly Thr Leu Val
                100                 105                 110

Thr Val Thr Ser
        115

<210> SEQ ID NO 84
<211> LENGTH: 114
<212> TYPE: PRT
<213> ORGANISM: Oryctolagus cuniculus

<400> SEQUENCE: 84

Gln Glu Gln Leu Glu Glu Ser Gly Gly Gly Leu Val Thr Pro Gly Thr
1               5                   10                  15

Pro Leu Thr Leu Thr Cys Thr Ala Ser Gly Phe Ser Leu Asp Ser Tyr
                20                  25                  30

Tyr Met Ile Trp Val Arg Gln Ala Pro Gly Glu Gly Leu Glu Trp Ile
            35                  40                  45

Gly Ile Ile Gly Gly Gly Asp Thr Ala Tyr Ala Ser Trp Ala Lys
        50                  55                  60

Gly Arg Phe Thr Ile Ser Lys Thr Ser Thr Thr Val Asp Leu Lys Met
65                  70                  75                  80

Thr Ser Leu Thr Thr Glu Asp Thr Ala Thr Tyr Phe Cys Ala Arg Asp
                85                  90                  95

Val Asp Gly Gly Tyr Ala Leu Trp Gly Pro Gly Thr Leu Val Thr Val
                100                 105                 110

Thr Ser

<210> SEQ ID NO 85
<211> LENGTH: 121
<212> TYPE: PRT
<213> ORGANISM: Oryctolagus cuniculus

<400> SEQUENCE: 85

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
                20                  25                  30

Met Thr Trp Val Arg Gln Ala Pro Gly Glu Gly Leu Glu Trp Ile Gly
            35                  40                  45

Thr Ile Ser Thr Gly Gly Ser Thr Tyr Phe Ala Ser Trp Ala Lys Gly
        50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
                100                 105                 110

Pro Gly Thr Leu Val Thr Val Thr Ser
        115                 120

<210> SEQ ID NO 86
<211> LENGTH: 119
<212> TYPE: PRT
<213> ORGANISM: Oryctolagus cuniculus
```

<400> SEQUENCE: 86

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Asn Asn Tyr Ala
            20                  25                  30

Met Gly Trp Val Arg Gln Ala Pro Gly Lys Gly Leu Glu Tyr Ile Gly
        35                  40                  45

Ile Ile Ser Tyr Gly Gly Ser Ala Tyr Tyr Ala Ser Trp Ala Lys Gly
    50                  55                  60

Arg Phe Thr Ile Ser Arg Thr Ser Thr Thr Val Asp Leu Lys Ile Thr
65              70                  75                  80

Ser Pro Thr Thr Glu Asp Thr Ala Thr Tyr Phe Cys Ala Arg Gly Asp
            85                  90                  95

Tyr Asp Asn Tyr Gly Tyr Gly Tyr Ala Ile Asn Phe Trp Gly Pro Gly
            100                 105                 110

Thr Leu Val Thr Val Thr Ser
        115

<210> SEQ ID NO 87
<211> LENGTH: 112
<212> TYPE: PRT
<213> ORGANISM: Oryctolagus cuniculus

<400> SEQUENCE: 87

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Pro
            20                  25                  30

Met Gly Trp Val Arg Gln Ala Pro Gly Lys Gly Leu Glu Tyr Ile Gly
        35                  40                  45

Ile Ile Ser Asp Ser Asp Asn Thr Tyr Tyr Ala Ser Trp Ala Lys Gly
    50                  55                  60

Arg Phe Thr Ile Ser Lys Thr Ser Thr Thr Val Asp Leu Lys Ile Thr
65              70                  75                  80

Ser Pro Thr Thr Glu Asp Thr Ala Thr Tyr Phe Cys Ala Arg Gly Trp
            85                  90                  95

Leu Tyr Phe Asp Leu Trp Gly Pro Gly Thr Leu Val Thr Val Thr Ser
            100                 105                 110

<210> SEQ ID NO 88
<211> LENGTH: 117
<212> TYPE: PRT
<213> ORGANISM: Oryctolagus cuniculus

<400> SEQUENCE: 88

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Asn Ser Tyr Ala
            20                  25                  30

Met Gly Trp Val Arg Gln Ala Pro Gly Glu Gly Leu Glu Trp Ile Gly
        35                  40                  45

Ile Ile Thr Ser Ser Ser Ile Thr Tyr Tyr Ala Ser Trp Ala Lys Gly
    50                  55                  60

Arg Phe Thr Ile Ser Lys Thr Ser Thr Thr Val Asp Leu Lys Met Thr
65              70                  75                  80

-continued

Ser Leu Thr Thr Glu Asp Thr Ala Thr Tyr Phe Cys Ala Arg Gly Asp
            85                  90                  95

Tyr Asn Asn Asn Trp Asp Tyr Phe Asn Leu Trp Gly Pro Gly Thr Leu
        100                 105                 110

Val Thr Val Thr Ser
        115

<210> SEQ ID NO 89
<211> LENGTH: 116
<212> TYPE: PRT
<213> ORGANISM: Oryctolagus cuniculus

<400> SEQUENCE: 89

Gln Ser Val Glu Glu Ser Gly Gly Arg Leu Val Thr Pro Gly Thr Pro
1               5                   10                  15

Leu Thr Leu Thr Cys Thr Ile Ser Gly Phe Ser Leu Asn Ile Tyr Glu
            20                  25                  30

Ile Asn Trp Val Arg Gln Ala Pro Gly Lys Gly Leu Glu Trp Ile Ala
        35                  40                  45

Ala Ile Trp Arg Glu Gly His Thr Asp Tyr Ser Asn Trp Ala Lys Gly
    50                  55                  60

Arg Phe Thr Ile Ser Lys Ser Ser Thr Thr Val Glu Leu Arg Met Thr
65                  70                  75                  80

Ser Leu Thr Thr Glu Asp Thr Ala Thr Tyr Phe Cys Ala Arg Tyr Ser
                85                  90                  95

Gly Asp Asn Gly Gly Thr Phe Asn Leu Trp Gly Pro Gly Thr Leu Val
            100                 105                 110

Thr Val Thr Ser
        115

<210> SEQ ID NO 90
<211> LENGTH: 118
<212> TYPE: PRT
<213> ORGANISM: Oryctolagus cuniculus

<400> SEQUENCE: 90

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Asn Trp Val Arg Gln Ala Pro Gly Lys Gly Leu Glu Trp Ile Thr
        35                  40                  45

Phe Ile Gly Thr Gly Gly Asp Ile Tyr Tyr Ala Asn Trp Ala Lys Gly
    50                  55                  60

Arg Phe Thr Ile Ser Lys Thr Ser Thr Thr Val Asp Leu Lys Ile Ala
65                  70                  75                  80

Ser Pro Thr Thr Glu Asp Thr Ala Thr Tyr Phe Cys Ala Arg Gly Asp
                85                  90                  95

Thr Gly Gly Ser Leu Tyr Arg His Phe Asn Leu Trp Gly Pro Gly Thr
            100                 105                 110

Leu Val Thr Val Thr Ser
        115

<210> SEQ ID NO 91
<211> LENGTH: 19
<212> TYPE: PRT
<213> ORGANISM: Oryctolagus cuniculus -continued

```
<400> SEQUENCE: 91

Ala Thr Arg Tyr Asp Ser Tyr Gly Tyr Ala Tyr Asn Tyr Trp Phe Gly
1               5                   10                  15

Thr Leu Trp

<210> SEQ ID NO 92
<211> LENGTH: 17
<212> TYPE: PRT
<213> ORGANISM: Oryctolagus cuniculus

<400> SEQUENCE: 92

Ala Arg Gly Asn Ile Gly Ile Gly Trp Gly Ser Tyr Tyr Phe Asn Phe
1               5                   10                  15

Trp

<210> SEQ ID NO 93
<211> LENGTH: 17
<212> TYPE: PRT
<213> ORGANISM: Oryctolagus cuniculus

<400> SEQUENCE: 93

Ala Arg Gly Asp Tyr Asp Asn Tyr Gly Tyr Gly Tyr Ala Ile Asn Phe
1               5                   10                  15

Trp

<210> SEQ ID NO 94
<211> LENGTH: 16
<212> TYPE: PRT
<213> ORGANISM: Oryctolagus cuniculus

<400> SEQUENCE: 94

Ala Arg Gly Asp Thr Gly Gly Ser Leu Tyr Arg His Phe Asn Leu Trp
1               5                   10                  15

<210> SEQ ID NO 95
<211> LENGTH: 15
<212> TYPE: PRT
<213> ORGANISM: Oryctolagus cuniculus

<400> SEQUENCE: 95

Ala Arg Gly Gly Ala Gly Tyr Asn Thr Val Gly Leu Asn Leu Trp
1               5                   10                  15

<210> SEQ ID NO 96
<211> LENGTH: 15
<212> TYPE: PRT
<213> ORGANISM: Oryctolagus cuniculus

<400> SEQUENCE: 96

Ala Arg Gly Asp Tyr Asn Asn Asn Trp Asp Tyr Phe Asn Leu Trp
1               5                   10                  15

<210> SEQ ID NO 97
<211> LENGTH: 14
<212> TYPE: PRT
<213> ORGANISM: Oryctolagus cuniculus

<400> SEQUENCE: 97

Ala Arg Ala Asp Tyr Asn Thr Val Ala Tyr Phe Asp Leu Trp
1               5                   10

<210> SEQ ID NO 98
```

-continued

<210> SEQ ID NO 98
<211> LENGTH: 14
<212> TYPE: PRT
<213> ORGANISM: Oryctolagus cuniculus

<400> SEQUENCE: 98

Val Arg Ala Asp Tyr Asn Thr Val Ser Tyr Phe Asp Leu Trp
1               5                   10

<210> SEQ ID NO 99
<211> LENGTH: 14
<212> TYPE: PRT
<213> ORGANISM: Oryctolagus cuniculus

<400> SEQUENCE: 99

Ala Arg Ala Ile Gly Asp Asn Gly Gly Tyr Phe Asn Leu Trp
1               5                   10

<210> SEQ ID NO 100
<211> LENGTH: 14
<212> TYPE: PRT
<213> ORGANISM: Oryctolagus cuniculus

<400> SEQUENCE: 100

Ala Arg Tyr Ser Gly Asp Asn Gly Gly Thr Phe Asn Leu Trp
1               5                   10

<210> SEQ ID NO 101
<211> LENGTH: 13
<212> TYPE: PRT
<213> ORGANISM: Oryctolagus cuniculus

<400> SEQUENCE: 101

Ala Arg Ala Gly Asp Ser Val Ser Thr Leu Ala Leu Trp
1               5                   10

<210> SEQ ID NO 102
<211> LENGTH: 13
<212> TYPE: PRT
<213> ORGANISM: Oryctolagus cuniculus

<400> SEQUENCE: 102

Ala Thr Ala Leu Tyr Ala Asp Asp Gly Asn Thr Leu Trp
1               5                   10

<210> SEQ ID NO 103
<211> LENGTH: 13
<212> TYPE: PRT
<213> ORGANISM: Oryctolagus cuniculus

<400> SEQUENCE: 103

Ala Lys Asn Asp Asp Pro Phe Glu Thr Tyr Asp Leu Trp
1               5                   10

<210> SEQ ID NO 104
<211> LENGTH: 12
<212> TYPE: PRT
<213> ORGANISM: Oryctolagus cuniculus

<400> SEQUENCE: 104

Val Arg Gly Val Ile Gly Ala Thr Gly Asp Leu Trp
1               5                   10

<210> SEQ ID NO 105
<211> LENGTH: 12
<212> TYPE: PRT

<213> ORGANISM: Oryctolagus cuniculus

<400> SEQUENCE: 105

Val Arg His Asp Asp Leu Thr Phe Asn Leu Trp
1               5                   10

<210> SEQ ID NO 106
<211> LENGTH: 11
<212> TYPE: PRT
<213> ORGANISM: Oryctolagus cuniculus

<400> SEQUENCE: 106

Ala Arg Asp Val Asp Gly Gly Tyr Ala Leu Trp
1               5                   10

<210> SEQ ID NO 107
<211> LENGTH: 10
<212> TYPE: PRT
<213> ORGANISM: Oryctolagus cuniculus

<400> SEQUENCE: 107

Ala Arg Gly Trp Leu Tyr Phe Asp Leu Trp
1               5                   10

<210> SEQ ID NO 108
<211> LENGTH: 121
<212> TYPE: PRT
<213> ORGANISM: Oryctolagus cuniculus

<400> SEQUENCE: 108

Gln Ser Val Lys Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Ser Trp Val Arg Gln Ala Pro Gly Glu Gly Leu Glu Trp Ile Gly
        35                  40                  45

Thr Ile Ser Thr Val Gly Lys Thr Tyr Phe Ala Ser Trp Ala Lys Gly
    50                  55                  60

Arg Phe Thr Ile Ser Lys Thr Ser Thr Val Asp Leu Arg Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
        115                 120

<210> SEQ ID NO 109
<211> LENGTH: 122
<212> TYPE: PRT
<213> ORGANISM: Oryctolagus cuniculus

<400> SEQUENCE: 109

Gln Gln Gln Leu Met Glu Ser Gly Gly Arg Leu Val Thr Pro Gly Thr
1               5                   10                  15

Pro Leu Thr Leu Thr Cys Thr Val Ser Gly Ile Asp Leu Ser Ser Asn
            20                  25                  30

Ala Met Thr Trp Val Arg Gln Ala Pro Gly Glu Gly Leu Glu Trp Ile
        35                  40                  45

Gly Thr Ile Ser Thr Gly Gly Ser Thr Tyr Phe Ala Ser Trp Ala Lys

```
            50                  55                  60
Gly Arg Phe Thr Ile Ser Lys Thr Ser Thr Thr Val Asp Leu Lys Ile
 65                  70                  75                  80

Thr Ser Pro Thr Thr Glu Asp Thr Ala Thr Tyr Phe Cys Ala Thr Arg
                 85                  90                  95

Tyr Asp Ser Tyr Gly Tyr Ala Tyr Asn Tyr Trp Phe Gly Thr Leu Trp
            100                 105                 110

Gly Pro Gly Thr Leu Val Thr Val Thr Ser
        115                 120

<210> SEQ ID NO 110
<211> LENGTH: 112
<212> TYPE: PRT
<213> ORGANISM: Oryctolagus cuniculus

<400> SEQUENCE: 110

Gln Ser Leu Glu Glu Ser Gly Gly Arg Leu Val Thr Pro Gly Gly Ser
 1               5                  10                  15

Leu Thr Leu Thr Cys Thr Ala Ser Gly Phe Ser Leu Ser Ala Tyr Asp
                20                  25                  30

Ile Asn Trp Val Arg Gln Ala Pro Gly Lys Gly Leu Glu Trp Ile Gly
            35                  40                  45

Met Ile Ser Gly Ser Gly Ser Thr Tyr Tyr Ala Ser Trp Ala Lys Gly
         50                 55                  60

Arg Phe Thr Ile Ser Lys Thr Ser Thr Thr Val Asp Leu Lys Met Thr
 65                  70                  75                  80

Ser Leu Thr Ala Ala Asp Thr Ala Thr Tyr Phe Cys Ala Arg Gly Phe
                 85                  90                  95

Asp Asn Tyr Asn Leu Trp Gly Pro Gly Thr Leu Val Thr Val Thr Ser
            100                 105                 110

<210> SEQ ID NO 111
<211> LENGTH: 122
<212> TYPE: PRT
<213> ORGANISM: Oryctolagus cuniculus

<400> SEQUENCE: 111

Gln Gln Gln Leu Met Glu Ser Gly Gly Arg Leu Val Thr Pro Gly Thr
 1               5                  10                  15

Pro Leu Thr Leu Thr Cys Thr Val Ser Gly Ile Asp Leu Ser Ser Asn
                20                  25                  30

Ala Met Thr Trp Val Arg Gln Ala Pro Gly Glu Gly Leu Glu Trp Ile
            35                  40                  45

Gly Thr Ile Ser Thr Gly Gly Ser Thr Tyr Phe Ala Ser Trp Ala Lys
         50                 55                  60

Gly Arg Phe Thr Ile Ser Lys Thr Ser Thr Thr Val Asp Leu Lys Ile
 65                  70                  75                  80

Thr Ser Pro Thr Thr Glu Asp Thr Ala Thr Tyr Phe Cys Ala Thr Arg
                 85                  90                  95

Tyr Asp Ser Tyr Gly Tyr Ala Tyr Asn Tyr Trp Phe Gly Thr Leu Trp
            100                 105                 110

Gly Pro Gly Thr Leu Val Thr Val Thr Ser
        115                 120

<210> SEQ ID NO 112
<211> LENGTH: 121
<212> TYPE: PRT
```

<213> ORGANISM: Oryctolagus cuniculus

<400> SEQUENCE: 112

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Thr Trp Val Arg Gln Ala Pro Gly Glu Gly Leu Glu Trp Ile Gly
        35                  40                  45

Thr Ile Ser Thr Gly Gly Ser Thr Tyr Phe Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
        115                 120

<210> SEQ ID NO 113
<211> LENGTH: 121
<212> TYPE: PRT
<213> ORGANISM: Oryctolagus cuniculus

<400> SEQUENCE: 113

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Thr Trp Val Arg Gln Ala Pro Gly Glu Gly Leu Glu Trp Ile Gly
        35                  40                  45

Thr Ile Ser Thr Gly Gly Ser Thr Tyr Phe Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
        115                 120

<210> SEQ ID NO 114
<211> LENGTH: 121
<212> TYPE: PRT
<213> ORGANISM: Oryctolagus cuniculus

<400> SEQUENCE: 114

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Asn Asn Ala
            20                  25                  30

Met Ser Trp Val Arg Gln Ala Pro Gly Glu Gly Leu Glu Trp Ile Gly
        35                  40                  45

Thr Ile Ser Thr Gly Gly Ser Ala Tyr Tyr Ala Ser Trp Ala Lys Gly
    50                  55                  60

Arg Phe Thr Ile Ser Lys Ser Thr Thr Val Asp Leu Lys Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
        115                 120

<210> SEQ ID NO 115
<211> LENGTH: 122
<212> TYPE: PRT
<213> ORGANISM: Oryctolagus cuniculus

<400> SEQUENCE: 115

Gln Gln Gln Leu Met Glu Ser Gly Gly Arg Leu Val Thr Pro Gly Thr
1               5                   10                  15

Pro Leu Thr Leu Thr Cys Thr Val Ser Gly Ile Asp Leu Ser Ser Asn
            20                  25                  30

Ala Met Thr Trp Val Arg Gln Ala Pro Gly Glu Gly Leu Glu Trp Ile
            35                  40                  45

Gly Thr Ile Ser Thr Gly Gly Ser Thr Tyr Phe Ala Ser Trp Ala Lys
        50                  55                  60

Gly Arg Phe Thr Ile Ser Lys Thr Ser Thr Val Asp Leu Lys Ile
65                  70                  75                  80

Thr Ser Pro Thr Thr Glu Asp Thr Ala Thr Tyr Phe Cys Ala Thr Arg
                85                  90                  95

Tyr Asp Ser Tyr Gly Tyr Ala Tyr Asn Tyr Trp Phe Gly Thr Leu Trp
            100                 105                 110

Gly Pro Gly Thr Leu Val Thr Val Thr Ser
        115                 120

<210> SEQ ID NO 116
<211> LENGTH: 121
<212> TYPE: PRT
<213> ORGANISM: Oryctolagus cuniculus

<400> SEQUENCE: 116

Gln Ser Val Lys Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Ser Trp Val Arg Gln Ala Pro Gly Glu Gly Leu Glu Trp Ile Gly
            35                  40                  45

Thr Ile Ser Thr Val Gly Lys Thr Tyr Phe Ala Ser Trp Ala Lys Gly
        50                  55                  60

Arg Phe Thr Ile Ser Lys Thr Ser Thr Val Asp Leu Arg Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
        115                 120

<210> SEQ ID NO 117

```
<211> LENGTH: 121
<212> TYPE: PRT
<213> ORGANISM: Oryctolagus cuniculus

<400> SEQUENCE: 117
```

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Thr Trp Val Arg Gln Ala Pro Gly Glu Gly Leu Glu Trp Ile Gly
        35                  40                  45

Thr Ile Ser Thr Gly Gly Ser Thr Tyr Phe Ala Ser Trp Ala Lys Gly
    50                  55                  60

Arg Phe Thr Ile Ser Lys Thr Ser Thr Val Asp Leu Lys Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
        115                 120

```
<210> SEQ ID NO 118
<211> LENGTH: 121
<212> TYPE: PRT
<213> ORGANISM: Oryctolagus cuniculus

<400> SEQUENCE: 118
```

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Thr Trp Val Arg Gln Ala Pro Gly Glu Gly Leu Glu Trp Ile Gly
        35                  40                  45

Thr Ile Ser Thr Gly Gly Ser Thr Tyr Phe Ala Ser Trp Ala Lys Gly
    50                  55                  60

Arg Phe Thr Ile Ser Lys Thr Ser Thr Val Asp Leu Lys Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
        115                 120

```
<210> SEQ ID NO 119
<211> LENGTH: 122
<212> TYPE: PRT
<213> ORGANISM: Oryctolagus cuniculus

<400> SEQUENCE: 119
```

Gln Gln Gln Leu Met Glu Ser Gly Gly Arg Leu Val Thr Pro Gly Thr
1               5                   10                  15

Pro Leu Thr Leu Thr Cys Thr Val Ser Gly Ile Asp Leu Ser Ser Asn
            20                  25                  30

Ala Met Thr Trp Val Arg Gln Ala Pro Gly Glu Gly Leu Glu Trp Ile
        35                  40                  45

```
Gly Thr Ile Ser Thr Gly Gly Ser Thr Tyr Phe Ala Ser Trp Ala Lys
 50                  55                  60

Gly Arg Phe Thr Ile Ser Lys Thr Ser Thr Val Asp Leu Lys Ile
 65                  70                  75                  80

Thr Ser Pro Thr Thr Glu Asp Thr Ala Thr Tyr Phe Cys Ala Thr Arg
                     85                  90                  95

Tyr Asp Ser Tyr Gly Tyr Ala Tyr Asn Tyr Trp Phe Gly Thr Leu Trp
                100                 105                 110

Gly Pro Gly Thr Leu Val Thr Val Thr Ser
            115                 120

<210> SEQ ID NO 120
<211> LENGTH: 117
<212> TYPE: PRT
<213> ORGANISM: Oryctolagus cuniculus

<400> SEQUENCE: 120

Gln Ser Val Glu Glu Ser Gly Arg Leu Val Ser Pro Gly Thr Pro
 1               5                  10                  15

Leu Thr Leu Thr Cys Thr Val Ser Gly Phe Ser Leu Ser Ser Tyr Tyr
                 20                  25                  30

Met Ile Trp Val Arg Gln Ala Pro Gly Lys Gly Leu Glu Tyr Ile Gly
             35                  40                  45

Met Ile Asp Gly Tyr Gly Gly Asn Ala Tyr Tyr Ala Asn Trp Ala Lys
 50                  55                  60

Gly Arg Phe Thr Val Ser Lys Ala Ala Thr Thr Val Asp Leu Lys Met
 65                  70                  75                  80

Thr Ser Leu Thr Thr Glu Asp Thr Ala Thr Tyr Phe Cys Val Arg Ala
                 85                  90                  95

Asp Tyr Asn Thr Val Ser Tyr Phe Asp Leu Trp Gly Pro Gly Thr Leu
                100                 105                 110

Val Thr Val Thr Ser
            115

<210> SEQ ID NO 121
<211> LENGTH: 121
<212> TYPE: PRT
<213> ORGANISM: Oryctolagus cuniculus

<400> SEQUENCE: 121

Gln Ser Leu Glu Glu Ser Gly Arg Leu Val Thr Pro Gly Thr Pro
 1               5                  10                  15

Leu Thr Leu Thr Cys Thr Val Ser Gly Ile Asp Leu Ser Ser Asn Ala
                 20                  25                  30

Met Thr Trp Val Arg Gln Ala Pro Gly Glu Gly Leu Glu Trp Ile Gly
             35                  40                  45

Thr Ile Ser Thr Gly Gly Ser Thr Tyr Phe Ala Ser Trp Ala Lys Gly
 50                  55                  60

Arg Phe Thr Ile Ser Lys Thr Ser Thr Val Asp Leu Lys Ile Thr
 65                  70                  75                  80

Ser Pro Thr Thr Glu Asp Thr Ala Thr Tyr Phe Cys Ala Thr Arg Tyr
                 85                  90                  95

Asp Ser Tyr Gly Tyr Ala Tyr Asn Tyr Trp Phe Gly Thr Leu Trp Gly
                100                 105                 110

Pro Gly Thr Leu Val Thr Val Thr Ser
            115                 120
```

<210> SEQ ID NO 122
<211> LENGTH: 121
<212> TYPE: PRT
<213> ORGANISM: Oryctolagus cuniculus

<400> SEQUENCE: 122

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Thr Trp Val Arg Gln Ala Pro Gly Glu Gly Leu Glu Trp Ile Gly
        35                  40                  45

Thr Ile Ser Thr Gly Gly Ser Thr Tyr Phe Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
            115                 120

<210> SEQ ID NO 123
<211> LENGTH: 121
<212> TYPE: PRT
<213> ORGANISM: Oryctolagus cuniculus

<400> SEQUENCE: 123

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Thr Trp Val Arg Gln Ala Pro Gly Glu Gly Leu Glu Trp Ile Gly
        35                  40                  45

Thr Ile Ser Thr Gly Gly Ser Thr Tyr Phe Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
            115                 120

<210> SEQ ID NO 124
<211> LENGTH: 122
<212> TYPE: PRT
<213> ORGANISM: Oryctolagus cuniculus

<400> SEQUENCE: 124

Gln Gln Gln Leu Met Glu Ser Gly Gly Arg Leu Val Thr Pro Gly Thr
1               5                   10                  15

Pro Leu Thr Leu Thr Cys Thr Val Ser Gly Ile Asp Leu Ser Ser Asn
            20                  25                  30

Ala Met Thr Trp Val Arg Gln Ala Pro Gly Glu Gly Leu Glu Trp Ile

```
                    35                  40                  45
Gly Thr Ile Ser Thr Gly Gly Ser Thr Tyr Phe Ala Ser Trp Ala Lys
            50                  55                  60
Gly Arg Phe Thr Ile Ser Lys Thr Ser Thr Val Asp Leu Lys Ile
 65                  70                  75                  80
Thr Ser Pro Thr Thr Glu Asp Thr Ala Thr Tyr Phe Cys Ala Thr Arg
                 85                  90                  95
Tyr Asp Ser Tyr Gly Tyr Ala Tyr Asn Tyr Trp Phe Gly Thr Leu Trp
                100                 105                 110
Gly Pro Gly Thr Leu Val Thr Val Thr Ser
            115                 120

<210> SEQ ID NO 125
<211> LENGTH: 121
<212> TYPE: PRT
<213> ORGANISM: Oryctolagus cuniculus

<400> SEQUENCE: 125

Gln Ser Val Glu Glu Ser Gly Gly Arg Leu Val Thr Pro Gly Thr Pro
 1               5                  10                  15
Leu Thr Leu Thr Cys Thr Val Ser Gly Ile Asp Leu Ser Ser Asn Ala
                20                  25                  30
Met Thr Trp Val Arg Gln Ala Pro Gly Glu Gly Leu Glu Trp Ile Gly
            35                  40                  45
Thr Ile Ser Thr Gly Gly Ser Thr Tyr Phe Ala Ser Trp Ala Lys Gly
        50                  55                  60
Arg Phe Thr Ile Ser Lys Thr Ser Thr Val Asp Leu Lys Ile Thr
 65                  70                  75                  80
Ser Pro Thr Thr Glu Asp Thr Ala Thr Tyr Phe Cys Ala Thr Arg Tyr
                 85                  90                  95
Asp Ser Tyr Gly Tyr Ala Tyr Asn Tyr Trp Phe Gly Thr Leu Trp Gly
                100                 105                 110
Pro Gly Thr Leu Val Thr Val Thr Ser
            115                 120

<210> SEQ ID NO 126
<211> LENGTH: 117
<212> TYPE: PRT
<213> ORGANISM: Oryctolagus cuniculus

<400> SEQUENCE: 126

Gln Ser Val Glu Glu Ser Gly Gly Arg Leu Val Ser Pro Gly Thr Pro
 1               5                  10                  15
Leu Thr Leu Thr Cys Thr Ala Ser Gly Phe Ser Leu Ser Thr Tyr Tyr
                20                  25                  30
Met Ile Trp Val Arg Gln Ala Pro Gly Lys Gly Leu Glu Tyr Ile Gly
            35                  40                  45
Ser Ile Asp Gly Tyr Asp Gly Asp Thr Tyr Tyr Ala Thr Trp Ala Lys
        50                  55                  60
Gly Arg Phe Thr Val Ser Lys Thr Ala Thr Val Asp Leu Lys Met
 65                  70                  75                  80
Thr Ser Leu Thr Thr Glu Asp Thr Ala Thr Tyr Phe Cys Ala Arg Ala
                 85                  90                  95
Asp Tyr Asn Thr Val Ala Tyr Phe Asp Leu Trp Gly Pro Gly Thr Leu
                100                 105                 110
Val Thr Val Thr Ser
```

<210> SEQ ID NO 127
<211> LENGTH: 121
<212> TYPE: PRT
<213> ORGANISM: Oryctolagus cuniculus

<400> SEQUENCE: 127

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Thr Trp Val Arg Gln Ala Pro Gly Glu Gly Leu Glu Trp Ile Gly
        35                  40                  45

Thr Ile Ser Thr Gly Gly Ser Thr Tyr Phe Ala Ser Trp Ala Lys Gly
    50                  55                  60

Arg Phe Thr Ile Ser Lys Thr Ser Thr Val Asp Leu Lys Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
        115                 120

<210> SEQ ID NO 128
<211> LENGTH: 121
<212> TYPE: PRT
<213> ORGANISM: Oryctolagus cuniculus

<400> SEQUENCE: 128

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Thr Trp Val Arg Gln Ala Pro Gly Glu Gly Leu Glu Trp Ile Gly
        35                  40                  45

Thr Ile Ser Thr Gly Gly Ser Thr Tyr Phe Ala Ser Trp Ala Lys Gly
    50                  55                  60

Arg Phe Thr Ile Ser Lys Thr Ser Thr Val Asp Leu Lys Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
        115                 120

<210> SEQ ID NO 129
<211> LENGTH: 122
<212> TYPE: PRT
<213> ORGANISM: Oryctolagus cuniculus

<400> SEQUENCE: 129

Gln Gln Gln Leu Met Glu Ser Gly Gly Arg Leu Val Thr Pro Gly Thr
1               5                   10                  15

Pro Leu Thr Leu Thr Cys Thr Val Ser Gly Ile Asp Leu Ser Ser Asn
            20                  25                  30

Ala Met Thr Trp Val Arg Gln Ala Pro Gly Glu Gly Leu Glu Trp Ile
            35                  40                  45

Gly Thr Ile Ser Thr Gly Gly Ser Thr Tyr Phe Ala Ser Trp Ala Lys
 50                  55                  60

Gly Arg Phe Thr Ile Ser Lys Thr Ser Thr Thr Val Asp Leu Lys Ile
 65                  70                  75                  80

Thr Ser Pro Thr Thr Glu Asp Thr Ala Thr Tyr Phe Cys Ala Thr Arg
                 85                  90                  95

Tyr Asp Ser Tyr Gly Tyr Ala Tyr Asn Tyr Trp Phe Gly Thr Leu Trp
                100                 105                 110

Gly Pro Gly Thr Leu Val Thr Val Thr Ser
            115                 120

<210> SEQ ID NO 130
<211> LENGTH: 122
<212> TYPE: PRT
<213> ORGANISM: Oryctolagus cuniculus

<400> SEQUENCE: 130

Gln Gln Gln Leu Met Glu Ser Gly Gly Arg Leu Val Thr Pro Gly Thr
1               5                   10                  15

Pro Leu Thr Leu Thr Cys Thr Val Ser Gly Ile Asp Leu Ser Ser Asn
            20                  25                  30

Ala Met Thr Trp Val Arg Gln Ala Pro Gly Glu Gly Leu Glu Trp Ile
            35                  40                  45

Gly Thr Ile Ser Thr Gly Gly Ser Thr Tyr Phe Ala Ser Trp Ala Lys
 50                  55                  60

Gly Arg Phe Thr Ile Ser Lys Thr Ser Thr Thr Val Asp Leu Lys Ile
 65                  70                  75                  80

Thr Ser Pro Thr Thr Glu Asp Thr Ala Thr Tyr Phe Cys Ala Thr Arg
                 85                  90                  95

Tyr Asp Ser Tyr Gly Tyr Ala Tyr Asn Tyr Trp Phe Gly Thr Leu Trp
                100                 105                 110

Gly Pro Gly Thr Leu Val Thr Val Thr Ser
            115                 120

<210> SEQ ID NO 131
<211> LENGTH: 121
<212> TYPE: PRT
<213> ORGANISM: Oryctolagus cuniculus

<400> SEQUENCE: 131

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Asn Asn Ala
            20                  25                  30

Met Ser Trp Val Arg Gln Ala Pro Gly Glu Gly Leu Glu Trp Ile Gly
            35                  40                  45

Thr Ile Ser Thr Gly Gly Ser Ala Tyr Tyr Ala Ser Trp Ala Lys Gly
 50                  55                  60

Arg Phe Thr Ile Ser Lys Thr Ser Thr Thr Val Asp Leu Lys Ile Thr
 65                  70                  75                  80

Ser Pro Thr Thr Glu Asp Thr Ala Thr Tyr Phe Cys Ala Thr Arg Tyr
                 85                  90                  95

Asp Ser Tyr Gly Tyr Ala Tyr Asn Tyr Trp Phe Gly Thr Leu Trp Gly
                100                 105                 110

```
Pro Gly Thr Leu Val Thr Val Thr Ser
        115                 120

<210> SEQ ID NO 132
<211> LENGTH: 122
<212> TYPE: PRT
<213> ORGANISM: Oryctolagus cuniculus

<400> SEQUENCE: 132

Gln Gln Gln Leu Met Glu Ser Gly Gly Arg Leu Val Thr Pro Gly Thr
1               5                   10                  15

Pro Leu Thr Leu Thr Cys Thr Val Ser Gly Ile Asp Leu Ser Ser Asn
            20                  25                  30

Ala Met Thr Trp Val Arg Gln Ala Pro Gly Glu Gly Leu Glu Trp Ile
        35                  40                  45

Gly Thr Ile Ser Thr Gly Gly Ser Thr Tyr Phe Ala Ser Trp Ala Lys
    50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Thr Arg
                85                  90                  95

Tyr Asp Ser Tyr Gly Tyr Ala Tyr Asn Tyr Trp Phe Gly Thr Leu Trp
            100                 105                 110

Gly Pro Gly Thr Leu Val Thr Val Thr Ser
        115                 120

<210> SEQ ID NO 133
<211> LENGTH: 117
<212> TYPE: PRT
<213> ORGANISM: Oryctolagus cuniculus

<400> SEQUENCE: 133

Gln Ser Val Lys Glu Ser Gly Gly Arg Leu Val Ser Pro Gly Thr Pro
1               5                   10                  15

Leu Thr Leu Thr Cys Thr Val Ser Gly Phe Ser Leu Ser Ser Tyr Tyr
            20                  25                  30

Met Ile Trp Val Arg Gln Ala Pro Gly Lys Gly Leu Glu Tyr Ile Gly
        35                  40                  45

Ser Ile Asp Gly Tyr Asp Gly Asp Thr Tyr Tyr Ala Thr Trp Ala Lys
    50                  55                  60

Gly Arg Phe Thr Val Ser Lys Thr Ala Thr Thr Val Asp Leu Lys Met
65                  70                  75                  80

Thr Ser Leu Thr Thr Glu Asp Thr Ala Thr Tyr Phe Cys Ala Arg Ala
                85                  90                  95

Asp Tyr Asn Thr Val Ala Tyr Phe Asp Leu Trp Gly Pro Gly Thr Leu
            100                 105                 110

Val Thr Val Thr Ser
        115

<210> SEQ ID NO 134
<211> LENGTH: 121
<212> TYPE: PRT
<213> ORGANISM: Oryctolagus cuniculus

<400> SEQUENCE: 134

Gln Ser Leu Glu Glu Ser Gly Gly Arg Leu Val Thr Pro Gly Thr Pro
1               5                   10                  15
```

Leu Thr Leu Thr Cys Thr Val Ser Gly Ile Asp Leu Ser Ser Asn Ala
            20                  25                  30

Met Thr Trp Val Arg Gln Ala Pro Gly Glu Gly Leu Glu Trp Ile Gly
        35                  40                  45

Thr Ile Ser Thr Gly Gly Ser Thr Tyr Phe Ala Ser Trp Ala Lys Gly
    50                  55                  60

Arg Phe Thr Ile Ser Lys Thr Ser Thr Val Asp Leu Lys Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
        115                 120

<210> SEQ ID NO 135
<211> LENGTH: 121
<212> TYPE: PRT
<213> ORGANISM: Oryctolagus cuniculus

<400> SEQUENCE: 135

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Thr Trp Val Arg Gln Ala Pro Gly Glu Gly Leu Glu Trp Ile Gly
        35                  40                  45

Thr Ile Ser Thr Ile Gly Thr Thr Tyr Phe Ala Ser Trp Ala Lys Gly
    50                  55                  60

Arg Phe Thr Ile Ser Lys Thr Ser Thr Val Asp Leu Lys Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
        115                 120

<210> SEQ ID NO 136
<211> LENGTH: 117
<212> TYPE: PRT
<213> ORGANISM: Oryctolagus cuniculus

<400> SEQUENCE: 136

Gln Ser Leu Glu Glu Ser Gly Gly Arg Leu Val Ser Pro Gly Thr Pro
1               5                   10                  15

Leu Thr Leu Thr Cys Thr Val Ser Gly Phe Ser Leu Ser Thr Tyr Tyr
            20                  25                  30

Met Ile Trp Val Arg Gln Ala Pro Gly Lys Gly Leu Glu Tyr Ile Gly
        35                  40                  45

Ser Ile Asp Gly Tyr Gly Gly Asn Ala Tyr Tyr Ala Thr Trp Ala Lys
    50                  55                  60

Gly Arg Phe Thr Ile Ser Lys Thr Ala Thr Thr Val Asp Leu Lys Met
65                  70                  75                  80

Thr Ser Leu Thr Thr Glu Asp Thr Ala Thr Tyr Phe Cys Ala Arg Ala
                85                  90                  95

```
Asp Tyr Asn Thr Ala Ala Tyr Phe Asp Leu Trp Gly Pro Gly Thr Leu
            100                 105                 110
Val Thr Val Thr Ser
        115

<210> SEQ ID NO 137
<211> LENGTH: 121
<212> TYPE: PRT
<213> ORGANISM: Oryctolagus cuniculus

<400> SEQUENCE: 137

Gln Ser Leu Glu Glu Ser Gly Gly Arg Leu Val Thr Pro Gly Thr Pro
1               5                   10                  15
Leu Thr Leu Thr Cys Thr Val Ser Gly Ile Asp Leu Ser Ser Asn Ala
            20                  25                  30
Met Thr Trp Val Arg Gln Ala Pro Gly Glu Gly Leu Glu Trp Ile Gly
        35                  40                  45
Thr Ile Ser Thr Gly Gly Ser Thr Tyr Phe Ala Ser Trp Ala Lys Gly
    50                  55                  60
Arg Phe Thr Ile Ser Lys Thr Ser Thr Thr Val Asp Leu Lys Ile Thr
65                  70                  75                  80
Ser Pro Thr Thr Glu Asp Thr Ala Thr Tyr Phe Cys Ala Thr Arg Tyr
                85                  90                  95
Asp Ser Tyr Gly Tyr Ala Tyr Asn Tyr Trp Phe Gly Thr Leu Trp Gly
            100                 105                 110
Pro Gly Thr Leu Val Thr Val Thr Ser
        115                 120

<210> SEQ ID NO 138
<211> LENGTH: 121
<212> TYPE: PRT
<213> ORGANISM: Oryctolagus cuniculus

<400> SEQUENCE: 138

Gln Ser Leu Glu Glu Ser Gly Gly Arg Leu Val Thr Pro Gly Thr Pro
1               5                   10                  15
Leu Thr Leu Thr Cys Thr Val Ser Gly Ile Asp Leu Ser Ser Asn Ala
            20                  25                  30
Met Thr Trp Val Arg Gln Ala Pro Gly Glu Gly Leu Glu Trp Ile Gly
        35                  40                  45
Thr Ile Ser Thr Gly Gly Ser Thr Tyr Phe Ala Ser Trp Ala Lys Gly
    50                  55                  60
Arg Phe Thr Ile Ser Lys Thr Ser Thr Thr Val Asp Leu Lys Ile Thr
65                  70                  75                  80
Ser Pro Thr Thr Glu Asp Thr Ala Thr Tyr Phe Cys Ala Thr Arg Tyr
                85                  90                  95
Asp Ser Tyr Gly Tyr Ala Tyr Asn Tyr Trp Phe Gly Thr Leu Trp Gly
            100                 105                 110
Pro Gly Thr Leu Val Thr Val Thr Ser
        115                 120

<210> SEQ ID NO 139
<211> LENGTH: 117
<212> TYPE: PRT
<213> ORGANISM: Oryctolagus cuniculus

<400> SEQUENCE: 139

Gln Ser Leu Glu Glu Ser Gly Gly Arg Leu Val Thr Pro Gly Thr Pro
```

```
              1               5                  10                 15
Leu Thr Leu Thr Cys Thr Val Ser Gly Phe Ser Leu Ser Ser Tyr Tyr
             20                 25                 30

Met Ile Trp Val Arg Gln Ala Pro Gly Lys Gly Leu Glu Tyr Ile Gly
             35                 40                 45

Ser Ile Asp Gly Tyr Gly Ser Ala Tyr Tyr Ala Thr Trp Ala Lys
    50                 55                 60

Gly Arg Phe Thr Val Ser Lys Thr Ala Thr Val Asp Leu Lys Met
65                  70                 75                  80

Thr Ser Leu Thr Thr Glu Asp Thr Ala Thr Tyr Phe Cys Ala Arg Ala
                85                 90                 95

Asp Tyr Asn Thr Ala Ala Tyr Phe Asp Leu Trp Gly Pro Gly Thr Leu
                100                105                110

Val Thr Val Thr Ser
        115

<210> SEQ ID NO 140
<211> LENGTH: 19
<212> TYPE: PRT
<213> ORGANISM: Oryctolagus cuniculus

<400> SEQUENCE: 140

Ala Thr Arg Tyr Asp Ser Tyr Gly Tyr Ala Tyr Asn Tyr Trp Phe Gly
1               5                   10                  15

Thr Leu Trp

<210> SEQ ID NO 141
<211> LENGTH: 14
<212> TYPE: PRT
<213> ORGANISM: Oryctolagus cuniculus

<400> SEQUENCE: 141

Ala Arg Ala Asp Tyr Asn Thr Val Ala Tyr Phe Asp Leu Trp
1               5                   10

<210> SEQ ID NO 142
<211> LENGTH: 14
<212> TYPE: PRT
<213> ORGANISM: Oryctolagus cuniculus

<400> SEQUENCE: 142

Ala Arg Ala Asp Tyr Asn Thr Ala Ala Tyr Phe Asp Leu Trp
1               5                   10

<210> SEQ ID NO 143
<211> LENGTH: 14
<212> TYPE: PRT
<213> ORGANISM: Oryctolagus cuniculus

<400> SEQUENCE: 143

Val Arg Ala Asp Tyr Asn Thr Val Ser Tyr Phe Asp Leu Trp
1               5                   10

<210> SEQ ID NO 144
<211> LENGTH: 10
<212> TYPE: PRT
<213> ORGANISM: Oryctolagus cuniculus

<400> SEQUENCE: 144

Ala Arg Gly Phe Asp Asn Tyr Asn Leu Trp
1               5                   10
```

<210> SEQ ID NO 145
<211> LENGTH: 121
<212> TYPE: PRT
<213> ORGANISM: Oryctolagus cuniculus

<400> SEQUENCE: 145

```
Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Thr Trp Val Arg Gln Ala Pro Gly Glu Gly Leu Glu Trp Ile Gly
        35                  40                  45

Thr Ile Ser Thr Gly Gly Ser Thr Tyr Phe Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
        115                 120
```

<210> SEQ ID NO 146
<211> LENGTH: 121
<212> TYPE: PRT
<213> ORGANISM: Oryctolagus cuniculus

<400> SEQUENCE: 146

```
Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Thr Trp Val Arg Gln Ala Pro Gly Glu Gly Leu Glu Trp Ile Gly
        35                  40                  45

Thr Ile Ser Thr Gly Gly Ser Thr Tyr Phe Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Thr Arg Tyr
                85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
        115                 120
```

<210> SEQ ID NO 147
<211> LENGTH: 121
<212> TYPE: PRT
<213> ORGANISM: Oryctolagus cuniculus

<400> SEQUENCE: 147

```
Gln Ser Val Lys Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30
```

```
Met Ser Trp Val Arg Gln Ala Pro Gly Glu Gly Leu Glu Trp Ile Gly
         35                  40                  45

Thr Ile Ser Thr Val Gly Lys Thr Tyr Phe Ala Ser Trp Ala Lys Gly
 50                  55                  60

Arg Phe Thr Ile Ser Lys Thr Ser Thr Val Asp Leu Arg Ile Thr
 65                  70                  75                  80

Ser Pro Thr Thr Glu Asp Thr Ala Thr Tyr Phe Cys Ala Thr Arg Tyr
                 85                  90                  95

Asp Ser Tyr Gly Tyr Ala Tyr Asn Tyr Trp Phe Gly Thr Leu Trp Gly
            100                 105                 110

Pro Gly Thr Leu Val Thr Val Thr Ser
        115                 120
```

<210> SEQ ID NO 148
<211> LENGTH: 19
<212> TYPE: PRT
<213> ORGANISM: Artificial Sequence
<220> FEATURE:
<223> OTHER INFORMATION: Synthetic: heavy-chain CDR3

<400> SEQUENCE: 148

```
Ala Thr Arg Tyr Asp Ser Tyr Gly Tyr Ala Tyr Asn Tyr Trp Phe Gly
 1               5                  10                  15

Thr Leu Trp
```

<210> SEQ ID NO 149
<211> LENGTH: 15
<212> TYPE: PRT
<213> ORGANISM: Artificial Sequence
<220> FEATURE:
<223> OTHER INFORMATION: Synthetic: heavy-chain CDR3

<400> SEQUENCE: 149

```
Gly Ser Tyr Tyr Asp Ser His Gly Tyr Ala Tyr Val Ser Leu Trp
 1               5                  10                  15
```

<210> SEQ ID NO 150
<211> LENGTH: 15
<212> TYPE: PRT
<213> ORGANISM: Artificial Sequence
<220> FEATURE:
<223> OTHER INFORMATION: Synthetic: heavy-chain CDR3

<400> SEQUENCE: 150

```
Ala Thr Asp Tyr Gly Ile Tyr Gly Tyr Ala Tyr Gly His Leu Trp
 1               5                  10                  15
```

<210> SEQ ID NO 151
<211> LENGTH: 14
<212> TYPE: PRT
<213> ORGANISM: Artificial Sequence
<220> FEATURE:
<223> OTHER INFORMATION: Synthetic: heavy-chain CDR3

<400> SEQUENCE: 151

```
Ala Arg Tyr Ser Gly Asp Asn Gly Gly Ala Leu Asn Leu Trp
 1               5                  10
```

<210> SEQ ID NO 152
<211> LENGTH: 14
<212> TYPE: PRT
<213> ORGANISM: Artificial Sequence
<220> FEATURE:
<223> OTHER INFORMATION: Synthetic: heavy-chain CDR3

<400> SEQUENCE: 152

Ala Arg Tyr Ser Gly Asp Asn Gly Gly Thr Leu Asn Leu Trp
1               5                   10

<210> SEQ ID NO 153
<211> LENGTH: 9
<212> TYPE: PRT
<213> ORGANISM: Artificial Sequence
<220> FEATURE:
<223> OTHER INFORMATION: Synthetic: heavy-chain CDR1

<400> SEQUENCE: 153

Ser Gly Ile Asp Leu Ser Ser Asn Ala
1               5

<210> SEQ ID NO 154
<211> LENGTH: 7
<212> TYPE: PRT
<213> ORGANISM: Artificial Sequence
<220> FEATURE:
<223> OTHER INFORMATION: Synthetic: heavy-chain CDR2

<400> SEQUENCE: 154

Ile Ser Thr Val Gly Lys Thr
1               5

<210> SEQ ID NO 155
<211> LENGTH: 6
<212> TYPE: PRT
<213> ORGANISM: Artificial Sequence
<220> FEATURE:
<223> OTHER INFORMATION: Synthetic: light-chain CDR1

<400> SEQUENCE: 155

Glu Asn Ile Asn Ser Glu
1               5

<210> SEQ ID NO 156
<211> LENGTH: 12
<212> TYPE: PRT
<213> ORGANISM: Artificial Sequence
<220> FEATURE:
<223> OTHER INFORMATION: Synthetic: light-chain CDR3

<400> SEQUENCE: 156

Gln Ser Thr Tyr Tyr Asp Gly Asn Tyr Val Tyr Ala
1               5                   10

<210> SEQ ID NO 157
<211> LENGTH: 7
<212> TYPE: PRT
<213> ORGANISM: Artificial Sequence
<220> FEATURE:
<223> OTHER INFORMATION: Synthetic: heavy-chain CDR2

<400> SEQUENCE: 157

Ile Ser Thr Gly Gly Ser Thr
1               5

<210> SEQ ID NO 158
<211> LENGTH: 6
<212> TYPE: PRT
<213> ORGANISM: Artificial Sequence
<220> FEATURE:
<223> OTHER INFORMATION: Synthetic: light-chain CDR1

<400> SEQUENCE: 158

Gln Asn Ile Asn Asn Glu
1               5

<210> SEQ ID NO 159
<211> LENGTH: 9
<212> TYPE: PRT
<213> ORGANISM: Artificial Sequence
<220> FEATURE:
<223> OTHER INFORMATION: Synthetic: heavy-chain CDR1

<400> SEQUENCE: 159

Ser Gly Phe Ser Leu Ser Arg Tyr Ala
1               5

<210> SEQ ID NO 160
<211> LENGTH: 7
<212> TYPE: PRT
<213> ORGANISM: Artificial Sequence
<220> FEATURE:
<223> OTHER INFORMATION: Synthetic: heavy-chain CDR2

<400> SEQUENCE: 160

Ile Gly Ser Gly Gly Ser Thr
1               5

<210> SEQ ID NO 161
<211> LENGTH: 6
<212> TYPE: PRT
<213> ORGANISM: Artificial Sequence
<220> FEATURE:
<223> OTHER INFORMATION: Synthetic: light-chain CDR1

<400> SEQUENCE: 161

Gln Ser Ile Ser Thr Ala
1               5

<210> SEQ ID NO 162
<211> LENGTH: 11
<212> TYPE: PRT
<213> ORGANISM: Artificial Sequence
<220> FEATURE:
<223> OTHER INFORMATION: Synthetic: light-chain CDR3

<400> SEQUENCE: 162

Gln Ser Tyr Tyr Gly Ser Ser Ser Asp Asn Ala
1               5                   10

<210> SEQ ID NO 163
<211> LENGTH: 9
<212> TYPE: PRT
<213> ORGANISM: Artificial Sequence
<220> FEATURE:
<223> OTHER INFORMATION: Synthetic: heavy-chain CDR1

<400> SEQUENCE: 163

Ser Gly Ile Asp Leu Ser Ser Tyr Ala
1               5

<210> SEQ ID NO 164
<211> LENGTH: 7
<212> TYPE: PRT
<213> ORGANISM: Artificial Sequence
<220> FEATURE:
<223> OTHER INFORMATION: Synthetic: heavy-chain CDR2

<400> SEQUENCE: 164

Ile Gly Ser Gly Gly Gly Thr
1               5

<210> SEQ ID NO 165
<211> LENGTH: 11
<212> TYPE: PRT
<213> ORGANISM: Artificial Sequence
<220> FEATURE:
<223> OTHER INFORMATION: Synthetic: light-chain CDR3

<400> SEQUENCE: 165

Gln Thr Tyr Phe Gly Ser Asp Thr Asp Asn Ala
1               5                   10

<210> SEQ ID NO 166
<211> LENGTH: 9
<212> TYPE: PRT
<213> ORGANISM: Artificial Sequence
<220> FEATURE:
<223> OTHER INFORMATION: Synthetic: heavy-chain CDR1

<400> SEQUENCE: 166

Ser Gly Phe Ser Leu Ser Ser Tyr Ala
1               5

<210> SEQ ID NO 167
<211> LENGTH: 7
<212> TYPE: PRT
<213> ORGANISM: Artificial Sequence
<220> FEATURE:
<223> OTHER INFORMATION: Synthetic: heavy-chain CDR2

<400> SEQUENCE: 167

Ile Ser Ser Ser Gly Ser Thr
1               5

<210> SEQ ID NO 168
<211> LENGTH: 6
<212> TYPE: PRT
<213> ORGANISM: Artificial Sequence
<220> FEATURE:
<223> OTHER INFORMATION: Synthetic: light-chain CDR1

<400> SEQUENCE: 168

Gln His Ile Arg Ser Tyr
1               5

<210> SEQ ID NO 169
<211> LENGTH: 12
<212> TYPE: PRT
<213> ORGANISM: Artificial Sequence
<220> FEATURE:
<223> OTHER INFORMATION: Synthetic: light-chain CDR3

<400> SEQUENCE: 169

Gln Arg Tyr Tyr Asp Ile Arg Asn Tyr Gly Asn Gly
1               5                   10

<210> SEQ ID NO 170
<211> LENGTH: 9
<212> TYPE: PRT
<213> ORGANISM: Artificial Sequence
<220> FEATURE:
<223> OTHER INFORMATION: Synthetic: heavy-chain CDR1

<400> SEQUENCE: 170

```
Ser Gly Ile Asp Leu Arg Arg Tyr Ala
1               5

<210> SEQ ID NO 171
<211> LENGTH: 7
<212> TYPE: PRT
<213> ORGANISM: Artificial Sequence
<220> FEATURE:
<223> OTHER INFORMATION: Synthetic: heavy-chain CDR2

<400> SEQUENCE: 171

Ile Ala Ser Gly Asn Thr Asp
1               5

<210> SEQ ID NO 172
<211> LENGTH: 6
<212> TYPE: PRT
<213> ORGANISM: Artificial Sequence
<220> FEATURE:
<223> OTHER INFORMATION: Synthetic: light-chain CDR1

<400> SEQUENCE: 172

Gln Ser Ile Ser Ser Tyr
1               5

<210> SEQ ID NO 173
<211> LENGTH: 12
<212> TYPE: PRT
<213> ORGANISM: Artificial Sequence
<220> FEATURE:
<223> OTHER INFORMATION: Synthetic: light-chain CDR3

<400> SEQUENCE: 173

Gln Ser Tyr Tyr Ser Ile Ser Ser Tyr Gly Asn Thr
1               5                   10
```

SEPARATING AGENT FOR HUMAN SERUM-DERIVED IGG POLYCLONAL ANTIBODIES, AND METHOD FOR SEPARATING HUMAN SERUM-DERIVED IGG POLYCLONAL ANTIBODIES USING SAME

REFERENCE TO SEQUENCE LISTING SUBMITTED VIA EFS-WEB

This application includes an electronically submitted sequence listing in .txt format. The .txt file contains a sequence listing entitled "2021-04-17_1261-0209PUS1_ST25.txt" created on Apr. 17, 2021, and is 16,673 bytes in size. The sequence listing contained in this .txt file is part of the specification and is hereby incorporated by reference herein in its entirety.

TECHNICAL FIELD

The present invention relates to a method for screening a single-chain antibody and a single-chain antibody.

BACKGROUND ART

Various forms of molecular targeted drugs have been studied and developed, including antibody drugs and low molecular weight drugs, as well as peptide drugs, in vivo protein preparations such as cytokines, siRNAs and aptamers (see Patent Document 1, for example). The use of antibodies as therapeutic agents are useful, because of their specificities, in the treatment of pathological conditions in which diseased cells express specific antigens. Antibodies bind to proteins expressed on the cell surface as antigens, and effectively act on the cells to which they are bound. Antibodies are characterized by having a long half-life in blood and high specificity for antigens, and are extremely useful also as antitumor drugs.

To obtain such an antibody, a technique is known in which an antibody is obtained by panning (referred to as "panning" by making an analogy to "washing out gold dust from the pebbles") using an antibody library. For example, a method is known in which the variable region of a human antibody is expressed as a single-chain antibody (scFv) on phage surface by the phage display method, and a phage which binds to an antigen is selected. By analyzing the gene of the selected phage, it is possible to determine the DNA sequence encoding the variable region of the human antibody which binds to the antigen. Once the DNA sequence of the scFv which binds to the antigen is determined, a suitable expression vector containing the sequence can be prepared to easily produce the human antibody (see Patent Documents 2 and 3, for example).

As described above, a method for obtaining an antibody as a candidate for an antibody drug by panning using an antibody library, and the like are known. However, such a method requires a blocking operation, since an antigen is usually immobilized on a tube or plate made of polystyrene when allowing phages to bind to the antigen, in the technical field, and in addition, there are cases where a protein adsorbed on the tube and the like may be denatured. As a result, some of the phages in a phage library bind to a protein used for blocking, or bind the denatured protein, resulting in a problem that phages which bind to antigens other than the antigen of interest are obtained.

On the other hand, in contrast to the above described method for obtaining an antibody, a method has been developed in which multilamellar liposomes are used to obtain a peptide which binds to a specific antibody from a peptide library (Non-patent Document 1). In Non-patent Document 1, it has been confirmed that, when a library of peptides which are expressed on the surface of phages by the phage display method is applied for an anti-octapeptide (FVNQHLCK, SEQ ID NO: 35) antibody immobilized on multilamellar liposomes, as a model, the octapeptide (FVNQHLCK, SEQ ID NO: 35) can be selectively obtained.

RELATED ART DOCUMENTS

Patent Documents

Patent Document 1: JP 2015-145366 A
Patent Document 2: JP 2015-097496 A
Patent Document 3: JP H9-506508 A

Non-Patent Documents

Non-patent Document 1: Journal of Chromatography A, 1080 (2005) 22-28

SUMMARY OF THE INVENTION

Problems to be Solved by the Invention

An object of the present invention is to provide a method for screening a single-chain antibody having a high separation efficiency and an extremely high antigen-binding capacity, as well as a single-chain antibody obtained by the screening method.

Means for Solving the Problems

The present inventors have found out that, in the case of obtaining an antibody of interest by panning using an antibody library prepared by the phage display method, it is possible to solve the problem that phages which bind to antigens other than the antigen of interest are likely to be obtained, which is a problem associated with the use of a conventional method in which an antigen is immobilized on a tube or the like, by the use of a method in which an antigen is coupled to multilamellar liposomes. The present invention is as follows.

[1] A method for screening a single-chain antibody which binds to an antigen, the method including the steps of:
  preparing an antigen coupled to multilamellar liposomes;
  preparing a phage library presenting single-chain antibodies; and
  selecting a phage presenting the single-chain antibody which binds to the antigen coupled to multilamellar liposomes; from the phage library.

[2] The method according to [1], wherein the single-chain antibody is derived from a rabbit.

[3] The method according to [1] or [2], wherein the antigen is a protein.

[4] The method according to [3], wherein the protein is an antibody.

[5] The method according to [4], wherein the antibody is a human serum-derived IgG polyclonal antibody or a human serum-derived IgA polyclonal antibody.

[6] The method according to [4] or [5], wherein the single-chain antibody is a single-chain antibody which binds to the L chain of a human-derived antibody.

[7] A method for producing an antibody, the method including the steps of:

performing screening by the method according to any one of [1] to [6];

determining the amino acid sequence of the screened single-chain antibody;

preparing a DNA sequence encoding the antibody based on the sequence of the variable region of the determined amino acid sequence;

expressing the prepared DNA sequence in a host cell.

[8] The method according to [7], wherein the DNA sequence encoding the antibody encodes a humanized antibody.

[9] A single-chain antibody having a dissociation constant for a human serum-derived IgG polyclonal antibody of not more than $3.0 \times 10^{-8}$ M.

[10] The single-chain antibody according to [9], which also binds to a human serum-derived IgA polyclonal antibody.

[11] A single-chain antibody having a dissociation rate constant for a human serum-derived IgA polyclonal antibody of not more than $1.0 \times 10^{-3}$ s$^{-1}$.

[12] A single-chain antibody having a dissociation rate constant for the L chain of a human-derived antibody of not more than $1.0 \times 10^{-3}$ s$^{-1}$.

Effect of the Invention

According to the present invention, it is possible to provide a method for screening a single-chain antibody having a high separation efficiency and an extremely high antigen-binding capacity, as well as a single-chain antibody obtained by the screening method.

Since multilamellar liposomes have a good dispersibility, the method using multilamellar liposomes allows for efficiently bringing an antibody with an antigen coupled to the multilamellar liposomes as compared to a conventional method, and it also allows for easy recovery of the antibody by centrifugation. Further, the use of multilamellar liposomes enables to reduce phages which are non-specifically adsorbed on a carrier, to an extremely low level. In addition, since the antigen can laterally diffuse on the membrane surface of the multilamellar liposomes, the antigen exhibits a high binding capacity with phages in a library. Accordingly, the present method allows for obtaining a single-chain antibody having a high separation efficiency and an extremely high antigen-binding capacity.

BRIEF DESCRIPTION OF THE DRAWINGS

FIG. 7-1 is a graph showing the results of the antigen-binding activity evaluation carried out for rabbit-derived single-chain antibodies obtained from 96 colonies collected at the completion of Round 3 in Example 3-2.

FIG. 7-2 is a graph showing the results of the antigen-binding activity evaluation carried out for rabbit-derived single-chain antibodies obtained from 96 colonies collected at the completion of Round 3 in Example 3-2.

FIG. 7-3 is a graph showing the results of the antigen-binding activity evaluation carried out for rabbit-derived single-chain antibodies obtained from 96 colonies collected at the completion of Round 3 in Example 3-2.

FIG. 7-4 is a graph showing the results of the antigen-binding activity evaluation carried out for rabbit-derived single-chain antibodies obtained from 96 colonies collected at the completion of Round 3 in Example 3-2.

FIG. 7-5 is a graph showing the results of the antigen-binding activity evaluation carried out for rabbit-derived single-chain antibodies obtained from 96 colonies collected at the completion of Round 3 in Example 3-2.

FIG. 7-6 is a graph showing the results of the antigen-binding activity evaluation carried out for rabbit-derived single-chain antibodies obtained from 96 colonies collected at the completion of Round 3 in Example 3-2.

FIG. 7-7 is a graph showing the results of the antigen-binding activity evaluation carried out for rabbit-derived single-chain antibodies obtained from 96 colonies collected at the completion of Round 3 in Example 3-2.

FIG. 7-8 is a graph showing the results of the antigen-binding activity evaluation carried out for rabbit-derived single-chain antibodies obtained from 96 colonies collected at the completion of Round 3 in Example 3-2.

FIG. 8-1 shows the amino acid sequences of the rabbit-derived single-chain antibody genes determined in Example 5.

FIG. 8-2 shows the amino acid sequences of the rabbit-derived single-chain antibody genes determined in Example 5.

FIG. 9-1 is a graph showing the results of the antigen-binding activity evaluation carried out in Example 6 and Comparative Example 6-1.

FIG. 9-2 is a graph showing the results of the antigen-binding activity evaluation carried out in Example 6 and Comparative Example 6-2.

FIG. 17-1 shows the amino acid sequences of the single-chain antibodies obtained from 32 colonies collected at the completion of Round 1, determined from the gene sequences of the $V_H$ domains, in Example 10.

FIG. 17-2 shows the analysis results of the amino acid sequences of the single-chain antibodies obtained from 32 colonies collected at the completion of Round 1, determined from the gene sequences of the $V_H$ domains, in Example 10.

FIG. 17-3 shows the amino acid sequences of the single-chain antibodies obtained from 32 colonies collected at the completion of Round 2, determined from the gene sequences of the $V_H$ domains, in Example 10.

FIG. 17-4 shows the analysis results of the amino acid sequences of the single-chain antibodies obtained from 32 colonies collected at the completion of Round 2, determined from the gene sequences of the $V_H$ domains, in Example 10.

FIG. 17-5 shows the amino acid sequences of the single-chain antibodies obtained from 32 colonies collected at the completion of Round 3, determined from the gene sequences of the $V_H$ domains, in Example 10.

FIG. 17-6 shows the analysis results of the amino acid sequences of the single-chain antibodies obtained from 32 colonies collected at the completion of Round 3, determined from the gene sequences of the $V_H$ domains, in Example 10.

FIG. 17-7 shows the amino acid sequences of the rabbit-derived single-chain antibody genes used as references in Example 10.

FIG. 17-8 is a table showing the numbers of common clones obtained at the completion of Round 1, determined in Example 10.

FIG. 17-9 is a table showing the numbers of common clones obtained at the completion of Round 2, determined in Example 10.

FIG. 17-10 is a table showing the numbers of common clones obtained at the completion of Round 3, determined in Example 10.

MODE FOR CARRYING OUT THE INVENTION

Figure 1:
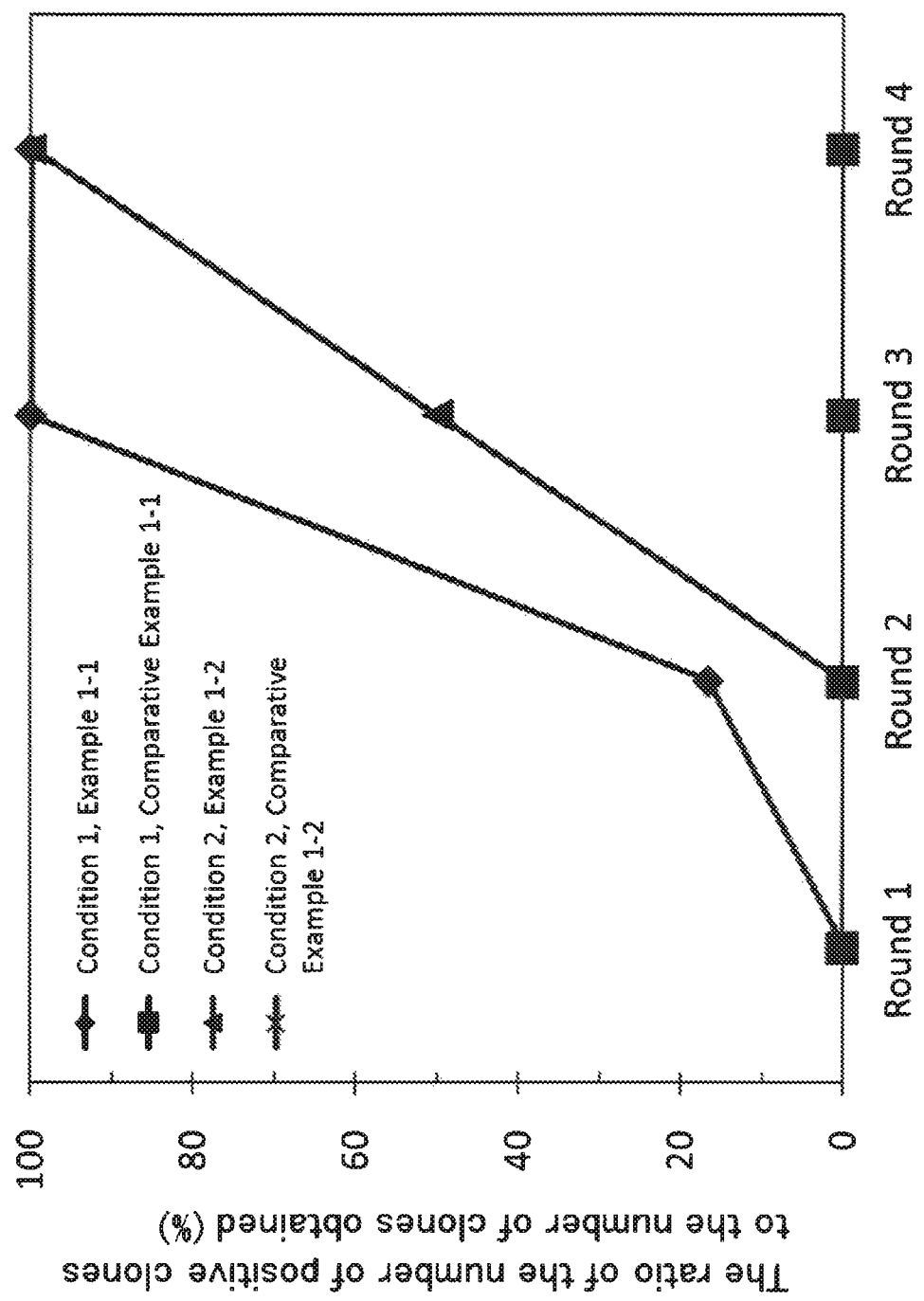
FIG. 1 is a graph showing the ratio of the number of positive clones to the total number of clones obtained in each of Example 1-1, Example 1-2, Comparative Example 1-1, and Comparative Example 1-2.

The present invention includes a first invention relating to a method for screening a single-chain antibody, and a second invention relating to a single-chain antibody. In the present specification, multilamellar liposomes are sometimes referred to as MLVs (multilamellar liposome vesicles). Further, single-chain antibodies are sometimes referred to as scFvs (single chain Fvs). The single-chain antibodies (scFvs) in the present invention are sometimes referred to as "single chain Fvs" or the like in the technical filed, as one type of low molecular weight antibodies.

The following description includes a description regarding the use of a rabbit-derived single-chain antibody as the single-chain antibody in the present invention. However, such a description is merely an example of the case where the single-chain antibody used is derived from a rabbit, and the single-chain antibody to be used in the present invention is not limited to a rabbit-derived single-chain antibody.

<1. First Invention>

The first invention of the present invention includes the following first and second embodiments.

The first embodiment: a method for screening a single-chain antibody which binds to an antigen, the method including the steps of: preparing an antigen coupled to multilamellar liposomes; preparing a phage library presenting single-chain antibodies; and selecting a phage presenting the single-chain antibody which binds to the antigen coupled to multilamellar liposomes; from the phage library.

The second embodiment: a method for producing an antibody, the method including the steps of: performing screening by the screening method according the first embodiment; determining the amino acid sequence of the screened single-chain antibody; preparing a DNA sequence encoding the antibody based on the sequence of the variable region of the determined amino acid sequence; expressing the prepared DNA sequence in a host cell.

1-1. First Embodiment in First Invention

The first embodiment in the first invention of the present invention is a method for screening a single-chain antibody which binds to an antigen, the method including the steps of: preparing an antigen coupled to multilamellar liposomes; preparing a phage library presenting single-chain antibodies; and selecting a phage presenting the single-chain antibody which binds to the antigen coupled to multilamellar liposomes; from the phage library.

The present screening method may be a method for screening a candidate for a single-chain antibody which binds to the above described antigen.

<(1) Step of Preparing Antigen Coupled to Multilamellar Liposomes>

[Multilamellar Liposomes (MLVs)]

Multilamellar liposomes are not particularly limited as long as an antigen can be coupled thereto. For example, multilamellar liposomes can be prepared by a known method such as the method described in Journal of Biotechnology 131 (2007) 144-149. Specifically, multilamellar liposomes can be prepared, for example, by hydrating appropriate amounts of dipalmitoylphosphatidylcholine (DPPC), dicetyl phosphate (DCP), and N-(4-(p-maleimidophenyl) butyryl)dipalmitoylphosphatidylethanolamine (MPB-DPPE).

At this time, multilamellar liposomes and unilamellar liposomes are often obtained in a mixed state, by performing hydration alone. Thus, multilamellar liposomes are preferably separated by centrifugation before use. The conditions of centrifugation are not particularly limited as long as the multilamellar liposomes can be separated. The centrifugation may be carried out, for example at 25° C. for two minutes, at 20,000 g.

[Antigen]

The antigen to be used is not particularly limited as long as it is a substance to which a single-chain antibody to be screened by the screening method according to the present embodiment binds. Examples thereof include cells, proteins, lipids, and sugar chains. Among these, a protein is preferred, and among proteins, an antibody is preferred. The antigen can be selected as appropriate depending on the application of the single-chain antibody to be obtained.

The biological species of the antibody to be used as an antigen is not particularly limited, and can be selected as appropriate depending on the application of the single-chain antibody to be obtained. Examples thereof include humans, rats, mice, rabbits, chickens, goats, sheep, cows, horses, dogs, cats, and monkeys. Preferred are humans, rats, mice, rabbits, chickens, and goats. The antibody to be used as an antigen may be a monoclonal antibody or a polyclonal antibody, and it can be selected as appropriate depending on the application of the single-chain antibody to be obtained.

Further, the antibody to be used as an antigen may be one type or two or more types selected from the group consisting of IgG, IgM, IgA, IgD and IgE antibodies. Further, an antibody belonging to a subclass of each type of antibody may also be used, and one type or two or more types of such subclass antibodies may be used.

In cases where the antibody to be used as an antigen is a human IgG antibody, examples of its subclass antibody include a human IgG1 antibody, a human IgG2 antibody, a human IgG3 antibody, and a human IgG4 antibody. Any one type, two or more types, three or more types, or all four types of these antibodies may be used.

In cases where the antibody to be used as an antigen is a human serum-derived IgG polyclonal antibody, examples of its subclass antibody include a human serum-derived IgG1 polyclonal antibody, a human serum-derived IgG2 polyclonal antibody, a human serum-derived IgG3 polyclonal antibody, and a human serum-derived IgG4 polyclonal antibody. Any one type, two or more types, three or more types, or all four types of these antibodies may be used.

Further, if a single-chain antibody selected by the present screening method binds to an antigen coupled to multilamellar liposomes, and does not bind to other antigens, the single-chain antibody can be used as a highly specific single-chain antibody. On the other hand, a single-chain antibody selected by the present screening method has a possibility of binding to an antigen coupled to multilamellar liposomes, as well as to other antigens. Such a single-chain antibody can be used as a single-chain antibody which binds to a common region of two or more different antigens, or as a single-chain antibody which binds to two or more different sites in the same amino acid sequence. Any of these single-chain antibodies can be selected and used depending on the application, and any of these are preferred embodiment(s).

The single-chain antibody which binds to a common region of two or more different antigens can be determined, for example, by performing screenings for two or more different antigens, individually, and then comparing the amino acid sequences of the single-chain antibodies selected by the respective screenings. This can be easily understood by those skilled in the art.

Further, the single-chain antibody which binds to two or more different sites in the same amino acid sequence can be determined, for example, by confirming the binding capacity of the single-chain antibody which has been selected by a screening using a certain antigen, for other antigens. This can be easily understood by those skilled in the art.

Examples of the single-chain antibody which binds to a common region of two or more different antibodies include a single-chain antibody which binds to a common region included in the light chains (L chains), specifically, the lambda chains or the kappa chains, of two or more different antibodies. In particular, since the amino acid sequence of the lambda chain or the kappa chain does not vary depending on the isotype, if a single-chain antibody which binds to an amino acid sequence contained in the lambda chain or the kappa chain is selected, the selected single-chain antibody recognizes and binds to the amino acid sequence regardless of the isotype. This can be easily understood by those skilled in the art.

Those skilled in the art can confirm that the selected single-chain antibody binds to an amino acid sequence contained in the light chain (L chain) of an antibody, specifically, that it binds to an amino acid sequence contained in the lambda chain or the kappa chain, for example, by a known method such as Western blotting.

There is no particular limitation on the antibody to be used as an antigen for selecting a single-chain antibody which binds to an amino acid sequence contained in the light chain (L chain) regardless of the isotype. However, preferred is an IgA antibody, such as, for example, a human serum-derived IgA polyclonal antibody.

The reason for this is as follows. In view of the fact that IgA antibodies do not have a complement activity while IgG antibodies and IgM antibodies have a complement activity, for example, IgA antibodies, rather than IgM antibodies, are thought to have functions and structures significantly different from those of the IgG antibodies, when considered based on IgG antibodies. Accordingly, the use of an IgA antibody, rather than the use of an IgM antibody, for example, facilitates the selection of a single-chain antibody which binds to an amino acid sequence contained in the light chain (L chain).

Further, it is also because, IgA antibodies forming monomers or dimers have a lower molecular weight as compared to IgM antibodies forming pentamers, for example, and have a higher dispersibility on multilamellar liposomes, and accordingly, the use of an IgA antibody, rather than the use of an IgM antibody, results in a higher screening efficiency.

In addition, IgA antibodies can be used as antibody drugs which have a high therapeutic effect in the mucous membrane.

[Step of Coupling Antigen to Multilamellar Liposomes]

Coupling of an antigen to multilamellar liposomes can be performed by any method without particular limitation, as long as the coupled antigen is not liberated form the multilamellar liposomes. For example, the coupling can be carried out by a known method such as the method disclosed in Non-patent Document 1. Specific examples of the method include one in which an excessive amount of 2-iminothiolane hydrochloride, in molar ratio, is added to a mixed liquid of an antigen and multilamellar liposomes, and a reaction is allowed to proceed while stirring. The coupling may be carried out, for example, by adding to the mixed liquid of an antigen and multilamellar liposomes, 2-iminothiolane hydrochloride in amount 10 times the amount of the antigen, in molar ratio, and allowing a reaction to proceed at 25° C. for three hours or more, while stirring.

<(2) Step of Preparing Phage Library Presenting Single-Chain Antibodies>

[Phage Library Presenting Single-Chain Antibodies]

The phage library to be prepared is not particularly limited as long as it is a library of phages presenting single-chain antibodies, and a known library or a commercially available library may be used. There is no particular limitation on the animal from which a single-chain antibody is derived. However, the single-chain antibody preferably has a high antigen-binding capacity, and is derived from an animal, such as, for example, a human, a rat, a mouse, a rabbit, a chicken, a goat, a sheep, a cow, a horse, a dog, a cat, or a monkey. The single-chain antibody is more preferably derived from an animal, such as, for example, a human, a rat, a mouse, a rabbit, a chicken, or a goat, still more preferably derived from a mouse or a rabbit, and particularly preferably derived from a rabbit.

The construction of a phage library can be carried out by a known method, such as the method disclosed in Japanese Patent Application No. 2013-233096.

In the case of using an immunized animal, the construction of a phage library can be carried out, for example, as follows. A specific antigen is administered to an animal to be immunized, and the total RNA is obtained from the spleen of the thus immunized animal, and then a cDNA library is constructed by reverse transcription polymerase chain reaction (RT-PCR). Subsequently, specific primers are used to amplify the gene of the variable region ($V_H$ domain) of the heavy chain (H chain), and the gene of the variable region ($V_L$ domain) of the light chain (L chain), by PCR.

There is no particular limitation on the primers to be used in cases where a rabbit is used as the immunized animal, as long as the primers allow for specifically amplifying the genes of interest by PCR. Examples of sense primers to be used for amplifying the gene of the variable region ($V_H$ domain) of the heavy chain (H chain) include:

5'-AAAAAGGCCATGGCCCAGTCGGTGGAGGAGTC-CRGG-3' (SEQ ID NO: 1, sometimes referred to as Nco-VH1 S in the present specification);
5'-AAAAAGGCCATGGCCCAGTCGGT-GAAGGAGTCCGAG-3' (SEQ ID NO: 2, sometimes referred to as Nco-VH2 S in the present specification);
5'-AAAAAGGCCATGGCCCAGTCGYTGGAG-GAGTCCGGG-3' (SEQ ID NO: 3, sometimes referred to as Nco-VH3 S in the present specification); and
5'-AAAAAGGCCATGGCCCAGSAGCAGCTGRWG-GAGTCCGG-3' (SEQ ID NO: 4, sometimes referred to as Nco-VH4 S in the present specification).

Examples of antisense primers to be used include:
5'-TCCACCACTAGTGACGGTGACSAGGGT-3'(SEQ ID NO: 5, sometimes referred to as VH-Spe AS in the present specification).

Examples of sense primers to be used for amplifying the gene of the variable region ($V_L$ domain) of the light chain (L chain) include:
5'-AATTAAGGATCCGAGCTCGTGMTGACCCA-GACTSCA-3' (SEQ ID NO: 6, sometimes referred to as Bam-VK1 in the present specification);
5'-AATTAAGGATCCGAGCTCGATMTGACCCA-GACTSCA-3' (SEQ ID NO: 7, sometimes referred to as Bam-VK2 S in the present specification);
5'-AATTAAGGATCCGAGCTCGTGATGACCCA-GACTGCA-3' (SEQ ID NO: 8, sometimes referred to as Bam-VK3 S in the present specification); and
5'-AAT-TAAGGATCCGAGCTCGTGCTGACTCAGTCGY-CCTC-3' (SEQ ID NO: 9, sometimes referred to as Bam-Vλ4 S in the present specification).

Examples of antisense primers to be used include:
5'-TATATATGCGGCCGCCGAACSTKTGAYSWCCAC-3' (SEQ ID NO: 10, sometimes referred to as Vκ-Not AS in the present specification); and
5'-TTTAAAT-TTGCGGCCGCCGAACCTGTGACGGTCAG-3'(SEQ ID NO: 11, sometimes referred to as Vλ-Not AS in the present specification).

Note that, in the above described sequences, W represents A or T, R represents A or G, M represents A or C, K represents T or G, Y represents T or C, S represents G or C, H represents A, C or T, B represents G, C or T, V represents A, G or C, D represents A, G or T, and N represents A, G, C or T, based on the IUPAC nomenclature of bases.

Next, the thus produced PCR products are subjected to a treatment by specific restriction enzymes, and the like, so that they can be inserted into a phagemid vector. Further, the phagemid vector to be used is also subjected to a treatment by specific restriction enzymes, and the like. Subsequently, each of the genes treated by the restriction enzymes are inserted into the phagemid vector treated by the restriction enzymes.

In this manner, a recombinant phagemid vector into which the gene of the variable region ($V_H$ domain) of the heavy chain (H chain), and the gene of the variable region ($V_L$ domain) of the light chain (L chain) are inserted, is introduced into host cells, such as, for example, cells of *Escherichia coli*. The transfected host cells are further infected with a helper phage, followed by culturing, to obtain a library of phages presenting rabbit-derived single-chain antibodies, in the resulting culture supernatant. The type of the helper phage to be used above is not particularly limited, and examples thereof include VCSM13.

<(3) Step of Selecting Phage Presenting Single-Chain Antibody which Binds to Antigen Coupled to Multilamellar Liposomes from Phage Library (Selection Step)>

The present step (selection step) includes: a step of allowing the antigen to bind to the single-chain antibodies expressed on the surface of phages in the phage library (binding step); a step of removing phages presenting single-chain antibodies which did not bind to the antigen coupled to multilamellar liposomes, by washing (washing step); and a step of dissociating (eluting) the phage presenting the single-chain antibody bound to the antigen coupled to multilamellar liposomes, from the antigen (elution step).

<(3-1) Binding Step>

The present step is a step of allowing the antigen to bind to the single-chain antibodies expressed on the surface of phages in the phage library. The method for carrying out the binding step is not particularly limited, as long as the method allows for sufficient binding between the antigen and the single-chain antibodies. The binding step can be carried out, for example, under the following conditions.

(Quantitative Ratio of Antigen and Phage Library)

The quantitative ratio of the antigen and the phages in the library is not particularly limited, as long as the ratio allows for a sufficient binding between the two. The quantitative ratio of the number of total phages in the library vs the number of antigen molecules is usually 1:5 or more, preferably 1:100 or more, and more preferably 1:1000 or more. When the quantitative ratio is within the above range, the number of antigen molecules will be sufficient relative to the number of the single-chain antibodies expressed on the phage surface, and a sufficient binding between the antigen and the single-chain antibodies can be expected.

(Solvent)

The type of the solvent to be used when allowing the antigen to bind to the single-chain antibodies expressed on the surface of phages in the phage library is not particularly limited, as long as the solvent allows for a sufficient binding between the two. For example, it is possible to use a solvent commonly used in the field, such as phosphate buffered saline (PBS).

(Temperature)

The temperature for allowing the antigen to bind to the single-chain antibodies expressed on the surface of phages in the phage library is not particularly limited, as long as the temperature allows for a sufficient binding between the two. However, in order to avoid degradation, denaturation and the like, the binding is preferably carried out at, for example, at room temperature, such as 25° C., and more preferably at a low temperature, such as 4° C.

(Period of Time)

The period of time for allowing the antigen to bind to the single-chain antibodies expressed on the surface of phages in the phage library is not particularly limited, as long as it allows for a sufficient binding between the two. However, the binding is carried out, for example, for 30 minutes or more, preferably one hour or more, and still more preferably overnight.

(Other Matters)

The binding reaction of the antigen and the single-chain antibodies expressed on the surface of phages in the phage library is preferably carried out, for example, while rotating, so that the antigen molecules and the phages can be sufficiently stirred during the reaction. Further, a reaction vessel such as a tube to be used for binding the antigen and the single-chain antibodies is preferably subjected to blocking, in advance. Examples of blocking agents include known blocking agents, such as those supplemented with bovine serum albumin (BSA). In addition, such a blocking agent can be added to the solvent to be used for the binding reaction, in advance.

<(3-2) Washing Step>

The present step is a step of removing phages presenting single-chain antibodies which did not bind to the antigen coupled to multilamellar liposomes, by washing. The method for carrying out the washing step is not particularly limited, as long as the phages presenting single-chain antibodies which did not bind to the antigen can be removed by washing. The washing step can be carried out, for example, under the following conditions.

(Centrifugation and Solvent Replacement)

After the binding reaction of the antigen and the single-chain antibodies expressed on the surface of phages in the phage library, the phages bound to the antigen coupled to multilamellar liposomes are precipitated by centrifugation, and the phages which did not bind to the antigen are contained in the supernatant. Therefore, the phages bound to the antigen coupled to multilamellar liposomes can be selectively obtained, by removing the supernatant, and then adding a solvent to the pellets to prepare a suspension.

The solvent to be used at this time is not particularly limited. However, the solvent is preferably the same as that used in the above described "(3-1) Binding Step", and PBS or the like can be used, for example. Further, a blocking agent such as BSA can be added to the solvent, in advance. Further, in cases where the suspension obtained by adding such a solvent to the pellets is transferred to a vessel such as a fresh tube, it is preferred that the vessel be also subjected to blocking in advance. Further, such a blocking agent can be added to the solvent to be used for the binding reaction, in advance.

The conditions of centrifugation is not particularly limited, as long as the phages bound to the antigen coupled to multilamellar liposomes can be separated from the phages which did not bind to the antigen. The centrifugation may be carried out, for example, at 4° C. for two minutes, at 20,000 g. The centrifugation and solvent replacement may be carried out once, or repeated a plurality of times. However, the centrifugation and solvent replacement are usually repeated twice or more, and preferably repeated three times or more.

<(3-3) Elution Step>

The present step is a step of dissociating (eluting) the phage presenting the single-chain antibody bound to the antigen coupled to multilamellar liposomes, from the antigen. The method for carrying out the elution step is not particularly limited. The elution step can be carried out, for example, according to a known method such as the method disclosed in Non-patent Document 1.

As a solution to be used for eluting the phages, a glycine-hydrochloric acid buffer solution or the like can be used, for example. Further, after eluting the phages, the resulting solution may be neutralized, and a tris-hydrochloric acid buffer solution or the like, for example, can be used for the neutralization.

<(3-4) Optional Steps>

The present selection step may include optional steps, as appropriate, in addition to the above described three steps (the binding step, the washing step, and the elution step). Examples of the optional steps include: a step of amplifying the selected phage (amplification step); a step of repeating the above described selection step (repetition step); a step of determining the gene sequence of the selected phage (gene sequencing step); a step of selecting a clone based on the sequence determined in the gene sequencing step (clone selection step), and a step of evaluating the binding activity for the antigen of the single-chain antibody presented by the selected phage (antigen-binding activity evaluation step).

[Amplification Step]

The present step is a step of amplifying the phage selected in the selection step. The method for carrying out the amplification step is not particularly limited. The amplification step can be carried out, for example, under the following conditions.

(Infection of Host Cells with Phage, and Culture of Host Cells Infected with Phage)

The phage selected in the selection step can be amplified by infecting host cells with the phage. The method therefor is not particularly limited, and the infection and amplification can be achieved, for example, according to a known method such as the method disclosed in Non-patent Document 1. The host cells to be used are not particularly limited, as long as the phage can be grown. The host cells may be, for example, *Escherichia coli* cells, and strains such as TG1 strain or XL-1 Blue strain may be used, for example. Further, it is preferred that the host cells be cultured in advance, and those in the middle stage of the exponential growth be used. The conditions for culturing the host cells which have been infected with the phage are not particularly limited, and the host cells may be cultured, for example, at 37° C. with shaking at 200 rpm.

(Infection of Host Cells with Helper Phage and Production of Phages in Culture Supernatant)

By infecting the host cells which have been infected with the phage, further with a helper phage, and then culturing the infected host cells, it is possible to allow the secretion of the phage presenting the single-chain antibody, and the single-chain antibody, in the culture supernatant. The method therefor is not particularly limited, and the secretion of the phage and the single-chain antibody can be achieved for example, according to a known method such as the method disclosed in Non-patent Document 1. The helper phage to be used at this time is not particularly limited, and examples thereof include VCSM13. Further, the culture conditions are not particularly limited, and the cells may be cultured, for example, at 37° C. with shaking at 200 rpm.

[Repetition Step]

The above described selection step may be repeated, using a library of the phages selected in the above described selection step, or a library of the phages amplified in the above described amplification step.

By repeating one "round", which consists of the above described selection step, it is possible to further select a phage having a higher binding capacity for the antigen. The number of rounds is not particularly limited. A larger number of rounds leads to obtaining a phage having an extremely high binding capacity for the antigen; whereas a smaller number of rounds enables a quick and efficient screening, and thus is useful. The present method is useful in that it allows for obtaining a phage having an extremely high binding capacity for the antigen, with a smaller number of rounds as compared to a conventional technique.

The number of times for carrying out the repetition step is usually three times or less, preferably twice or less, more preferably once or less, and still more preferably 0 times. When the number of times for carrying out the repetition step is 0 times, it means that the selection step is carried out only once.

[Gene Sequencing Step]

The present step is a step of determining the gene sequence of the variable region ($V_H$ domain) of the heavy chain (H chain) and the gene sequence of the variable region ($V_L$ domain) of the light chain (L chain) of each phage, using a library of the phages selected in the above described selection step. The present step may be carried out as the final round, and/or carried out between the rounds.

The method therefor is not particularly limited, and the gene sequences can be determined according to a known method such as the method disclosed in Non-patent Document 1. For example, the gene sequences can be determined, for example, by the following method.

By the method described in the section of "Infection of Host Cells with Phage, and Culture of Host Cells Infected with Phage" in the above described amplification step, *Escherichia coli* cells infected with the phages are allowed to form single colonies, and each colony is subcloned. Subsequently, the sequences of the gene of the variable region ($V_H$ domain) of the heavy chain (H chain), and the gene of the variable region ($V_L$ domain) of the light chain (L chain) can be analyzed and determined for each colony. The gene sequences can be analyzed using a known technique. If the gene sequences can be determined, the amino acid sequences encoded by the gene sequences can also be determined. When the gene sequences are determined in this manner, it is also possible to monitor the efficiency of screening.

[Clone Selection Step]

The present step is a step of selecting a clone, based on each sequence determined in the gene sequencing step. This step is a step of selecting a clone of host cells infected with the phage containing a desired gene sequence of the variable region ($V_H$ domain) of the heavy chain (H chain) and a desired gene sequence of the ($V_L$ domain) of the light chain (L chain). This step is also effective for eliminating overlapping clones.

The present step may be carried out as the final round, and/or carried out between the rounds. If such a clone can be selected, it is possible to select a host cell infected with a phage having a higher binding capacity for the antigen, thereby allowing for a more efficient screening.

[Antigen-Binding Activity Evaluation Step]

The present step is a step of evaluating the binding activity for the antigen of the antibody presented by the selected phage. The method therefor is not limited, as long as the binding activity for the antigen of the antibody presented by the phage can be evaluated.

The evaluation can be carried out, for example, by the method to be described in Example 3-2. Specifically, host cells containing a phagemid are allowed to form a single colony, and the supernatant obtained after cell lysis is applied on a plate on which an antigen is immobilized. Subsequently, the absorbance is measured using a microplate reader.

The present step may be carried out as the final round, and/or carried out between the rounds. If a clone containing the gene of the antibody having a high binding capacity for the antigen can be selected, a more efficient screening can be carried out using the clone.

In addition, the dissociation rate constant $k_{off}$ or the dissociation constant $K_D$ measured using a Biacore, or the like, as will be described in Example 4 and Example 6, can be used as an index.

The method for preparing a sample to be used in the measurement of the dissociation rate constant $k_{off}$ or the dissociation constant $K_D$ is not particularly limited. For example, as will be shown in Examples, cells obtained from a colony of phagemid-containing host cells are cultured, followed by cell lysis, and the supernatant obtained after centrifugation can be used as a sample.

In addition, whether the phage and the single-chain antibody have been secreted from the host cells, or whether they are present within the periplasm, can be confirmed as follows. For example, as will be shown in Examples, when a DNA fragment containing the gene of the single-chain antibody is amplified using a phagemid vector, and the amplified fragment is inserted into an appropriate vector, such as a pET22 vector (manufactured by Merck KGaA), the single-chain antibody will be expressed in the form in which a pelB leader signal sequence is fused to the N-terminus, and a histidine tag (6×His-tag) is fused to the C-terminus. After culturing the host cells containing the above described recombinant vector, it is possible to obtain the culture supernatant, and the intracellular soluble fraction from the cells, by an appropriate method. The thus obtained culture supernatant and the intracellular soluble fraction are each eluted using a column capable of trapping a histidine tag, or the like, and the dissociation constant $K_D$ can be measured using the resulting eluants.

The dissociation rate constant $k_{off}$ and the dissociation constant $K_D$ will be described below.

[Dissociation Rate Constant $k_{off}$]

Definition

In the present specification, the dissociation rate constant $k_{off}$ for the binding of the single-chain antibody to the antigen is defined as follows. The dissociation rate constant $k_{off}$ is usually not more than $3.0 \times 10^{-3}$ s$^{-1}$, preferably not more than $1.0 \times 10^{-3}$ s$^{-1}$, more preferably not more than $4.0 \times 10^{-4}$ s$^{-1}$, still more preferably not more than $2.0 \times 10^{-4}$ s$^{-1}$, further still more preferably not more than $5.0 \times 10^{-5}$ s$^{-1}$, particularly preferably not more than $4.0 \times 10^{-5}$ s$^{-1}$, and more particularly preferably not more than $3.0 \times 10^{-5}$ s$^{-1}$. A lower dissociation rate constant $k_{off}$ indicates a higher binding capacity for the antigen, and thus, a higher usefulness as an antibody.

In cases where an antigen is represented as Ag, the concentration of the antigen as [Ag], an antibody as Ab, the concentration of the antibody as [Ab], an antigen-antibody complex as Ag·Ab, the concentration of the antigen-antibody complex as [Ag·Ab], a binding rate constant as $k_{on}$, and the dissociation rate constant as $k_{off}$, the binding reaction between the antigen and the single-chain antibody is represented by the following equations (1) and (2):

[Equation 1]

$$Ag + Ab \underset{k_{off}}{\overset{k_{on}}{\rightleftharpoons}} Ag \cdot Ab \quad (1)$$

[Equation 2]

$$\frac{d[Ag \cdot Ab]}{dt} = k_{on}[Ag][Ab] - k_{off}[Ag \cdot Ab] \quad (2)$$

These equations can be converted to the following equation (3):

[Equation 3]

$$-\frac{d[Ag \cdot Ab]}{dt} = k_{off}[Ag \cdot Ab] - k_{on}[Ag][Ab] \quad (3)$$

In a liquid delivery system such as Biacore, the value of [Ab] is 0 at the time of washing the sensor chip, and thus, the above described equation (3) is represented as the following equation (4):

[Equation 4]

$$-\frac{d[Ag \cdot Ab]}{dt} = k_{off}[Ag \cdot Ab] \quad (4)$$

Further, when the [Ag·Ab] at the time t=0 is represented as [Ag·Ab]$_0$, it can be represented as the following equation (5):

[Equation 5]

$$\ln\frac{[Ag \cdot Ab]}{[Ag \cdot Ab]_0} = -k_{off}t. \quad (5)$$

In the case of calculating the dissociation rate constant for the binding of the single-chain antibody to the antigen, using a liquid delivery system such as Biacore, the dissociation rate constant can be obtained by: drawing a measurement graph, in which the time: t is plotted on the horizontal axis, and

[Equation 6]

$$\ln\frac{[Ag \cdot Ab]}{[Ag \cdot Ab]_0}$$

is plotted on the vertical axis; and calculating the dissociation rate constant from the slope of the graph.

(Method for Measuring Dissociation Rate Constant $k_{off}$)

The method for measuring the dissociation rate constant is not particularly limited, and the measurement can be carried out, for example, using a known apparatus such as BiacoreX-100 (manufactured by GE Healthcare Inc.) as a measuring apparatus, and by drawing a measurement graph as described above and calculating the dissociation rate constant from the slope of the graph.

[Dissociation Constant $K_D$]

The dissociation constant $K_D$ is usually not more than $3.0 \times 10^{-8}$ M, preferably not more than $1.0 \times 10^{-8}$ M, more preferably not more than $6.0 \times 10^{-9}$ M, still more preferably not more than $1.0 \times 10^{-9}$ M, further still more preferably not more than $6.0 \times 10^{-10}$ M, and particularly preferably not more than $1.0 \times 10^{-10}$ M. A lower dissociation constant indicates a higher binding capacity for the antigen, and thus, a higher usefulness as an antibody. Note that a common antibody has a $K_D$ of about 10 nM, whereas the single-chain antibody in the present embodiment has a $K_D$ within the above described range. This indicates that the single-chain antibody has a markedly higher binding capacity as compared to a common antibody.

(Method for Measuring Dissociation Constant $K_D$)

The method for measuring the dissociation constant $K_D$ is not particularly limited, and a known method can be used. For example, Biacore X-100 (manufactured by GE Healthcare Inc.) can be used as a measuring apparatus.

[Complementarity Determining Regions (CDRs) of $V_H$ Chain of Single-Chain Antibody]

The complementarity determining regions (CDRs) of the $V_H$ chain of a single-chain antibody includes CDR1, CDR2, and CDR3. As is well known, the amino acid sequence of CDR3, among the above described CDRs, contributes the most to the binding capacity for an antigen.

The amino acid sequences of the CDRs of the $V_H$ chain of the single-chain antibody in the present embodiment are not particularly limited, as long as an antibody constructed using the CDR sequences binds to an antigen. Of the amino acid sequences of the CDRs, the amino acid sequence of CDR3 is preferably the amino acid sequence of CDR3 of any one of the $V_H$ chains described in Examples in the present specification, in cases where the present method is carried out using a human serum-derived IgG polyclonal antibody or a human serum-derived IgA polyclonal antibody as the antigen, and a rabbit-derived single-chain antibody as the single-chain antibody. This is because an antibody constructed using such a CDR3 sequence has a high binding capacity for the antigen. Further, among these sequences, more preferred is an amino acid sequence which allows an antibody constructed therewith to have a higher binding capacity for the antigen.

The same applies to the amino acid sequence of CDR1 and the amino acid sequence of CDR2. The amino acid sequences of CDR1 and CDR2 are preferably the amino acid sequences of CDR1 and CDR2, respectively, of any one of the $V_H$ chains described in Examples in the present specification, in cases where the present method is carried out using a human serum-derived IgG polyclonal antibody or a human serum-derived IgA polyclonal antibody as the antigen, and a rabbit-derived single-chain antibody as the single-chain antibody. This is because an antibody constructed using such CDR1 and CDR2 sequences has a high binding capacity for the antigen. Further, among these sequences, more preferred are amino acid sequences which allow an antibody constructed therewith to have a higher binding capacity for the antigen.

[Amino Acid Sequences Substantially Homologous to Amino Acid Sequences of CDRs of $V_H$ Chain]

Each of the amino acid sequences of CDR1, CDR2, and CDR3 of the $V_H$ chain in the present embodiment is not particularly limited, as long as an antibody constructed using the CDR sequences binds to an antigen. In cases where the present method is carried out using a human serum-derived IgG polyclonal antibody or a human serum-derived IgA polyclonal antibody as the antigen, and a rabbit-derived single-chain antibody as the single-chain antibody, the amino acid sequences of CDR1, CDR2, and CDR3 of the $V_H$ chain may be amino acid sequences having an identity of 80% or more, preferably 90% or more, and more preferably 95% or more to the amino acid sequences of CDR1, CDR2, and CDR3, respectively, of any one of the $V_H$ chains described in Examples in the present specification.

Further, in cases where the present method is carried out using a human serum-derived IgG polyclonal antibody or a human serum-derived IgA polyclonal antibody as the antigen, and a rabbit-derived single-chain antibody as the single-chain antibody, the CDR1, CDR2, and CDR3 of the $V_H$ chain may have the same amino acid sequences as the amino acid sequences of CDR1, CDR2, and CDR3, respectively, of any one of the $V_H$ chains described in Examples in the present specification, except that one to several amino acids are substituted, deleted, inserted and/or added. The expression "one to several" as used herein refers preferably to a number from 1 to 5, and more preferably from 1 to 3.

The above described substitution is preferably a conservative substitution, and a conservative mutation is a mutation in which substitution takes place mutually among Phe, Trp, and Tyr, if the substitution site is an aromatic amino acid; among Leu, Ile, and Val, if the substitution site is a hydrophobic amino acid; between Gln and Asn, if the substitution site is a polar amino acid; among Lys, Arg, and His, if the substitution site is a basic amino acid; between Asp and Glu, if the substitution site is an acidic amino acid; and between Ser and Thr, if the substitution site is an amino acid having a hydroxyl group.

Examples of the conservative substitution include: substitution of Ala with Ser or Thr; substitution of Arg with Gln, His or Lys; substitution of Asn with Glu, Gln, Lys, His, or Asp; substitution of Asp with Asn, Glu or Gln; substitution of Cys with Ser or Ala; substitution of Gln with Asn, Glu, Lys, His, Asp, or Arg; substitution of Glu with Gly, Asn, Gln, Lys, or Asp; substitution of Gly with Pro; substitution of His with Asn, Lys, Gln, Arg, or Tyr; substitution of Ile with Leu, Met, Val, or Phe; substitution of Leu with Ile, Met, Val, or Phe; substitution of Lys with Asn, Glu, Gln, His, or Arg; substitution of Met with Ile, Leu, Val, or Phe; substitution of Phe with Trp, Tyr, Met, Ile, or Leu; substitution of Ser with Thr or Ala; substitution of Thr with Ser or Ala; substitution of Trp with Phe or Tyr; substitution of Tyr with His, Phe, or Trp; and substitution of Val with Met, Ile, or Leu.

The amino acid sequence(s) may be modified, as long as an antibody constructed using the modified sequence(s) binds to an antigen. Examples of the modification include amidation, addition of a lipid chain (aliphatic acylation (such as palmitoylation and myristoylation), prenylation (such as farnesylation and geranylgeranylation) and the like), phosphorylation (phosphorylation on a serine residue, a threonine residue, a tyrosine residue, etc.), acetylation, and addition of a sugar chain (such as N-glycosylation and O-glycosylation).

[Complementarity Determining Regions (CDRs) of $V_L$ Chain of Single-Chain Antibody]

The complementarity determining regions (CDRs) of the $V_L$ chain of a single-chain antibody includes CDR1, CDR2, and CDR3. As is well known, the amino acid sequences of the CDRs of the $V_L$ chain also contribute to the binding capacity for an antigen.

The amino acid sequences of the CDRs of the $V_L$ chain of the single-chain antibody in the present embodiment are not particularly limited, as long as an antibody constructed using the CDR sequences binds to an antigen. The amino acid sequences of CDR1, CDR2, and CDR3 are preferably the amino acid sequences of CDR1, CDR2, and CDR3, respectively, of any one of the $V_L$ chains described in Examples in the present specification, in cases where the present method is carried out using a human serum-derived IgG polyclonal antibody or a human serum-derived IgA polyclonal antibody as the antigen, and a rabbit-derived single-chain antibody as the single-chain antibody. This is because an antibody constructed using such CDR sequences has a high binding capacity for the antigen. Further, among these sequences, more preferred are amino acid sequences which allow an antibody constructed therewith to have a higher binding capacity for the antigen.

[Amino Acid Sequences Substantially Homologous to Amino Acid Sequences of CDRs of $V_L$ Chain]

The description to be given here is the same as that given above in the section of "Amino Acid Sequences Substantially Homologous to Amino Acid Sequences of CDRs of $V_H$ Chain".

[Framework Regions (FR) of $V_H$ Chain of Single-Chain Antibody]

The framework regions (FRs) of the $V_H$ chain of a single-chain antibody includes FR1, FR2, FR3, and FR4. As is well known, the amino acid sequences of the FRs of the $V_H$ chain also contribute to the binding capacity for an antigen.

The amino acid sequences of the FRs of the $V_H$ chain of the single-chain antibody in the present embodiment are not particularly limited, as long as an antibody constructed using the FR sequences binds to an antigen. The amino acid sequences of FR1, FR2, FR3, and FR4 are preferably the amino acid sequences of FR1, FR2, FR3, and FR4, respectively, of any one of the $V_H$ chains described in Examples in the present specification, in cases where the present method is carried out using a human serum-derived IgG polyclonal antibody or a human serum-derived IgA polyclonal antibody as the antigen, and a rabbit-derived single-chain antibody as the single-chain antibody. This is because an antibody constructed using such FR sequences has a high binding capacity for the antigen. Further, among these sequences, more preferred are amino acid sequences which allow an antibody constructed therewith to have a higher binding capacity for the antigen.

[Amino Acid Sequences Substantially Homologous to Amino Acid Sequences of FRs of $V_H$ Chain]

The description to be given here is the same as that given above in the section of "Amino Acid Sequences Substantially Homologous to Amino Acid Sequences of CDRs of $V_H$ Chain".

[Framework Regions (FR) of $V_L$ Chain of Single-Chain Antibody]

The framework regions (FRs) of the $V_L$ chain of a single-chain antibody includes FR1, FR2, FR3, and FR4. As is well known, the amino acid sequences of the FRs of the $V_L$ chain also contribute to the binding capacity for an antigen.

The amino acid sequences of the FRs of the $V_L$ chain of the single-chain antibody in the present embodiment are not particularly limited, as long as an antibody constructed using the FR sequences binds to an antigen. The amino acid sequences of FR1, FR2, FR3, and FR4 are preferably the amino acid sequences of FR1, FR2, FR3, and FR4, respectively, of any one of the $V_L$ chains described in Examples in the present specification, in cases where the present method is carried out using a human serum-derived IgG polyclonal antibody or a human serum-derived IgA polyclonal antibody as the antigen, and a rabbit-derived single-chain antibody as the single-chain antibody. This is because an antibody constructed using such FR sequences has a high binding capacity for the antigen. Further, among these sequences, more preferred are amino acid sequences which allow an antibody constructed therewith to have a higher binding capacity for the antigen.

[Amino Acid Sequences Substantially Homologous to Amino Acid Sequences of FRs of $V_L$ Chain]

The description to be given here is the same as that given above in the section of "Amino Acid Sequences Substantially Homologous to Amino Acid Sequences of CDRs of $V_H$ Chain".

1-2. Second Embodiment in First Invention

The second embodiment in the first invention of the present invention is a method for producing an antibody, the method including the steps of:

performing screening by the screening method according the first embodiment;

determining the amino acid sequence of the screened single-chain antibody;

preparing a DNA sequence encoding the antibody based on the sequence of the variable region of the determined amino acid sequence;

expressing the prepared DNA sequence in a host cell.

<(1) Step of Performing Screening by Screening Method According to First Embodiment>

The present step is a step of performing screening by the screening method according the first embodiment. The description previously given for the first embodiment applies to the description of the present step.

<(2) Step of Determining Amino Acid Sequence of Screened Single-Chain Antibody>

The present step is a step of determining the amino acid sequence of the screened single-chain antibody. The method therefor is not limited, as long as the amino acid sequence of the screened single-chain antibody can be determined.

For example, the amino acid sequence can be determined based on the gene sequence determined by the previously described "gene sequencing step".

<(3) Step of Preparing DNA Sequence Encoding Antibody Based on Sequence of Variable Region of Determined Amino Acid Sequence>

In the present step, the method for preparing a DNA sequence is not limited, as long as a DNA sequence encoding the antibody can be prepared, based on the sequence of the variable region of the determined amino acid sequence. Since codons encoding the respective amino acids are well known, the base sequence of DNA encoding a specific amino acid sequence can be easily identified.

There are a number of known methods for preparing a DNA sequence encoding the antibody. The DNA sequence can be prepared, for example, by ligating the DNA sequence encoding the variable region (V domain) of the amino acid sequence determined in the step of determining the amino acid sequence to DNA encoding a desired constant region (C domain), and the ligated DNA is incorporated into an expression vector. Alternatively, the DNA encoding the variable region (V domain) of the antibody can be incorporated into an expression vector containing DNA encoding the constant region. At this time, the DNA is incorporated into an expression vector, for example, so as to be expressed under the control of an expression regulatory region, such as an enhancer or promoter, and a host cell can be transformed with the thus prepared expression vector to produce the antibody.

The amino acid sequence of the constant region (C domain) to be used at this time may be derived from any animal, and there is no particular limitation on the animal. The amino acid sequence of the constant region (C domain) may be derived from an animal different from the animal from which the amino acid of the variable region (V domain) is derived. In cases where such a combination of amino acid sequences is used to produce an antibody, the resulting antibody is a chimeric antibody. Examples of the animal include humans, rats, mice, goats, sheep, cows, horses, dogs, cats, and monkeys. Among these, a human is preferred. In cases where the amino acid of the variable region (V domain) is derived from an animal other than a human, and the amino acid sequence of the constant region (C domain) is derived from a human, the resulting antibody produced by such a combination is a humanized antibody.

Further, an antibody to be encoded by the DNA sequence need not be an immunoglobulin, and may be, for example, an scFv, Fv, Fab, Fab', or F(ab')$_2$.

(Encoding Humanized Antibody, DNA Sequence)

A description will be given below with reference to a DNA sequence encoding a humanized antibody. As described above, the animal from which the amino acid sequence of the constant region (C domain) is derived is not limited.

A humanized antibody is a modified antibody which is also referred to as a reshaped human antibody. In the present embodiment, a humanized antibody can be constructed by grafting the CDRs of the single-chain antibody screened by the screening method according to the first embodiment into the complementarity determining regions of a human antibody. Common genetic engineering techniques for producing such a humanized antibody are also known. For example, these methods can be found in WO 2013/125654, European Patent Application No. EP 239400, WO 96/02576, and the like.

In the present embodiment, a humanized antibody can be constructed, for example, as follows. Specifically, a DNA sequence designed to ligate the CDRs of the single-chain antibody screened by the screening method according to the first embodiment to the FRs of a human antibody is synthesized by PCR from several oligonucleotides prepared to have terminal overlapping regions. The resulting DNA sequence is ligated to the DNA sequence encoding the constant region of the human antibody. The ligated DNA is inserted into an expression vector, which is then incorporated into a host cell to allow the production of a humanized antibody.

The FRs of the human antibody to be ligated via the CDRs are selected in such a manner that the complementarity determining regions form an appropriate antigen-binding site. If necessary, amino acids in the framework regions of the variable region in the humanized antibody may be substituted so that the complementarity determining regions of the humanized antibody forms an appropriate antigen-binding site. The method therefor is disclosed, for example, in Sato K. et al., Cancer Research 1993, 53: 851-856, and the like. Further, the FRs may be replaced with framework regions derived from a human antibody of a different class or a subclass. The method therefor is disclosed, for example, in WO 99/51743.

When producing a humanized antibody, amino acids in the variable region (for example, FRs) and the constant region may be substituted with other amino acids. For example, the method described in The Journal of Japanese Society on Thrombosis and Hemostasis 4 (3): 193-200, 1993 may be used. As described in the above document, the determined amino acid sequence of the variable region may be compared with the amino acid sequences of the variable regions of human antibodies found in data banks to select a human antibody gene having a skeleton (FRs) with the highest similarity to that of the determined sequence, and then the higher order structure of the selected gene is analyzed using computer graphics, thereby determining the optimum amino acid sequence of the variable region. Further, it is also possible to carry out the substitution of amino acids, and the like, which are necessary for achieving an efficient antibody production, when inserting the DNA into an expression vector and then incorporating the vector into a host cell to produce an antibody.

The substitution of amino acids is, for example, a substitution of less than 15, less than 10, 8 or less, 7 or less, 6 or less, 5 or less, 4 or less, 3 or less, or 2 or less amino acids, preferably a substitution of 1 to 5 amino acids, and more preferably a substitution of 1 or 2 amino acids, and a substituted antibody should be functionally equivalent to an unsubstituted antibody. The substitution is preferably a conservative amino acid substitution, which is a substitution between amino acids having similar properties, such as those having similar electric charge, side chains, polarity, aromaticity, etc. Amino acids having similar properties can be classified, for example, into: basic amino acids (arginine, lysine, and histidine), acidic amino acids (aspartic acid and glutamic acid), uncharged polar amino acids (glycine, asparagine, glutamine, serine, threonine, cysteine, and tyrosine), non-polar amino acids (leucine, isoleucine, alanine, valine, proline, phenylalanine, tryptophan, and methionine), branched-chain amino acids (leucine, valine, and isoleucine), aromatic amino acids (phenylalanine, tyrosine, tryptophan, and histidine), and the like.

<(4) Step of Expressing Prepared DNA Sequence in Host Cell>

In the present step, the method for carrying out the step is not limited, as long as the DNA sequence prepared in the step of preparing a DNA sequence encoding the antibody can be expressed in a host cell.

For example, many of the host cells used for antibody production are derived from mammals, and those skilled in the art can select as appropriate a specific type of host cells which is most suitable for expressing a desired gene product. Examples of host cell lines which are commonly used include CHO-derived cell lines (Chinese hamster ovary cell lines), CV1 (monkey kidney cell line), COS (a derivative of CV1 doing SV40T antigen), SP2/0 (mouse myeloma cell line), P3x63-Ag3.653 (mouse myeloma cell line), 293 (human kidney cell line), and 293T (a derivative of 293 expressing SV40T antigen), but not particularly limited thereto. Host cell lines are available from various manufacturers, organizations such as ATCC, or organizations publishing papers cited in literature.

<(5) Optional Steps>

After the expression step in a host cell, a step of separating and purifying the resulting antibody may be carried out. The method therefor is not particularly limited, and any of known separation and purification methods may be combined as appropriate to carry out the separation and purification of the antibody.

Examples of the method include: methods utilizing a difference in electric charge, such as ion-exchange chromatography; methods primarily utilizing a difference in molecular weight, such as dialysis, ultrafiltration, gel filtration, and SDS-polyacrylamide gel electrophoresis; methods utilizing specific affinity, such as affinity chromatography; methods utilizing a difference in hydrophobicity, such as reverse-phase high performance liquid chromatography; methods utilizing a difference in isoelectric point such as isoelectric focusing; and the like.

<2. Second Invention>

The second invention of the present invention includes the following first to sixth embodiments.

The first embodiment: a single-chain antibody having a dissociation constant for a human serum-derived IgG polyclonal antibody of not more than $3.0 \times 10^{-8}$ M.

The second embodiment: a separation agent for separating a human serum-derived IgG polyclonal antibody, the separation agent including: a carrier; and the single-chain antibody according to the first embodiment, which binds to the surface of the carrier via a chemical bond.

The third embodiment: a single-chain antibody having a dissociation rate constant for a human serum-derived IgA polyclonal antibody of not more than $1.0 \times 10^{-3}$ s$^{-1}$ The fourth embodiment: a separation agent for separating a human serum-derived IgA polyclonal antibody, the separation agent including: a carrier; and the single-chain antibody according to the third embodiment, which binds to the surface of the carrier via a chemical bond.

The fifth embodiment: a single-chain antibody having a dissociation rate constant for the L chain of a human-derived antibody of not more than $1.0 \times 10^{-3}$ s$^{-1}$ The sixth embodiment: a separation agent for separating a human-derived antibody, the separation agent including: a carrier; and the single-chain antibody according to the fifth embodiment, which binds to the surface of the carrier via a chemical bond.

2-1. First Embodiment in Second Invention

The first embodiment in the second invention of the present invention is a single-chain antibody having a dissociation constant for a human serum-derived IgG polyclonal antibody of not more than $3.0 \times 10^{-8}$ M.

The above described single-chain antibody is preferably also an antibody against a human serum-derived IgA polyclonal antibody, and more preferably has a dissociation rate constant for the human serum-derived IgA polyclonal antibody of not more than $1.0 \times 10^{-3}$ s$^{-1}$. Further, the single-chain antibody preferably binds to the L chain of such an antibody, and more preferably binds to the kappa chain of such an antibody.

The description previously given for the first invention applies to the description regarding other matters in the present embodiment.

2-2. Second Embodiment in Second Invention

The second embodiment in the second invention of the present invention is a separation agent for separating a human serum-derived IgG polyclonal antibody, the separation agent including: a carrier; and the single-chain antibody according to the first embodiment in the second invention, which binds to the surface of the carrier via a chemical bond.

[Separation Agent for Separating Human Serum-Derived IgG Polyclonal Antibody]

The single-chain antibody according to the first embodiment can be used as a separation agent for separating a human serum-derived IgG polyclonal antibody, utilizing the capacity of the single-chain antibody to bind to the antibody. The above described separation agent can be used for the purification or removal of the antibody, as well as for the diagnosis, treatment, examination and the like utilizing the antibody.

The separation agent according to the present embodiment has a form in which the single-chain antibody according to the first embodiment is immobilized on a solid phase support which is insoluble in water.

[Water-Insoluble Carrier]

Examples of the water-insoluble carrier to be used include: inorganic carriers such as glass beads and silica gels; organic carriers composed of synthetic polymers such as crosslinked polyvinyl alcohols, crosslinked polyacrylates, crosslinked polyacrylamides and crosslinked polystyrenes, and/or polysaccharides such as crystalline cellulose, crosslinked cellulose, crosslinked agarose and crosslinked dextran; as well as composite carriers obtained by combining these carriers, such as organic-organic and organic-inorganic composite carriers. Among these, a hydrophilic carrier is preferred because it has a relatively low non-specific adsorption, and a good selectivity for the single-chain antibody according to the first embodiment. The hydrophilic carrier as used herein refers to a carrier which has a contact angle with water, as measured when the compound(s) constituting the carrier is/are formed into a plate-like shape, of 60 degrees or lower. Representative examples of such a carrier include carriers composed of: polysaccharides such as cellulose, chitosan and dextran; polyvinyl alcohol; a saponified product of ethylene-vinyl acetate copolymer; polyacrylamide; polyacrylic acid; polymethacrylic acid; polymethylmethacrylate; polyacrylic acid-grafted polyethylene; polyacrylamide-grafted polyethylene; and glass.

Examples of commercially available products thereof include: GCL2000 and GC700, which are porous cellulose gels; Sephacryl S-1000, obtained by covalently crosslinking allyl dextran and methylene bisacrylamide; Toyopearl, which is an acrylate-based carrier; Sepharose CL4B, which is an agarose-based crosslinked carrier; Eupergit C250L, which is a polymethacrylamide activated with epoxy groups; and the like. Note, however, that the carrier to be used in the present embodiment is not limited only to these carriers and activated carriers. Each of the above described carriers may be used alone, or arbitrarily selected two or more kinds of these carriers may be mixed for use. Further, the water-insoluble carrier to be used in the present embodiment preferably has a large surface area, in terms of the purposes and methods of using the present separation agent. In other words, the carrier to be used is preferably a porous carrier which has a number of pores of an appropriate size.

The form of the carrier can be selected arbitrarily, and any of the carriers in the form of beads, fibers, membranes (including hollow fibers) and the like can be used. Among these, a carrier in the form of beads is particularly preferably used, because one having a specific exclusion limit molecular weight can be easily formed. A carrier in the form of beads having an average particle size of from 10 to 2,500 µm is easy to use. In particular, preferred is a carrier in the form of beads having an average particle size within the range of from 25 µm to 800 µm, because the immobilization reaction of the single-chain antibody on such a carrier can be easily performed.

In addition, if a functional group which can be used for the immobilization reaction of the single-chain antibody are present on the carrier surface, it is convenient for the immobilization of the single-chain antibody. Representative examples of the functional group include hydroxyl group, amino group, aldehyde group, carboxyl group, thiol group, silanol group, amide group, epoxy group, succinylimide group, acid anhydride groups, iodoacetyl group, and the like.

When the single-chain antibody is immobilized on the carrier as described above, it is preferred that the steric hindrance of the single-chain antibody be reduced so as to improve the separation efficiency. In addition, it is more preferred that the single-chain antibody be immobilized on the carrier via a hydrophilic spacer, so as to reduce non-specific binding. As the hydrophilic spacer, it is preferable to use, for example, a polyalkylene oxide derivative substituted at both ends with a carboxyl group, an amino group, an aldehyde group, an epoxy group, etc.

The method and conditions for immobilizing the single-chain antibody to be incorporated into the carrier and an organic compound to be used as a spacer, are not particularly limited. Methods commonly used for immobilizing a protein or a peptide on a carrier will be exemplified below. For example, the immobilization may be carried out by a method in which a carrier is allowed to react with cyanic bromide, epichlorohydrin, diglycidyl ether, tosyl chloride, tresyl chloride, hydrazine or the like to activate the carrier (namely, functional groups originally present on the carrier are replaced with functional groups which more easily react with the single-chain antibody), thereby allowing the carrier to react with the single-chain antibody and the single-chain antibody to be immobilized on the carrier. Alternatively, a method may be used in which a condensation reagent such as carbodiimide, or a reagent containing a plurality of functional groups within the molecule, such as glutaraldehyde, is added to a system in which a carrier and the single-chain antibody are present, followed by condensation and crosslinking, thereby immobilizing the single-chain antibody on the carrier. However, it is more preferable to use a method which allows the single-chain antibody to be immobilized on a carrier such that the single-chain antibody is not easily desorbed from the carrier during the sterilization or use of the separation agent.

Specific Examples

Specific examples of the separation agent for separating a human serum-derived IgG polyclonal antibody and the method for producing the same include HiTrap NHS-activated HP Columns (manufactured by GE Healthcare Inc.), and the method for immobilizing the single-chain antibody according to the first embodiment, using the same, as will be described in Example 8. Stated simply, the carboxyl group of the Sepharose (an agarose carrier in the form of beads) in the column is esterified with NHS, and allowed to form an amide bond with an amino group of the single-chain antibody according to the first embodiment which has been purified, thereby immobilizing the single-chain antibody. Unreacted NHS esters can be blocked by addition of ethanolamine.

[Other Matters]

The descriptions previously given for the first invention and the first embodiment in the second invention apply to the description regarding other matters in the present embodiment.

2-3. Third Embodiment in Second Invention

The third embodiment in the second invention of the present invention is a single-chain antibody having a dissociation rate constant for a human serum-derived IgA polyclonal antibody of not more than $1.0 \times 10^{-3}$ $s^{-1}$.

The above described single-chain antibody is preferably also an antibody against a human serum-derived IgG polyclonal antibody, and more preferably has a dissociation constant for the human serum-derived IgG polyclonal antibody of not more than $3.0 \times 10^{-8}$ M. Further, the single-chain antibody preferably binds to the L chain of such an antibody, and more preferably binds to the kappa chain of such an antibody.

The description previously given for the first invention applies to the description regarding other matters in the present embodiment.

2-4. Fourth Embodiment in Second Invention

The fourth embodiment in the second invention of the present invention is a separation agent for separating a human serum-derived IgA polyclonal antibody, the separation agent including: a carrier; and the single-chain antibody according to the third embodiment in the second invention, which binds to the surface of the carrier via a chemical bond.

The descriptions previously given for the first invention, the second embodiment in the second invention, and the third embodiment in the second invention apply to the description regarding other matters in the present embodiment.

2-5. Fifth Embodiment in Second Invention

The fifth embodiment in the second invention of the present invention is a single-chain antibody having a dissociation rate constant for the L chain of a human-derived antibody of not more than $1.0 \times 10^{-3}$ $s^{-1}$ The above described single-chain antibody is preferably an antibody against a human serum-derived IgG polyclonal antibody and/or a human serum-derived IgA polyclonal antibody, and more preferably has a dissociation constant for the human serum-derived IgG polyclonal antibody of not more than $3.0 \times 10^{-8}$ M, and/or a dissociation rate constant for the human serum-derived IgA polyclonal antibody of not more than $1.0 \times 10^{-3}$ $s^{-1}$. Further, the single-chain antibody preferably binds to the kappa chain of such an antibody.

The description previously given for the first invention applies to the description regarding other matters in the present embodiment.

2-6. Sixth Embodiment in Second Invention

The sixth embodiment in the second invention of the present invention is a separation agent for separating a human-derived antibody, the separation agent including: a carrier; and the single-chain antibody according to the fifth embodiment in the second invention, which binds to the surface of the carrier via a chemical bond.

The descriptions previously given for the first invention, the second embodiment in the second invention, and the fifth embodiment in the second invention apply to the description regarding other matters in the present embodiment.

EXAMPLES

The present invention will now be described more specifically by way of Examples. However, the present invention is in no way limited by the following Examples, as long as the gist of the present invention is not deviated. Note that there are cases where Examples and Comparative Examples are not described in their numerical order, for convenience sake.

<1. Model Study>

Before describing Examples of the screening method according to the first invention of the present invention, a description will be given below regarding the method for screening a mouse-derived single-chain antibody which binds to a human serum-derived IgG polyclonal antibody (hereinafter, sometimes referred to as an "anti-human serum-derived IgG polyclonal antibody-mouse-derived single-chain antibody"), from a phage library. A description will also be given regarding the case in which a library of phages not presenting the mouse-derived single-chain antibody is used, as a comparative study. Further, for each of the above cases, a study in which multilamellar liposomes were used and a study in which an immunotube was used will be described.

<1-1. Coupling of Human Serum-Derived IgG Polyclonal Antibody to Multilamellar Liposomes>

A quantity of 10 μmol of dipalmitoylphosphatidylcholine (DPPC), 1 μmol of dicetyl phosphate (DCP), 0.5 μmol of N-(4-(p-maleimidophenyl)butyryl)dipalmitoylphosphatidylethanolamine (MPB-DPPE) were dissolved in 5 ml of chloroform. Then the chloroform in the resulting solution was removed by distillation in a 100 ml eggplant flask, under reduced pressure.

Subsequently, the resulting thin film of phospholipid formed on the inner wall of the flask was hydrated with 3 ml of PBS at 50° C., to form multilamellar liposomes (MLVs). The resultant was centrifuged at 20,000 g and at 25° C. for two minutes, and the supernatant was removed. This operation was repeated two more times.

The resulting multilamellar liposomes were suspended in 3 ml of PBS and stored at 4° C. (the resultant is sometimes referred to as "reactive MLVs"). A quantity of 1 ml of reactive MLVs was centrifuged at 20,000 g and at 25° C. for two minutes. A human serum-derived IgG polyclonal antibody (#I4506; manufactured by Sigma-Aldrich Co. LLC.) was dissolved in PBS to a concentration of 1 mg/ml, and to the resulting solution, the pellets of the reactive MLVs obtained after the centrifugation were dispersed.

To the resultant, 2-iminothiolane hydrochloride (manufactured by Sigma-Aldrich Co. LLC.) was added, in an amount 10 times the amount of the human serum-derived IgG polyclonal antibody, in molar ratio, followed by incubation at 25° C. for three hours or more, while stirring. Thereafter, centrifugation was carried out at 20,000 g and at 25° C. for two minutes, the supernatant was removed, and the resultant was suspended in 1 ml of PBS. An operational process consisting of the above described centrifugation, removal of supernatant, and suspension in 1 ml of PBS, as one unit, was repeated three more times.

The resulting suspension was stored at 4° C., to be used as human serum-derived IgG polyclonal antibody-immobilized MLVs. The amount of the human serum-derived IgG polyclonal antibody immobilized on the MLVs was quantified using DC Protein Assay.

<1-2. Immobilization of Human Serum-Derived IgG Polyclonal Antibody on Tube>

A quantity of 1 ml of a solution of a human serum-derived IgG polyclonal antibody (#I4506; manufactured by Sigma-Aldrich Co. LLC.), prepared with PBS to a concentration of 10 μg/ml, was added to an immunotube (Maxisorp (registered trademark); manufactured by Nunc), followed by incubation at 4° C. overnight. Subsequently, the tube was washed with PBS five times, and 1 ml of 2% BSA-PBS was added thereto, followed by incubation for one hour.

Before mixing with a phage library, the tube was washed with PBS five more times, and then a phage library solution was added thereto and mixed for use.

It has been shown in Non-patent Document 1 that, although it is the result obtained in the case of using a rabbit-serum derived IgG polyclonal antibody, the ratio of the antibody non-specifically bound to a tube when the antibody is immobilized on the tube, is markedly higher as compared to the ratio of the antibody non-specifically bound to multilamellar liposomes when the antibody is immobilized on the multilamellar liposomes. Those skilled in the art can easily understand that the same applies to the case in which a human serum-derived IgG polyclonal antibody is used.

<1-3. Preparation of Library of Phages Presenting Anti-Human Serum-Derived IgG Polyclonal Antibody-Mouse-Derived Single-Chain Antibody>

A DNA containing a gene sequence of pelB leader, an Nco I site, an Spe I site, a gene sequence of flexible linker $(G_4S)_3$, a BamH I site, a Not I site, a gene sequence of FLAG-tag, a gene sequence of c-myc-tag, an Amber stop codon (TAG), and a gene sequence of gIIIp coat protein (250 amino acid residues on the N-terminus are deleted) was synthesized by a commissioned service, and the DNA was inserted into the Xba I/BamH I sites of pT7 Blue (manufactured by Merck KGaA). The thus obtained pT7 Blue recombinant phagemid vector was named as pPLFMAΔ250gIIIp, and used in a series of studies using the phage display method.

The gene of the anti-human serum-derived IgG polyclonal antibody-mouse-derived single-chain antibody determined by a mouse hybridoma CRL-1786 cell line (ATCC) was amplified by PCR, and inserted into the Nco I/Not I sites of the recombinant phagemid vector pPLFMAA250gIIIp.

The recombinant phagemid vector was used to transform *Escherichia coli* TG1 cells, and the transformed cells were inoculated in 10 ml of 2×YT medium (containing 1% glucose and 50 mg/L ampicillin). The cells were cultured overnight in a 200 ml Erlenmeyer flask, at 200 rpm and at 37° C. (preculture).

The precultured liquid was inoculated in 50 ml of 2×YT medium (containing 1% glucose and 50 mg/L ampicillin) so as to achieve an OD 600 of 0.1, followed by culturing at 30° C. with shaking at 200 rpm. After culturing the cells until the OD reached around 1.0, a helper phage, VCSM13 was added to the culture liquid so as to achieve a multiplicity of infection (MOI) of 20, followed by incubation at 37° C. for 30 minutes. Following centrifugation at 3,000 g and at 37° C. for 10 minutes, the supernatant was removed, and the resulting cells were gently suspended in 50 ml of 2×YT medium (containing 50 mg/L ampicillin and 35 mg/L kanamycin). The resulting suspension was shaken at 200 rpm and at 30° C. for 12 hours or more, thereby allowing phages presenting the anti-human serum-derived IgG polyclonal antibody-mouse-derived single-chain antibody to be produced in the culture supernatant.

The supernatant was collected by centrifugation, concentrated by PEG precipitation, and resuspended in 1 ml of PBS, to obtain a library of phages presenting the anti-human serum-derived IgG polyclonal antibody-mouse-derived single-chain antibody.

<1-4. Preparation of Library of Non-Presenting Phages>

The same procedure as in the above described section 1-3 was carried out, except that the recombinant phagemid vector pPLFMAA250gIIIp into which the gene of the anti-human serum-derived IgG polyclonal antibody-mouse-derived single-chain antibody was not inserted, was used to transform *Escherichia coli* TG1 cells, thereby obtaining non-presenting phages, namely, phages not presenting the anti-human serum-derived IgG polyclonal antibody-mouse-derived single-chain antibody.

<1-5. Panning>

(Preparation of Pseudo-Phage Library)

The library of phages presenting the anti-human serum-derived IgG polyclonal antibody-mouse-derived single-chain antibody, and the library of non-presenting phages, obtained in the above described sections 1-3 and 1-4, respectively, were mixed at the ratios shown in Table 1, to prepare pseudo-phage libraries.

TABLE 1

| Composition of the pseudo-phage library | | | |
|---|---|---|---|
| Condition | | cfu/ml | cfu/ml ratio |
| Condition 1 | Library of phages presenting anti-human serum-derived IgG polyclonal antibody-mouse-derived single-chain antibody | $8.8 \times 10^8$ | 1 |
| | Non-presenting phages | $4.7 \times 10^{14}$ | 540,000 |
| Condition 2 | Library of phages presenting anti-human serum-derived IgG polyclonal antibody-mouse-derived single-chain antibody | $8.8 \times 10^7$ | 1 |
| | Non-presenting phages | $4.7 \times 10^{14}$ | 5,400,000 |

Example 1-1

(Panning Using Human Serum-Derived IgG Polyclonal Antibody-Immobilized MLVs)

Panning was carried out as follows, using the pseudo-phage library prepared according to Condition 1, and using the human serum-derived IgG polyclonal antibody-immobilized MLVs prepared in the above section 1-1.

(Rounds)

First, operations to be carried out in each of the rounds will be described.

The human serum-derived IgG polyclonal antibody-immobilized MLVs were added in an amount to achieve an IgG content of 10 μg, followed by vortexing. Following centrifugation at 20,000 g and at 25° C. for two minutes, the supernatant was removed, and then 0.9 ml of 2% BSA-PBS was added to the resultant for resuspension.

Meanwhile, a solution of the pseudo-phage library was centrifuged at 20,000 g and at 25° C. for two minutes, and the supernatant was collected. A quantity of 100 μl of the supernatant was added to a tube, followed by vortexing. The resultant was then inversion mixed at 25° C. for one hour using a rotator, to allow a binding reaction between the human serum-derived IgG polyclonal antibody-immobilized MLVs and the pseudo-phage library to proceed.

The binding reaction liquid obtained above and 1 ml of 2% BSA-PBS were mixed, and the mixture was centrifuged at 20,000 g and at 25° C. for two minutes to remove the supernatant (washing). The washing operation was repeated five times.

(Recovery of Phages Selected by Panning)

To the human serum-derived IgG polyclonal antibody-immobilized MLVs in the above described tube, 0.9 ml of 10 mM glycine-HCl (pH 1.5) was added for suspension, and the resulting suspension was transferred to a BSA-blocked tube. Subsequently, the tube was further inversion mixed at room temperature (or at 4° C.) for 10 minutes, thereby eluting the phages.

A quantity of 0.9 ml of the phage eluent collected from the above tube and 0.1 ml of a 2M Tris-HCl solution were mixed to neutralize the phage eluent.

Meanwhile, a culture liquid of *Escherichia coli* TG1 cells were inoculated in 10 ml of fresh LB medium so as to achieve an OD of 0.1, followed by culturing at 30° C.

A quantity of 1 ml of the neutralized eluent and 1 ml of the culture liquid of *Escherichia coli* TG1 cells which had been cultured were mixed, followed by incubation at 37° C. for one hour. After the incubation, the cells was added to 2×YT medium (containing 1% glucose and 50 mg/L ampicillin), and cultured at 30° C. and at 200 rpm, until the OD 600 reached 1.0.

To the resulting culture liquid, a helper phage VCSM13 was added to achieve a multiplicity of infection (MOI) of 20, followed by incubation at 37° C. for 30 minutes. After centrifuging the culture liquid at 1,500 rpm and at 30° C. for 15 minutes, the supernatant was discarded, and the cells were redispersed in 50 ml of 2×YT medium (containing 50 mg/L ampicillin and 50 mg/L kanamycin). The cells were then cultured at 30° C. and at 200 rpm for 12 hours, to allow phages to be produced in the culture supernatant.

Following subsequent centrifugation at 1,500 rpm and at 30° C. for 15 minutes, the supernatant was collected, and then concentrated and purified by PEG precipitation. Finally, the resultant was dispersed in 1 ml of PBS, followed by centrifugation to remove aggregates.

A series of operations up to this point are defined as one round. When the above described operations were carried out, it is regarded that Round 1 has been completed.

Thereafter, the above described round was repeated three more times. In other words, the procedure up to Round 4 was carried out. From the colonies obtained in each of the rounds, phagemid DNAs were recovered.

Example 1-2

The same procedure as in Example 1-1 was carried out as Example 1-2, except that the pseudo-phage library prepared according to Condition 2 was used.

Comparative Example 1-1

Panning was carried out as follows, using the pseudo-phage library prepared according to Condition 1, and using the human serum-derived IgG polyclonal antibody-immobilized tube prepared in the above section 1-2, instead of the human serum-derived IgG polyclonal antibody-immobilized MLVs.

(Rounds)

Operations to be carried out in each of the rounds will be described.

As described in the above 1-2, 1 ml of a solution of a human serum-derived IgG polyclonal antibody (#I4506; manufactured by Sigma-Aldrich Co. LLC.), prepared with PBS to a concentration of 10 μg/ml, was added to an immunotube (Maxisorp (registered trademark); manufactured by Nunc), followed by incubation at 4° C. overnight. Subsequently, the tube was washed with PBS five times, and 1 ml of 2% BSA-PBS was added thereto, followed by incubation for one hour.

Thereafter, the tube was washed with PBST five times, and 900 μl of 2% BSA-PBST, and then 100 μl of a solution of the pseudo-phage library were added thereto, followed by incubation at 25° C. for one hour.

(Recovery of Phages Selected by Panning)

A culture liquid of *Escherichia coli* TG1 cells were inoculated in 10 ml of fresh LB medium so as to achieve an OD of 0.1, followed by culturing at 30° C.

A quantity of 1 ml of the eluent and 1 ml of the culture liquid of *Escherichia coli* TG1 cells which had been cultured were mixed, followed by incubation at 37° C. for one hour. After the incubation, the cells was added to 2×YT medium (containing 1% glucose and 50 mg/L ampicillin), and cultured at 30° C. and at 200 rpm, until the OD 600 reached 1.0.

To the resulting culture liquid, a helper phage VCSM13 was added to achieve a multiplicity of infection (MOI) of 20, followed by incubation at 37° C. for 30 minutes. After centrifuging the culture liquid at 1,500 rpm and at 30° C. for 15 minutes, the supernatant was discarded, and the cells were redispersed in 50 ml of 2×YT medium (containing 50 mg/L ampicillin and 50 mg/L kanamycin). The cells were then cultured at 30° C. and at 200 rpm for 12 hours, to allow phages to be produced in the culture supernatant.

Following subsequent centrifugation at 1,500 rpm and at 30° C. for 15 minutes, the supernatant was collected, and then concentrated and purified by PEG precipitation. Finally, the resultant was dispersed in 1 ml of PBS, followed by centrifugation to remove aggregates.

A series of operations up to this point are defined as one round. When the above described operations were carried out, it is regarded that Round 1 has been completed.

Thereafter, the above described round was repeated three more times. In other words, the procedure up to Round 4 was carried out. From the colonies obtained in each of the rounds, phagemid DNAs were recovered.

Comparative Example 1-2

The same procedure as in Comparative Example 1-1 was carried out as Comparative Example 1-2, except that the pseudo-phage library prepared according to Condition 2 was used.

<1-6. Confirmation of Presence or Absence of Gene of Anti-Human Serum-Derived IgG Polyclonal Antibody-Mouse-Derived Single-Chain Antibody>

The presence or absence of the gene of the anti-human serum-derived IgG polyclonal antibody-mouse-derived single-chain antibody was confirmed in the phagemid DNAs recovered in Example 1-1, Example 1-2, Comparative Example 1-1, and Comparative Example 1-2.

The obtained phagemid DNAs were separated by electrophoresis using 1% agarose gel, and visualized by ethidium bromide staining. The migration distances of the phagemid DNAs were compared against the migration distance of the DNA of the phagemid vector (pPLFMAA250gIIIp) into which the gene of the anti-human serum-derived IgG polyclonal antibody-mouse-derived single-chain antibody was not inserted, and the presence or absence of the gene of the anti-human serum-derived IgG polyclonal antibody-mouse-derived single-chain antibody was visually confirmed.

<1-7. Panning Results>

Table 2-1 and Table 2-2 show the number of phages before and after the panning, and the recovery rate of the phages, which is the rate of the number of the phages after the panning to the number of the phages before the panning, in each of the rounds 1 to 4.

Further, Table 3 shows the ratio of the number of positive clones (namely, the number of clones containing the gene of the anti-human serum-derived IgG polyclonal antibody-mouse-derived single-chain antibody), with respect to the total number of clones obtained, in each of the rounds 1 to 4. The above described ratio is shown in FIG. 1.

TABLE 2-1

|  |  | Round 1 | | | Round 2 | | |
| --- | --- | --- | --- | --- | --- | --- | --- |
|  |  | Before Panning (cfu/ml) | After Panning (cfu/ml) | Recovery Rate (%) | Before Panning (cfu/ml) | After Panning (cfu/ml) | Recovery Rate (%) |
| Condition 1 | Example 1-1 | 4.7E+14 | 2.8E+04 | 6.0E−09 | 4.2E+12 | 1.1E+06 | 2.6E−05 |
|  | Comparative Example 1-1 | 4.7E+14 | 8.1E+05 | 1.7E−07 | 1.9E+12 | 1.4E+06 | 7.4E−05 |
| Condition 2 | Example 1-2 | 4.7E+14 | 7.4E+04 | 1.6E−08 | 3.1E+13 | 1.5E+05 | 4.8E−07 |
|  | Comparative Example 1-2 | 4.7E+14 | 1.3E+05 | 2.8E−08 | 4.0E+12 | 6.0E+06 | 1.5E−04 |

TABLE 2-2

|  |  | Round 3 | | | Round 4 | | |
| --- | --- | --- | --- | --- | --- | --- | --- |
|  |  | Before Panning (cfu/ml) | After Panning (cfu/ml) | Recovery Rate (%) | Before Panning (cfu/ml) | After Panning (cfu/ml) | Recovery Rate (%) |
| Condition 1 | Example 1-1 | 2.8E+12 | 1.3E+07 | 4.6E−04 | 1.2E+14 | 2.4E+06 | 2.0E−06 |
|  | Comparative Example 1-1 | 5.2E+12 | 2.0E+06 | 3.8E−05 | 2.0E+12 | 9.8E+06 | 4.9E−04 |
| Condition 2 | Example 1-2 | 6.4E+12 | 5.9E+05 | 9.2E−06 | 1.0E+14 | 8.4E+06 | 8.3E−06 |
|  | Comparative Example 1-2 | 3.2E+12 | 1.2E+06 | 3.8E−05 | 7.3E+12 | 2.1E+06 | 2.9E−05 |

TABLE 3

|  |  | Round 1 | | Round 2 | | Round 3 | | Round 4 | |
| --- | --- | --- | --- | --- | --- | --- | --- | --- | --- |
|  |  | Number of positive clones | Ratio (%) | Number of positive clones | Ratio (%) | Number of positive clones | Ratio (%) | Number of positive clones | Ratio (%) |
| Condition 1 | Example 1-1 | 0 | 0 | 1 | 17 | 6 | 100 | 6 | 100 |
|  | Comparative Example 1-1 | 0 | 0 | 0 | 0 | 0 | 0 | 0 | 0 |
| Condition 2 | Example 1-2 | 0 | 0 | 0 | 0 | 3 | 50 | 6 | 100 |
|  | Comparative Example 1-2 | 0 | 0 | 0 | 0 | 0 | 0 | 0 | 0 |

The above results revealed that the use of the method in which the human serum-derived IgG polyclonal antibody as an antigen was coupled to multilamellar liposomes enables a more efficient panning, as compared to using the method in which the human serum-derived IgG polyclonal antibody was immobilized on a tube.

<2. Method for Screening Rabbit-Derived Single-Chain Antibody which Binds to Human Serum-Derived IgG Polyclonal Antibody>

A description will be given below regarding the method for screening a rabbit-derived single-chain antibody which binds to a human serum-derived IgG polyclonal antibody (hereinafter, sometimes referred to as an "anti-human serum-derived IgG polyclonal antibody-rabbit-derived single-chain antibody"), from a phage library.

<1-2. Coupling of Human Serum-Derived IgG Polyclonal Antibody to Multilamellar Liposomes>

Human serum-derived IgG polyclonal antibody-immobilized MLVs were prepared in the same manner as described in the above section 1-1.

<2-2. Preparation of Library of Phages Presenting Anti-Human Serum-Derived IgG Polyclonal Antibody-Rabbit-Derived Single-Chain Antibodies>

First, a European rabbit was immunized with a human serum-derived IgG polyclonal antibody (#I4506; manufactured by Sigma-Aldrich Co. LLC.) by a known method. The total RNA was extracted from the spleen of the immunized rabbit.

Using Superscript (registered trademark) IV Reverse Transcriptase (manufactured by Thermo Fisher Scientific) as a reverse transcriptase, cDNA was prepared from the total RNA. Using the cDNA as a template, and the sequences of SEQ ID NOs: 1 to 11 as primers, the genes of the variable regions ($V_H$ domains) of the heavy chains (H chains), and genes of the variable regions ($V_L$ domains) of the light chains (L chains) were amplified.

The thus amplified $V_L$ genes were introduced into the BamH I/Not I sites of pPLFMAΔgIIIp vectors, to be used as $V_L$ library vectors. Escherichia coli TG1 cells were used as the host cells.

Next, the $V_L$ library vectors were purified from the Escherichia coli cells, and the amplified $V_H$ genes were introduced into the Nco I/Spe I sites, to obtain phage library vectors ($2.0 \times 10^7$ colonies) presenting anti-human serum-derived IgG polyclonal antibody-rabbit-derived single-chain antibodies. The host cells used at this time were also Escherichia coli TG1 cells.

Subsequently, the Escherichia coli TG1 cells containing the phage library vectors were inoculated in 50 ml of 2×YT medium (containing 1% glucose and 50 mg/L ampicillin), and then cultured at 30° C. with shaking at 200 rpm, until the OD reached 1. To the resulting culture liquid, a helper phage VCSM13 was added to achieve a multiplicity of infection: MOI of 20, followed by incubation at 37° C. for one hour. Following centrifugation at 1,500 rpm and at 30° C. for 15 minutes, the supernatant was discarded, and the cells were suspended in 50 ml of 2×YT medium (containing 50 mg/L ampicillin and 50 mg/L kanamycin), and cultured at 30° C. and at 200 rpm for 12 hours or more, to allow phages to be produced in the culture supernatant.

The resultant was centrifuged twice at 10,000 g and at 4° C. for 15 minutes, and the supernatant was collected as a phage library. Subsequently, the phage library is concentrated by PEG precipitation, and then dispersed in 1 ml of 1×PBS.

<2-3. Panning>

Example 2

Panning was carried out as follows, using the phage library prepared in the above section 2-2, and the human serum-derived IgG polyclonal antibody-immobilized MLVs prepared in the above section 2-1.

(Rounds)

Operations to be carried out in each of the rounds will be described.

To a 1.5 ml eppendorf tube, 1 ml of 2% BSA-PBS was added, and blocking was carried out at room temperature for one hour or more. The above described blocking was performed for all the tubes to be used. The human serum-derived IgG polyclonal antibody-immobilized MLVs were added in an amount to achieve an IgG content of 10 µg, followed by vortexing. Following centrifugation at 20,000 g and at 4° C. for two minutes, the supernatant was removed. The phage library diluted 10-fold with 1 ml of 2% BSA-PBS was added to the resultant, and the mixture was incubated overnight at 4° C. under inversion rotation.

Subsequently, the resultant was centrifuged at 20,000 g at 4° C. for two minutes, and the supernatant was removed. A quantity of 1 ml of 2% BSA-PBS was added to the resultant for suspension, and the mixture was transferred to another eppendorf tube. An operational process consisting of the above described centrifugation, removal of supernatant, suspension with 2% BSA-PBS, and transfer to another eppendorf tube, as one unit, was repeated three times in total.

(Recovery of Phages Selected by Panning)

Subsequently, the tube was centrifuged at 20,000 g and at 4° C. for two minutes, and the supernatant was removed. A quantity of 0.9 ml of 10 mM glycine-HCl (pH 1.5) was added to the tube for suspension, and the resulting solution was transferred to another eppendorf tube. The tube was incubated at 4° C. for 10 minutes under inversion rotation, thereby eluting the phages.

The resultant was centrifuged at 20,000 g and at 4° C. for two minutes, and the supernatant was transferred to another eppendorf tube. Further, 0.1 ml of 2M Tris-HCl (pH 8.0) was added to the resultant, thereby neutralizing the phage eluent.

To the neutralized phage eluent, 1 ml of the culture liquid of *Escherichia coli* TG1 cells which had been cultured in advance, which cells were in the middle stage of the exponential growth, were added, followed by incubation at 37° C. for 30 minutes.

The resulting solution was suspended in 2×YT medium (containing 1% glucose and 50 mg/L ampicillin), followed by culturing at 30° C. with shaking at 200 rpm. After growing the cells until the OD reached around 1.0, VCSM13 was added to the cells so as to achieve a multiplicity of infection (MOI) of 20, and the mixture was incubated at 37° C. for 30 minutes, followed by centrifugation at 3,000 g and at 30° C. for 10 minutes.

Following centrifugation at 1,500 rpm and at 30° C. for 15 minutes, the supernatant was removed, and the *E. coli* cells were suspended in 50 ml of 2×YT medium (containing 50 mg/L ampicillin and 50 mg/L kanamycin). Thereafter, the cells were cultured at 200 rpm and at 30° C. for 12 hours, to allow phages to be produced in the culture supernatant.

Subsequently, the resultant was centrifuged at 20,000 g at 4° C. for two minutes, the supernatant was collected, and PEG precipitation was carried out (twice), followed by dispersion in 1 ml of PBS. Finally, the resulting dispersion was centrifuged at 20,000 g and at 4° C. for two minutes, and the supernatant was collected as a phage solution.

A series of operations up to this point are defined as one round. When the above described operations were carried out, it is regarded that Round 1 has been completed.

Thereafter, the above described round was repeated two more times. In other words, the procedure up to Round 3 was carried out. From the colonies obtained in each of the rounds, phagemid DNAs were recovered.

Comparative Example 2

The same procedure as in Example 2 was carried out as Comparative Example 2, except that multilamellar liposomes which had not been coupled with the human serum-derived IgG polyclonal antibody were used.

<2-4. Recovery of Phages to Gene Sequencing>

The presence or absence of the genes of the anti-human serum-derived IgG polyclonal antibody-rabbit-derived single-chain antibodies was confirmed in the phagemid DNAs recovered in Example 2 and Comparative Example 2.

The obtained phagemid DNAs were separated by electrophoresis using 1% agarose gel, and visualized by ethidium bromide staining. The migration distances of the phagemid DNAs were compared against the migration distance of the DNA of the phagemid vector (pPLFMAA250gIIIp) into which none of the genes of the anti-human serum-derived IgG polyclonal antibody-rabbit-derived single-chain antibodies was inserted, and the presence or absence of the genes of the anti-human serum-derived IgG polyclonal antibody-rabbit-derived single-chain antibodies was visually confirmed. The sequencing of the phagemid vectors in which the insertion of the genes was confirmed was carried out by DNA sequence analysis (by a commissioned service).

The determination of the CDRs in the above genes was carried out using Vquest search engine available at IMGT (http://www.imgt.org/).

<2-5. Panning Results>

Figure 2:
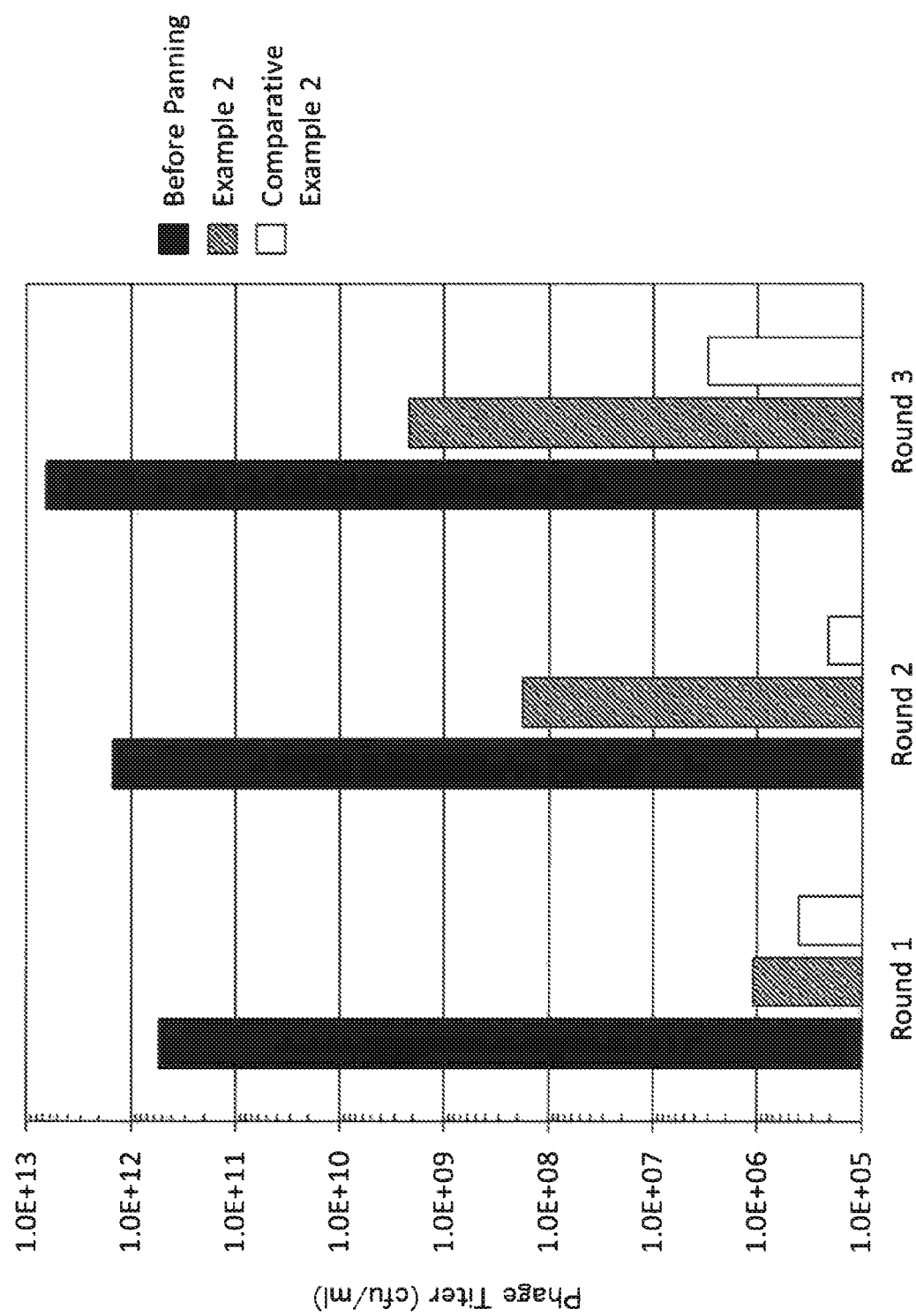
FIG. 2 is a graph showing the number of phages before panning, at the completion of Round 1, at the completion of Round 2, and at the completion of Round 3, in each of Example 2 and Comparative Example 2.

FIG. 2 shows the number of phages before the panning, at the completion of Round 1, at the completion of Round 2, and at the completion of Round 3, in each of Example 2 and Comparative Example 2.

Figure 3:
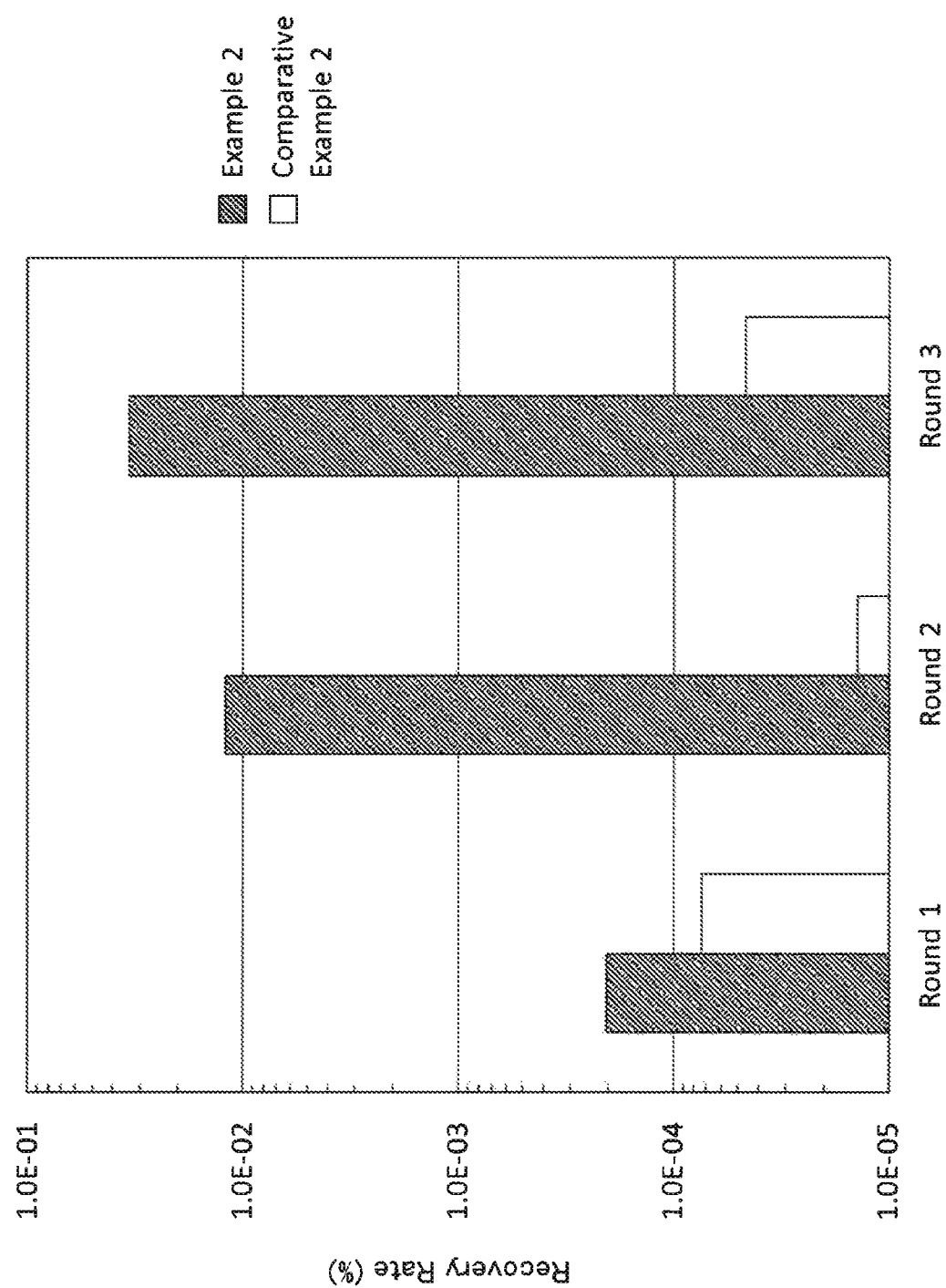
FIG. 3 is a graph showing the recovery rate (%), obtained by dividing each of the numbers of phages at the completion of Round 1, at the completion of Round 2, and at the completion of Round 3 by the number of phages before the panning in each round, in Example 2 and Comparative Example 2.

FIG. 3 shows the recovery rate (%), obtained by dividing each of the numbers of phages at the completion of Round 1, at the completion of Round 2, and at the completion of Round 3 by the number of phages before the panning in each round, in Example 2 and Comparative Example 2.

The above results revealed that, in Example 2, a marked increase in the recovery rate was already observed at the completion of Round 2. It is to be noted that, in the method using a common immunotube, such a high recovery rate (%) cannot be obtained at least until the completion of Round 3 to Round 4. In other words, it has been found out that the use of multilamellar liposomes allows for a markedly efficient panning as compared to using a conventional technique.

<3-1. Evaluation of Antigen-Binding Activity 1>

Example 3-1

For the rabbit-derived single-chain antibodies obtained from the pellet portion of the phagemid-containing *Escherichia coli* cells (namely, the entire phages contained in the *Escherichia coli* cells which did not form single colonies and contained in the pellets) collected in each of the rounds, the evaluation of the antigen-binding activity was carried out as follows.

To Maxisorp (registered trademark) (manufactured by Thermo Fisher Scientific) plates, 100 μl of PBS was added, such that a human IgG1 (#I5154; manufactured by Sigma-Aldrich Co. LLC.), a human IgG2 (#I5404; manufactured by Sigma-Aldrich Co. LLC.), a human IgG3 (#I5654; manufactured by Sigma-Aldrich Co. LLC.), a human IgG4 (#I4639; manufactured by Sigma-Aldrich Co. LLC.), and a human IgA (#I4036; manufactured by Sigma-Aldrich Co. LLC.), each achieved a final concentration of 5 μg/ml, and the plates were incubated overnight at 4° C. (immobilization of antigen).

Subsequently, the antigen-immobilized plates were washed with PBS, and 300 μl of 10% Blocking One-PBS (manufactured by Nakalai Tesque, Inc.) was added to the plates. The plates were then incubated at 25° C. for one hour (blocking), and washed with PBST.

Meanwhile, to 25 ml of each of the phagemid-containing *Escherichia coli* pellets obtained before the panning, at the completion of Round 1, at the completion of Round 2, and at the completion of Round 3 in Example 2, 2.5 ml of Bugbuster (registered trademark) (manufactured by Merck KGaA) and 2.5 μL Benzonase Nuclease (registered trademark) (manufactured by Merck KGaA) were added to lyse the cells. Then, the resultants were centrifuged at 10,000 g and at 4° C. for 15 minutes, and the supernatants were collected.

The supernatants were each diluted 10-fold with 10% Blocking One-PBST, and 100 μl each of the diluted supernatants were added to the above described plates which had been blocked and washed with PBST, followed by incubation at 25° C. for one hour.

Subsequently, the plates were washed with PBST, and 100 μl of an HRP-labeled anti-c-myc antibody diluted 10,000-fold with 10% Blocking One-PBST was added to each of the plates, followed by incubation at 25° C. for one hour.

The plates were then washed with PBST, and 100 μl of a TMB solution was added to each plate, followed by incubation for five minutes. Thereafter, 100 μl of 0.3 M sulfuric acid was added to each plate to terminate the reaction.

The absorbance at 450 nm was measured using a microplate reader. At this time, a wavelength of 650 nm was used as the secondary wavelength.

Figure 4:
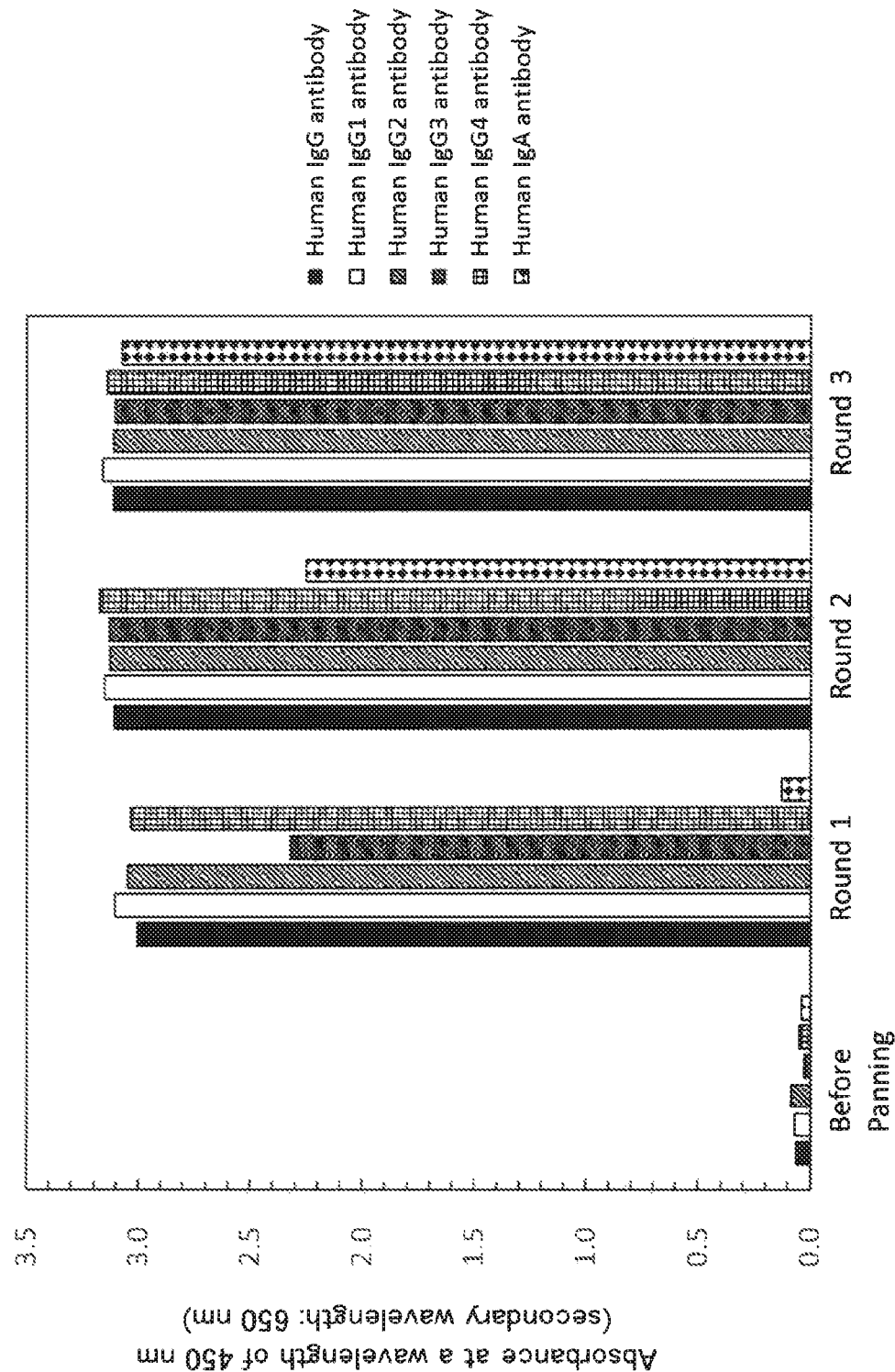
FIG. 4 is a graph showing the absorbance at a wavelength of 450 nm (secondary wavelength: 650 nm), when the evaluation of the antigen-binding activity was carried out for the pellet portion of phagemid-containing *Escherichia coli* cells collected before the panning, at the completion of Round 1, at the completion of Round 2, and at the completion of Round 3 in Example 2.

The results are shown in FIG. 4. It can be seen from FIG. 4 that a high absorbance, which indicates a high binding activity, was observed by performing just one round of panning operation, for each of the human IgG1 antibody, the human IgG2 antibody, the human IgG3 antibody, and the human IgG4 antibody. In other words, it has been found out that phages which specifically bind to the antigens are concentrated by carrying out just one round of the panning operation.

Further, it has been confirmed that the phages which also bind specifically to the human IgA antibody, in addition to the human IgG1 antibody, the human IgG2 antibody, the human IgG3 antibody, and the human IgG4 antibody, are concentrated at the completion of Round 2.

<3-2. Evaluation of Antigen-Binding Activity 2>

Example 3-2

The evaluation of the antigen-binding activity was carried out for the rabbit-derived single-chain antibodies obtained from the colonies of the phagemid-containing *Escherichia coli* cells collected in each of the rounds, as follows.

Each of the colonies of the phagemid-containing *Escherichia coli* cells collected before the panning, at the completion of Round 1, at the completion of Round 2, and at the completion of Round 3 in Example 2 was inoculated in a well of a 96-well deep well plate, in 1 ml of Overnight Express (registered trademark; manufactured by Merck KGaA) medium, and cultured at 1,600 rpm and at 30° C. for 24 hours, followed by centrifugation to remove the supernatant. To each of the resultants, 0.2 ml of Bugbuster and 0.2 μL of Benzonase Nuclease were added to lyse the cells. The resulting lysates were then centrifuged, and the supernatants were collected. The subsequent operations are the same as those described in the above section 3-1.

Figure 5:
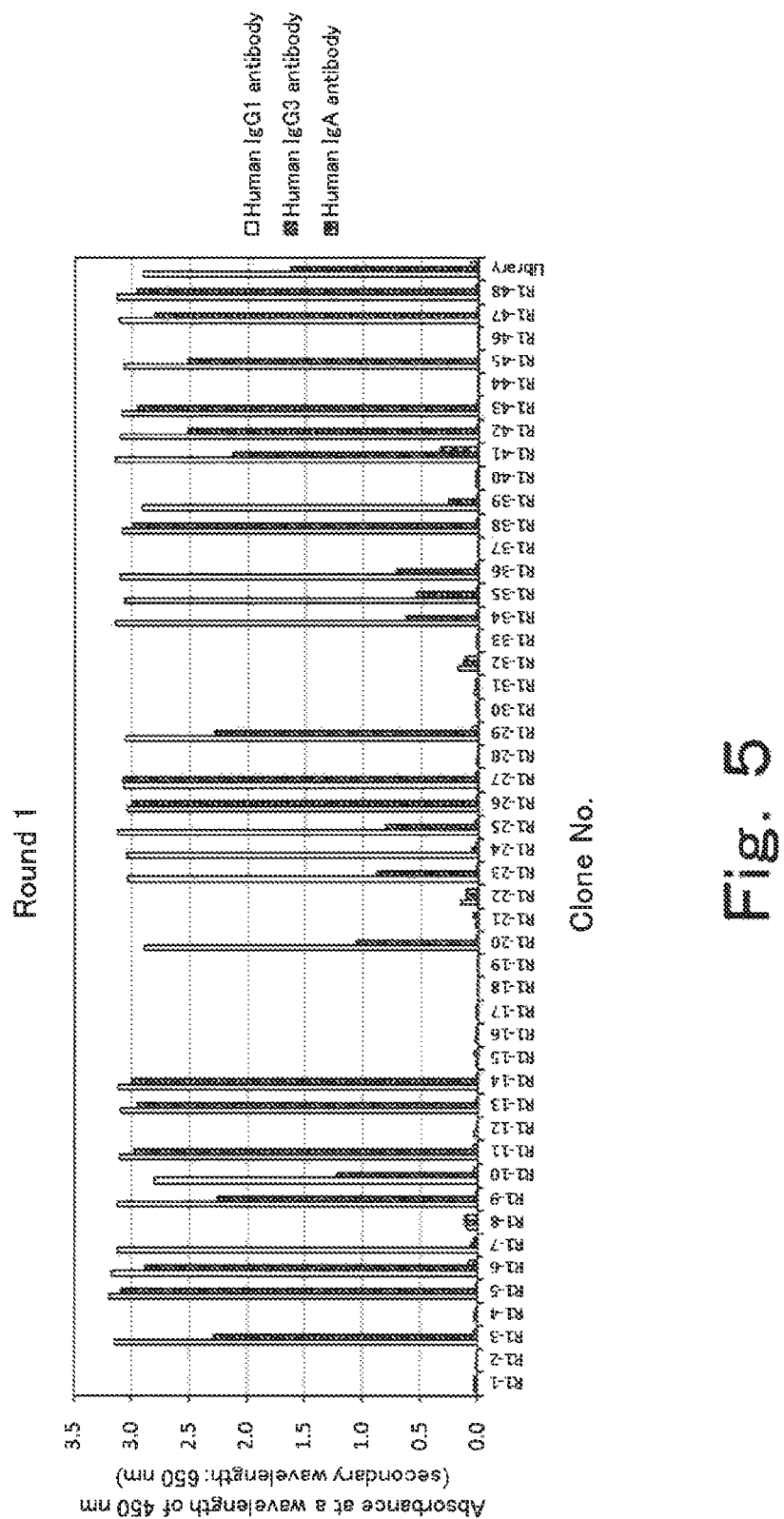
FIG. 5 is a graph showing the results of the antigen-binding activity evaluation carried out for rabbit-derived single-chain antibodies obtained from 48 colonies collected at the completion of Round 1 in Example 3-2.

FIG. 5, Table 4-1, and Table 4-2 show the evaluation results of the antigen-binding activities of the rabbit-derived single-chain antibodies obtained from 48 colonies collected at the completion of Round 1. Note that the "Library" in each of the FIGS. and Tables represents the results of the antigen-binding activity evaluation carried out for the rabbit-derived single-chain antibodies obtained from the pellet portion of the phagemid-containing *Escherichia coli* cells (namely, the entire phages contained in the *Escherichia coli* cells which did not form single colonies and contained in the pellets). The clones having an OD value of 0.1 or more were defined as positive clones, and those having an OD of less than 0.1 were defined as negative clones.

It is also noted that, regarding the names of the clones obtained by the method for screening a rabbit-derived single-chain antibody which binds to a human serum-derived IgG polyclonal antibody, the clone of "Clone No. 1 obtained at the completion of Round 1", for example, is sometimes referred to as "R1-1" or "I-1" in abbreviation. In the same manner, the clone of "Clone No. 1 obtained at the completion of Round 2", for example, is sometimes referred to as "R2-1" or "II-1", and the clone of "Clone No. 1 obtained at the completion of Round 3" is sometimes referred to as "R3-1" or "III-1", in abbreviation.

TABLE 4-1

| Clone No. | IgG1 | IgG3 | IgA |
| --- | --- | --- | --- |
| R1-1 | 0.0330 | 0.0290 | 0.0330 |
| R1-2 | 0.0200 | 0.0150 | 0.0160 |
| R1-3 | 3.1470 | 2.2850 | 0.0410 |
| R1-4 | 0.0300 | 0.0290 | 0.0250 |
| R1-5 | 3.1910 | 3.0870 | 0.0230 |
| R1-6 | 3.1740 | 2.8820 | 0.0780 |
| R1-7 | 3.1240 | 0.0660 | 0.0360 |
| R1-8 | 0.1010 | 0.1200 | 0.1200 |
| R1-9 | 3.1220 | 2.2560 | 0.0200 |
| R1-10 | 2.8020 | 1.2220 | 0.0360 |
| R1-11 | 3.1100 | 2.9800 | 0.0480 |
| R1-12 | 0.0350 | 0.0230 | 0.0140 |
| R1-13 | 3.1020 | 2.9500 | 0.0200 |
| R1-14 | 3.1160 | 3.0010 | 0.0220 |
| R1-15 | 0.0170 | 0.0130 | 0.0360 |
| R1-16 | 0.0310 | 0.0240 | 0.0240 |
| R1-17 | 0.0220 | 0.0200 | 0.0230 |

TABLE 4-1-continued

| Clone No. | IgG1 | IgG3 | IgA |
|---|---|---|---|
| R1-18 | 0.0160 | 0.0090 | 0.0120 |
| R1-19 | 0.0110 | 0.0100 | 0.0090 |
| R1-20 | 2.8940 | 1.0570 | 0.0190 |
| R1-21 | 0.0270 | 0.0150 | 0.0450 |
| R1-22 | 0.1530 | 0.1110 | 0.1040 |
| R1-23 | 3.0390 | 0.8750 | 0.0170 |
| R1-24 | 3.0480 | 0.0530 | 0.0270 |
| R1-25 | 3.1200 | 0.7990 | 0.0310 |
| R1-26 | 3.0350 | 3.0000 | 0.0200 |
| R1-27 | 3.0730 | 3.0820 | 0.0290 |
| R1-28 | 0.0170 | 0.0100 | 0.0140 |
| R1-29 | 3.0530 | 2.2800 | 0.0530 |
| R1-30 | 0.0190 | 0.0170 | 0.0290 |
| R1-31 | 0.0360 | 0.0300 | 0.0340 |
| R1-32 | 0.1900 | 0.1350 | 0.1150 |
| R1-33 | 0.0170 | 0.0180 | 0.0170 |
| R1-34 | 3.1380 | 0.6290 | 0.0250 |
| R1-35 | 3.0660 | 0.5400 | 0.0170 |
| R1-36 | 3.1030 | 0.7110 | 0.0310 |
| R1-37 | 0.0080 | 0.0080 | 0.0120 |
| R1-38 | 3.0930 | 2.9980 | 0.0210 |
| R1-39 | 2.9170 | 0.2600 | 0.0170 |
| R1-40 | 0.0330 | 0.0330 | 0.0320 |
| R1-41 | 3.1450 | 2.1250 | 0.3290 |
| R1-42 | 3.1050 | 2.5150 | 0.0170 |
| R1-43 | 3.0910 | 2.9530 | 0.0200 |
| R1-44 | 0.0090 | 0.0060 | 0.0120 |
| R1-45 | 3.0720 | 2.5140 | 0.0130 |
| R1-46 | 0.0080 | 0.0070 | 0.0130 |
| R1-47 | 3.1160 | 2.8050 | 0.0190 |
| R1-48 | 3.1370 | 2.9600 | 0.0290 |
| Library | 2.9090 | 1.6280 | 0.0710 |

TABLE 4-2

|  | IgG1 | IgG3 | IgA |
|---|---|---|---|
| Number of positive clones | 30 | 28 | 4 |
| Number of negative clones | 18 | 20 | 44 |
| The ratio of the number of positive clones with respect to the total 48 clones (%) | 62.5 | 58.3 | 8.3 |
| OD ≥ 2.5 | 27 | 13 | 0 |
| 1 ≤ OD < 2.5 | 0 | 6 | 0 |
| 0.1 ≤ OD < 1 | 3 | 9 | 4 |

Figure 6:
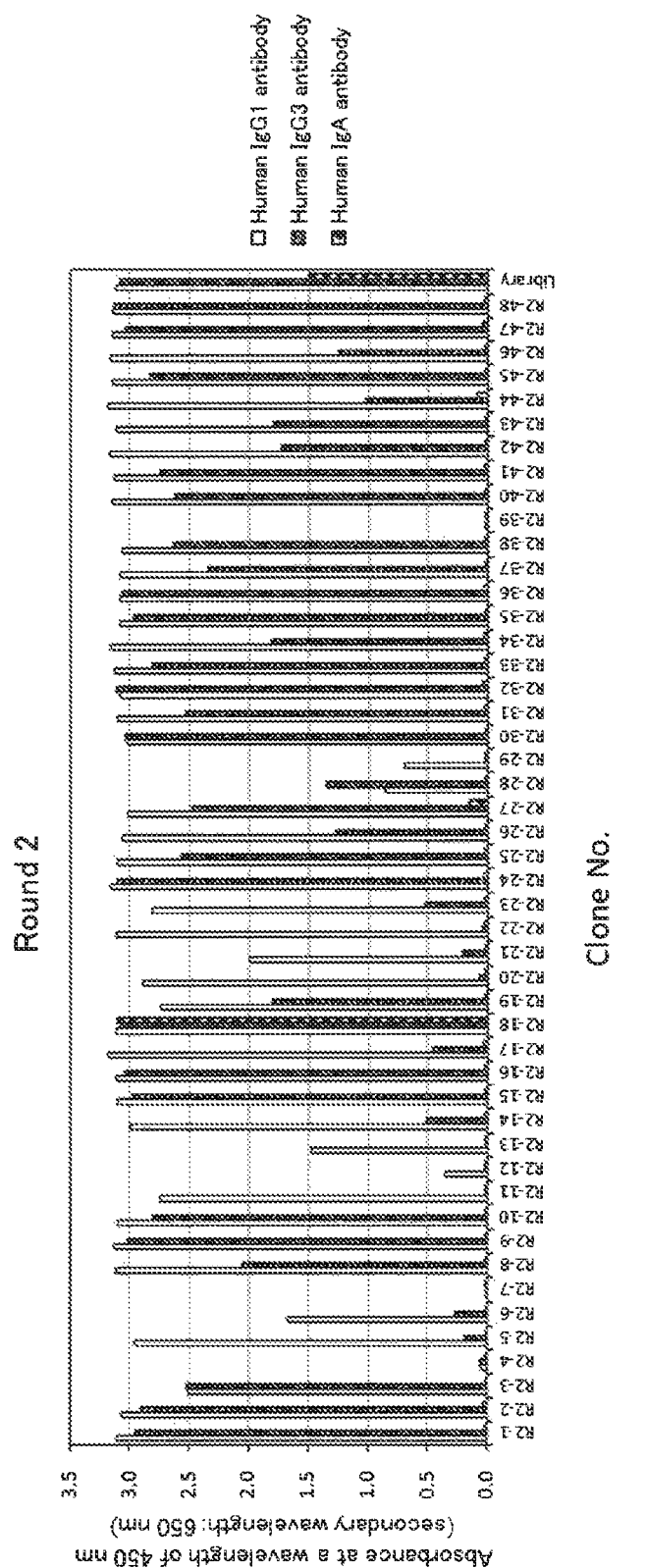
FIG. 6 is a graph showing the results of the antigen-binding activity evaluation carried out for rabbit-derived single-chain antibodies obtained from 48 colonies collected at the completion of Round 2 in Example 3-2.

In the same manner as above, FIG. 6, Table 5-1, and Table 5-2 show the evaluation results of the antigen-binding activities of the rabbit-derived single-chain antibodies obtained from 48 colonies collected at the completion of Round 2. Here, the evaluation results of the binding activities for the human IgG1 antibody, the human IgG3 antibody, and the human IgA antibody are shown. Note that the "Library" in each of the FIGS. and Tables represents, in the same manner as described above, the results of the antigen-binding activity evaluation carried out for the rabbit-derived single-chain antibodies obtained from the pellet portion of the phagemid-containing *Escherichia coli* cells (namely, the entire phages contained in the *Escherichia coli* cells which did not form single colonies and contained in the pellets). The clones having an OD value of 0.1 or more were defined as positive clones, and those having an OD of less than 0.1 were defined as negative clones.

TABLE 5-1

| Clone No. | IgG1 | IgG3 | IgA |
|---|---|---|---|
| R2-1 | 3.1060 | 2.9480 | 0.0250 |
| R2-2 | 3.0650 | 2.9030 | 0.0370 |
| R2-3 | 2.5150 | 2.5170 | 0.0100 |
| R2-4 | 0.0490 | 0.0630 | 0.0160 |
| R2-5 | 2.9640 | 0.1920 | 0.0130 |
| R2-6 | 1.6750 | 0.2710 | 0.0120 |
| R2-7 | 0.0090 | 0.0090 | 0.0140 |
| R2-8 | 3.1140 | 2.0550 | 0.0190 |
| R2-9 | 3.1330 | 3.0210 | 0.0200 |
| R2-10 | 3.1010 | 2.8040 | 0.0210 |
| R2-11 | 2.7430 | 0.0210 | 0.0180 |
| R2-12 | 0.3590 | 0.0300 | 0.0150 |
| R2-13 | 1.4750 | 0.0130 | 0.0170 |
| R2-14 | 2.9970 | 0.5070 | 0.0220 |
| R2-15 | 3.1040 | 2.9740 | 0.0200 |
| R2-16 | 3.1150 | 3.0470 | 0.0260 |
| R2-17 | 3.1850 | 0.4590 | 0.0350 |
| R2-18 | 3.1140 | 3.0750 | 3.1080 |
| R2-19 | 2.7350 | 1.8010 | 0.0210 |
| R2-20 | 2.8910 | 0.0680 | 0.0190 |
| R2-21 | 1.9870 | 0.2040 | 0.0160 |
| R2-22 | 3.1160 | 0.0400 | 0.0250 |
| R2-23 | 2.8150 | 0.5180 | 0.0220 |
| R2-24 | 3.1600 | 3.1080 | 0.0380 |
| R2-25 | 3.1110 | 2.5610 | 0.0270 |
| R2-26 | 3.0630 | 1.2730 | 0.0180 |
| R2-27 | 3.0220 | 2.4760 | 0.1570 |
| R2-28 | 0.8610 | 1.3530 | 0.0210 |
| R2-29 | 0.6900 | 0.0170 | 0.0180 |
| R2-30 | 3.0180 | 3.0400 | 0.0210 |
| R2-31 | 3.1040 | 2.5360 | 0.0220 |
| R2-32 | 3.0850 | 3.1180 | 0.0470 |
| R2-33 | 3.1310 | 2.8100 | 0.0240 |
| R2-34 | 3.1600 | 1.8090 | 0.0360 |
| R2-35 | 3.0810 | 2.9710 | 0.0200 |
| R2-36 | 3.0860 | 3.0690 | 0.0310 |
| R2-37 | 3.0820 | 2.3490 | 0.0170 |
| R2-38 | 3.0670 | 2.6320 | 0.0180 |
| R2-39 | 0.0170 | 0.0110 | 0.0150 |
| R2-40 | 3.1540 | 2.6190 | 0.0200 |
| R2-41 | 3.1320 | 2.7460 | 0.0300 |
| R2-42 | 3.1680 | 1.7200 | 0.0210 |
| R2-43 | 3.1190 | 1.7940 | 0.0200 |
| R2-44 | 3.1840 | 1.0250 | 0.0830 |
| R2-45 | 3.1430 | 2.8320 | 0.0180 |
| R2-46 | 3.1590 | 1.2460 | 0.0180 |
| R2-47 | 3.1440 | 3.0400 | 0.0420 |
| R2-48 | 3.1430 | 3.1320 | 0.0260 |
| Library | 3.1130 | 3.0780 | 1.4940 |

TABLE 5-2

|  | IgG1 | IgG3 | IgA |
|---|---|---|---|
| Number of positive clones | 45 | 39 | 2 |
| Number of negative clones | 3 | 9 | 46 |
| The ratio of the number of positive clones with respect to the total 48 clones (%) | 93.8 | 81.3 | 4.2 |
| OD ≥ 2.5 | 39 | 22 | 1 |
| 1 ≤ OD < 2.5 | 3 | 11 | 0 |
| 0.1 ≤ OD < 1 | 3 | 6 | 1 |

Figures 1, 7:
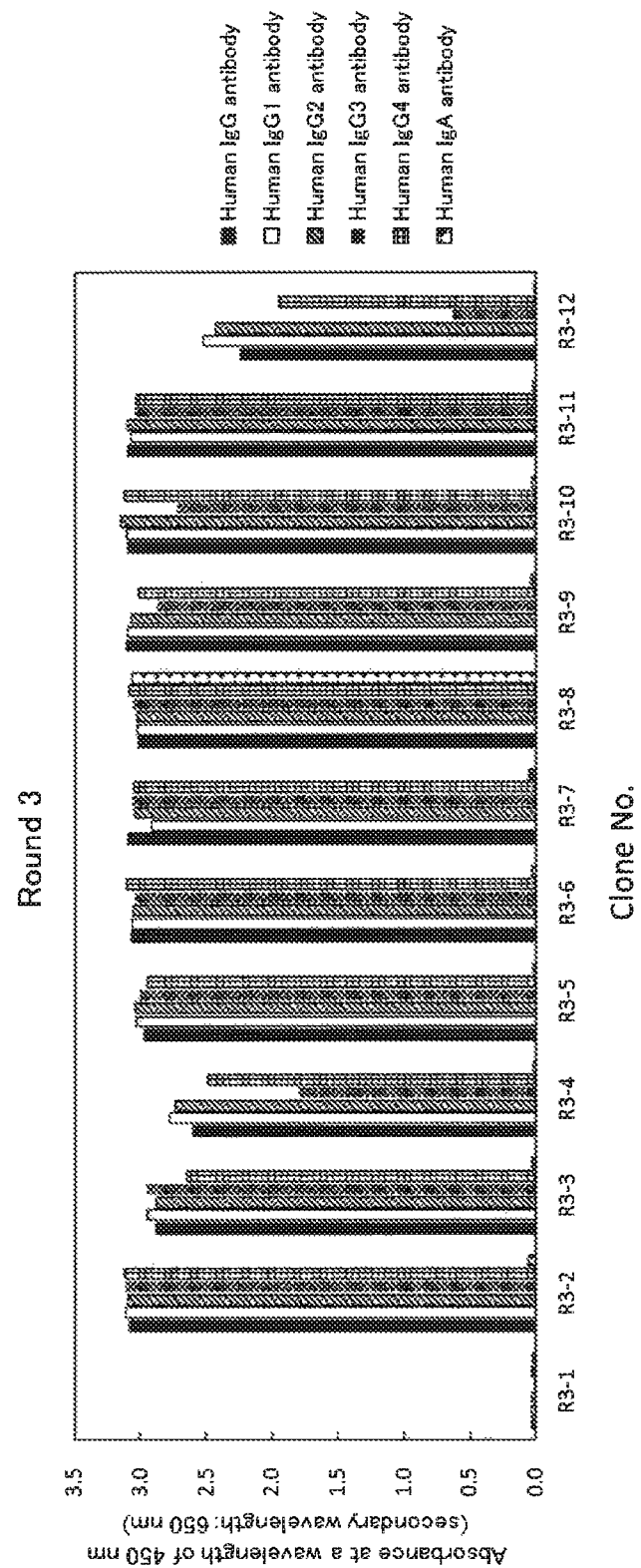
Figures 2, 7:
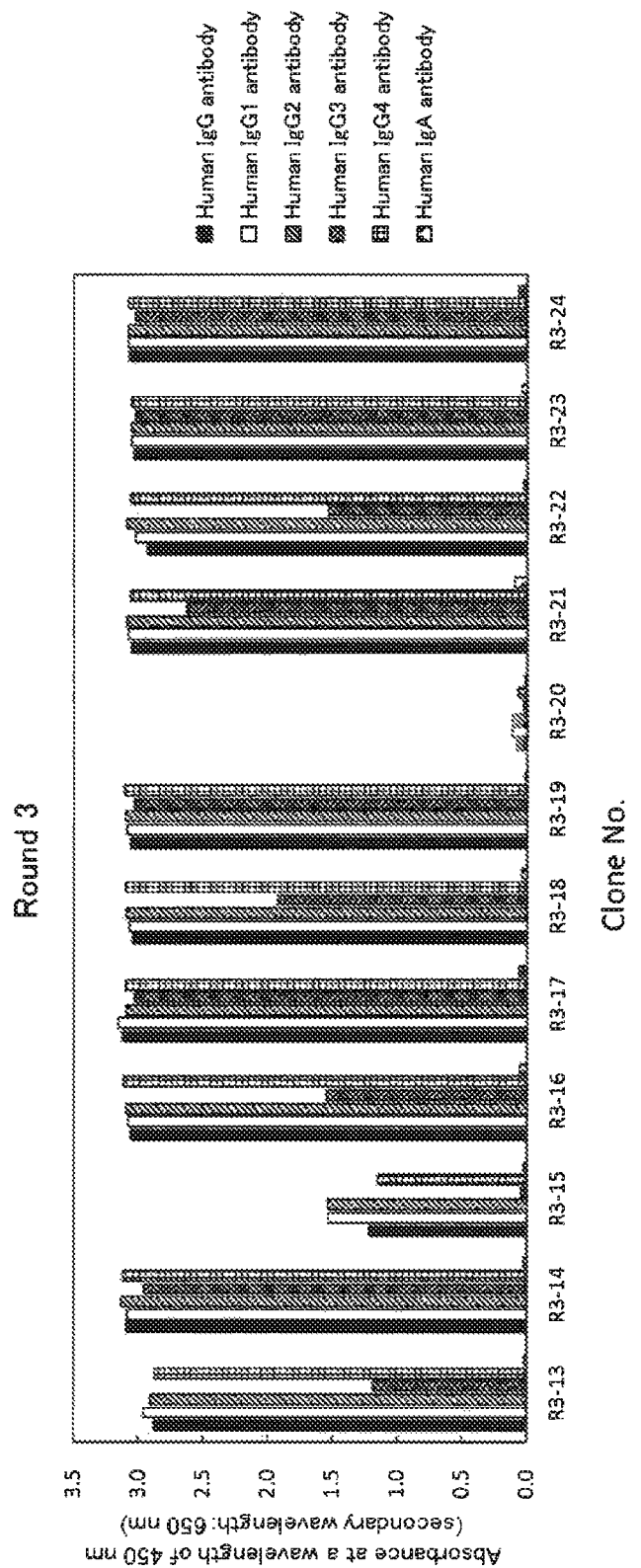
Figures 3, 7:
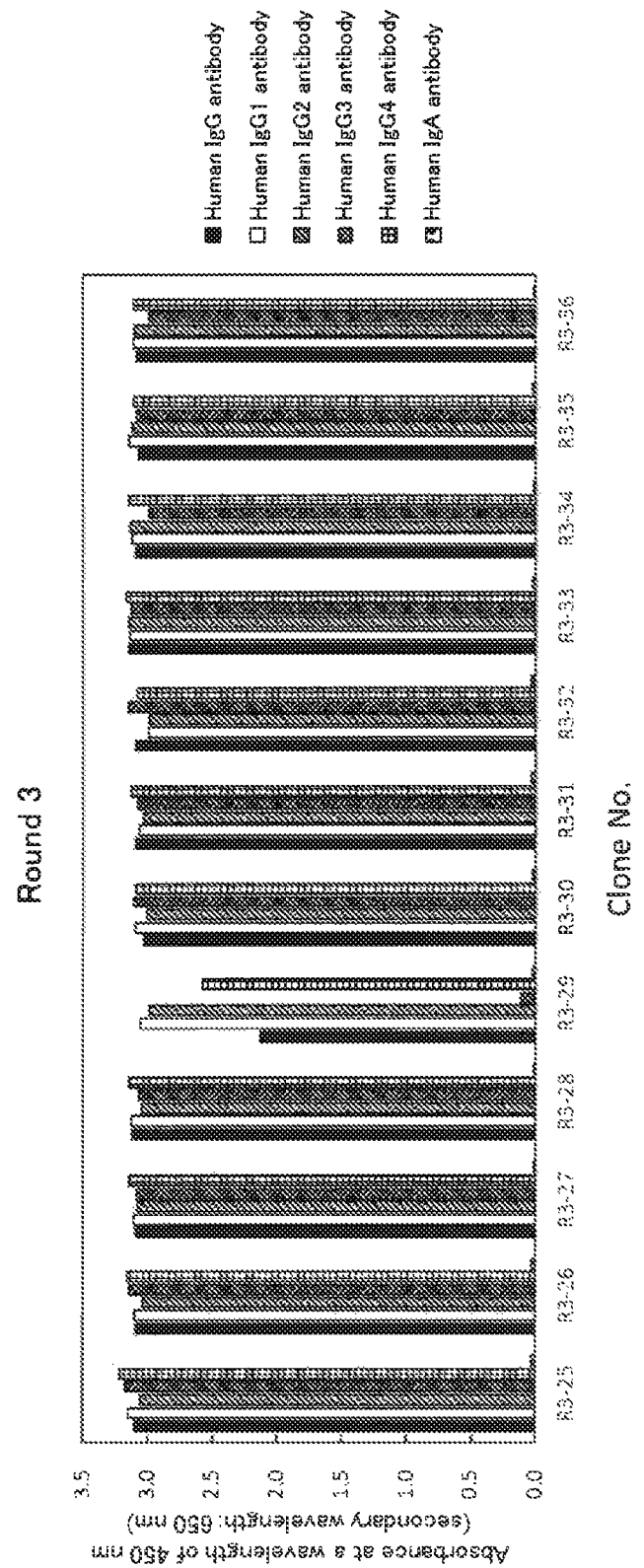
Figures 4, 7:
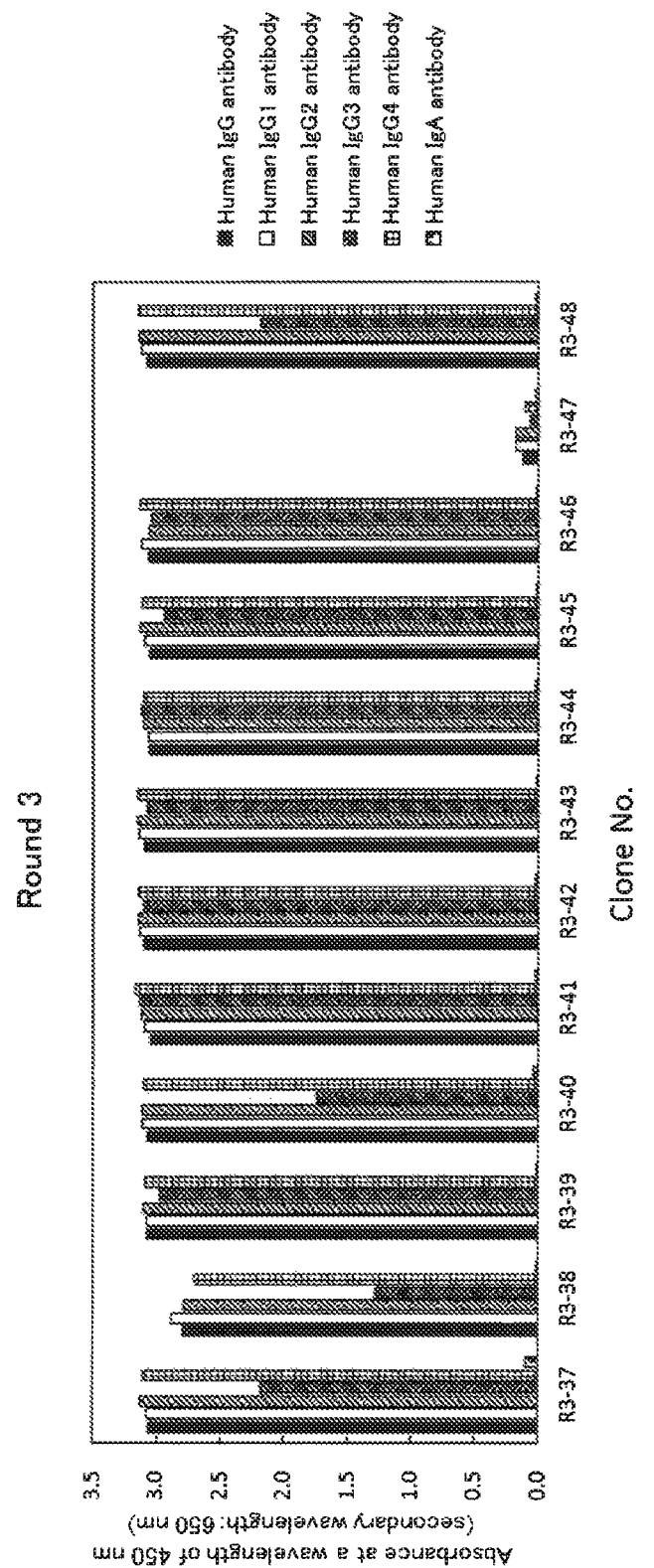
Figures 5, 7:
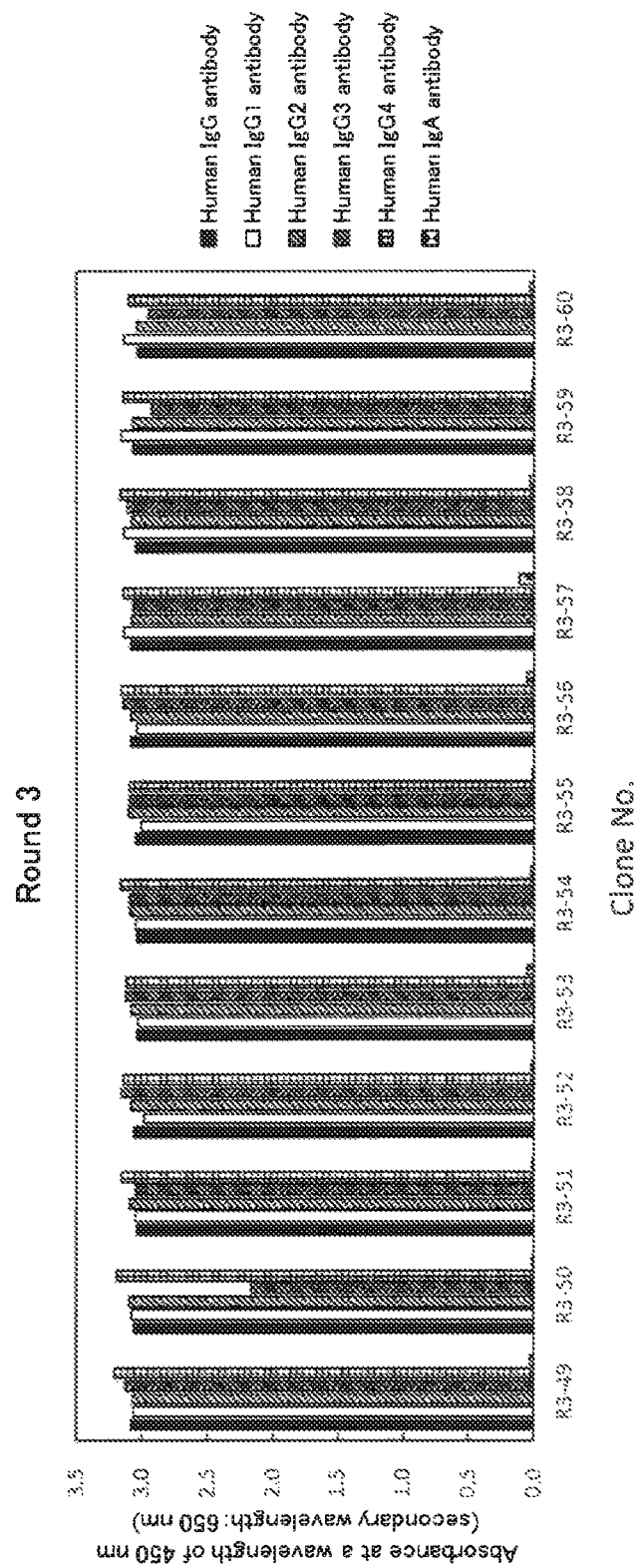
Figures 6, 7:
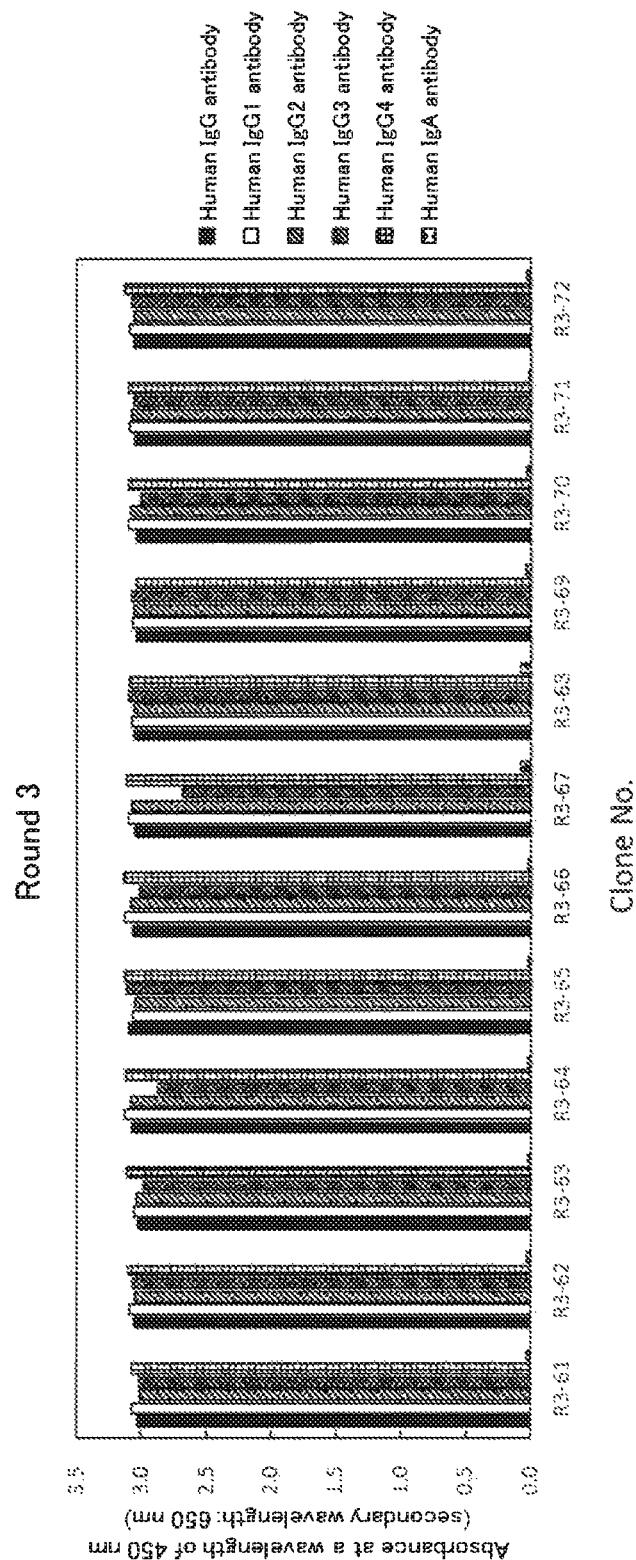
Figure 7:
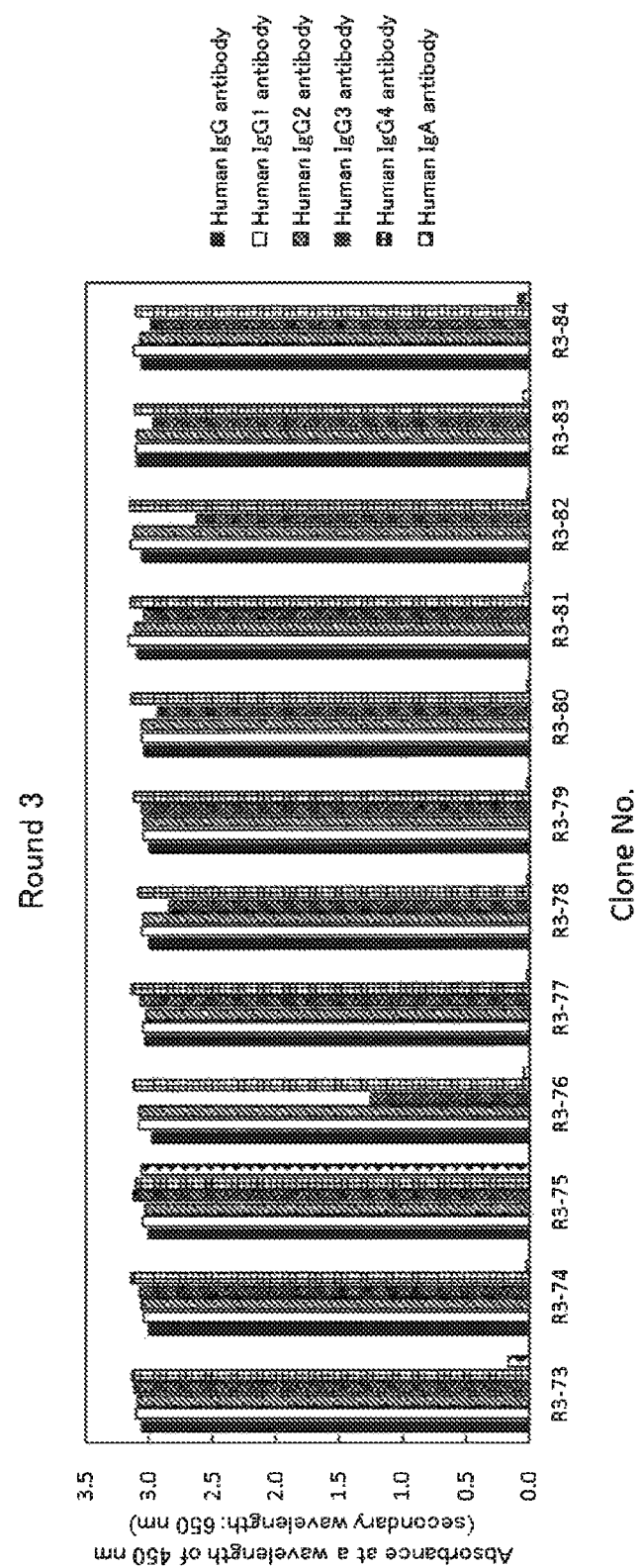
Figures 7, 8:
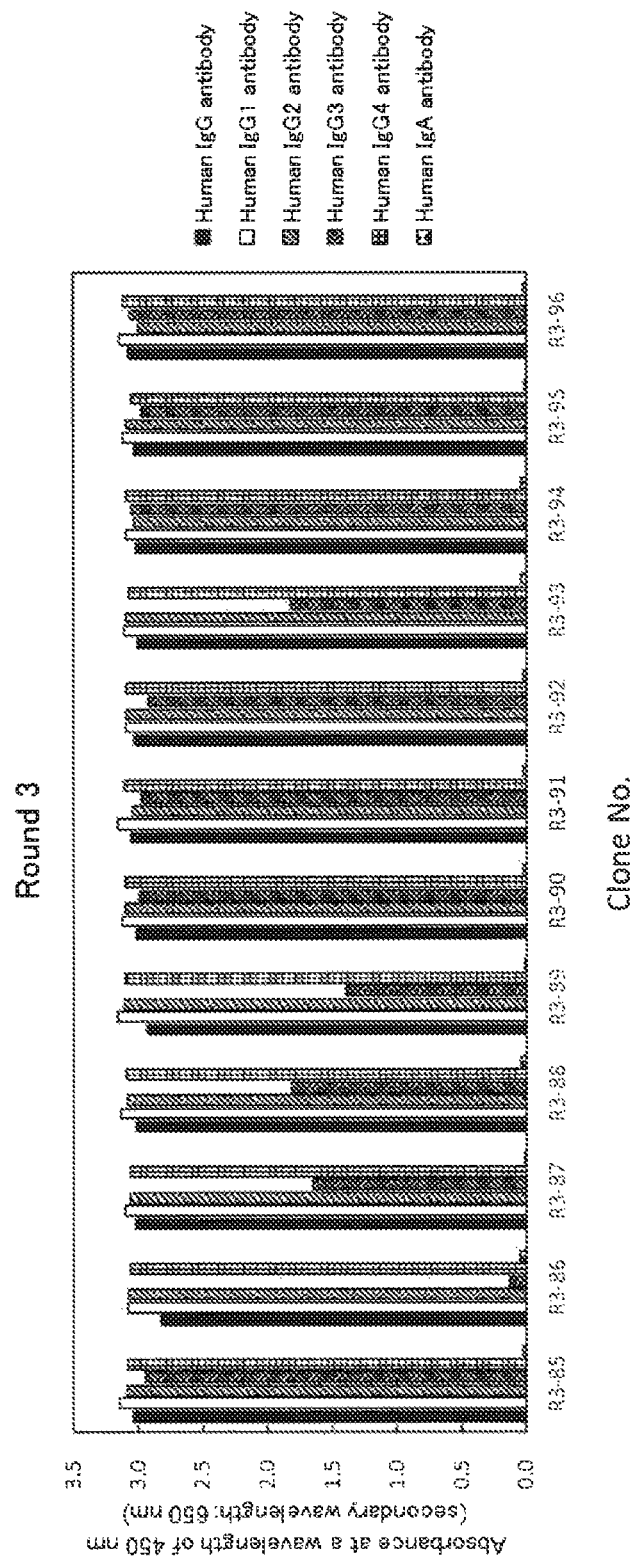

In the same manner as above, FIG. 7-1 to FIG. 7-8, Table 6-1 to Table 6-5 show the evaluation results of the antigen-binding activities of the rabbit-derived single-chain antibodies obtained from 96 colonies collected at the completion of Round 3. The clones having an OD value of 0.1 or more were defined as positive clones, and those having an OD of less than 0.1 were defined as negative clones.

TABLE 6-1

| Clone No. | IgG | IgG1 | IgG2 | IgG3 | IgG4 | IgA |
|---|---|---|---|---|---|---|
| R3-1 | 0.0310 | 0.0370 | 0.0360 | 0.0180 | 0.0370 | 0.0240 |
| R3-2 | 3.0800 | 3.1090 | 3.0940 | 3.1140 | 3.1180 | 0.0590 |
| R3-3 | 2.8830 | 2.9510 | 2.8880 | 2.9560 | 2.6520 | 0.0340 |
| R3-4 | 2.5980 | 2.7860 | 2.7350 | 1.7970 | 2.4910 | 0.0260 |
| R3-5 | 2.9690 | 3.0340 | 3.0400 | 3.0120 | 2.9450 | 0.0280 |
| R3-6 | 3.0750 | 3.0610 | 3.0590 | 3.0430 | 3.1060 | 0.0380 |
| R3-7 | 3.0980 | 2.9180 | 3.0420 | 3.0640 | 3.0510 | 0.0550 |
| R3-8 | 3.0140 | 3.0280 | 3.0250 | 3.0600 | 3.0920 | 3.0630 |
| R3-9 | 3.1070 | 3.0960 | 3.0760 | 2.8800 | 3.0170 | 0.0420 |
| R3-10 | 3.0930 | 3.1050 | 3.1540 | 2.7160 | 3.1220 | 0.0310 |
| R3-11 | 3.0930 | 3.0690 | 3.0950 | 3.0400 | 3.0350 | 0.0280 |
| R3-12 | 2.2380 | 2.5210 | 2.4300 | 0.6300 | 1.9520 | 0.0200 |
| R3-13 | 2.8830 | 2.9640 | 2.9040 | 1.1880 | 2.8740 | 0.0200 |
| R3-14 | 3.0970 | 3.0880 | 3.1320 | 2.9640 | 3.1210 | 0.0280 |
| R3-15 | 1.2220 | 1.5330 | 1.5390 | 0.0480 | 1.1510 | 0.0280 |
| R3-16 | 3.0640 | 3.0810 | 3.0930 | 1.5460 | 3.1160 | 0.0610 |
| R3-17 | 3.1290 | 3.1580 | 3.0970 | 3.0340 | 3.1070 | 0.0650 |
| R3-18 | 3.0470 | 3.0680 | 3.0980 | 1.9300 | 3.1070 | 0.0400 |
| R3-19 | 3.0610 | 3.0910 | 3.1060 | 3.0340 | 3.1140 | 0.0230 |
| R3-20 | 0.0820 | 0.1120 | 0.1160 | 0.0310 | 0.0730 | 0.0180 |
| R3-21 | 3.0520 | 3.0760 | 3.0870 | 2.6270 | 3.0640 | 0.0970 |
| R3-22 | 2.9310 | 3.0260 | 3.0840 | 1.5340 | 3.0600 | 0.0240 |
| R3-23 | 3.0370 | 3.0550 | 3.0560 | 3.0220 | 3.0560 | 0.0440 |
| R3-24 | 3.0680 | 3.0780 | 3.0790 | 3.0220 | 3.0820 | 0.0680 |

TABLE 6-2

| Clone No. | IgG | IgG1 | IgG2 | IgG3 | IgG4 | IgA |
|---|---|---|---|---|---|---|
| R3-25 | 3.1060 | 3.1460 | 3.0560 | 3.1750 | 3.2120 | 0.0320 |
| R3-26 | 3.0960 | 3.1000 | 3.0370 | 3.1440 | 3.1580 | 0.0370 |
| R3-27 | 3.0960 | 3.1090 | 3.0770 | 3.0890 | 3.1390 | 0.0220 |
| R3-28 | 3.1190 | 3.1290 | 3.0440 | 3.0720 | 3.1380 | 0.0220 |
| R3-29 | 2.1340 | 3.0510 | 2.9840 | 0.1170 | 2.5800 | 0.0260 |
| R3-30 | 3.0330 | 3.0940 | 3.0100 | 3.1070 | 3.0930 | 0.0300 |
| R3-31 | 3.0970 | 3.0660 | 3.0280 | 3.0780 | 3.1250 | 0.0370 |
| R3-32 | 3.0950 | 2.9880 | 2.9860 | 3.1500 | 3.0800 | 0.0380 |
| R3-33 | 3.1380 | 3.1370 | 3.1400 | 3.1270 | 3.1660 | 0.0260 |
| R3-34 | 3.0970 | 3.1190 | 3.1370 | 2.9870 | 3.1430 | 0.0200 |
| R3-35 | 3.0740 | 3.1400 | 3.1190 | 3.0850 | 3.1080 | 0.0280 |
| R3-36 | 3.0880 | 3.1110 | 3.1020 | 2.9920 | 3.1130 | 0.0180 |
| R3-37 | 3.0650 | 3.0820 | 3.1260 | 2.1810 | 3.1020 | 0.0940 |
| R3-38 | 2.7950 | 2.8820 | 2.7880 | 1.2760 | 2.7010 | 0.0180 |
| R3-39 | 3.0760 | 3.0750 | 3.1010 | 2.9760 | 3.0900 | 0.0190 |
| R3-40 | 3.0700 | 3.1080 | 3.1080 | 1.7450 | 3.1040 | 0.0400 |
| R3-41 | 3.0470 | 3.0970 | 3.1200 | 3.1280 | 3.1680 | 0.0270 |
| R3-42 | 3.1050 | 3.1300 | 3.1430 | 3.1020 | 3.1400 | 0.0200 |
| R3-43 | 3.0960 | 3.1390 | 3.1510 | 3.0700 | 3.1530 | 0.0190 |
| R3-44 | 3.0560 | 3.0620 | 3.1000 | 3.1210 | 3.1030 | 0.0220 |
| R3-45 | 3.0570 | 3.0920 | 3.1290 | 2.9400 | 3.1150 | 0.0160 |
| R3-46 | 3.0660 | 3.1220 | 3.0540 | 3.0390 | 3.1270 | 0.0170 |
| R3-47 | 0.1210 | 0.1750 | 0.1800 | 0.0630 | 0.1080 | 0.0250 |
| R3-48 | 3.0760 | 3.1180 | 3.1320 | 2.1820 | 3.1440 | 0.0200 |

TABLE 6-3

| Clone No. | IgG | IgG1 | IgG2 | IgG3 | IgG4 | IgA |
|---|---|---|---|---|---|---|
| R3-49 | 3.0920 | 3.0680 | 3.0740 | 3.1260 | 3.2050 | 0.0330 |
| R3-50 | 3.0680 | 3.0770 | 3.0960 | 2.1670 | 3.1910 | 0.0200 |
| R3-51 | 3.0400 | 3.0480 | 3.0990 | 3.0520 | 3.1630 | 0.0150 |
| R3-52 | 3.0640 | 2.9840 | 3.0860 | 3.1580 | 3.1460 | 0.0220 |
| R3-53 | 3.0380 | 3.0300 | 3.0860 | 3.1260 | 3.1210 | 0.0580 |
| R3-54 | 3.0390 | 3.0520 | 3.0950 | 3.0980 | 3.1660 | 0.0280 |
| R3-55 | 3.0520 | 3.0110 | 3.1080 | 3.0960 | 3.1000 | 0.0150 |
| R3-56 | 3.0850 | 3.0440 | 3.0910 | 3.1430 | 3.1590 | 0.0540 |
| R3-57 | 3.0850 | 3.1320 | 3.0830 | 3.0730 | 3.1420 | 0.1160 |
| R3-58 | 3.0460 | 3.1360 | 3.0790 | 3.1140 | 3.1690 | 0.0300 |
| R3-59 | 3.0720 | 3.1590 | 3.0710 | 2.9270 | 3.1420 | 0.0180 |
| R3-60 | 3.0310 | 3.1390 | 3.0440 | 2.9530 | 3.1010 | 0.0350 |
| R3-61 | 3.0360 | 3.0780 | 3.0130 | 3.0230 | 3.0780 | 0.0320 |
| R3-62 | 3.0580 | 3.0910 | 3.0490 | 3.0700 | 3.1060 | 0.0320 |
| R3-63 | 3.0300 | 3.0620 | 3.0450 | 2.9870 | 3.1170 | 0.0240 |

TABLE 6-3-continued

| Clone No. | IgG | IgG1 | IgG2 | IgG3 | IgG4 | IgA |
|---|---|---|---|---|---|---|
| R3-64 | 3.0750 | 3.1320 | 3.0800 | 2.8780 | 3.1220 | 0.0220 |
| R3-65 | 3.1030 | 3.0710 | 3.0540 | 3.1120 | 3.1280 | 0.0270 |
| R3-66 | 3.0640 | 3.1340 | 3.0810 | 3.0090 | 3.1370 | 0.0230 |
| R3-67 | 3.0520 | 3.0990 | 3.0780 | 2.6830 | 3.1160 | 0.0780 |
| R3-68 | 3.0610 | 3.0780 | 3.0630 | 3.0960 | 3.0890 | 0.0760 |
| R3-69 | 3.0400 | 3.0640 | 3.0600 | 3.0720 | 3.0470 | 0.0360 |
| R3-70 | 3.0430 | 3.0990 | 3.0800 | 3.0040 | 3.0960 | 0.0300 |
| R3-71 | 3.0520 | 3.0930 | 3.0790 | 3.0600 | 3.0980 | 0.0170 |
| R3-72 | 3.0610 | 3.0880 | 3.0630 | 3.0740 | 3.1290 | 0.0340 |

TABLE 6-4

| Clone No. | IgG | IgG1 | IgG2 | IgG3 | IgG4 | IgA |
|---|---|---|---|---|---|---|
| R3-73 | 3.0550 | 3.1000 | 3.0920 | 3.1200 | 3.1370 | 0.1650 |
| R3-74 | 3.0070 | 3.0470 | 3.0610 | 3.0800 | 3.1430 | 0.0250 |
| R3-75 | 3.0110 | 3.0500 | 3.0400 | 3.1240 | 3.1070 | 3.0610 |
| R3-76 | 2.9820 | 3.0840 | 3.0820 | 1.2550 | 3.1270 | 0.0490 |
| R3-77 | 3.0360 | 3.0540 | 3.0300 | 3.0740 | 3.1430 | 0.0280 |
| R3-78 | 3.0060 | 3.0580 | 3.0560 | 2.8450 | 3.0970 | 0.0300 |
| R3-79 | 3.0070 | 3.0510 | 3.0490 | 3.0620 | 3.1290 | 0.0280 |
| R3-80 | 3.0410 | 3.0570 | 3.0630 | 2.9360 | 3.1410 | 0.0230 |
| R3-81 | 3.0990 | 3.1640 | 3.1200 | 3.0440 | 3.1530 | 0.0410 |
| R3-82 | 3.0570 | 3.1510 | 3.1250 | 2.6310 | 3.1620 | 0.0270 |
| R3-83 | 3.1000 | 3.1090 | 3.1050 | 2.9730 | 3.1160 | 0.0570 |
| R3-84 | 3.0610 | 3.1290 | 3.0800 | 2.9890 | 3.1080 | 0.0930 |
| R3-85 | 3.0390 | 3.1480 | 3.0880 | 2.9480 | 3.0770 | 0.0270 |
| R3-86 | 2.8250 | 3.0800 | 3.0730 | 0.1340 | 3.0630 | 0.0540 |
| R3-87 | 3.0220 | 3.1040 | 3.0650 | 1.6500 | 3.0650 | 0.0210 |
| R3-88 | 3.0200 | 3.1380 | 3.0920 | 1.8170 | 3.0970 | 0.0430 |
| R3-89 | 2.9340 | 3.1590 | 3.1150 | 1.3950 | 3.1080 | 0.0170 |
| R3-90 | 3.0200 | 3.1280 | 3.1080 | 2.9950 | 3.1010 | 0.0240 |
| R3-91 | 3.0580 | 3.1570 | 3.0490 | 2.9740 | 3.1160 | 0.0280 |
| R3-92 | 3.0360 | 3.0980 | 3.0980 | 2.9290 | 3.0950 | 0.0280 |
| R3-93 | 3.0100 | 3.1110 | 3.0990 | 1.8240 | 3.0700 | 0.0470 |
| R3-94 | 3.0280 | 3.0970 | 3.0310 | 3.0530 | 3.0950 | 0.0400 |
| R3-95 | 3.0360 | 3.1210 | 3.1000 | 2.9770 | 3.0560 | 0.0230 |
| R3-96 | 3.0810 | 3.1460 | 3.0000 | 3.0610 | 3.1210 | 0.0250 |

TABLE 6-5

| | IgG | IgG1 | IgG2 | IgG3 | IgG4 | IgA |
|---|---|---|---|---|---|---|
| Number of positive clones | 94 | 95 | 95 | 92 | 94 | 4 |
| Number of negative clones | 2 | 1 | 1 | 4 | 2 | 92 |
| The ratio of the number of positive clones with respect to the total 96 clones (%) | 97.9 | 99 | 99 | 95.8 | 97.9 | 4.2 |
| OD ≥ 2.5 | 90 | 92 | 91 | 74 | 90 | 2 |
| 1 ≤ OD < 2.5 | 3 | 1 | 2 | 15 | 3 | 0 |
| 0.1 ≤ OD < 1 | 1 | 2 | 2 | 3 | 1 | 2 |

The above results revealed as follows.

The use of the human serum-derived IgG polyclonal antibody-immobilized MLVs enabled to efficiently collect the phages which bind extremely specifically to the human serum-derived IgG polyclonal antibodies. It is to be noted here that the ratios of the number of positive clones with respect to the total number of the clones exceeded 50% by performing just one round of panning, and such a result is extremely rare, and difficult to achieve with a conventional technique. Further, since the number of positive clones and the amount of binding for each antibody are both markedly increased as the number of rounds performed increases, it can be said that the screening method according to the present invention which uses multilamellar liposomes is an extremely efficient screening technique.

In addition, many of the isolated rabbit-derived single-chain antibodies had a binding specificity for two or more selected from the group consisting of the human IgG1 antibody, the human IgG2 antibody, the human IgG3 antibody, and the human IgG4 antibody. In particular, it is considered that the rabbit-derived single-chain antibodies in which the amounts of binding for the human IgG1 antibody and the human IgG3 antibody are the same, have a high possibility of serving as an affinity ligand which could replace Protein A.

Moreover, although not many in numbers, some of the rabbit-derived single-chain antibodies showed an approximately the same level of absorbance for the human IgA, as the absorbances for the human IgG1 antibody, the human IgG2 antibody, the human IgG3 antibody, and the human IgG4 antibody. This result is thought to suggest that these single-chain antibodies bind specifically to the L chains of the antibodies.

<4. Measurement of Dissociation Rate Constant $k_{off}$>

Example 4

Among the 48 colonies collected at the completion of Round 1, the 48 colonies collected at the completion of Round 2, and the 96 colonies collected at the completion of Round 3, the colonies which showed an absorbance exceeding 2.5 in the "Evaluation of Antigen-binding Activity 2" were selected; and the measurement of the dissociation rate constant $k_{off}$ was performed for each of the selected colonies, using Biacore X-100 (manufactured by GE Healthcare Inc.).

(Sample Preparation)

Each of the colonies of the phagemid-containing *Escherichia coli* cells was inoculated in a well of a 96-well deep well plate, in 1 ml of Overnight Express (registered trademark; manufactured by Merck KGaA) medium, and cultured at 1,600 rpm and at 30° C. for 24 hours, followed by centrifugation to remove the supernatant. To each of the resultants, 0.2 ml of Bugbuster and 0.2 μL of Benzonase Nuclease were added to lyse the cells. The resulting lysates were then centrifuged, and the supernatants were collected. The collected supernatants were each diluted 10-fold with PBST.

(Measuring Method)

The measurement was carried out under the following measurement conditions.
Sensor Chip: human IgG-coupled CM5 (15000 RU)
Running buffer: PBST
Binding time: 300 sec
Dissociation time: 180 sec
Elution: 10 mM Glycine, pH 1.5

According to the method for calculating the dissociation rate constant $k_{off}$ as previously described, the calculations of the dissociation rate constant $k_{off}$ were performed. The calculated results were ranked in the order of descending dissociation rate constant $k_{off}$ values, from Rank 1 to Rank 140, and the results are shown in Table 7-1 to Table 7-5.

TABLE 7-1

| Rank | Clone No. | koff (s^-1) | IgG1 | IgG3 | IgA |
|---|---|---|---|---|---|
| 1 | R3-75 | 2.78E-04 | 3.0500 | 3.1240 | 3.0610 |
| 2 | R3-23 | 4.08E-04 | 3.0550 | 3.0220 | 0.0440 |
| 3 | R3-26 | 5.71E-04 | 3.1000 | 3.1440 | 0.0370 |
| 4 | R3-43 | 6.41E-04 | 3.1390 | 3.0700 | 0.0190 |
| 5 | R3-58 | 7.42E-04 | 3.1360 | 3.1140 | 0.0300 |
| 6 | R2-18 | 8.00E-04 | 3.1140 | 3.0750 | 3.1080 |
| 7 | R2-16 | 8.38E-04 | 3.1150 | 3.0470 | 0.0260 |
| 8 | R1-27 | 8.59E-04 | 3.0730 | 3.0820 | 0.0290 |
| 9 | R3-42 | 8.62E-04 | 3.1300 | 3.1020 | 0.0200 |

TABLE 7-1-continued

| Rank | Clone No. | koff (s^-1) | IgG1 | IgG3 | IgA |
|---|---|---|---|---|---|
| 10 | R3-44 | 8.74E-04 | 3.0620 | 3.1210 | 0.0220 |
| 11 | R3-8 | 8.80E-04 | 3.0280 | 3.0600 | 3.0630 |
| 12 | R3-24 | 8.80E-04 | 3.0780 | 3.0220 | 0.0680 |
| 13 | R3-2 | 8.97E-04 | 3.1090 | 3.1140 | 0.0590 |
| 14 | R3-74 | 9.32E-04 | 3.0470 | 3.0800 | 0.0250 |
| 15 | R3-25 | 9.40E-04 | 3.1460 | 3.1750 | 0.0320 |
| 16 | R3-33 | 9.42E-04 | 3.1370 | 3.1270 | 0.0260 |
| 17 | R3-31 | 9.55E-04 | 3.0660 | 3.0780 | 0.0370 |
| 18 | R3-28 | 9.60E-04 | 3.1290 | 3.0720 | 0.0220 |
| 19 | R3-41 | 9.71E-04 | 3.0970 | 3.1280 | 0.0270 |
| 20 | R3-52 | 9.73E-04 | 2.9840 | 3.1580 | 0.0220 |
| 21 | R3-54 | 1.00E-03 | 3.0520 | 3.0980 | 0.0280 |
| 22 | R3-62 | 1.05E-03 | 3.0910 | 3.0700 | 0.0320 |
| 23 | R3-78 | 1.07E-03 | 3.0580 | 2.8450 | 0.0300 |
| 24 | R3-59 | 1.08E-03 | 3.1590 | 2.9270 | 0.0180 |
| 25 | R3-5 | 1.11E-03 | 3.0340 | 3.0120 | 0.0280 |
| 26 | R3-92 | 1.11E-03 | 3.0980 | 2.9290 | 0.0280 |
| 27 | R3-56 | 1.12E-03 | 3.0440 | 3.1430 | 0.0540 |
| 28 | R3-61 | 1.13E-03 | 3.0780 | 3.0230 | 0.0320 |
| 29 | R3-77 | 1.13E-03 | 3.0540 | 3.0740 | 0.0280 |
| 30 | R3-6 | 1.21E-03 | 3.0610 | 3.0430 | 0.0380 |

TABLE 7-2

| Rank | Clone No. | koff (s^-1) | IgG1 | IgG3 | IgA |
|---|---|---|---|---|---|
| 31 | R3-68 | 1.22E-03 | 3.0780 | 3.0960 | 0.0760 |
| 32 | R3-64 | 1.24E-03 | 3.1320 | 2.8780 | 0.0220 |
| 33 | R2-3 | 1.25E-03 | 2.5150 | 2.5170 | 0.0100 |
| 34 | R3-3 | 1.27E-03 | 2.9510 | 2.9560 | 0.0340 |
| 35 | R3-7 | 1.32E-03 | 2.9180 | 3.0640 | 0.0550 |
| 36 | R3-85 | 1.34E-03 | 3.1480 | 2.9480 | 0.0270 |
| 37 | R3-32 | 1.34E-03 | 2.9880 | 3.1500 | 0.0380 |
| 38 | R3-39 | 1.36E-03 | 3.0750 | 2.9760 | 0.0190 |
| 39 | R3-34 | 1.39E-03 | 3.1190 | 2.9870 | 0.0200 |
| 40 | R2-32 | 1.39E-03 | 3.0850 | 3.1180 | 0.0470 |
| 41 | R3-95 | 1.40E-03 | 3.1210 | 2.9770 | 0.0230 |
| 42 | R3-21 | 1.41E-03 | 3.0760 | 2.6270 | 0.0970 |
| 43 | R2-1 | 1.42E-03 | 3.1060 | 2.9480 | 0.0250 |
| 44 | R3-73 | 1.42E-03 | 3.1000 | 3.1200 | 0.1650 |
| 45 | R3-46 | 1.48E-03 | 3.1220 | 3.0390 | 0.0170 |
| 46 | R2-24 | 1.49E-03 | 3.1600 | 3.1080 | 0.0380 |
| 47 | R3-90 | 1.51E-03 | 3.1280 | 2.9950 | 0.0240 |
| 48 | R3-91 | 1.52E-03 | 3.1570 | 2.9740 | 0.0280 |
| 49 | R3-60 | 1.52E-03 | 3.1390 | 2.9530 | 0.0350 |
| 50 | R3-80 | 1.53E-03 | 3.0570 | 2.9360 | 0.0230 |
| 51 | R3-82 | 1.54E-03 | 3.1510 | 2.6310 | 0.0270 |
| 52 | R2-25 | 1.57E-03 | 3.1110 | 2.5610 | 0.0270 |
| 53 | R3-84 | 1.57E-03 | 3.1290 | 2.9890 | 0.0930 |
| 54 | R1-43 | 1.60E-03 | 3.0910 | 2.9530 | 0.0200 |
| 55 | R3-63 | 1.62E-03 | 3.0620 | 2.9870 | 0.0240 |
| 56 | R3-51 | 1.63E-03 | 3.0480 | 3.0520 | 0.0150 |
| 57 | R2-31 | 1.64E-03 | 3.1040 | 2.5360 | 0.0220 |
| 58 | R3-27 | 1.64E-03 | 3.1090 | 3.0890 | 0.0220 |
| 59 | R3-55 | 1.65E-03 | 3.0110 | 3.0960 | 0.0150 |
| 60 | R1-5 | 1.66E-03 | 3.1910 | 3.0870 | 0.0230 |

TABLE 7-3

| Rank | Clone No. | koff (s^-1) | IgG1 | IgG3 | IgA |
|---|---|---|---|---|---|
| 61 | R3-49 | 1.67E-03 | 3.0680 | 3.1260 | 0.0330 |
| 62 | R3-83 | 1.68E-03 | 3.1090 | 2.9730 | 0.0570 |
| 63 | R3-45 | 1.69E-03 | 3.0920 | 2.9400 | 0.0160 |
| 64 | R3-14 | 1.71E-03 | 3.0880 | 2.9640 | 0.0280 |
| 65 | R3-65 | 1.73E-03 | 3.0710 | 3.1120 | 0.0270 |
| 66 | R3-36 | 1.73E-03 | 3.1110 | 2.9920 | 0.0180 |
| 67 | R3-94 | 1.74E-03 | 3.0970 | 3.0530 | 0.0400 |
| 68 | R1-7 | 1.75E-03 | 3.1240 | 0.0660 | 0.0360 |
| 69 | R3-9 | 1.76E-03 | 3.0960 | 2.8800 | 0.0420 |
| 70 | R2-22 | 1.86E-03 | 3.1160 | 0.0400 | 0.0250 |
| 71 | R3-67 | 1.86E-03 | 3.0990 | 2.6830 | 0.0780 |
| 72 | R3-96 | 1.86E-03 | 3.1460 | 3.0610 | 0.0250 |

TABLE 7-3-continued

| Rank | Clone No. | koff (s^-1) | IgG1 | IgG3 | IgA |
|---|---|---|---|---|---|
| 73 | R2-33 | 1.86E-03 | 3.1310 | 2.8100 | 0.0240 |
| 74 | R1-36 | 1.87E-03 | 3.0660 | 0.5400 | 0.0170 |
| 75 | R3-70 | 1.87E-03 | 3.0990 | 3.0040 | 0.0300 |
| 76 | R3-53 | 1.88E-03 | 3.0300 | 3.1260 | 0.0580 |
| 77 | R3-81 | 1.93E-03 | 3.1640 | 3.0440 | 0.0410 |
| 78 | R3-17 | 1.94E-03 | 3.1580 | 3.0340 | 0.0650 |
| 79 | R3-71 | 1.94E-03 | 3.0930 | 3.0600 | 0.0170 |
| 80 | R3-57 | 1.95E-03 | 3.1320 | 3.0730 | 0.1160 |
| 81 | R3-30 | 1.97E-03 | 3.0940 | 3.1070 | 0.0300 |
| 82 | R2-14 | 2.04E-03 | 2.9970 | 0.5070 | 0.0220 |
| 83 | R2-26 | 2.05E-03 | 3.0630 | 1.2730 | 0.0180 |
| 84 | R3-79 | 2.06E-03 | 3.0510 | 3.0620 | 0.0280 |
| 85 | R1-29 | 2.08E-03 | 3.0530 | 2.2800 | 0.0530 |
| 86 | R2-15 | 2.09E-03 | 3.1040 | 2.9740 | 0.0200 |
| 87 | R3-19 | 2.10E-03 | 3.0910 | 3.0340 | 0.0230 |
| 88 | R2-10 | 2.11E-03 | 3.1010 | 2.8040 | 0.0210 |
| 89 | R1-42 | 2.11E-03 | 3.1050 | 2.5150 | 0.0170 |
| 90 | R3-11 | 2.18E-03 | 3.0690 | 3.0400 | 0.0280 |

TABLE 7-4

| Rank | Clone No. | koff (s^-1) | IgG1 | IgG3 | IgA |
|---|---|---|---|---|---|
| 91 | R1-38 | 2.22E-03 | 3.0930 | 2.9980 | 0.0210 |
| 92 | R2-8 | 2.22E-03 | 3.1140 | 2.0550 | 0.0190 |
| 93 | R1-39 | 2.22E-03 | 2.9170 | 0.2600 | 0.0170 |
| 94 | R2-27 | 2.28E-03 | 3.0220 | 2.4760 | 0.1570 |
| 95 | R2-30 | 2.31E-03 | 3.0180 | 3.0400 | 0.0210 |
| 96 | R2-5 | 2.33E-03 | 2.9640 | 0.1920 | 0.0130 |
| 97 | R1-25 | 2.33E-03 | 3.1200 | 0.7990 | 0.0310 |
| 98 | R2-23 | 2.36E-03 | 2.8150 | 0.5180 | 0.0220 |
| 99 | R2-34 | 2.36E-03 | 3.1600 | 1.8090 | 0.0360 |
| 100 | R3-10 | 2.38E-03 | 3.1050 | 2.7160 | 0.0310 |
| 101 | R3-66 | 2.42E-03 | 3.1340 | 3.0090 | 0.0230 |
| 102 | R1-47 | 2.44E-03 | 3.1160 | 2.8050 | 0.0190 |
| 103 | R3-72 | 2.44E-03 | 3.0880 | 3.0740 | 0.0340 |
| 104 | R2-9 | 2.44E-03 | 3.1330 | 3.0210 | 0.0200 |
| 105 | R1-13 | 2.47E-03 | 3.1020 | 2.9500 | 0.0200 |
| 106 | R1-23 | 2.48E-03 | 3.0390 | 0.8750 | 0.0170 |
| 107 | R1-41 | 2.48E-03 | 3.1450 | 2.1250 | 0.3290 |
| 108 | R2-35 | 2.48E-03 | 3.0810 | 2.9710 | 0.0200 |
| 109 | R3-35 | 2.53E-03 | 3.1400 | 3.0850 | 0.0280 |
| 110 | R1-6 | 2.53E-03 | 3.1740 | 2.8820 | 0.0780 |
| 111 | R2-17 | 2.55E-03 | 3.1850 | 0.4590 | 0.0350 |
| 112 | R3-69 | 2.59E-03 | 3.0640 | 3.0720 | 0.0360 |
| 113 | R1-35 | 2.60E-03 | 3.1030 | 0.7110 | 0.0310 |
| 114 | R2-37 | 2.60E-03 | 3.0820 | 2.3490 | 0.0170 |
| 115 | R1-9 | 2.65E-03 | 3.1220 | 2.2560 | 0.0200 |
| 116 | R2-19 | 2.67E-03 | 2.7350 | 1.8010 | 0.0210 |
| 117 | R1-24 | 2.68E-03 | 3.0480 | 0.0530 | 0.0270 |
| 118 | R2-2 | 2.82E-03 | 3.0650 | 2.9030 | 0.0370 |
| 119 | R1-3 | 2.85E-03 | 3.1470 | 2.2850 | 0.0410 |
| 120 | R1-20 | 2.86E-03 | 2.8940 | 1.0570 | 0.0190 |

TABLE 7-5

| Rank | Clone No. | koff (s^-1) | IgG1 | IgG3 | IgA |
|---|---|---|---|---|---|
| 121 | R2-11 | 2.96E-03 | 2.7430 | 0.0210 | 0.0180 |
| 122 | R2-45 | 3.09E-03 | 3.1430 | 2.8320 | 0.0180 |
| 123 | R2-48 | 3.14E-03 | 3.1430 | 3.1320 | 0.0260 |
| 124 | R1-34 | 3.27E-03 | 3.1380 | 0.6290 | 0.0250 |
| 125 | R1-48 | 3.45E-03 | 3.1370 | 2.9600 | 0.0290 |
| 126 | R1-45 | 3.47E-03 | 3.0720 | 2.5140 | 0.0130 |
| 127 | R1-26 | 3.63E-03 | 3.0350 | 3.0000 | 0.0200 |
| 128 | R1-14 | 3.66E-03 | 3.1160 | 3.0010 | 0.0220 |
| 129 | R2-42 | 3.87E-03 | 3.1680 | 1.7200 | 0.0210 |
| 130 | R1-10 | 4.00E-03 | 2.8020 | 1.2220 | 0.0360 |
| 131 | R2-44 | 4.06E-03 | 3.1840 | 1.0250 | 0.0830 |
| 132 | R2-47 | 4.11E-03 | 3.1440 | 3.0400 | 0.0420 |
| 133 | R1-11 | 4.38E-03 | 3.1100 | 2.9800 | 0.0480 |
| 134 | R2-40 | 4.88E-03 | 3.1540 | 2.6190 | 0.0200 |
| 135 | R2-46 | 6.78E-03 | 3.1590 | 1.2460 | 0.0180 |

TABLE 7-5-continued

| Rank | Clone No. | koff (s^-1) | IgG1 | IgG3 | IgA |
|---|---|---|---|---|---|
| 136 | R2-41 | 6.94E-03 | 3.1320 | 2.7460 | 0.0300 |
| 137 | R2-43 | 6.95E-03 | 3.1190 | 1.7940 | 0.0200 |
| 138 | R2-38 | 9.89E-03 | 3.0670 | 2.6320 | 0.0180 |
| 139 | R2-20 | Unmeasurable | 2.8910 | 0.0680 | 0.0190 |
| 140 | R2-36 | Unmeasurable | 3.0860 | 3.0690 | 0.0310 |

<5. Determination of Amino Acid Sequences of Genes of Rabbit-Derived Single-Chain Antibodies which Bind to Human Serum-Derived IgG Polyclonal Antibodies>

Example 5

For the clones which had been ranked as Rank 1 (R3-75), Rank 2 (R3-23), Rank 3 (R3-26), Rank 4 (R3-43), Rank 5 (R3-58), Rank 6 (R2-18), Rank 7 (R2-16), Rank 8 (R1-27), Rank 11 (R3-8), and Rank 68 (R1-7) based on the measurement results of the dissociation rate constant $k_{off}$, the amino acid sequences were determined from the gene sequences of the rabbit-derived single-chain antibody genes. The clone ranked as Rank 4 (R3-43) could not be sequenced.

FIG. 8-1 and FIG. 8-2 show the amino acid sequences determined. The results revealed the following. It is to be noted that, regarding the genes of the variable regions ($V_H$ domains) of the heavy chains (H chains) shown in FIG. 8-1, the sequence of Rank 1 (R3-75) is defined as SEQ ID NO: 12, the sequence of Rank 2 (R3-23) as SEQ ID NO: 13; the sequence of Rank 3 (R3-26) as SEQ ID NO: 14; the sequence of Rank 5 (R3-58) as SEQ ID NO: 15; the sequence of Rank 6 (R2-18) as SEQ ID NO: 16; the sequence of Rank 7 (R2-16) as SEQ ID NO: 17; the sequence of Rank 8 (R1-27) as SEQ ID NO: 18; the sequence of Rank 11 (R3-8) as SEQ ID NO: 19; and the sequence of Rank 68 (R1-7) as SEQ ID NO: 20.

Further, regarding the genes of the variable regions ($V_L$ domains) of the light chains (L chains) shown in FIG. 8-2, the sequence of Rank 1 (III-75) is defined as SEQ ID NO: 21; the sequence of Rank 2 (III-23) as SEQ ID NO: 22; the sequence of Rank 3 (III-26) as SEQ ID NO: 23; the sequence of Rank 5 (III-58) as SEQ ID NO: 24; the sequence of Rank 6 (II-18) as SEQ ID NO: 25; the sequence of Rank 7 (II-16) as SEQ ID NO: 26; the sequence of Rank 8 (I-27) as SEQ ID NO: 27; the sequence of Rank 11 (III-8) as SEQ ID NO: 28; and the sequence of Rank 68 (I-7) as SEQ ID NO: 29.

The rabbit-derived single-chain antibody genes obtained from Rank 1 (R3-75), Rank 6 (R2-18), and Rank 11 (R3-8) were found to contain the sequence "ATRYDSYG-YAYNYWFGTLW (SEQ ID NO: 30, 19 residues)" as CDR3. The rabbit-derived single-chain antibodies derived from these colonies are those which bind to the human IgG1 antibody, the human IgG2 antibody, the human IgG3 antibody, the human IgG4 antibody, and the human IgA antibody.

The rabbit-derived single-chain antibody gene obtained from Rank 2 (R3-23) was found to contain the sequence "GSYYDSHGYAYVSLW (SEQ ID NO: 31, 15 residues)" as CDR3. The rabbit-derived single-chain antibody obtained from this colony is one which binds to the human IgG1 antibody, the human IgG2 antibody, the human IgG3 antibody, and the human IgG4 antibody.

The rabbit-derived single-chain antibody gene obtained from Rank 3 (R3-26) was found to contain the sequence "ATDYGIYGYAYGHLW (SEQ ID NO: 32, 15 residues)" as CDR3. The rabbit-derived single-chain antibody obtained from this colony is one which binds to the human IgG1 antibody, the human IgG2 antibody, the human IgG3 antibody, and the human IgG4 antibody.

The rabbit-derived single-chain antibody genes obtained from Rank 5 (R3-58) and Rank 8 (R1-27) were found to contain the sequence "ARYSGDNGGTLNLW (SEQ ID NO: 33, 14 residues)" as CDR3. The rabbit-derived single-chain antibodies obtained from these colonies are those which bind to the human IgG1 antibody, the human IgG2 antibody, the human IgG3 antibody, and the human IgG4 antibody.

The rabbit-derived single-chain antibody gene obtained from Rank 7 (R2-16) was found to contain the sequence "ARYSGDNGGALNLW (SEQ ID NO: 34, 14 residues)" as CDR3. The rabbit-derived single-chain antibody obtained from this colony is one which binds to the human IgG1 antibody, the human IgG2 antibody, the human IgG3 antibody, and the human IgG4 antibody.

<6. Measurement of Binding Capacity for Human IgG1 Antibody>

Example 6

The binding capacity for the human IgG1 antibody was measured, for each of the rabbit-derived single-chain antibodies obtained from the colonies which had been ranked as Rank 1 (R3-75), Rank 2 (R3-23), Rank 6 (R2-18), Rank 7 (R2-16), Rank 8 (R1-27), and Rank 68 (R1-7) based on the measurement results of the dissociation rate constant $k_{off}$, using Biacore X-100 (manufactured by GE Healthcare Inc.).

(Sample Preparation Method)

Each of the collected colonies of the phagemid-containing *Escherichia coli* cells was inoculated in a 500-ml flask equipped with a baffle, in 50 ml of Overnight Express (registered trademark; manufactured by Merck KGaA) medium, and cultured at 30° C. and at 200 rpm for 24 hours, followed by centrifugation to remove the supernatant. To each of the resultants, 5 ml of Bugbuster and 0.2 μL of Benzonase Nuclease were added to lyse the cells. The resulting lysates were then centrifuged, and the supernatants were collected. The supernatants were each diluted 10-fold with PBST, to be used as measurement samples.

(Measuring Method)

The measurement was carried out under the following measurement conditions.
Sensor Chip: human IgG1-coupled CM5 (5000 RU)
Running buffer: PBST
Binding time: 540 sec
Dissociation time: 120 sec
Elution: 10 mM Glycine, pH 1.5

Comparative Example 6-1

The same procedure as in Example 6 was carried out as Comparative Example 6-1, except that Protein A (29435-14; manufactured by Nakalai Tesque, Inc.) prepared with PBST to a final concentration of 10 g/mL was used, instead of the sample.

Comparative Example 6-2

The same procedure as in Example 6 was carried out as Comparative Example 6-2, except that a mouse scFv-FM (soluble fraction was diluted 10-fold with PBST) was used, instead of the sample.

The obtained colony of the phagemid-containing *Escherichia coli* cells was inoculated in a 500-ml flask equipped with a baffle, in 50 ml of Overnight Express (registered trademark; manufactured by Merck KGaA) medium, and cultured at 30° C. and at 200 rpm for 24 hours, followed by centrifugation to remove the supernatant. To the resultant, 5 ml of Bugbuster and 0.2 μL of Benzonase Nuclease were added to lyse the cells. The resulting lysate was then centrifuged, and the supernatant was collected. The supernatant was diluted 10-fold with PBST, and used in the measurement.

Figures 1, 9:
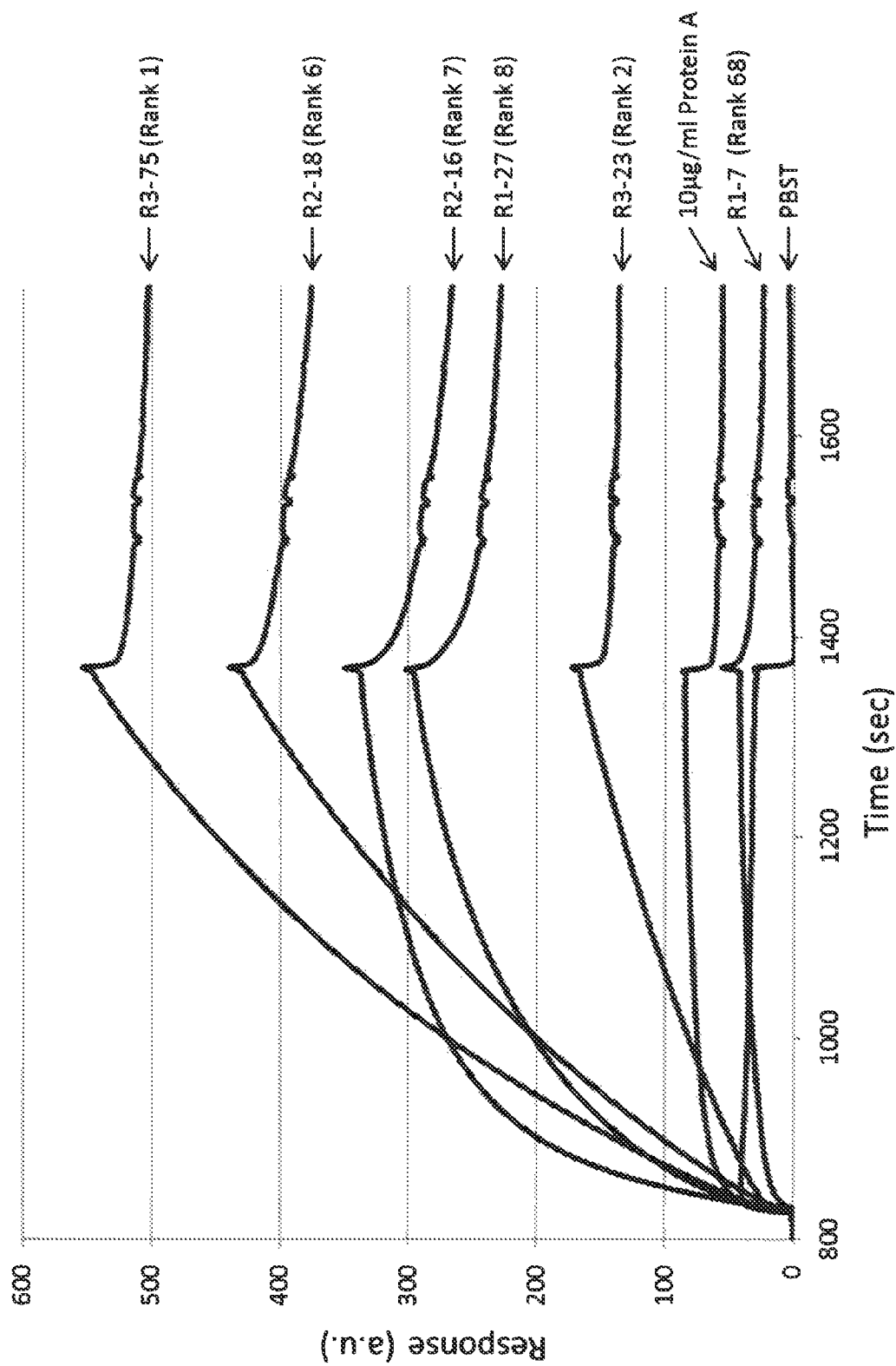
Figures 2, 9:
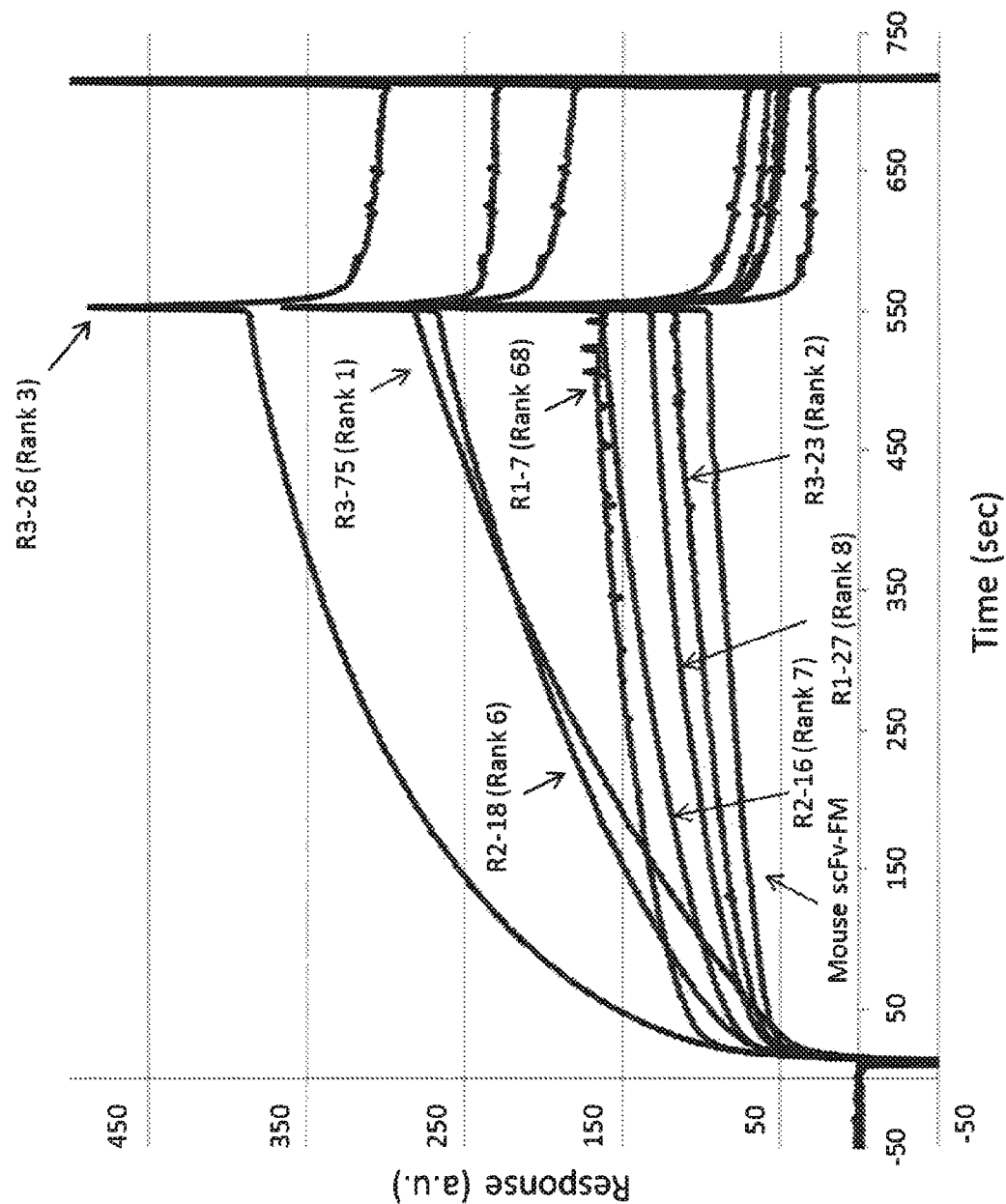

Measurement results are shown in FIG. 9-1 and FIG. 9-2. It has been found out that each of the rabbit-derived single-chain antibodies has a binding capacity for the human IgG1 antibody that is markedly higher than the binding capacity of Protein A in Comparative Example 6-1 and that of the mouse scFv-FM in Comparative Example 6-2.

<7. Measurement of Dissociation Constant $K_D$ for Human IgG1 Antibody>

Example 7

The dissociation constant $K_D$ for the human IgG1 antibody was measured, for each of the rabbit-derived single-chain antibodies obtained from the colonies which had been ranked as Rank 1 (R3-75), Rank 2 (R3-23), Rank 3 (R3-26), Rank 6 (R2-18), Rank 7 (R2-16), Rank 8 (R1-27), and Rank 68 (R1-7) based on the measurement results of the dissociation rate constant $k_{off}$, using Biacore X-100 (manufactured by GE Healthcare Inc.).

(Sample Preparation Method)

A DNA fragment containing the rabbit-derived single-chain antibody gene was amplified by PCR from the phagemid vector of each colony, using T7 promoter primer and M13 primer. After purification, the DNA fragment was digested with restriction enzymes Xba I and Not I, and inserted into the Xba I/Not I sites of a pET22 vector (manufactured by Merck KGaA). The thus constructed rabbit-derived single-chain antibody expression vector allows the rabbit-derived single-chain antibody to be expressed in the form in which a pelB leader signal sequence is fused to the N-terminus, and a histidine tag (6×His-tag) is fused to the C-terminus. After the expression, the rabbit-derived single-chain antibody migrates to the periplasm and the pelB leader sequence is cleaved by a signal peptidase.

The thus constructed rabbit-derived single-chain antibody-His expression vector was used to transform *Escherichia coli* Rosetta (DE3) cells, and the transformed cells were cultured on an LB agar plate (containing 50 mg/L ampicillin and 35 mg/L kanamycin). The resulting single colony was cultured overnight in 10 ml of an LB medium (containing 50 mg/L ampicillin and 35 mg/L kanamycin). The obtained culture liquid was inoculated in 50 ml of Overnight Express TB medium (manufactured by Merck KGaA) and cultured at 37° C. and at 200 rpm for 24 hours.

The resulting culture liquid was centrifuged (10,000 rpm, 4° C., 15 minutes), and the culture supernatant was obtained. Further, the cells were suspended in 5 ml of lysis buffer containing Bugbuster, lysozyme, and Benzonase Nuclease, and incubated at 37° C. for one hour to lyse the cells. Following centrifugation at 10,000 rpm and at 4° C. for 15 minutes, the supernatant was collected as the intracellular soluble fraction.

The above described culture supernatant and the intracellular soluble fraction were each applied to a His-Trap HP column (manufactured by GE Healthcare), and subjected to a gradient elution using 0.4 M imidazole, to collect the rabbit-derived single-chain antibody-His. For each of the obtained eluants, the protein concentration was quantified by DC Protein assay (Biorad). Further, the purity of the rabbit-derived single-chain antibody-His in each eluant was confirmed by SDS-PAGE. When the purity of the rabbit-derived single-chain antibody-His in the eluant was not sufficient, the eluant was further purified by a human IgG-coupled column, and then quantified. The collected eluants were each diluted 10-fold or more with PBST, and the measurement of the dissociation constant $K_D$ was carried out using Biacore X-100.

(Measuring Method)

The measurement was carried out under the following measurement conditions.

Sensor Chip: human IgG1-coupled CM5 (5000 RU)
Running buffer: PBST
Binding time: 180 sec
Dissociation time: 600 sec
Elution: 10 mM Glycine, pH 1.5
Mode: Single cycle kinetics mode The properties of the thus obtained rabbit-derived single-chain antibodies, including the measurement results of the dissociation constant $K_D$, are summarized in Table 8. The dissociation constant $K_D$ of the rabbit-derived single-chain antibody of Rank 1 (R3-75) for the human IgG1 antibody was found out to be $5.5 \times 10^{-10}$ M. In view of the fact that the dissociation constant $K_D$ of Protein A for the human IgG1 antibody is around 5 to 10 nM, the rabbit-derived single-chain antibody of Rank 1 (R3-75) is thought to bind extremely strongly to the human IgG1 antibody.

Further, in the column "Location" in Table 8, one whose activity was confirmed using a sample of culture supernatant is indicated as "Supernatant", and one whose activity was confirmed using a sample of soluble fraction is indicated as "Periplasm". When indicated as "Supernatant", it means that the phage or rabbit-derived single-chain antibody was secreted from the *Escherichia coli*, and when indicated as "Periplasm", it means that the phage or rabbit-derived single-chain antibody was present in the periplasm of *Escherichia coli*.

[Table 8]

TABLE 8

| Rank | Clone No. | $k_{on}$ ($M^{-1}s^{-1}$) | $k_{off}$ ($s^{-1}$) | $K_D$ (M) | $R_{max}$ (RU) | Location |
|---|---|---|---|---|---|---|
| 1 | R3-75 | $6.7 \times 10^4$ | $3.7 \times 10^{-5}$ | $5.5 \times 10^{-10}$ | 342.2 | Supernatant |
| 2 | R3-23 | $1.1 \times 10^4$ | $1.3 \times 10^{-4}$ | $1.1 \times 10^{-8}$ | 364.1 | Periplasm |
| 3 | R3-26 | $2.1 \times 10^4$ | $4.3 \times 10^{-5}$ | $2.1 \times 10^{-9}$ | 329.4 | Supernatant |
| 6 | R2-18 | $2.5 \times 10^4$ | $1.2 \times 10^{-4}$ | $4.8 \times 10^{-9}$ | 364.1 | Supernatant |
| 7 | R2-16 | $1.3 \times 10^5$ | $3.2 \times 10^{-4}$ | $2.5 \times 10^{-9}$ | 241.8 | Periplasm |
| 8 | R1-27 | $9.9 \times 10^3$ | $4.0 \times 10^{-4}$ | $4.0 \times 10^{-8}$ | 530.6 | Periplasm |
| 68 | R1-07 | $7.1 \times 10^4$ | $1.7 \times 10^{-3}$ | $2.4 \times 10^{-8}$ | 79.9 | Periplasm |

The rabbit-derived single-chain antibodies of Rank 1 (R3-75), Rank 3 (R3-26), and Rank 6 (R2-18) were found to be secreted in the culture supernatant.

<8. Separation Agent for Separating Human Serum-Derived IgG Polyclonal Antibody>

Example 8

(Preparation of Single-Chain Antibody)

The single-chain antibody of "R3-26" was mass produced, by fed-batch culture using a Jar Fermenter. Further, the single-chain antibody secreted in the culture supernatant was purified using a HisTrap HP column (manufactured by GE Healthcare Inc.) by immobilized metal ion affinity chromatography (IMAC). Further, a Hi Trap Desalting column (manufactured by GE Healthcare Inc.) for desalting and buffer replacement was used to replace the buffer with 0.1 M carbonate buffer (pH 8.3) containing 0.5 M NaCl, and then concentrated by ultrafiltration. Finally, the single-chain antibody having a concentration of 1 mg/ml and a volume of 10 ml was obtained.

(Immobilization of Single-Chain Antibody on Carrier)

The carboxyl group of Sepharose (agarose carrier in the form of beads), which is the carrier in a 5 ml HiTrap NHS column (manufactured by GE Healthcare Inc.), was esterified with NHS, and the purified single-chain antibody described above was supplied to the column so that an amino group of the single-chain antibody forms an amide bond with the carboxyl group, thereby immobilizing the single-chain antibody on the column. Ethanolamine was added to the column to block the unreacted NHS esters.

(Separation of Human Serum-Derived IgG Polyclonal Antibody)

The 5 ml column on which the single-chain antibody was immobilized was set in a chromatography system, AKTA Purifier UPC 10 (manufactured by GE Healthcare Inc.), and equilibrated with PBS. To the column, 10 ml of a human serum-derived IgG polyclonal antibody (#I4506; manufactured by Sigma-Aldrich Co. LLC.) prepared to a concentration of 1 mg/ml was supplied at a flow velocity of 1 ml/min. Subsequently, the column was washed with PBS. After confirming that the value of UV280 reached the baseline, 0.5 M arginine (pH 1.5) was supplied to the column, to elute the human serum-derived IgG polyclonal antibody from the column.

Figure 10:
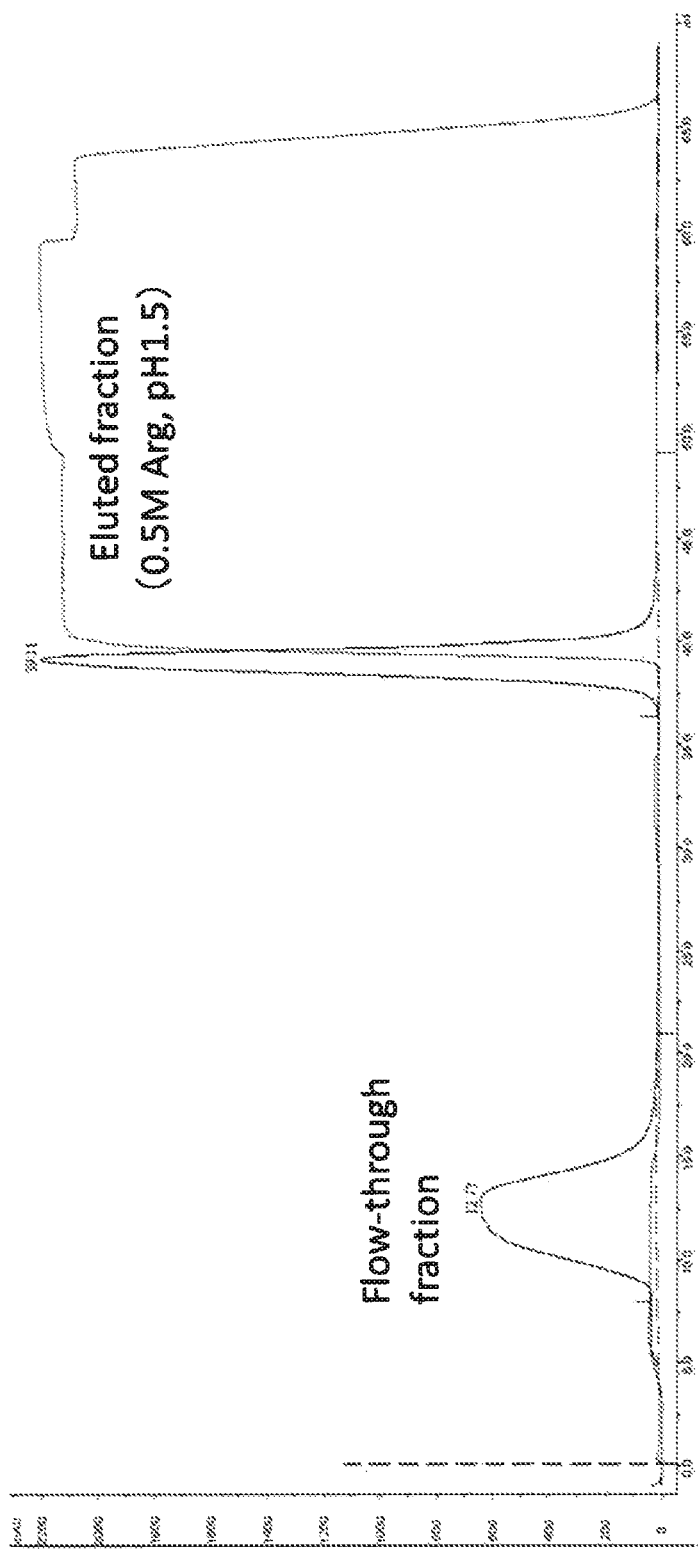
FIG. 10 is a graph showing the breakthrough curve obtained in Example 8.

As a result, the breakthrough curve as shown in FIG. 10 was obtained. Further, when 0.5 M arginine (pH 1.5) was used to forcibly dissociate the human serum-derived IgG polyclonal antibody from the column, it was possible to isolate the IgG polyclonal antibody at a high purity. It can be seen from the peak area ratio of the flow-through fraction and the eluted fraction that about 53% (5.3 mg) of the IgG (10 mg) supplied was adsorbed to the column and eluted.

The above results suggested the usability of a single-chain antibody selected by the screening method according to the present invention as a separation agent for separating a human serum-derived IgG polyclonal antibody.

<9. Method for Screening Rabbit-Derived Single-Chain Antibody which Specifically Binds to L Chain of Human Antibody>

The previously examined evaluation results of the antigen specificity and the amino acid sequence, carried out for each of the total 192 clones obtained in Rounds 1 to 3 in the panning using the human serum-derived IgG polyclonal antibody-immobilized MLVs, revealed that 3 clones (R2-18, R3-8, and R3-75) strongly bind not only to the human IgG antibodies, but also to the human IgA antibody.

Further, the analysis of the antigen specificities of these single-chain antibodies by Western blotting revealed that these single-chain antibodies recognize the light chains (L chains), specifically, the kappa chains, of the human antibodies. When the amino acid sequences of the constant regions are compared between a human IgG antibody and a human IgA antibody, the amino acid sequences of the heavy chains (H chains) are completely different between the two. In contrast, the light chains (L chains) are broadly classified into lambda and kappa chains, and the amino acid sequences of the lambda chains are common between IgG and IgA, and so are the amino acid sequences of the kappa chains. This also applies to the case of a human IgM antibody, a human IgE antibody, a human IgD antibody, and the like. Thus, it has been suggested that these 3 clones are antibodies with an extremely high added value, which are capable of specifically binding not only to a human IgG antibody and a human IgA antibody, but also to all types of the human antibodies including a human IgM antibody, a human IgE antibody, a human IgD antibody, and the like.

Therefore, in order to collect such a rabbit-derived single-chain antibody which specifically binds to the L chain of a human antibody, in a highly efficient manner, from the previously prepared library of phages presenting the anti-human serum-derived IgG polyclonal antibody-rabbit-derived single-chain antibodies, the panning as described below was further performed.

A description will be given below regarding the method for screening a rabbit-derived single-chain antibody which specifically binds to the L chain of a human antibody (hereinafter, sometimes referred to as an "anti-human antibody L chain-rabbit-derived single-chain antibody") from a phage library.

It is noted that, regarding the names of clones obtained by the method for screening an anti-human antibody L chain-rabbit-derived single-chain antibody, the clone of "Clone No. 1 obtained at the completion of Round 1", for example, is sometimes referred to as "IgA R1-1" or "IgA I-1" in abbreviation. In the same manner, the clone of "Clone No. 1 obtained at the completion of Round 2", for example, is sometimes referred to as "IgA R2-1" or "IgA II-1", and the clone of "Clone No. 1 obtained at the completion of Round 3" is sometimes referred to as "IgA R3-1" or "IgA III-1", in abbreviation.

<9-1. Coupling of Human Serum-Derived IgA Polyclonal Antibody to Multilamellar Liposomes>

Human serum-derived IgA polyclonal antibody-immobilized MLVs were prepared in the same manner as described in the above section 1-1. As the human serum-derived IgA polyclonal antibody, #I4036 manufactured by Sigma-Aldrich Co. LLC. was used.

<9-2. Preparation of Library of Phages Presenting Anti-Human Serum-Derived IgG Polyclonal Antibody-Rabbit-Derived Single-Chain Antibodies>

A library of phages presenting the anti-human serum-derived IgG polyclonal antibody-rabbit-derived single-chain antibodies was prepared, in the same manner as described in the above described section 2-2.

<9-3. Panning>

Example 9-1

Panning was carried out in the same manner as in the above 2-3, using the phage library prepared in the above 9-2 and the human serum-derived IgA polyclonal antibody-immobilized MLVs prepared in the above 9-1.

Comparative Example 9-1

The same procedure as in Example 9-1 was carried out as Comparative Example 9-1, except that multilamellar liposomes on which the human serum-derived IgA polyclonal antibody had not been immobilized were used.

<9-4. Recovery of Phages to Gene Sequencing>

The presence or absence of the genes of anti-human serum-derived IgA polyclonal antibody-rabbit-derived single-chain antibodies was confirmed in the phagemid DNAs recovered in Example 9-1 and Comparative Example 9-1, in the same manner as described in the above described 2-2.

<9-5. Panning Results>

Figure 11:
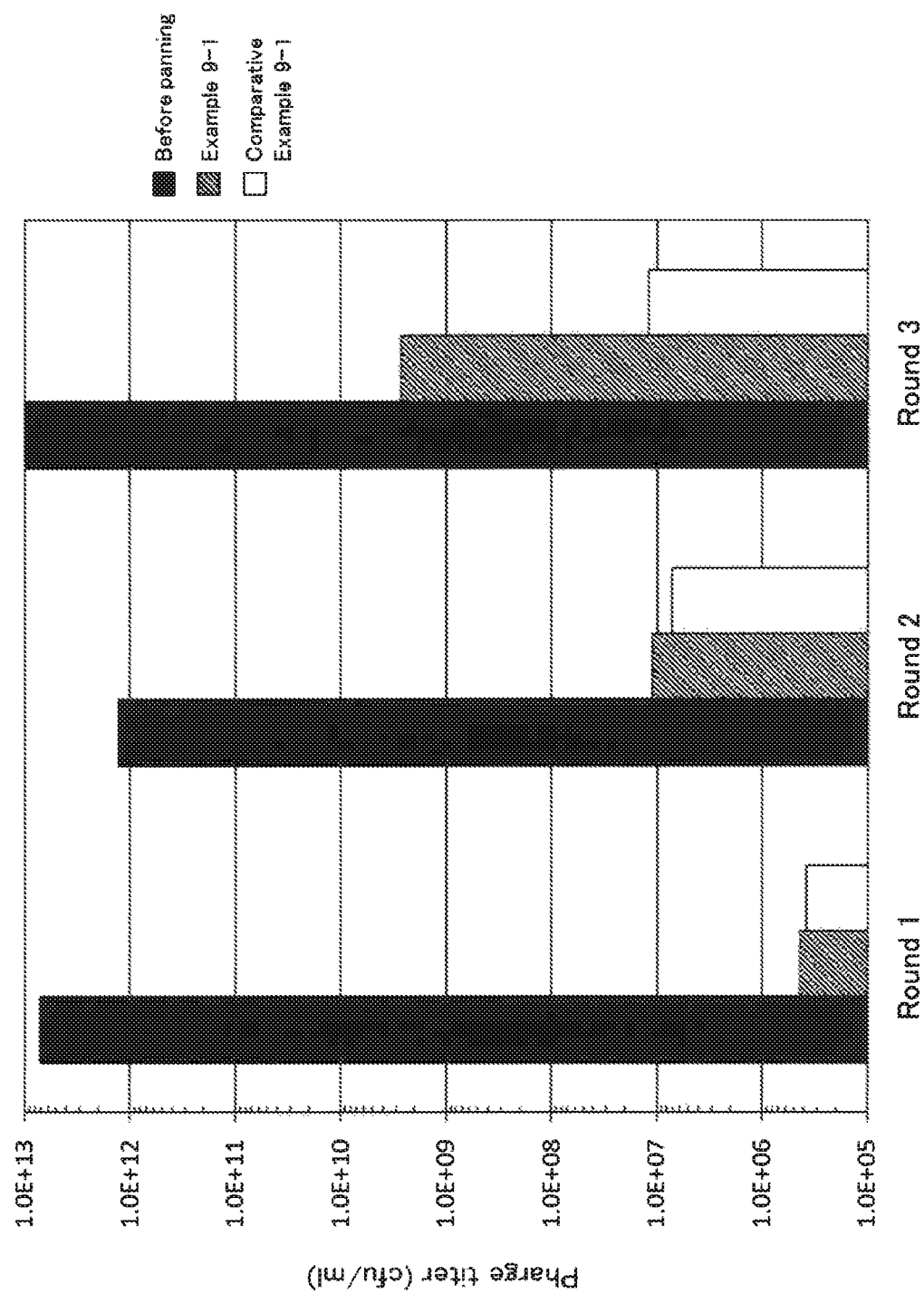
FIG. 11 is a graph showing the number of phages before panning, at the completion of Round 1, at the completion of Round 2, and at the completion of Round 3, in each of Example 9-1 and Comparative Example 9-1.

FIG. 11 shows the number of phages before the panning, at the completion of Round 1, at the completion of Round 2, and at the completion of Round 3, in each of Example 9-1 and Comparative Example 9-1.

Figure 12:
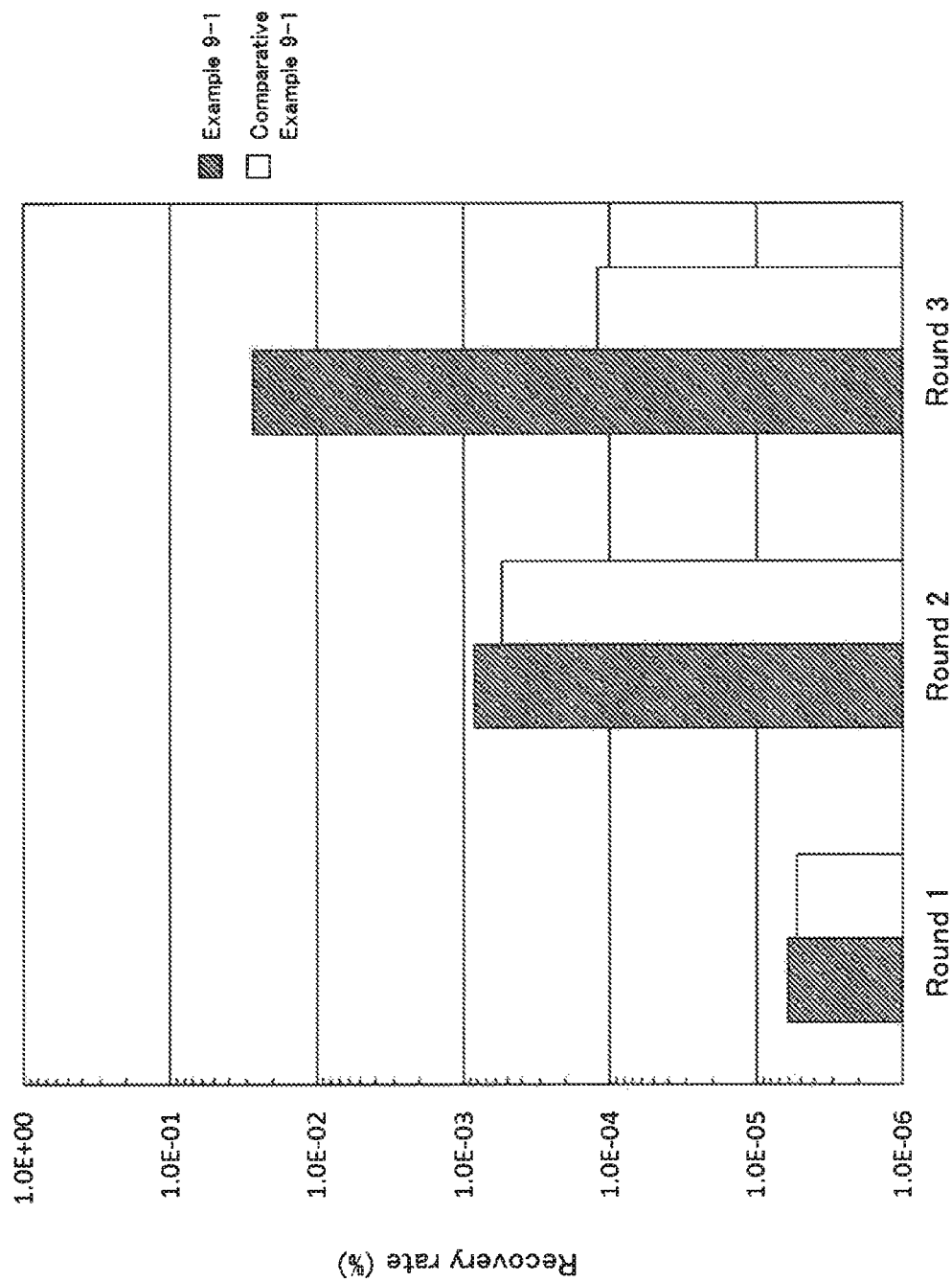
FIG. 12 is a graph showing the recovery rate (%), obtained by dividing each of the numbers of phages at the completion of Round 1, at the completion of Round 2, and at the completion of Round 3 by the number of phages before the panning in each round, in Example 9-1 and Comparative Example 9-1.

FIG. 12 shows the recovery rate (%), obtained by dividing each of the numbers of phages at the completion of Round 1, at the completion of Round 2, and at the completion of Round 3 by the number of phages before the panning in each round, in Example 9-1 and Comparative Example 9-1.

It can be seen from the above results that the recovery rate markedly increased in Round 3 in Example 9-1, to a level not less than 100-times the recovery rate in Comparative Example 9-1. This has confirmed that it is possible to carry out an efficient panning, also in the case of using the human serum-derived IgA polyclonal antibody-immobilized MLVs.

<9-6. Evaluation of Antigen-Binding Activity 1>

Example 9-2

In the same manner as in the above section 3-1, the evaluation of the antigen-binding activity was carried out for the rabbit-derived single-chain antibodies obtained from the pellet portion of the phagemid-containing *Escherichia coli* cells (namely, the entire phages contained in the *Escherichia coli* cells which did not form single colonies and contained in the pellets) collected in each of the rounds, as follows. Note, however, that the human IgA antibody (#I4036; manufactured by Sigma-Aldrich Co. LLC.) alone was used as the antigen to be immobilized on plates, and the evaluation of the antigen-binding activity was also performed only for the human IgA antibody. In other words, the immobilization of the human IgG1 antibody and the like, and the evaluation of the antigen-binding activity for the human IgG1 antibody and the like, were not carried out.

Figure 13:
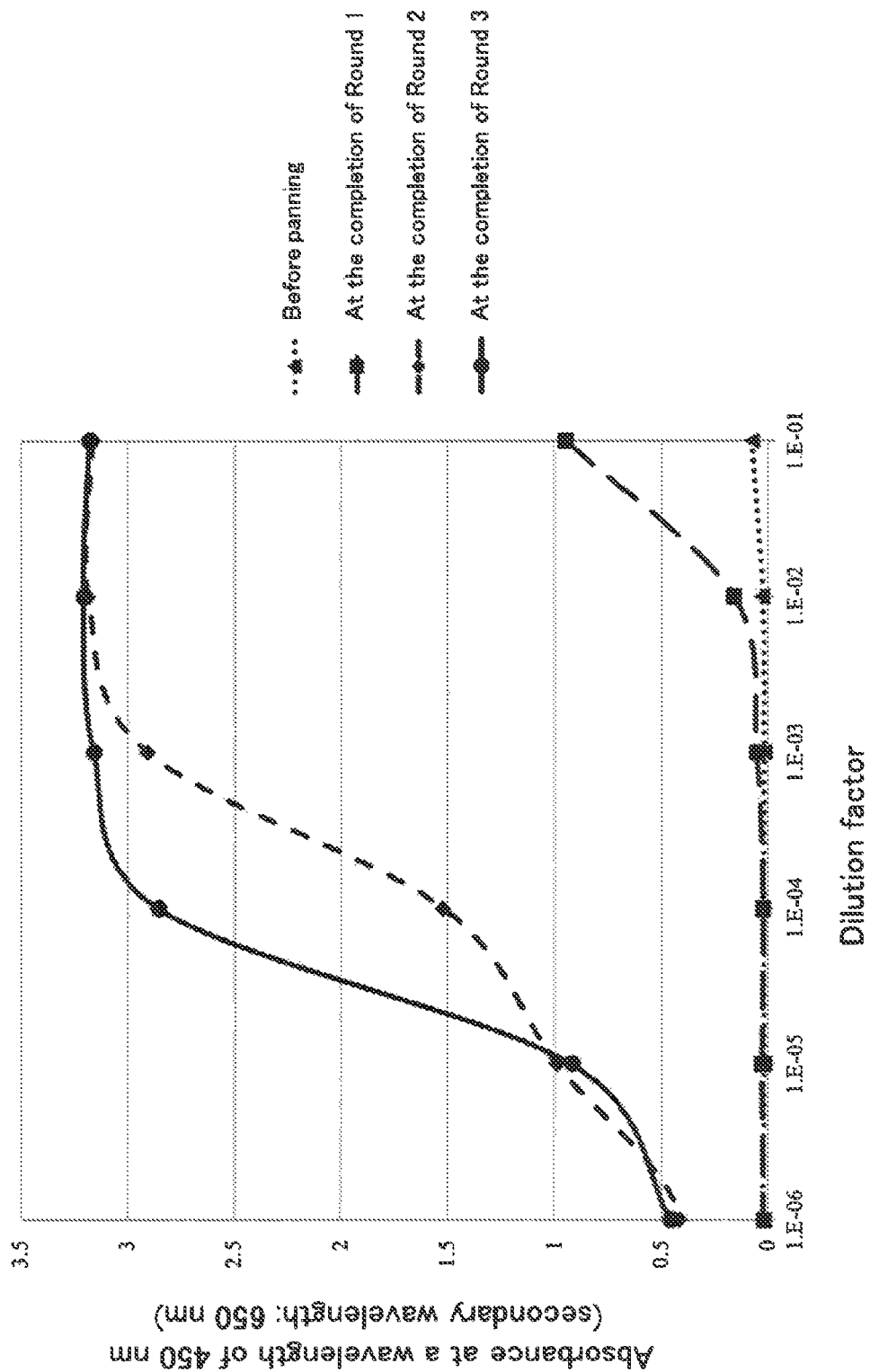
FIG. 13 is a graph showing the absorbance at a wavelength of 450 nm (secondary wavelength: 650 nm), when the evaluation of the antigen-binding activity was carried out for the pellet portion of phagemid-containing *Escherichia coli* cells collected before the panning, at the completion of Round 1, at the completion of Round 2, and at the completion of Round 3 in Example 9-2.

The results are shown in FIG. 13. It can be seen from FIG. 13 that the antigen-binding activity for the human IgA antibody increased exponentially in Round 2. Further, it can be seen that the antigen-binding activity for the human IgA antibody in Round 3 was even higher than that in Round 2. These results have revealed that phages which specifically bind to the human IgA antibody are concentrated, even in the case of carrying out the panning using the human serum-derived IgA polyclonal antibody-immobilized MLVs as the carrier.

<9-7. Evaluation of Antigen-Binding Activity 2>

Example 9-3

The evaluation of the antigen-binding activity was carried out for the rabbit-derived single-chain antibodies obtained from the colonies of the phagemid-containing *Escherichia coli* cells collected in each of the rounds, in the same manner as in the above section 3-2. Note that, in this Example, not only the human IgA antibody (#I4036; manufactured by Sigma-Aldrich Co. LLC.), but also the human IgG 1 antibody and the like were used as the antigens to be immobilized on plates, in the same manner as in the above 3-2. Likewise, the evaluation of the antigen-binding activity was carried out not only for the human IgA antibody, but also for the human IgG 1 antibody and the like.

Figure 14:
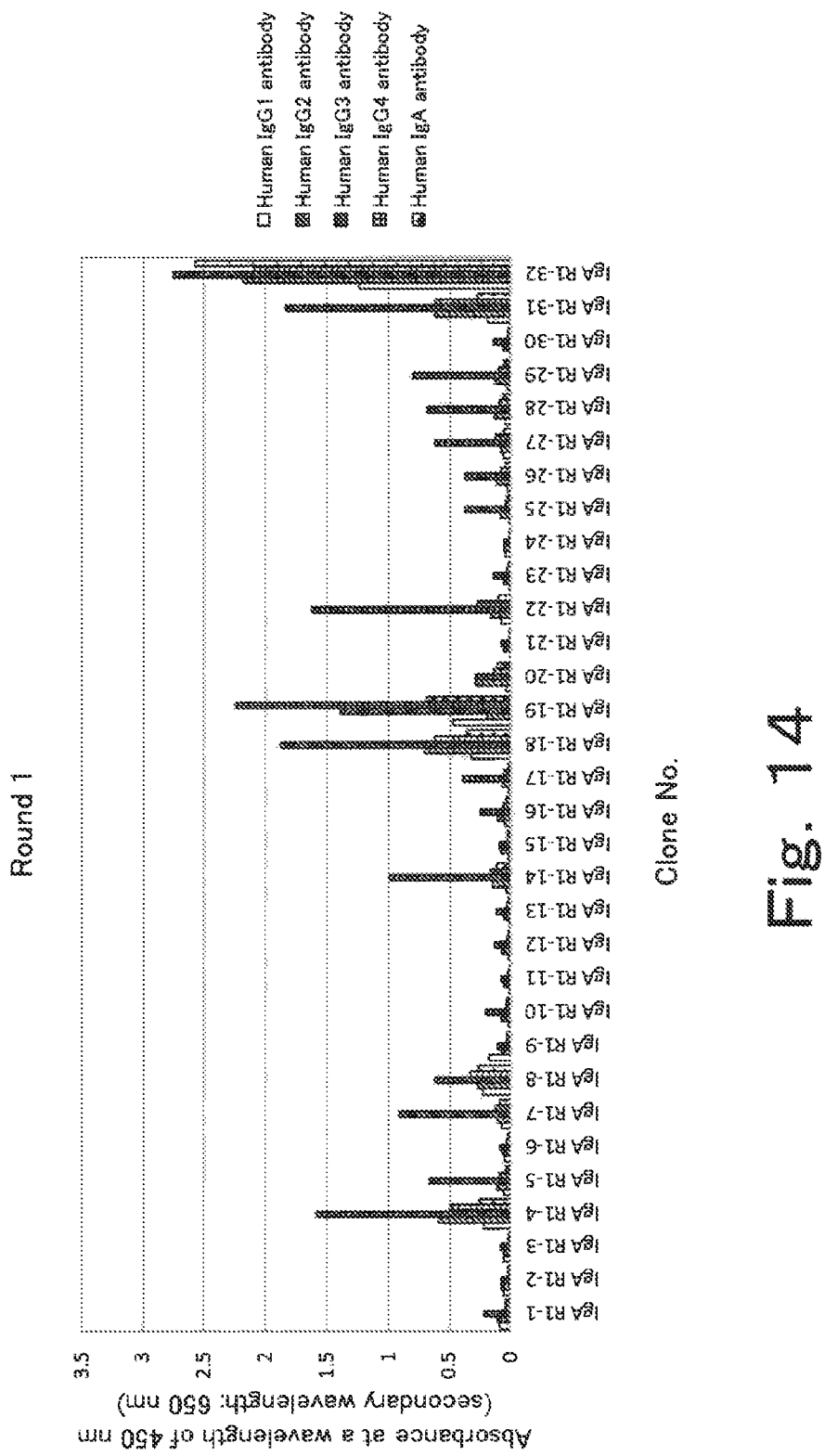
FIG. 14 is a graph showing the results of the antigen-binding activity evaluation carried out for rabbit-derived single-chain antibodies obtained from 32 colonies collected at the completion of Round 1 in Example 9-3.

FIG. 14, Table 9-1, and Table 9-2 show the evaluation results of the antigen-binding activities of the rabbit-derived single-chain antibodies obtained from the 32 colonies collected at the completion of Round 1. The clones having an OD value of 0.1 or more were defined as positive clones, and those having an OD of less than 0.1 were defined as negative clones.

TABLE 9-1

| Clone No | IgG1 | IgG2 | IgG3 | IgG4 | IgA |
|---|---|---|---|---|---|
| IgA R1-1 | 0.0850 | 0.1040 | 0.2120 | 0.0440 | 0.0380 |
| IgA R1-2 | 0.0600 | 0.0760 | 0.0690 | 0.0280 | 0.0240 |
| IgA R1-3 | 0.0540 | 0.0560 | 0.0790 | 0.0270 | 0.0200 |
| IgA R1-4 | 0.2200 | 0.5880 | 1.5880 | 0.5000 | 0.2600 |
| IgA R1-5 | 0.0600 | 0.1100 | 0.6720 | 0.0970 | 0.0440 |
| IgA R1-6 | 0.0500 | 0.0650 | 0.0850 | 0.0330 | 0.0270 |
| IgA R1-7 | 0.0730 | 0.1150 | 0.9080 | 0.1290 | 0.0920 |
| IgA R1-8 | 0.2330 | 0.2670 | 0.6240 | 0.3280 | 0.2690 |
| IgA R1-9 | 0.1810 | 0.0760 | 0.1100 | 0.0300 | 0.0310 |
| IgA R1-10 | 0.0270 | 0.0820 | 0.2070 | 0.0440 | 0.0320 |
| IgA R1-11 | 0.0180 | 0.0570 | 0.0770 | 0.0250 | 0.0210 |
| IgA R1-12 | 0.0220 | 0.0750 | 0.1360 | 0.0350 | 0.0270 |
| IgA R1-13 | 0.0190 | 0.0590 | 0.1230 | 0.0340 | 0.0260 |
| IgA R1-14 | 0.0450 | 0.1510 | 0.9870 | 0.1680 | 0.1210 |
| IgA R1-15 | 0.0220 | 0.0800 | 0.0950 | 0.0350 | 0.0300 |
| IgA R1-16 | 0.0520 | 0.1140 | 0.2510 | 0.0670 | 0.0430 |
| IgA R1-17 | 0.0240 | 0.0710 | 0.3950 | 0.0580 | 0.0290 |
| IgA R1-18 | 0.3240 | 0.7110 | 1.8720 | 0.6230 | 0.3630 |
| IgA R1-19 | 0.4750 | 0.2010 | 1.3900 | 2.2470 | 0.6940 |
| IgA R1-20 | 0.0390 | 0.2960 | 0.2900 | 0.1420 | 0.1120 |
| IgA R1-21 | 0.0120 | 0.0560 | 0.0820 | 0.0210 | 0.0170 |
| IgA R1-22 | 0.0830 | 0.1650 | 1.6250 | 0.2780 | 0.1050 |
| IgA R1-23 | 0.0200 | 0.0570 | 0.1450 | 0.0310 | 0.0230 |
| IgA R1-24 | 0.0460 | 0.0600 | 0.0600 | 0.0190 | 0.0210 |
| IgA R1-25 | 0.0210 | 0.0850 | 0.3760 | 0.0490 | 0.0310 |
| IgA R1-26 | 0.0330 | 0.1190 | 0.3780 | 0.0790 | 0.0500 |
| IgA R1-27 | 0.0630 | 0.0810 | 0.6180 | 0.1260 | 0.0540 |
| IgA R1-28 | 0.0490 | 0.1350 | 0.6880 | 0.1000 | 0.0640 |
| IgA R1-29 | 0.0320 | 0.1310 | 0.8010 | 0.1050 | 0.0610 |
| IgA R1-30 | 0.0130 | 0.0640 | 0.1430 | 0.0280 | 0.0220 |
| IgA R1-31 | 0.1870 | 0.6220 | 1.8370 | 0.6150 | 0.2750 |
| IgA R1-32 | 1.2300 | 2.1850 | 2.7570 | 2.0930 | 2.5720 |

TABLE 9-2

| | IgG1 | IgG2 | IgG3 | IgG4 | IgA |
|---|---|---|---|---|---|
| Number of positive clones | 7 | 16 | 25 | 13 | 9 |
| Number of negative clones | 25 | 16 | 7 | 19 | 23 |
| The ratio of the number of positive clones to the total 32 clones (%) | 21.9 | 500 | 78.1 | 406 | 28.1 |
| OD ≥ 2.5 | 0 | 0 | 1 | 0 | 1 |
| 1 ≤ OD < 2.5 | 1 | 1 | 5 | 2 | 0 |
| 0.1 ≤ OD < 1 | 6 | 15 | 19 | 11 | 8 |

Figure 15:
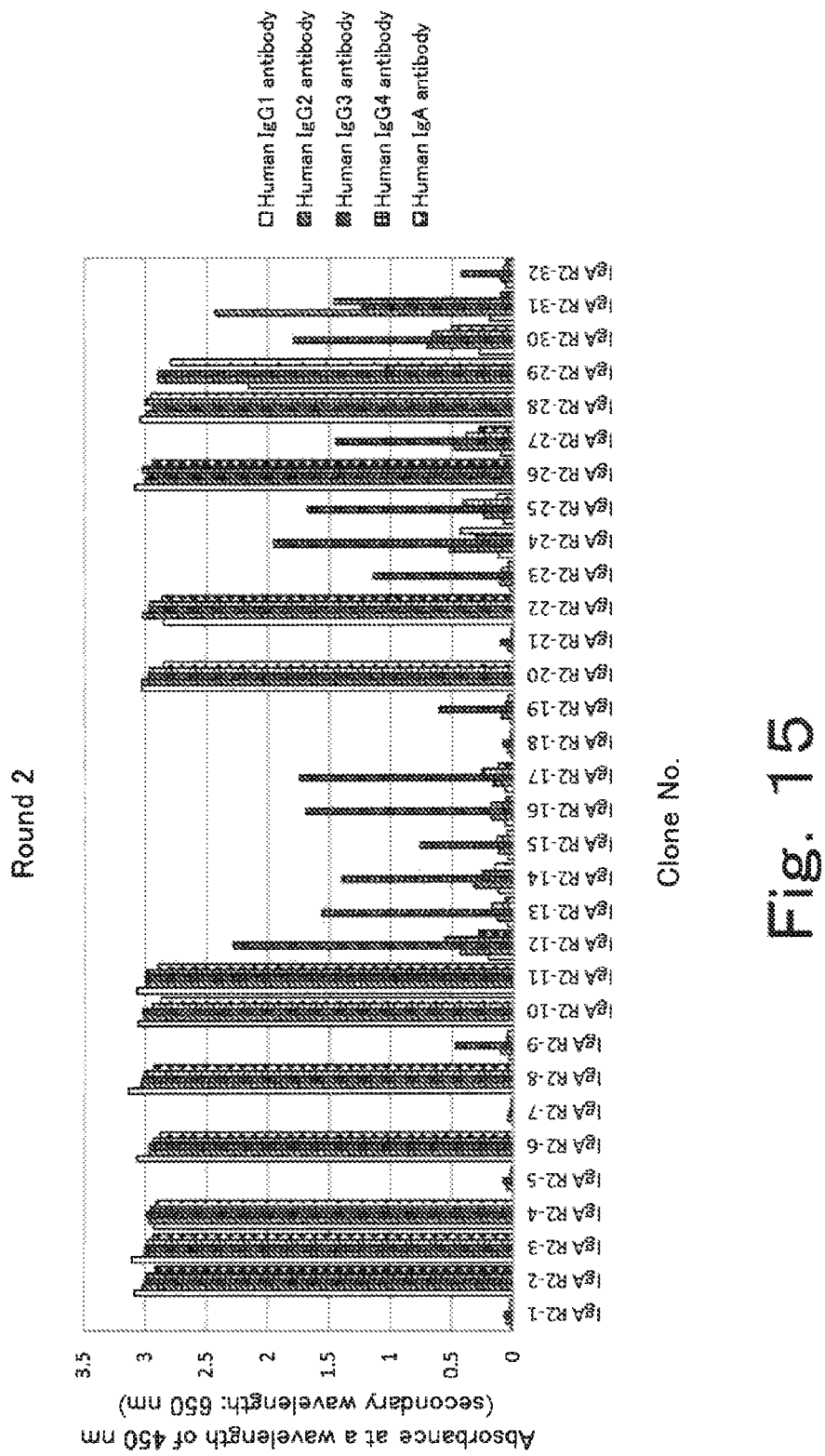
FIG. 15 is a graph showing the results of the antigen-binding activity evaluation carried out for rabbit-derived single-chain antibodies obtained from 32 colonies collected at the completion of Round 2 in Example 9-3.

Likewise, FIG. 15, Table 10-1, and Table 10-2 show the evaluation results of the antigen-binding activities of the rabbit-derived single-chain antibodies obtained from the 32 colonies collected at the completion of Round 2. The clones having an OD value of 0.1 or more were defined as positive clones, and those having an OD of less than 0.1 were defined as negative clones.

TABLE 10-1

| Clone No. | IgG1 | IgG2 | IgG3 | IgG4 | IgA |
|---|---|---|---|---|---|
| IgA R2-1 | 0.0140 | 0.0560 | 0.0710 | 0.0220 | 0.0200 |
| IgA R2-2 | 3.0900 | 3.0160 | 2.9940 | 2.9860 | 2.9130 |
| IgA R2-3 | 3.1110 | 2.9990 | 2.9910 | 2.9780 | 2.9280 |
| IgA R2-4 | 2.9270 | 2.9660 | 2.9890 | 2.9540 | 2.9070 |
| IgA R2-5 | 0.0100 | 0.0540 | 0.0760 | 0.0220 | 0.0180 |
| IgA R2-6 | 3.0640 | 2.9620 | 2.9640 | 2.9300 | 2.8760 |
| IgA R2-7 | 0.0090 | 0.0450 | 0.0270 | 0.0170 | 0.0180 |
| IgA R2-8 | 3.1390 | 3.0310 | 3.0200 | 3.0030 | 2.9220 |
| IgA R2-9 | 0.0330 | 0.0980 | 0.4670 | 0.0560 | 0.0450 |
| IgA R2-10 | 3.0600 | 3.0060 | 3.0150 | 2.9410 | 2.8700 |
| IgA R2-11 | 3.0650 | 2.9860 | 2.9960 | 2.9860 | 2.8940 |
| IgA R2-12 | 0.2040 | 0.4280 | 2.2810 | 0.5590 | 0.2790 |
| IgA R2-13 | 0.0430 | 0.1360 | 1.5570 | 0.1690 | 0.0660 |
| IgA R2-14 | 0.1150 | 0.3220 | 1.3980 | 0.2480 | 0.1490 |
| IgA R2-15 | 0.0380 | 0.1140 | 0.7580 | 0.1350 | 0.0550 |
| IgA R2-16 | 0.0720 | 0.1760 | 1.6820 | 0.1760 | 0.0630 |
| IgA R2-17 | 0.0690 | 0.1650 | 1.7400 | 0.2470 | 0.1160 |
| IgA R2-18 | 0.0120 | 0.0520 | 0.0850 | 0.0220 | 0.0210 |
| IgA R2-19 | 0.0250 | 0.0950 | 0.6030 | 0.0590 | 0.0380 |
| IgA R2-20 | 3.0290 | 3.0270 | 2.9720 | 2.9640 | 2.8480 |
| IgA R2-21 | 0.0080 | 0.0460 | 0.1020 | 0.0150 | 0.0170 |
| IgA R2-22 | 2.8440 | 3.0150 | 2.9650 | 2.9660 | 2.8580 |
| IgA R2-23 | 0.0320 | 0.1070 | 1.1400 | 0.0960 | 0.0410 |
| IgA R2-24 | 0.1180 | 0.5180 | 1.9500 | 0.3020 | 0.4330 |
| IgA R2-25 | 0.0810 | 0.2390 | 1.6760 | 0.4050 | 0.1340 |
| IgA R2-26 | 3.0840 | 2.9940 | 2.9820 | 3.0180 | 2.9360 |
| IgA R2-27 | 0.1000 | 0.4810 | 1.4420 | 0.3820 | 0.2800 |
| IgA R2-28 | 3.0400 | 2.9900 | 2.9300 | 2.9910 | 2.9560 |
| IgA R2-29 | 2.1590 | 2.8960 | 2.8920 | 1.0310 | 2.7930 |
| IgA R2-30 | 0.2730 | 0.6990 | 1.7850 | 0.6590 | 0.4920 |
| IgA R2-31 | 0.1900 | 2.4280 | 1.2270 | 1.4560 | 0.0990 |
| IgA R2-32 | 0.0620 | 0.1050 | 0.4250 | 0.0760 | 0.0650 |

TABLE 10-2

| | IgG1 | IgG2 | IgG3 | IgG4 | IgA |
|---|---|---|---|---|---|
| Number of positive clones | 18 | 25 | 28 | 23 | 19 |
| Number of negative clones | 14 | 7 | 4 | 9 | 13 |
| The ratio of the number of positive clones to the total 32 clones (%) | 56.3 | 78.1 | 87.5 | 71.9 | 59.4 |
| OD ≥ 2.5 | 11 | 12 | 12 | 11 | 12 |
| 1 ≤ OD < 2.5 | 1 | 1 | 11 | 2 | 0 |
| 0.1 ≤ OD < 1 | 6 | 12 | 5 | 10 | 7 |

Figure 16:
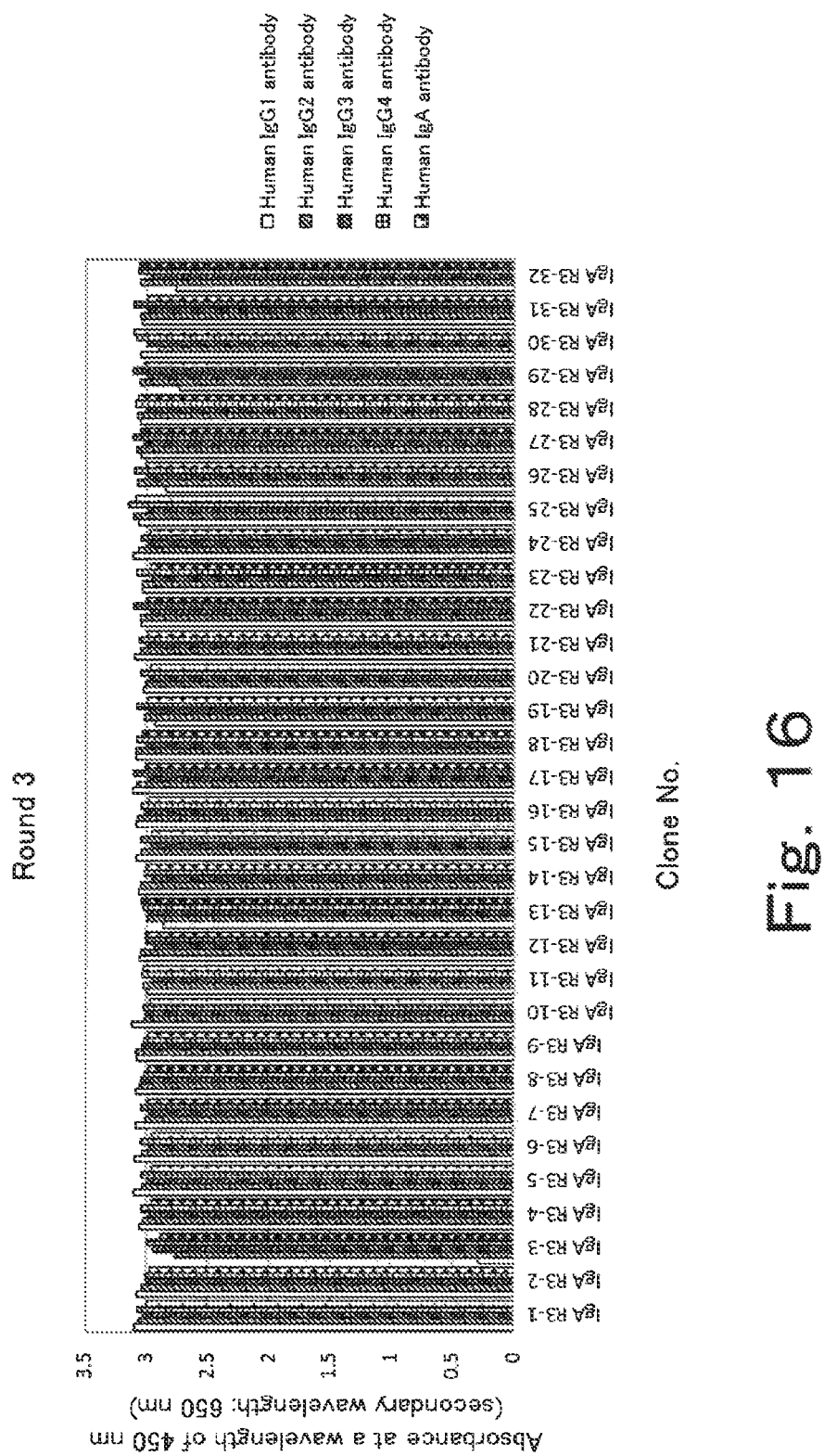
FIG. 16 is a graph showing the results of the antigen-binding activity evaluation carried out for rabbit-derived single-chain antibodies obtained from 32 colonies collected at the completion of Round 3 in Example 9-3.

Likewise, FIG. 16, Table 11-1, and Table 11-2 show the evaluation results of the antigen-binding activities of the rabbit-derived single-chain antibodies obtained from the 32 colonies collected at the completion of Round 3. The clones having an OD value of 0.1 or more were defined as positive clones, and those having an OD of less than 0.1 were defined as negative clones.

TABLE 11-1

| Clone No. | IgG1 | IgG2 | IgG3 | IgG4 | IgA |
|---|---|---|---|---|---|
| IgA R3-1 | 3.0930 | 3.0670 | 3.0240 | 3.0710 | 2.9960 |
| IgA R3-2 | 3.0790 | 3.0310 | 2.9910 | 3.0140 | 2.9740 |
| IgA R3-3 | 0.2860 | 2.7640 | 2.9480 | 2.9950 | 2.8860 |
| IgA R3-4 | 3.0610 | 3.0250 | 2.9770 | 3.0420 | 2.9520 |
| IgA R3-5 | 3.1030 | 3.0350 | 2.9900 | 3.0390 | 2.9580 |
| IgA R3-6 | 3.0930 | 3.0310 | 2.9770 | 3.0500 | 2.9540 |
| IgA R3-7 | 3.0870 | 3.0090 | 2.9810 | 3.0490 | 2.9950 |
| IgA R3-8 | 3.0920 | 3.0590 | 3.0440 | 3.0210 | 2.9840 |
| IgA R3-9 | 3.0780 | 3.0910 | 3.0370 | 3.0210 | 2.9860 |
| IgA R3-10 | 3.1220 | 3.0150 | 3.0140 | 3.0280 | 2.9690 |
| IgA R3-11 | 2.9950 | 3.0290 | 2.9600 | 3.0350 | 3.0260 |
| IgA R3-12 | 3.0610 | 3.0490 | 2.9380 | 3.0060 | 3.0120 |
| IgA R3-13 | 2.8620 | 2.9970 | 2.9940 | 3.0250 | 3.0410 |
| IgA R3-14 | 3.0680 | 3.0490 | 2.9530 | 3.0210 | 3.0010 |
| IgA R3-15 | 3.0920 | 3.0420 | 2.9610 | 3.0480 | 2.9550 |
| IgA R3-16 | 3.0900 | 3.0750 | 3.0210 | 3.0380 | 2.9770 |
| IgA R3-17 | 3.1130 | 3.0810 | 2.9750 | 3.1040 | 3.0100 |
| IgA R3-18 | 3.0910 | 3.0900 | 2.9910 | 3.0790 | 3.0340 |
| IgA R3-19 | 2.9280 | 3.0170 | 2.9810 | 3.0840 | 2.9920 |
| IgA R3-20 | 3.0290 | 3.0130 | 2.9810 | 3.0490 | 2.9650 |
| IgA R3-21 | 3.0950 | 3.0490 | 2.9920 | 3.0600 | 2.9960 |
| IgA R3-22 | 3.0400 | 3.0500 | 2.9610 | 3.1010 | 3.0010 |
| IgA R3-23 | 3.0360 | 3.0310 | 2.9540 | 3.0780 | 2.9660 |
| IgA R3-24 | 3.1110 | 3.0640 | 2.9940 | 3.0400 | 2.9730 |
| IgA R3-25 | 3.0670 | 3.1040 | 2.9840 | 3.1550 | 3.0870 |

TABLE 11-1-continued

| Clone No. | IgG1 | IgG2 | IgG3 | IgG4 | IgA |
|---|---|---|---|---|---|
| IgA R3-26 | 2.8440 | 3.0730 | 3.0000 | 3.0990 | 3.0030 |
| IgA R3-27 | 3.0450 | 3.0810 | 3.0150 | 3.1110 | 3.0520 |
| IgA R3-28 | 3.0470 | 3.0720 | 3.0050 | 3.0910 | 3.0640 |
| IgA R3-29 | 2.7280 | 3.0550 | 2.9890 | 3.1130 | 3.0150 |
| IgA R3-30 | 3.0490 | 2.9040 | 2.9910 | 3.0780 | 3.1070 |
| IgA R3-31 | 3.0370 | 3.0520 | 2.9900 | 3.1030 | 2.9870 |
| IgA R3-32 | 2.7580 | 3.0530 | 2.9610 | 3.0670 | 3.0590 |

TABLE 11-2

| | IgG1 | IgG2 | IgG3 | IgG4 | IgA |
|---|---|---|---|---|---|
| Number of positive clones | 32 | 32 | 32 | 32 | 32 |
| Number of negative clones | 0 | 0 | 0 | 0 | 0 |
| The ratio of the number of positive clones to the total 32 clones (%) | 100 | 100 | 100 | 100 | 100 |
| OD ≥ 2.5 | 31 | 32 | 32 | 32 | 32 |
| 1 ≤ OD < 2.5 | 0 | 0 | 0 | 0 | 0 |
| 0.1 ≤ OD < 1 | 1 | 0 | 0 | 0 | 0 |

The above results revealed as follows.

All of the single-chain antibodies collected at Round 3 bound to the human IgA antibody, with an extremely high binding activity. Further, these single-chain antibodies bound not only to the human IgA antibody, but also to all of the human IgG1 antibody, the human IgG2 antibody, the human IgG3 antibody, and the human IgG4 antibody. These results revealed that the panning has been carried out at an extremely high efficiency.

<9-8. Determination of Amino Acid Sequences of Genes of Rabbit-Derived Single-Chain Antibodies which Bind to Human Serum-Derived IgA Polyclonal Antibody>

Example 10

The amino acid sequences of the rabbit-derived single-chain antibodies obtained from the 32 colonies collected at the completion of Round 1, the 32 colonies collected at the completion of Round 2, and the 32 colonies collected at the completion of Round 3 were determined, from the gene sequences of the rabbit-derived single-chain antibody genes.

FIG. 17-1 shows the amino acid sequences of the rabbit-derived single-chain antibodies obtained from the 32 colonies collected at the completion of Round 1, determined from the gene sequences of the $V_H$ domains. SEQ ID NOs are assigned for the respective amino acid sequences, as shown in the FIGS. Note that the empty cells indicate that the corresponding sequences could not be determined.

Further, for the amino acid sequences of CDR3 of the $V_H$ domains, which greatly affect the specificity of the antigen-antibody reaction, the number of amino acid residues, the number of emergence of the sequence in 32 clones, and the probability of emergence in 32 clones are shown for each sequence in FIG. 17-2. The row indicated as "Negative clones" shows the results for the clones in which the amino acid sequences of CDR3 of the $V_H$ domains could not be determined. SEQ ID NOs are assigned for the respective amino acid sequences of CDR3.

Likewise, the results for the 32 colonies obtained at the at the completion of Round 2 are shown in FIG. 17-3 and FIG. 17-4, and the results for the 32 colonies obtained at the completion of Round 3 are shown in FIG. 17-5 and FIG. 17-6.

Further, the amino acid sequences of the $V_H$ domains of "R2-18", "R3-8" and "R3-75" obtained in the section of <2. Method for Screening Rabbit-derived Single-chain Antibody which Binds to Human Serum-derived IgG Polyclonal Antibody> described above are shown in FIG. 17-7, for reference.

Further, a plurality of clones in the FIGS. are indicated with the notation, for example, "Common 1" in the remarks column. This indicates that the clones denoted as "Common 1" are all identical clones. Likewise, the clones denoted as "Common 2" are all identical clones. Note, however, that these numbers are given merely for convenience sake.

Still further, there are clones which are indicated with the notation, for example, "Common 3 (identical to R3-75)", in the remarks column. This indicates that these clones are identical to the clone "R3-75" obtained in the section of <2. Method for Screening Rabbit-derived Single-chain Antibody which Binds to Human Serum-derived IgG Polyclonal Antibody>.

Further, the numbers of clones of "Common 1" to "Common 7" at the completion of Rounds 1 to 3 are summarized in FIG. 17-8, FIG. 17-9, and FIG. 17-10.

The above results revealed as follows.

As can be seen from the results shown in FIG. 17-6, 26 clones out of the total 32 clones obtained in Round 3 contained the $V_H$ domain containing the sequence "ATRYDSYGYAYNYWFGTLW (SEQ ID NO: 30; 19 residues), which is the amino acid sequence of CDR3 contained in each of "R2-18", "R3-8 (note, however, that this clone is identical to the clone R2-18)", and "R3-75" obtained in the section of <2. Method for Screening Rabbit-derived Single-chain Antibody which Binds to Human Serum-derived IgG Polyclonal Antibody>. In other words, 81.3% of the clones obtained in Round 3 contained the $V_H$ domain containing the sequence of SEQ ID NO: 30.

Among these, 12 clones were clones of Common 1, and 8 clones were clones of Common 2. Two other clones were clones of Common 4, which are identical with "R2-18 (Rank 6; note, however, that this clone is identical to the clone "R3-8")" obtained in the section of <2. Method for Screening Rabbit-derived Single-chain Antibody which Binds to Human Serum-derived IgG Polyclonal Antibody>.

Further, two other clones were clones of Common 3, which are identical to the clone "R3-75 (Rank 1)" obtained in the section of <2. Method for Screening Rabbit-derived Single-chain Antibody which Binds to Human Serum-derived IgG Polyclonal Antibody>.

In addition, a plurality of clones were also obtained, whose amino acid sequences of CDR3 of the $V_H$ domains are highly homologous with each other, such as the sequences "ARADYNTVAYFDLW (SEQ ID NO: 141; 14 residues)", "ARADYNTAAYFDLW (SEQ ID NO: 142; 14 residues)", and "VRADYNTVSYFDLW (SEQ ID NO: 143; 14 residues)".

The results of Western blotting have revealed that all the clones obtained in Round 3 bind to the light chains (L chains) of the human antibodies, specifically to the kappa chains, regardless of the length of the amino acid sequence of the CDR3 of the $V_H$ domain.

Based on the above results, it has been found out that, by carrying out panning using a human serum-derived IgA polyclonal antibody as an antigen to be immobilized on a carrier, it is possible to collect a single-chain antibody which binds to the light chain (L chain), specifically to the kappa chain, of a human antibody, which is a region common to both a human IgG antibody and a human IgA antibody, with an extremely high efficiency.

<9-9. Measurement of Dissociation Rate Constant $k_{off}$>

Example 11

Figure 18:
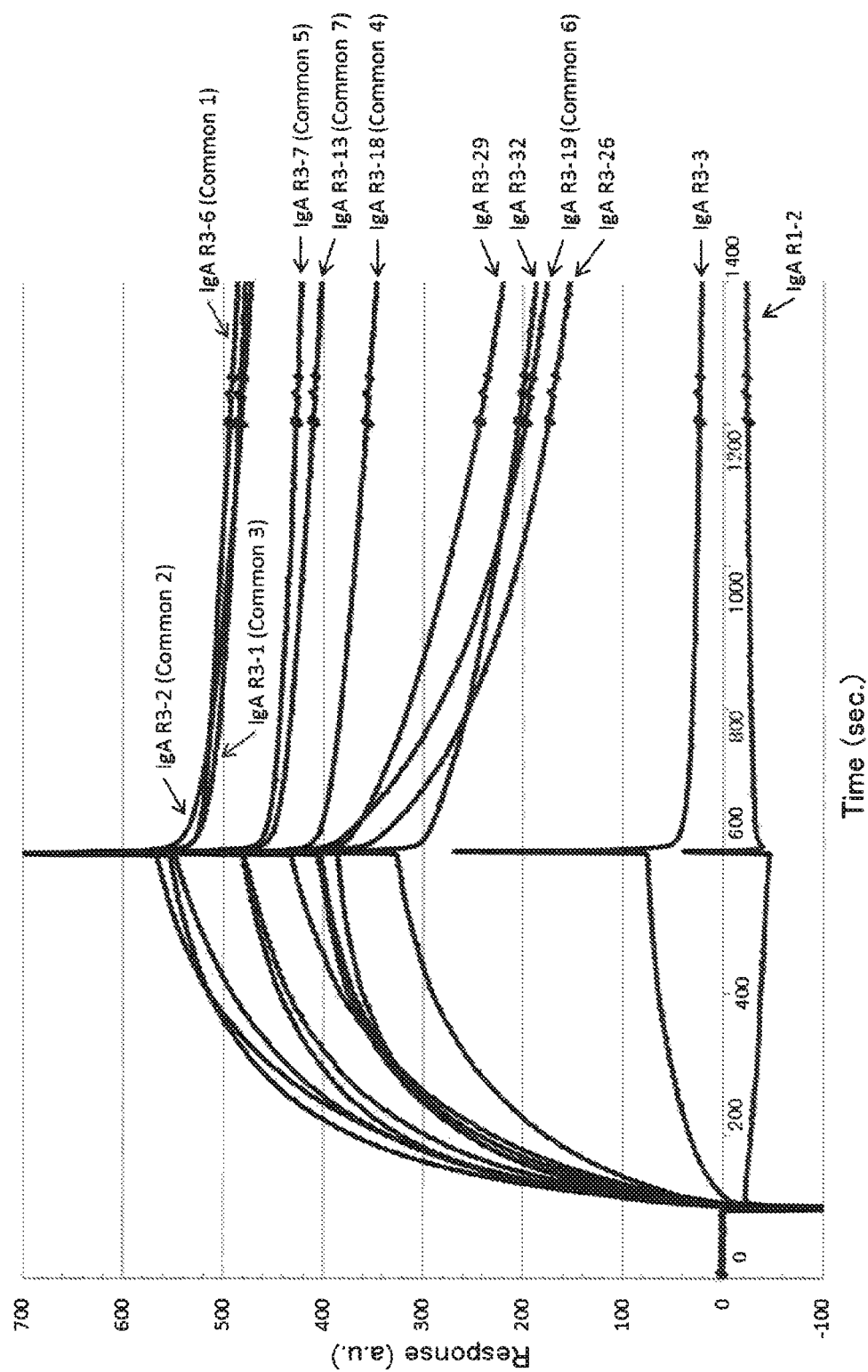
FIG. 18 is a graph showing the results of the antigen-binding activity evaluation carried out in Example 11 and Comparative Example 11.

The measurement of the dissociation rate constant $k_{off}$ was carried out for the 32 colonies obtained at the completion of Round 3, in the same manner as described in the section of <4. Measurement of Dissociation Rate Constant $k_{off}$> above, except that human IgA antibody immobilized CM5 was used as a sensor chip. These results are shown in FIG. 18 and Table 12. The $R^2$ are also shown.

Comparative Example 11

The same procedure as in Example 11 was carried out as Comparative Example 11, except for using "IgA R1-2" as a negative control.

TABLE 12

| Clone No. | koff (sec$^{-1}$) | $R^2$ | Remarks |
|---|---|---|---|
| IgA R3-6 | 8.69E−05 | 9.92E−01 | Common 1 |
| IgA R3-2 | 1.48E−04 | 9.92E−01 | Common 2 |
| IgA R3-1 | 9.88E−05 | 9.81E−01 | Common 3 |
| IgA R3-18 | 1.81E−04 | 9.93E−01 | Common 4 |
| IgA R3-7 | 9.56E−05 | 9.74E−01 | Common 5 |
| IgA R3-19 | 9.81E−04 | 9.84E−01 | Common 6 |
| IgA R3-13 | 1.31E−04 | 9.95E−01 | Common 7 |
| IgA R3-3 | 6.75E−04 | 9.53E−01 | |
| IgA R3-26 | 1.00E−03 | 9.86E−01 | |
| IgA R3-29 | 6.61E−04 | 9.97E−01 | |
| IgA R3-32 | 5.64E−04 | 9.99E−01 | |
| IgA R1-2 | — | — | |

It has been confirmed that all the clones obtained in Round 3 bind to the human IgA antibody. Further, as shown in Table 12, the most of the single-chain antibodies derived from the clones obtained in Round 3 had a dissociation rate constant $k_{off}$ within the order of from $10^{-5}$ to $10^{-4}$ sec$^{-1}$, which is extremely low. In particular, the dissociation rate constant $k_{off}$ of the single-chain antibody derived from "IgA R3-6 (Common 1)", which accounted for 12 clones out of 32 clones, was lower than the dissociation rate constant $k_{off}$ of the single-chain antibody derived from "IgA R3-1 (Common 3)", which is identical to the clone R3-75", suggesting a high affinity of the single-chain antibody derived from "IgA R3-6 (Common 1)".

Based on the above results, it has been found out that the present method is also capable of collecting a clone which is present at a low abundance in the library, at an extremely high efficiency, and is effective for collecting a single-chain antibody having a high affinity and specificity.

INDUSTRIAL APPLICABILITY

The present invention can be used, for example, in a method for producing an antibody drug.

The invention claimed is:

1. A separation agent for separating a human serum-derived IgG polyclonal antibody, the separation agent comprising: a carrier; and a single-chain antibody which has a dissociation constant for a human serum-derived IgG polyclonal antibody of not more than $3.0 \times 10^{-8}$ M and which binds to the surface of the carrier via a chemical bond,
wherein the single-chain antibody is selected from the following single-chain antibodies (a) to (e):
(a) the single-chain antibody having
the amino acid sequence of the heavy-chain CDR3: ATRYDSYGYAYNYWFGTLW (SEQ ID NO: 148);
wherein the single-chain antibody (a) further comprises the following amino acid sequence (a-1) or (a-2):
(a-1) the amino acid sequence of the heavy-chain CDR1: SGIDLSSNA (SEQ ID NO: 153),
the amino acid sequence of the heavy-chain CDR2: ISTVGKT (SEQ ID NO: 154),
the amino acid sequence of the light-chain CDR1: ENINSE (SEQ ID NO: 155),
the amino acid sequence of the light-chain CDR2: DAS, and
the amino acid sequence of the light-chain CDR3: QSTYYDGNYVYA (SEQ ID NO: 156); and
(a-2) the amino acid sequence of the heavy-chain CDR1: SGIDLSSNA (SEQ ID NO: 153),
the amino acid sequence of the heavy-chain CDR2: ISTGGST (SEQ ID NO: 157),
the amino acid sequence of the light-chain CDR1: QNINNE (SEQ ID NO: 158),
the amino acid sequence of the light-chain CDR2: DAS, and
the amino acid sequence of the light-chain CDR3: QSTYYDGNYVYA (SEQ ID NO: 156),
(b) the single-chain antibody having the amino acid sequence of the heavy-chain CDR3: GSYYDSHG-YAYVSLW (SEQ ID NO: 149);
wherein the single-chain antibody (b) further comprises the amino acid sequence of the heavy-chain CDR1: SGFSLSRYA (SEQ ID NO: 159),
the amino acid sequence of the heavy-chain CDR2: IGSGGST (SEQ ID NO: 160),
the amino acid sequence of the light-chain CDR1: QSISTA (SEQ ID NO: 161),
the amino acid sequence of the light-chain CDR2: SAS, and
the amino acid sequence of the light-chain CDR3: QSYYGSSSDNA (SEQ ID NO: 162);
(c) the single-chain antibody having
the amino acid sequence of the heavy-chain CDR3: ATDYGIYGYAYGHLW (SEQ ID NO: 150);
wherein the single-chain antibody (c) further comprises:
the amino acid sequence of the heavy-chain CDR1: SGIDLSSYA (SEQ ID NO: 163),
the amino acid sequence of the heavy-chain CDR2: IGSGGGT (SEQ ID NO: 164),
the amino acid sequence of the light-chain CDR1: QSISTA (SEQ ID NO: 161),
the amino acid sequence of the light-chain CDR2: DAS, and the amino acid sequence of the light-chain CDR3: QTYFGSDTDNA (SEQ ID NO: 165);
(d) the single-chain antibody having
the amino acid sequence of the heavy-chain CDR3: ARYSGDNGGALNLW (SEQ ID NO: 151);
wherein the single-chain antibody (d) further comprises:
the amino acid sequence of the heavy-chain CDR1: SGFSLSSYA (SEQ ID NO: 166),
the amino acid sequence of the heavy-chain CDR2: ISSSGST (SEQ ID NO: 167),
the amino acid sequence of the light-chain CDR1: QHIRSY (SEQ ID NO: 168),
the amino acid sequence of the light-chain CDR2: AAS, and
the amino acid sequence of the light-chain CDR3: QRYYDIRNYGNG (SEQ ID NO: 169), and
(e) the single-chain antibody having
the amino acid sequence of the heavy-chain CDR3: ARYSGDNGGTLNLW (SEQ ID NO: 152);
wherein the single-chain antibody (e) further comprises:
the amino acid sequence of the heavy-chain CDR1: SGIDLRRYA (SEQ ID NO: 170),
the amino acid sequence of the heavy-chain CDR2: IASGNTD (SEQ ID NO: 171),
the amino acid sequence of the light-chain CDR1: QSISSY (SEQ ID NO: 172),
the amino acid sequence of the light-chain CDR2: AAS, and
the amino acid sequence of the light-chain CDR3: QSYYSISSYGNT (SEQ ID NO: 173).

2. The separation agent according to claim 1, wherein the single-chain antibody is also an antibody against a human serum-derived IgA polyclonal antibody.

3. The separation agent according to claim 2, wherein the single-chain antibody has a dissociation rate constant for the human serum-derived IgA polyclonal antibody of not more than $1.0 \times 10^{-3}$ s$^{-1}$.

4. The separation agent according to claim 1, wherein the single-chain antibody is an antibody which binds to L chain.

5. The separation agent according to claim 1, wherein the single-chain antibody is an antibody which binds to kappa chain.

6. A method for separating a human serum-derived IgG polyclonal antibody from a mixed liquid of two or more kinds of substances, said mixed liquid comprising human serum-derived IgG polyclonal antibody, said method comprising the steps of: contacting said mixed liquid with a separation agent; and separating a human serum-derived IgG polyclonal antibody from said mixed liquid, the separation agent comprising: a carrier; and a single-chain antibody which has a dissociation constant for a human serum-derived IgG polyclonal antibody of not more than $3.0 \times 10^{-8}$ M and which binds to the surface of the carrier via a chemical bond,
wherein the single-chain antibody is selected from the following single-chain antibodies (a) to (e):
(a) the single-chain antibody having the amino acid sequence of the heavy-chain CDR3: ATRYDSYGYAYNYWFGTLW (SEQ ID NO: 148);
wherein the single-chain antibody (a) further comprises the following amino acid sequence (a-1) or (a-2):
(a-1) the amino acid sequence of the heavy-chain CDR1: SGIDLSSNA (SEQ ID NO: 153),
the amino acid sequence of the heavy-chain CDR2: ISTVGKT (SEQ ID NO: 154),
the amino acid sequence of the light-chain CDR1: ENINSE (SEQ ID NO: 155),
the amino acid sequence of the light-chain CDR2: DAS, and
the amino acid sequence of the light-chain CDR3: QSTYYDGNYVYA (SEQ ID NO: 156); and
(a-2) the amino acid sequence of the heavy-chain CDR1: SGIDLSSNA (SEQ ID NO: 153),
the amino acid sequence of the heavy-chain CDR2: ISTGGST (SEQ ID NO: 157),
the amino acid sequence of the light-chain CDR1: QNINNE (SEQ ID NO: 158),
the amino acid sequence of the light-chain CDR2: DAS, and
the amino acid sequence of the light-chain CDR3: QSTYYDGNYVYA (SEQ ID NO: 156),
(b) the single-chain antibody having the amino acid sequence of the heavy-chain CDR3: GSYYDSHGYAYVSLW (SEQ ID NO: 149);
wherein the single-chain antibody (b) further comprises
the amino acid sequence of the heavy-chain CDR1: SGFSLSRYA (SEQ ID NO: 159),
the amino acid sequence of the heavy-chain CDR2: IGSGGST (SEQ ID NO: 160),
the amino acid sequence of the light-chain CDR1: QSISTA (SEQ ID NO: 161),
the amino acid sequence of the light-chain CDR2: SAS, and
the amino acid sequence of the light-chain CDR3: QSYYGSSSDNA (SEQ ID NO: 162);
(c) the single-chain antibody having
the amino acid sequence of the heavy-chain CDR3: ATDYGIYGYAYGHLW (SEQ ID NO: 150);
wherein the single-chain antibody (c) further comprises:
the amino acid sequence of the heavy-chain CDR1: SGIDLSSYA (SEQ ID NO: 163),
the amino acid sequence of the heavy-chain CDR2: IGSGGGT (SEQ ID NO: 164),
the amino acid sequence of the light-chain CDR1: QSISTA (SEQ ID NO: 161),
the amino acid sequence of the light-chain CDR2: DAS, and
the amino acid sequence of the light-chain CDR3: QTYFGSDTDNA (SEQ ID NO: 165);
(d) the single-chain antibody having
the amino acid sequence of the heavy-chain CDR3: ARYSGDNGGALNLW (SEQ ID NO: 151);
wherein the single-chain antibody (d) further comprises:
the amino acid sequence of the heavy-chain CDR1: SGFSLSSYA (SEQ ID NO: 166),
the amino acid sequence of the heavy-chain CDR2: ISSSGST (SEQ ID NO: 167),
the amino acid sequence of the light-chain CDR1: QHIRSY (SEQ ID NO: 168),
the amino acid sequence of the light-chain CDR2: AAS, and
the amino acid sequence of the light-chain CDR3: QRYYDIRNYGNG (SEQ ID NO: 169), and
(e) the single-chain antibody having
the amino acid sequence of the heavy-chain CDR3: ARYSGDNGGTLNLW (SEQ ID NO: 152);
wherein the single-chain antibody (e) further comprises:
the amino acid sequence of the heavy-chain CDR1: SGIDLRRYA (SEQ ID NO: 170),
the amino acid sequence of the heavy-chain CDR2: IASGNTD (SEQ ID NO: 171),
the amino acid sequence of the light-chain CDR1: QSISSY (SEQ ID NO: 172), the amino acid sequence of the light-chain CDR2: AAS, and the amino acid sequence of the light-chain CDR3: QSYY-SISSYGNT (SEQ ID NO: 173).

7. The method according to claim 6, wherein the single-chain antibody is also an antibody against a human serum-derived IgA polyclonal antibody, and wherein the method further separates the human serum-derived IgA polyclonal antibody.

8. The method according to claim 7, wherein the single-chain antibody has a dissociation rate constant for the human serum-derived IgA polyclonal antibody of not more than $1.0 \times 10^{-3}$ $s^{-1}$.

9. The method according to claim 6, wherein the single-chain antibody is an antibody which binds to L chain.

10. The method according to claim 6, wherein the single-chain antibody is an antibody which binds to kappa chain.

* * * * *